(12) United States Patent
Igawa et al.

(10) Patent No.: US 11,359,194 B2
(45) Date of Patent: *Jun. 14, 2022

(54) ANTIGEN-BINDING MOLECULE CAPABLE OF BINDING TWO OR MORE ANTIGEN MOLECULES REPEATEDLY

(71) Applicant: Chugai Seiyaku Kabushiki Kaisha, Tokyo (JP)

(72) Inventors: Tomoyuki Igawa, Shizuoka (JP); Shinya Ishii, Shizuoka (JP); Atsuhiko Maeda, Shizuoka (JP); Takashi Nakai, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/020,497

(22) Filed: Sep. 14, 2020

(65) Prior Publication Data

US 2021/0079378 A1 Mar. 18, 2021

Related U.S. Application Data

(60) Continuation of application No. 15/952,951, filed on Apr. 13, 2018, which is a division of application No. 13/595,139, filed on Aug. 27, 2012, now abandoned, which is a continuation of application No. 12/936,587, filed as application No. PCT/JP2009/057309 on Apr. 10, 2009, now abandoned.

(30) Foreign Application Priority Data

Apr. 11, 2008 (JP) ................ 2008-104147
Sep. 26, 2008 (JP) ................ 2008-247713
Mar. 19, 2009 (JP) ................ 2009-068744

(51) Int. Cl.

| | |
|---|---|
| *C12N 15/10* | (2006.01) |
| *C07K 16/00* | (2006.01) |
| *C07K 16/24* | (2006.01) |
| *A61K 39/12* | (2006.01) |
| *A61K 39/145* | (2006.01) |
| *C07K 16/28* | (2006.01) |
| *G01N 33/68* | (2006.01) |
| *A61K 39/00* | (2006.01) |

(52) U.S. Cl.
CPC .......... *C12N 15/1037* (2013.01); *A61K 39/12* (2013.01); *A61K 39/145* (2013.01); *C07K 16/244* (2013.01); *C07K 16/248* (2013.01); *C07K 16/2866* (2013.01); *G01N 33/6854* (2013.01); *A61K 2039/505* (2013.01); *A61K 2039/544* (2013.01); *A61K 2039/545* (2013.01); *A61K 2039/552* (2013.01); *C07K 2317/24* (2013.01); *C07K 2317/56* (2013.01); *C07K 2317/565* (2013.01); *C07K 2317/622* (2013.01); *C07K 2317/76* (2013.01); *C07K 2317/77* (2013.01); *C07K 2317/92* (2013.01); *C12N 2760/16111* (2013.01); *C12N 2760/16134* (2013.01); *C12N 2770/20071* (2013.01); *G01N 2500/00* (2013.01)

(58) Field of Classification Search
None
See application file for complete search history.

(56) References Cited

U.S. PATENT DOCUMENTS

| | | |
|---|---|---|
| 4,689,299 A | 8/1987 | Insel et al. |
| 4,801,687 A | 1/1989 | Ngo |
| 5,126,250 A | 6/1992 | McDonough et al. |
| 5,202,253 A | 4/1993 | Esmon et al. |
| 5,322,678 A | 6/1994 | Morgan et al. |
| 5,468,634 A | 11/1995 | Liu |
| 5,501,854 A | 3/1996 | Raso |
| 5,585,089 A | 12/1996 | Queen et al. |
| 5,670,373 A | 9/1997 | Kishimoto |
| 5,795,965 A | 8/1998 | Tsuchiya et al. |
| 5,817,790 A | 10/1998 | Tsuchiya et al. |
| 5,827,733 A | 10/1998 | Lee et al. |
| 5,830,478 A | 11/1998 | Raso et al. |
| 5,935,935 A | 8/1999 | Connelly et al. |
| 5,945,311 A | 8/1999 | Lindhofer et al. |
| 5,994,524 A | 11/1999 | Matsushima et al. |
| 6,018,032 A | 1/2000 | Koike et al. |
| 6,024,956 A | 2/2000 | Matsushima et al. |
| 6,025,158 A | 2/2000 | Gonzalez et al. |

(Continued)

FOREIGN PATENT DOCUMENTS

| | | |
|---|---|---|
| AR | 068564 A | 11/2009 |
| AU | 2007/255753 | 12/2007 |

(Continued)

OTHER PUBLICATIONS

GE Healthcare Biacore Sensor Surface Handbook, pp. 1-100, 2005-2007 (Year: 2005).*
Jaeger 1990.
Riott 2000, 97-113.
Riott 2000, 373-4.
Yarilin 1999, 172-4.
Yarilin 1999, 175.
Wikipedia Rituximab Definition, 2018.
Final Office Action dated Mar. 2, 2018 in U.S. Appl. No. 13/637,415, Igawa, T., et al., filed Feb. 4, 2013.

(Continued)

*Primary Examiner* — Daniel E Kolker
*Assistant Examiner* — James L Rogers
(74) *Attorney, Agent, or Firm* — Nixon & Vanderhye P.C.

(57) ABSTRACT

The present inventors discovered that antibodies having weaker antigen-binding activity at the early endosomal pH in comparison with that at the pH of plasma are capable of binding to multiple antigen molecules with a single antibody molecule, have long half-lives in plasma, and have improved durations of time in which they can bind to antigen.

29 Claims, 29 Drawing Sheets

Specification includes a Sequence Listing.

(56) References Cited

U.S. PATENT DOCUMENTS

| | | |
|---|---|---|
| 6,074,642 A | 6/2000 | Wang et al. |
| 6,096,506 A | 8/2000 | Lee et al. |
| 6,165,745 A | 12/2000 | Ward et al. |
| 6,245,894 B1 | 6/2001 | Matsushima et al. |
| 6,309,636 B1 | 10/2001 | do Couto et al. |
| 6,329,511 B1 | 12/2001 | Vasquez et al. |
| 6,355,245 B1 | 3/2002 | Evans et al. |
| 6,458,355 B1 | 10/2002 | Hsei et al. |
| 6,723,319 B1 | 4/2004 | Ito et al. |
| 6,737,056 B1 | 5/2004 | Presta |
| 6,821,505 B2 | 11/2004 | Ward |
| 6,884,879 B1 | 4/2005 | Baca et al. |
| 7,052,873 B2 | 5/2006 | Tsuchiya |
| 7,247,302 B1 | 7/2007 | Rosok et al. |
| 7,261,893 B2 | 8/2007 | Geertruida et al. |
| 7,276,585 B2 | 10/2007 | Lazar et al. |
| 7,320,789 B2 | 1/2008 | Aghajanian et al. |
| 7,361,740 B2 | 4/2008 | Hinton et al. |
| 7,371,826 B2 | 5/2008 | Presta |
| 7,432,356 B2 | 10/2008 | Fung et al. |
| 7,479,543 B2 | 1/2009 | Tsuchiya et al. |
| 7,482,440 B2 | 1/2009 | Maeda et al. |
| 7,632,499 B2 | 12/2009 | Davies et al. |
| 7,632,924 B2 | 12/2009 | Cho et al. |
| 7,662,925 B2 | 2/2010 | Lazar et al. |
| 7,670,600 B2 | 3/2010 | Dall Acqua et al. |
| 7,785,791 B2 | 8/2010 | Presta |
| 7,807,159 B2 | 10/2010 | Chin et al. |
| 7,820,800 B2 | 10/2010 | Rossi et al. |
| 7,888,486 B2 | 2/2011 | Walsh et al. |
| 7,951,918 B2 | 5/2011 | Glaser et al. |
| 8,062,635 B2 | 11/2011 | Hattori et al. |
| 8,101,720 B2 | 1/2012 | Lazar et al. |
| 8,147,829 B2 | 4/2012 | Hariharan et al. |
| 8,188,231 B2 | 5/2012 | Lazar et al. |
| 8,323,962 B2 | 12/2012 | Dall Acqua et al. |
| 8,329,186 B2 | 12/2012 | Kim et al. |
| 8,329,867 B2 | 12/2012 | Lazar et al. |
| 8,367,805 B2 | 2/2013 | Chamberlain et al. |
| 8,388,955 B2 | 3/2013 | Lazar et al. |
| 8,415,459 B2 | 4/2013 | La Vallie et al. |
| 8,486,895 B2 | 7/2013 | Weaver et al. |
| 8,562,991 B2 | 10/2013 | Igawa et al. |
| 8,568,726 B2 | 10/2013 | Beaumont et al. |
| 8,568,992 B2 | 10/2013 | Walker et al. |
| 8,580,264 B2 | 11/2013 | Zhang et al. |
| 8,609,097 B2 | 12/2013 | Bohrmann et al. |
| 8,637,641 B2 | 1/2014 | Dahiyat et al. |
| 8,679,490 B2 | 3/2014 | Dennis et al. |
| 8,734,798 B2 | 5/2014 | Finney et al. |
| 8,753,629 B2 | 6/2014 | Lazar et al. |
| 8,778,345 B2 | 7/2014 | Zhang et al. |
| 8,883,158 B2 | 11/2014 | Diefenbach-Streiber et al. |
| 8,999,343 B2 | 4/2015 | Han et al. |
| 9,029,515 B2 | 5/2015 | Pons et al. |
| 9,051,373 B2 | 6/2015 | Lazar et al. |
| 9,079,949 B1 | 7/2015 | Andrien et al. |
| 9,096,651 B2 | 8/2015 | Igawa et al. |
| 9,206,251 B2 | 12/2015 | Andrien, Jr. et al. |
| 9,255,154 B2 | 2/2016 | Feldhaus et al. |
| 9,315,577 B2 | 4/2016 | Foltz et al. |
| 9,447,190 B2 | 9/2016 | Flanagan et al. |
| 9,481,725 B2 | 11/2016 | Dutzar et al. |
| 9,605,061 B2 | 3/2017 | Lazar et al. |
| 9,701,759 B2 | 7/2017 | Desjarlais et al. |
| 9,765,135 B2 | 9/2017 | Ruike et al. |
| 9,868,948 B2 | 1/2018 | Igawa et al. |
| 9,890,377 B2 | 2/2018 | Igawa et al. |
| 9,969,800 B2 | 5/2018 | Igawa et al. |
| 10,000,560 B2 | 6/2018 | Ruike et al. |
| 10,024,867 B2 | 7/2018 | Igawa et al. |
| 10,233,252 B2 | 3/2019 | Shusta et al. |
| 10,253,100 B2 | 4/2019 | Igawa et al. |
| 10,385,122 B2 | 8/2019 | Ruike et al. |
| 10,472,623 B2 | 11/2019 | Igawa et al. |
| 10,519,229 B2 | 12/2019 | Igawa et al. |
| 10,618,965 B2 | 4/2020 | Igawa et al. |
| 10,662,245 B2 | 5/2020 | Igawa et al. |
| 10,738,111 B2 | 8/2020 | Ruike et al. |
| 2001/0001663 A1 | 5/2001 | Kishimoto et al. |
| 2002/0082396 A1 | 6/2002 | Matsushima et al. |
| 2002/0142374 A1 | 10/2002 | Gallo et al. |
| 2002/0187150 A1 | 12/2002 | Mihara et al. |
| 2003/0059937 A1 | 3/2003 | Ruben et al. |
| 2003/0125520 A1 | 7/2003 | Maeda et al. |
| 2003/0215838 A1 | 11/2003 | Sprecher et al. |
| 2003/0224397 A1 | 12/2003 | Lowman et al. |
| 2003/0224487 A1 | 12/2003 | Sprecher et al. |
| 2004/0058393 A1 | 3/2004 | Fukishima et al. |
| 2004/0071706 A1 | 4/2004 | Ito et al. |
| 2004/0081651 A1 | 4/2004 | Karpusas et al. |
| 2004/0110226 A1 | 6/2004 | Lazar et al. |
| 2004/0133357 A1 | 7/2004 | Zhong et al. |
| 2004/0208873 A1 | 10/2004 | Teeling et al. |
| 2004/0223970 A1 | 11/2004 | Afar et al. |
| 2004/0236080 A1 | 11/2004 | Aburatani et al. |
| 2005/0014934 A1 | 1/2005 | Hinton et al. |
| 2005/0130224 A1 | 6/2005 | Saito et al. |
| 2005/0142635 A1 | 6/2005 | Tsuchiya et al. |
| 2005/0191293 A1 | 9/2005 | Deshpande et al. |
| 2005/0260711 A1 | 11/2005 | Datta et al. |
| 2005/0261229 A1 | 11/2005 | Gillies et al. |
| 2006/0014156 A1 | 1/2006 | Rabbani et al. |
| 2006/0019342 A1 | 1/2006 | Dall Acqua et al. |
| 2006/0134709 A1 | 6/2006 | Stavenhagen et al. |
| 2006/0141456 A1* | 6/2006 | Edwards ............ C07K 16/3007 435/6.16 |
| 2006/0153860 A1 | 7/2006 | Cho et al. |
| 2006/0182743 A1 | 8/2006 | Bilsborough |
| 2006/0194280 A1 | 8/2006 | Dillon et al. |
| 2006/0275282 A1 | 12/2006 | Moore et al. |
| 2006/0292147 A1 | 12/2006 | Yoshizaki et al. |
| 2007/0003546 A1 | 1/2007 | Lazar et al. |
| 2007/0009523 A1 | 1/2007 | Presta |
| 2007/0036785 A1 | 2/2007 | Kishimoto et al. |
| 2007/0037734 A1 | 2/2007 | Rossi et al. |
| 2007/0041978 A1 | 2/2007 | Hattori et al. |
| 2007/0135620 A1 | 6/2007 | Chamberlain et al. |
| 2007/0148164 A1 | 6/2007 | Farrington et al. |
| 2007/0160598 A1 | 7/2007 | Dennis et al. |
| 2007/0160611 A1 | 7/2007 | Yao et al. |
| 2007/0190056 A1 | 8/2007 | Kambadur et al. |
| 2007/0224188 A1 | 9/2007 | Allan et al. |
| 2007/0231329 A1 | 10/2007 | Lazar et al. |
| 2007/0237767 A1 | 10/2007 | Lazar et al. |
| 2007/0253951 A1 | 11/2007 | Ng et al. |
| 2007/0269371 A1 | 11/2007 | Krummen et al. |
| 2007/0280945 A1 | 12/2007 | Stevens et al. |
| 2008/0050370 A1 | 2/2008 | Glaser et al. |
| 2008/0075712 A1 | 3/2008 | Hattori et al. |
| 2008/0089892 A1 | 4/2008 | Allan et al. |
| 2008/0125579 A1 | 5/2008 | Owens et al. |
| 2008/0166756 A1 | 7/2008 | Tsuchiya et al. |
| 2008/0219971 A1 | 9/2008 | Smith et al. |
| 2009/0041770 A1 | 2/2009 | Chamberlain et al. |
| 2009/0117097 A1 | 5/2009 | Igawa et al. |
| 2009/0130110 A1 | 5/2009 | Babcook et al. |
| 2009/0131638 A1 | 5/2009 | Davies et al. |
| 2009/0136485 A1 | 5/2009 | Chu et al. |
| 2009/0142340 A1 | 6/2009 | Lazar et al. |
| 2009/0148436 A1 | 6/2009 | La Vallie et al. |
| 2009/0163699 A1 | 6/2009 | Chamberlain et al. |
| 2009/0263392 A1 | 10/2009 | Igawa et al. |
| 2009/0291076 A1 | 11/2009 | Morichika et al. |
| 2009/0324589 A1 | 12/2009 | Igawa et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0015133 A1 | 1/2010 | Igawa et al. |
| 2010/0055092 A1 | 3/2010 | Hasegawa et al. |
| 2010/0098730 A1 | 4/2010 | Lowman et al. |
| 2010/0099147 A1 | 4/2010 | Hariharan et al. |
| 2010/0129365 A1 | 5/2010 | Kim et al. |
| 2010/0166748 A1 | 7/2010 | Guild et al. |

(56) References Cited

U.S. PATENT DOCUMENTS

| | | |
|---|---|---|
| 2010/0216187 A1 | 8/2010 | Lasters et al. |
| 2010/0239577 A1 | 9/2010 | Igawa et al. |
| 2010/0247523 A1 | 9/2010 | Kano et al. |
| 2010/0249482 A1 | 9/2010 | Chung et al. |
| 2010/0292443 A1 | 11/2010 | Sabbadini et al. |
| 2010/0297697 A1 | 11/2010 | Ambrosius et al. |
| 2010/0298542 A1 | 11/2010 | Igawa et al. |
| 2010/0316636 A1 | 12/2010 | Radin et al. |
| 2011/0002931 A1 | 1/2011 | Tamburini |
| 2011/0044986 A1 | 2/2011 | Biere-Citron et al. |
| 2011/0059093 A1 | 3/2011 | Bohrmann et al. |
| 2011/0076275 A1 | 3/2011 | Igawa et al. |
| 2011/0098450 A1 | 4/2011 | Igawa et al. |
| 2011/0105724 A1 | 5/2011 | Clegg et al. |
| 2011/0111406 A1 | 5/2011 | Igawa et al. |
| 2011/0129459 A1 | 6/2011 | Kuramochi et al. |
| 2011/0135662 A1 | 6/2011 | Finney et al. |
| 2011/0150888 A1 | 6/2011 | Foltz et al. |
| 2011/0229459 A1 | 9/2011 | Kuramochi et al. |
| 2011/0229489 A1 | 9/2011 | Pons et al. |
| 2011/0236374 A1 | 9/2011 | Shitara et al. |
| 2011/0245473 A1 | 10/2011 | Igawa et al. |
| 2011/0287032 A1 | 11/2011 | Lazar et al. |
| 2012/0009188 A1 | 1/2012 | Behrens et al. |
| 2012/0065379 A1 | 3/2012 | Igawa et al. |
| 2012/0071634 A1 | 3/2012 | Igawa et al. |
| 2012/0121587 A1 | 5/2012 | Maeda et al. |
| 2012/0189639 A1 | 7/2012 | Schebye et al. |
| 2012/0237517 A1 | 9/2012 | Hattori et al. |
| 2012/0238729 A1 | 9/2012 | Kuramochi et al. |
| 2012/0253016 A1 | 10/2012 | Igawa et al. |
| 2012/0301460 A1 | 11/2012 | Bao et al. |
| 2012/0301488 A1 | 11/2012 | Zhang et al. |
| 2012/0303083 A1 | 11/2012 | Agnetti et al. |
| 2012/0315267 A1 | 12/2012 | Clegg et al. |
| 2012/0321620 A1 | 12/2012 | Chu et al. |
| 2013/0011866 A1 | 1/2013 | Igawa et al. |
| 2013/0018174 A1 | 1/2013 | Igawa et al. |
| 2013/0022624 A1 | 1/2013 | Weaver et al. |
| 2013/0064836 A1 | 3/2013 | Diefenbach-Streiber et al. |
| 2013/0085074 A1 | 4/2013 | Walker et al. |
| 2013/0101581 A1 | 4/2013 | Kuramochi et al. |
| 2013/0131319 A1 | 5/2013 | Igawa et al. |
| 2013/0142788 A1 | 6/2013 | Ashman et al. |
| 2013/0209489 A1 | 8/2013 | Han et al. |
| 2013/0247236 A1 | 9/2013 | McWhirter et al. |
| 2013/0302399 A1 | 11/2013 | Feldhaus et al. |
| 2013/0303396 A1 | 11/2013 | Igawa et al. |
| 2013/0317203 A1 | 11/2013 | Igawa et al. |
| 2013/0336963 A1 | 12/2013 | Igawa et al. |
| 2014/0056878 A1 | 2/2014 | McConnell et al. |
| 2014/0086916 A1 | 3/2014 | Zha |
| 2014/0105889 A1 | 4/2014 | Igawa et al. |
| 2014/0112926 A1 | 4/2014 | LIU et al. |
| 2014/0127209 A1 | 5/2014 | Grabstein et al. |
| 2014/0227292 A1 | 8/2014 | Flanagan et al. |
| 2014/0234340 A1 | 8/2014 | Igawa et al. |
| 2014/0255398 A1 | 9/2014 | Igawa et al. |
| 2014/0271459 A1 | 9/2014 | Dutzar et al. |
| 2014/0271617 A1 | 9/2014 | Igawa et al. |
| 2014/0335089 A1 | 11/2014 | Igawa et al. |
| 2014/0363426 A1 | 12/2014 | Moore et al. |
| 2014/0363428 A1 | 12/2014 | Igawa et al. |
| 2015/0050269 A1 | 2/2015 | Igawa et al. |
| 2015/0056182 A1 | 2/2015 | Igawa et al. |
| 2015/0079088 A1 | 3/2015 | Lowman et al. |
| 2015/0166654 A1 | 6/2015 | Igawa et al. |
| 2015/0166666 A1 | 6/2015 | Igawa et al. |
| 2015/0203577 A1 | 7/2015 | Igawa et al. |
| 2015/0239966 A1 | 8/2015 | Baciu |
| 2015/0247849 A1 | 9/2015 | Tamburini |
| 2015/0299296 A1 | 10/2015 | Katada et al. |
| 2015/0299305 A1 | 10/2015 | Andrien, Jr. et al. |
| 2015/0299313 A1 | 10/2015 | Igawa et al. |
| 2015/0315278 A1 | 11/2015 | Igawa et al. |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0068592 A1 | 3/2016 | Chung et al. |
| 2016/0176954 A1 | 6/2016 | Ruike et al. |
| 2016/0200807 A1 | 7/2016 | Ruike et al. |
| 2016/0229908 A1 | 8/2016 | Igawa et al. |
| 2016/0244526 A1 | 8/2016 | Igawa et al. |
| 2017/0002066 A1 | 1/2017 | Igawa et al. |
| 2017/0002080 A1 | 1/2017 | Igawa et al. |
| 2017/0022270 A1 | 1/2017 | Igawa et al. |
| 2017/0121412 A1 | 5/2017 | Igawa et al. |
| 2017/0174778 A1 | 6/2017 | Shusta et al. |
| 2017/0181987 A1 | 6/2017 | Svensson et al. |
| 2017/0226206 A1 | 8/2017 | Igawa et al. |
| 2018/0002415 A1 | 1/2018 | Ruike et al. |
| 2018/0016327 A1 | 1/2018 | Murata et al. |
| 2018/0148509 A1 | 5/2018 | Kakehi et al. |
| 2018/0258161 A1 | 9/2018 | Igawa et al. |
| 2018/0258163 A1 | 9/2018 | Igawa et al. |
| 2018/0282718 A1 | 10/2018 | Igawa et al. |
| 2018/0282719 A1 | 10/2018 | Igawa et al. |
| 2018/0319876 A1 | 11/2018 | Ruike et al. |
| 2018/0319877 A1 | 11/2018 | Ruike et al. |
| 2019/0002548 A1 | 1/2019 | Ruike et al. |
| 2019/0062413 A1 | 2/2019 | Ruike et al. |
| 2019/0085085 A1 | 3/2019 | Igawa et al. |
| 2019/0085095 A1 | 3/2019 | Natarajan et al. |
| 2019/0169286 A1 | 6/2019 | Kakiuchi et al. |
| 2019/0185557 A1 | 6/2019 | Igawa et al. |
| 2019/0218309 A1 | 7/2019 | Igawa et al. |
| 2019/0233525 A1 | 8/2019 | Igawa et al. |
| 2019/0352387 A1 | 11/2019 | Sampei |
| 2019/0367599 A1 | 12/2019 | Shinomiya et al. |
| 2020/0031913 A1 | 1/2020 | Ruike et al. |
| 2020/0048627 A1 | 2/2020 | Igawa et al. |
| 2020/0172610 A1 | 6/2020 | Igawa et al. |
| 2020/0199241 A1 | 6/2020 | Igawa et al. |
| 2020/0231688 A1 | 7/2020 | Igawa et al. |
| 2020/0317768 A1 | 10/2020 | Ruike et al. |
| 2020/0407432 A1 | 12/2020 | Shinomiya et al. |
| 2021/0017286 A1 | 1/2021 | Kakehi et al. |
| 2021/0079379 A1 | 3/2021 | Igawa et al. |
| 2021/0206862 A1 | 7/2021 | Igawa et al. |
| 2022/0041741 A1 | 2/2022 | Igawa et al. |

FOREIGN PATENT DOCUMENTS

| | | |
|---|---|---|
| AU | 2008332271 | 6/2009 |
| AU | 200929016 | 4/2010 |
| AU | 2010206050 A1 | 8/2010 |
| AU | 2011244851 A | 11/2011 |
| AU | 2010206050 B2 | 11/2013 |
| AU | 2014250434 A1 | 10/2015 |
| AU | 2015227424 A1 | 10/2015 |
| AU | 2014250434 B2 | 8/2019 |
| CA | 1 332 367 | 10/1994 |
| CA | 2 203 182 | 5/1996 |
| CA | 2 443 294 | 10/2002 |
| CA | 2 523 577 | 11/2004 |
| CA | 2 549 467 | 7/2005 |
| CA | 2 560 953 | 9/2005 |
| CA | 2 603 264 | 10/2006 |
| CA | 2 625 773 | 4/2007 |
| CA | 2 626 688 | 4/2007 |
| CA | 2 648 644 | 10/2007 |
| CA | 2911000 A1 | 10/2007 |
| CA | 2 700 394 | 4/2009 |
| CA | 2 700 498 | 4/2009 |
| CA | 2 708 065 | 6/2009 |
| CA | 2 708 532 | 6/2009 |
| CA | 2721052 A1 | 10/2009 |
| CA | 2 831 770 | 10/2012 |
| CA | 2 899 589 | 8/2014 |
| CN | 1156460 A | 8/1997 |
| CN | 1274289 A | 11/2000 |
| CN | 1763097 | 4/2006 |
| CN | 101098890 | 1/2008 |
| CN | 101230102 A | 7/2008 |

(56) References Cited

FOREIGN PATENT DOCUMENTS

| | | |
|---|---|---|
| CN | 101277976 | 10/2008 |
| CN | 101282992 | 10/2008 |
| CN | 100455598 C | 1/2009 |
| CN | 101479381 A | 7/2009 |
| CN | 101511871 A | 8/2009 |
| CN | 101849006 A | 9/2010 |
| CN | 102056946 A | 5/2011 |
| CN | 102271703 A | 12/2011 |
| CN | 102325793 A | 1/2012 |
| CN | 101511871 B | 7/2012 |
| CN | 102597005 A | 7/2012 |
| CN | 102844332 A | 12/2012 |
| CN | 102918057 A | 2/2013 |
| CN | 102993304 A | 3/2013 |
| CN | 101849006 B | 5/2013 |
| CN | 103097415 A | 5/2013 |
| CN | 103221426 A | 7/2013 |
| CN | 103328632 A | 9/2013 |
| CN | 103476793 A | 12/2013 |
| CN | 103492565 A | 1/2014 |
| CN | 103975060 A | 8/2014 |
| CN | 104302169 A | 1/2015 |
| CN | 101479381 B | 4/2015 |
| CN | 102844332 B | 8/2015 |
| CN | 102271703 B | 9/2015 |
| CN | 103221426 B | 1/2016 |
| CN | 106459189 A | 2/2017 |
| CN | 107108726 A | 8/2017 |
| CN | 104302169 B | 11/2017 |
| EA | 009026 | 10/2007 |
| EA | 200801027 A1 | 10/2008 |
| EA | 015589 B1 | 10/2011 |
| EA | 201100300 A1 | 12/2011 |
| EA | 027575 B1 | 8/2017 |
| EP | 0 182 495 | 5/1986 |
| EP | 0 361 902 | 4/1990 |
| EP | 0628639 A1 | 12/1994 |
| EP | 0770628 A1 | 5/1997 |
| EP | 0 783 893 | 7/1997 |
| EP | 0791359 A1 | 8/1997 |
| EP | 0628639 B1 | 6/1999 |
| EP | 0983767 A1 | 3/2000 |
| EP | 1004315 A1 | 5/2000 |
| EP | 1074268 A1 | 2/2001 |
| EP | 1 188 830 | 3/2002 |
| EP | 1334731 A1 | 8/2003 |
| EP | 1374900 A1 | 1/2004 |
| EP | 02708772.5 | 1/2004 |
| EP | 1 510 943 | 3/2005 |
| EP | 1509770 A1 | 3/2005 |
| EP | 1 693 448 | 8/2006 |
| EP | 1690550 A1 | 8/2006 |
| EP | 0 770 628 | 9/2006 |
| EP | 1707215 A1 | 10/2006 |
| EP | 1 728 801 | 12/2006 |
| EP | 1 733 740 | 12/2006 |
| EP | 1 601 697 | 5/2007 |
| EP | 1 870 459 | 12/2007 |
| EP | 1074268 B1 | 1/2008 |
| EP | 1334731 B1 | 2/2008 |
| EP | 1004315 B1 | 5/2008 |
| EP | 1941907 A1 | 7/2008 |
| EP | 1941908 A1 | 7/2008 |
| EP | 0983767 B1 | 9/2008 |
| EP | 1967207 A1 | 9/2008 |
| EP | 1967209 A1 | 9/2008 |
| EP | 1990060 A1 | 11/2008 |
| EP | 1992692 A1 | 11/2008 |
| EP | 07707458-1 | 11/2008 |
| EP | 2 006 381 | 12/2008 |
| EP | 2 031 064 | 3/2009 |
| EP | 2 047 863 | 4/2009 |
| EP | 2123302 A1 | 11/2009 |
| EP | 2174667 A1 | 4/2010 |
| EP | 2 194 066 | 6/2010 |
| EP | 2 196 541 | 6/2010 |
| EP | 2 202 245 | 6/2010 |
| EP | 2196220 A1 | 6/2010 |
| EP | 2 206 775 | 7/2010 |
| EP | 2206775 A1 | 7/2010 |
| EP | 2 236 604 | 10/2010 |
| EP | 2 241 332 | 10/2010 |
| EP | 2 275 443 | 1/2011 |
| EP | 2275443 A1 | 1/2011 |
| EP | 2305306 A1 | 4/2011 |
| EP | 2314618 A2 | 4/2011 |
| EP | 2 330 193 | 8/2011 |
| EP | 2 366 713 | 9/2011 |
| EP | 2 431 393 | 3/2012 |
| EP | 1707215 B1 | 3/2012 |
| EP | 1967209 B1 | 6/2012 |
| EP | 2471813 A1 | 7/2012 |
| EP | 1690550 B1 | 8/2012 |
| EP | 1992692 B1 | 1/2013 |
| EP | 2578233 A1 | 4/2013 |
| EP | 2 647 706 | 10/2013 |
| EP | 2 679 681 | 1/2014 |
| EP | 2679681 A1 | 1/2014 |
| EP | 2 698 431 | 2/2014 |
| EP | 1509770 B1 | 7/2014 |
| EP | 2 762 564 | 8/2014 |
| EP | 2762166 A1 | 8/2014 |
| EP | 2762493 A1 | 8/2014 |
| EP | 2762564 A1 | 8/2014 |
| EP | 2196220 B1 | 12/2014 |
| EP | 2471813 B1 | 12/2014 |
| EP | 2818183 A1 | 12/2014 |
| EP | 2 853 898 | 4/2015 |
| EP | 2889377 A1 | 7/2015 |
| EP | 1941908 B1 | 8/2015 |
| EP | 2 940 043 | 11/2015 |
| EP | 2123302 B1 | 12/2015 |
| EP | 2 975 055 | 1/2016 |
| EP | 2305306 B1 | 2/2016 |
| EP | 1941907 B1 | 3/2016 |
| EP | 1967207 B1 | 6/2016 |
| EP | 3042912 A1 | 7/2016 |
| EP | 2174667 B1 | 1/2017 |
| EP | 2578233 B1 | 4/2017 |
| EP | 3240804 A1 | 11/2017 |
| EP | 3263132 A1 | 1/2018 |
| EP | 2818183 B1 | 4/2020 |
| JP | S61-117457 | 6/1986 |
| JP | S63-52890 | 3/1988 |
| JP | H01-144991 | 6/1989 |
| JP | 2-028200 | 1/1990 |
| JP | H02-501112 | 4/1990 |
| JP | 2-163096 | 6/1990 |
| JP | H02-163085 | 6/1990 |
| JP | H03504332 A | 9/1991 |
| JP | H05504579 A | 7/1993 |
| JP | H08-217799 | 8/1996 |
| JP | 09-506001 | 6/1997 |
| JP | 2638680 B | 8/1997 |
| JP | 11-500915 | 1/1999 |
| JP | 2002-514406 | 5/2002 |
| JP | 2003-512019 | 4/2003 |
| JP | 200473210 A | 3/2004 |
| JP | 2004-511426 | 4/2004 |
| JP | 2005510212 A | 4/2005 |
| JP | 2005-532805 | 11/2005 |
| JP | 2005/537009 | 12/2005 |
| JP | 2006517525 A | 7/2006 |
| JP | 2006-519583 | 8/2006 |
| JP | 2007252368 A | 10/2007 |
| JP | 2007-532139 | 11/2007 |
| JP | 2008-510466 | 4/2008 |
| JP | 2008-519860 | 6/2008 |
| JP | 4179517 B | 11/2008 |
| JP | 2009516743 | 4/2009 |
| JP | 2009541352 A | 11/2009 |
| JP | 2010500020 A | 1/2010 |
| JP | 2010500226 | 1/2010 |
| JP | 2010-505436 | 2/2010 |

(56) References Cited

FOREIGN PATENT DOCUMENTS

| | | |
|---|---|---|
| JP | 4452077 B2 | 4/2010 |
| JP | 2010081866 A | 4/2010 |
| JP | 2010521194 A | 6/2010 |
| JP | 4547561 B2 | 9/2010 |
| JP | 2011-504096 | 2/2011 |
| JP | 2012552935 | 2/2011 |
| JP | 2011507963 A | 3/2011 |
| JP | 2011-184418 | 9/2011 |
| JP | 2011529700 A | 12/2011 |
| JP | 2012021004 A | 2/2012 |
| JP | 2012-505833 | 3/2012 |
| JP | 2012-512641 | 6/2012 |
| JP | 4961501 B2 | 6/2012 |
| JP | 2012116837 A | 6/2012 |
| JP | 5048866 B2 | 10/2012 |
| JP | 2012531418 A | 12/2012 |
| JP | 2013-518131 | 5/2013 |
| JP | 2013518606 A | 5/2013 |
| JP | 2013-521772 | 6/2013 |
| JP | 5229888 B | 7/2013 |
| JP | 2013-531486 | 8/2013 |
| JP | 2013217294 | 10/2013 |
| JP | 2013537425 A | 10/2013 |
| JP | 2013-541594 | 11/2013 |
| JP | 5421105 B2 | 2/2014 |
| JP | 201455145 A | 3/2014 |
| JP | 2014528906 A | 10/2014 |
| JP | 2015510769 A | 4/2015 |
| JP | 5726534 B2 | 6/2015 |
| JP | 5815403 B2 | 11/2015 |
| JP | 2016026190 A | 2/2016 |
| JP | 2017501706 A | 1/2017 |
| JP | 6082447 B2 | 2/2017 |
| JP | 6088703 | 3/2017 |
| JP | 2017509312 A | 4/2017 |
| JP | 2017-113013 | 6/2017 |
| JP | 6174782 B2 | 8/2017 |
| JP | 6228589 B2 | 11/2017 |
| JP | 6383122 B2 | 8/2018 |
| JP | 2018123125 A | 8/2018 |
| JP | 2018141025 A | 9/2018 |
| KR | 2006/0010765 | 2/2006 |
| KR | 2007/0035482 | 3/2007 |
| KR | 20100074220 A | 7/2010 |
| KR | 20110103431 A | 9/2011 |
| KR | 10-2012-0035192 A | 4/2012 |
| KR | 20140005864 A | 1/2014 |
| KR | 101575914 B1 | 12/2015 |
| KR | 20170092449 A | 8/2017 |
| KR | 101838645 B1 | 3/2018 |
| MX | 2013006109 A | 1/2014 |
| MX | 365235 B | 5/2019 |
| RU | 2147442 C1 | 4/2000 |
| RU | 2195960 | 1/2003 |
| RU | 2225721 | 3/2004 |
| RU | 2005130173 A | 3/2006 |
| RU | 2006127314 A | 2/2008 |
| RU | 2007/121679 | 12/2008 |
| RU | 2367667 | 9/2009 |
| RU | 2008128133 A | 1/2010 |
| RU | 2008139118 A | 4/2010 |
| RU | 2008139901 A | 4/2010 |
| RU | 2399381 C2 | 9/2010 |
| RU | 2009112723 A | 10/2010 |
| RU | 2422460 C2 | 6/2011 |
| RU | 2430111 | 9/2011 |
| RU | 2010/116152 | 11/2011 |
| RU | 2440824 C2 | 1/2012 |
| RU | 2445975 C2 | 3/2012 |
| RU | 2010150931 A | 6/2012 |
| RU | 2477137 C2 | 3/2013 |
| RU | 2495882 C2 | 10/2013 |
| RU | 2519645 C2 | 6/2014 |
| SG | 183867 | 10/2012 |
| TW | 416960 B | 1/2001 |
| TW | 2010/00127 | 1/2010 |
| TW | 2012/06466 | 2/2012 |
| TW | 201302219 A | 1/2013 |
| TW | 201632557 A | 9/2016 |
| TW | 201642902 A | 12/2016 |
| TW | 201643190 A | 12/2016 |
| TW | 201712032 A | 4/2017 |
| TW | I603738 B | 11/2017 |
| TW | I605057 B | 11/2017 |
| TW | 201808331 A | 3/2018 |
| TW | 201808992 A | 3/2018 |
| TW | I621628 B | 4/2018 |
| TW | 201819409 A | 6/2018 |
| TW | I656133 B | 4/2019 |
| TW | 202039553 A | 11/2020 |
| WO | WO-8303678 A1 * | 10/1983 ........... C07K 16/468 |
| WO | WO 88/04692 | 6/1988 |
| WO | WO9007524 A1 | 7/1990 |
| WO | WO9112023 A2 | 8/1991 |
| WO | WO 91/13631 | 9/1991 |
| WO | WO9207084 A1 | 4/1992 |
| WO | WO 92/19759 | 11/1992 |
| WO | WO-9317105 A1 | 9/1993 |
| WO | WO 94/10354 | 5/1994 |
| WO | WO 94/12215 | 6/1994 |
| WO | WO 94/21681 | 9/1994 |
| WO | WO 95/02187 | 1/1995 |
| WO | WO9514710 A1 | 6/1995 |
| WO | WO 95/29697 | 11/1995 |
| WO | WO 95/33844 | 12/1995 |
| WO | WO 96/01653 | 1/1996 |
| WO | WO 96/02576 | 2/1996 |
| WO | WO 96/11020 | 4/1996 |
| WO | WO 96/12503 | 5/1996 |
| WO | WO 96/23071 | 8/1996 |
| WO | WO 96/27011 | 9/1996 |
| WO | WO 97/10354 | 3/1997 |
| WO | WO-9720858 A1 | 6/1997 |
| WO | WO 97/34631 | 9/1997 |
| WO | WO 98/03546 | 1/1998 |
| WO | WO 98/05787 | 2/1998 |
| WO | WO-9842377 A1 | 10/1998 |
| WO | WO-9846257 A1 | 10/1998 |
| WO | WO 98/50431 | 11/1998 |
| WO | WWO 98/50431 | 11/1998 |
| WO | WO 99/03495 | 1/1999 |
| WO | WO-9908707 A1 | 2/1999 |
| WO | WO 99/018212 | 4/1999 |
| WO | WO-9947170 A1 | 9/1999 |
| WO | WO 99/51642 | 10/1999 |
| WO | WO 99/58572 | 11/1999 |
| WO | WO 2000/014220 | 3/2000 |
| WO | WO 00/34317 | 6/2000 |
| WO | WO 00/42072 | 7/2000 |
| WO | WO 00/75314 | 12/2000 |
| WO | WO 01/82899 | 11/2001 |
| WO | WO 02/09641 | 2/2002 |
| WO | WO 02/3 0985 | 4/2002 |
| WO | WO-0234292 A1 | 5/2002 |
| WO | WO 02/060919 | 8/2002 |
| WO | WO-02080969 A1 | 10/2002 |
| WO | WO 03/000883 | 1/2003 |
| WO | WO 03/015819 | 2/2003 |
| WO | WO 2003/027248 | 4/2003 |
| WO | WO 03/057881 | 7/2003 |
| WO | WO 03/060090 | 7/2003 |
| WO | WO 2003/070760 | 8/2003 |
| WO | WO 03/074679 | 9/2003 |
| WO | WO 03/105757 | 12/2003 |
| WO | WO 2003/107009 | 12/2003 |
| WO | WO 2004/007553 | 1/2004 |
| WO | WO 2004/008147 | 1/2004 |
| WO | WO 2004/020579 | 3/2004 |
| WO | WO 2004/024890 | 3/2004 |
| WO | WO 2004/029207 | 4/2004 |
| WO | WO 2004/035752 | 4/2004 |
| WO | WO 2004/037861 | 5/2004 |
| WO | WO 2004/039826 | 5/2004 |
| WO | WO 2004/058797 | 7/2004 |

(56) References Cited

FOREIGN PATENT DOCUMENTS

| | | |
|---|---|---|
| WO | WO 2004/085476 | 10/2004 |
| WO | WO 2004/091543 | 10/2004 |
| WO | WO 2004/092219 | 10/2004 |
| WO | WO 2004/096273 | 11/2004 |
| WO | WO 2004/099249 | 11/2004 |
| WO | WO 2004/108157 | 12/2004 |
| WO | WO 2004/113387 | 12/2004 |
| WO | WO-2005020936 A2 | 3/2005 |
| WO | WO-2005023193 A2 | 3/2005 |
| WO | WO 2005/035753 | 4/2005 |
| WO | WO 2005/035754 | 4/2005 |
| WO | WO 2005/035756 | 4/2005 |
| WO | WO 2005/037867 | 4/2005 |
| WO | WO-2005037315 A1 | 4/2005 |
| WO | WO 2005/047327 | 5/2005 |
| WO | WO-2005047307 A2 | 5/2005 |
| WO | WO 2005/056606 | 6/2005 |
| WO | WO 2005/056759 | 6/2005 |
| WO | WO-2005061000 A1 | 7/2005 |
| WO | WO-2005066204 A2 | 7/2005 |
| WO | WO 2005/070963 | 8/2005 |
| WO | WO 2005/074607 | 8/2005 |
| WO | WO 2005/077981 | 8/2005 |
| WO | WO 2005/080429 | 9/2005 |
| WO | WO 2005/090405 | 9/2005 |
| WO | WO 2005/092925 | 10/2005 |
| WO | WO 2005/094446 | 10/2005 |
| WO | WO 2005/115452 | 12/2005 |
| WO | WO 2005/123780 | 12/2005 |
| WO | WO 2006/004663 | 1/2006 |
| WO | WO 2006/019447 | 2/2006 |
| WO | WO 2006/020114 | 2/2006 |
| WO | WO 2006/023144 | 3/2006 |
| WO | WO 2006/023403 | 3/2006 |
| WO | WO 2006/031370 | 3/2006 |
| WO | WO 2006/047350 | 5/2006 |
| WO | WO 2006/050166 | 5/2006 |
| WO | WO 2006/053301 | 5/2006 |
| WO | WO 2006/066598 | 6/2006 |
| WO | WO 2006/067913 | 6/2006 |
| WO | WO 2006/070286 | 7/2006 |
| WO | WO 2006/071877 | 7/2006 |
| WO | WO 2006/083182 | 8/2006 |
| WO | WO 2006/083183 | 8/2006 |
| WO | WO 2006/085967 | 8/2006 |
| WO | WO 2006/088855 | 8/2006 |
| WO | WO-2006082052 A1 | 8/2006 |
| WO | WO 2006/102095 | 9/2006 |
| WO | WO 2006/105338 | 10/2006 |
| WO | WO 2006/106903 | 10/2006 |
| WO | WO 2006/106905 | 10/2006 |
| WO | WO 2006/109592 | 10/2006 |
| WO | WO 2006/113643 | 10/2006 |
| WO | WO 2006/116260 | 11/2006 |
| WO | WO 2006/116269 | 11/2006 |
| WO | WO 2006/118959 | 11/2006 |
| WO | WO 2006/119062 | 11/2006 |
| WO | WO 2006/119115 | 11/2006 |
| WO | WO-2006119107 A2 | 11/2006 |
| WO | WO 2006/130834 | 12/2006 |
| WO | WO 2007/001422 | 1/2007 |
| WO | WO 2007/008943 | 1/2007 |
| WO | WO 2007/021841 | 2/2007 |
| WO | WO 2007/024249 | 3/2007 |
| WO | WO 2007/024535 | 3/2007 |
| WO | WO 2007/041635 | 4/2007 |
| WO | WO 2007/044411 | 4/2007 |
| WO | WO 2007/044616 | 4/2007 |
| WO | WO 2007/047112 | 4/2007 |
| WO | WO-2007043641 A1 | 4/2007 |
| WO | WO-2007046489 A1 | 4/2007 |
| WO | WO 2007/060411 | 5/2007 |
| WO | WO-2007058194 A1 | 5/2007 |
| WO | WO-2007061029 A1 | 5/2007 |
| WO | WO-2007068411 A2 | 6/2007 |
| WO | WO 2007/074880 | 7/2007 |
| WO | WO 2007/076524 | 7/2007 |
| WO | WO-2007084253 A2 | 7/2007 |
| WO | WO 2007/092772 | 8/2007 |
| WO | WO-2007086490 A1 | 8/2007 |
| WO | WO 2007/106585 | 9/2007 |
| WO | WO 2007/108559 | 9/2007 |
| WO | WO-2007103134 A2 | 9/2007 |
| WO | WO-2007103549 A2 | 9/2007 |
| WO | WO 2007/114319 | 10/2007 |
| WO | WO 2007/114325 | 10/2007 |
| WO | WO 2007/133 816 | 11/2007 |
| WO | WO 2007/137984 | 12/2007 |
| WO | WO 2007/142325 | 12/2007 |
| WO | WO 2007/143168 | 12/2007 |
| WO | WO-2007150015 A2 | 12/2007 |
| WO | WO-2007150016 A2 | 12/2007 |
| WO | WO 2008/022152 | 2/2008 |
| WO | WO-2008017963 A2 | 2/2008 |
| WO | WO 2008/030706 | 3/2008 |
| WO | WO 2008/036688 | 3/2008 |
| WO | WO-2008031056 A2 | 3/2008 |
| WO | WO 2008/043822 | 4/2008 |
| WO | WO-2008043822 A2 | 4/2008 |
| WO | WO 2008/060785 | 5/2008 |
| WO | WO 2008/091798 | 5/2008 |
| WO | WO 2008/069889 | 6/2008 |
| WO | WO 2008/090960 | 7/2008 |
| WO | WO 2008/091954 | 7/2008 |
| WO | WO 2008/092117 | 7/2008 |
| WO | WO-2008090901 A1 | 7/2008 |
| WO | WO 2008/098115 | 8/2008 |
| WO | WO 2008/103432 | 8/2008 |
| WO | WO 2008/113834 | 9/2008 |
| WO | WO-2008115732 A2 | 9/2008 |
| WO | WO 2008/121160 | 10/2008 |
| WO | WO 2008/130969 | 10/2008 |
| WO | WO 2008/132453 | 11/2008 |
| WO | WO 2008/143954 | 11/2008 |
| WO | WO 2008/145141 | 12/2008 |
| WO | WO 2008/150494 | 12/2008 |
| WO | WO 2009/000098 | 12/2008 |
| WO | WO 2009/000099 | 12/2008 |
| WO | WO 2009/006338 | 1/2009 |
| WO | WO-2009014263 A1 | 1/2009 |
| WO | WO 2009/026117 | 2/2009 |
| WO | WO 2009/032145 | 3/2009 |
| WO | WO 2009/032782 | 3/2009 |
| WO | WO-2009039175 A2 | 3/2009 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/053358 | 4/2009 |
| WO | WO-2009044774 A1 | 4/2009 |
| WO | WO-2009047356 A1 | 4/2009 |
| WO | WO 2009/058346 | 5/2009 |
| WO | WO 2009/058492 | 5/2009 |
| WO | WO 2009/063965 | 5/2009 |
| WO | WO 2009/072598 | 6/2009 |
| WO | WO 2009/072604 | 6/2009 |
| WO | WO 2009/086320 | 7/2009 |
| WO | WO-2009089846 A1 | 7/2009 |
| WO | WO 2009/09523 5 | 8/2009 |
| WO | WO 2009/125825 | 10/2009 |
| WO | WO 2009/139822 | 11/2009 |
| WO | WO-2009137880 A1 | 11/2009 |
| WO | WO-2009148148 A1 | 12/2009 |
| WO | WO 2010/015608 | 2/2010 |
| WO | WO 2010/033736 | 3/2010 |
| WO | WO 2010/035769 | 4/2010 |
| WO | WO 2010/045193 | 4/2010 |
| WO | WO 2010/054403 | 5/2010 |
| WO | WO 2010/058860 | 5/2010 |
| WO | WO 2010/070094 | 6/2010 |
| WO | WO-2010065078 A1 | 6/2010 |
| WO | WO 2010/081173 | 7/2010 |
| WO | WO-2010085682 A2 | 7/2010 |

(56) References Cited

FOREIGN PATENT DOCUMENTS

| | | |
|---|---|---|
| WO | WO 2010/106180 | 9/2010 |
| WO | WO-2010106812 A1 | 9/2010 |
| WO | WO 2010/151338 | 12/2010 |
| WO | WO 2010/151792 | 12/2010 |
| WO | WO-2010151526 A1 | 12/2010 |
| WO | WO 2011/021009 | 2/2011 |
| WO | WO 2011/043643 | 4/2011 |
| WO | WO 2011/044368 | 4/2011 |
| WO | WO-2011063980 A1 | 6/2011 |
| WO | WO 2011/094593 | 8/2011 |
| WO | WO 2011/100271 | 8/2011 |
| WO | WO-2011094593 A2 | 8/2011 |
| WO | WO 2011/109338 | 9/2011 |
| WO | WO 2011/111007 | 9/2011 |
| WO | WO 2011/122011 | 10/2011 |
| WO | WO-2011122011 A2 | 10/2011 |
| WO | WO 2011/137362 | 11/2011 |
| WO | WO 2011/150008 | 12/2011 |
| WO | WO 2011/151432 | 12/2011 |
| WO | WO-2011149046 A1 | 12/2011 |
| WO | WO 2012/016227 | 2/2012 |
| WO | WO 2012/024242 | 2/2012 |
| WO | WO 2012/033953 | 3/2012 |
| WO | WO 2012/064627 | 5/2012 |
| WO | WO 2012/073992 | 6/2012 |
| WO | WO 2012/088247 | 6/2012 |
| WO | WO 2012/093704 | 7/2012 |
| WO | WO 2012/115241 | 8/2012 |
| WO | WO-2012118903 A2 | 9/2012 |
| WO | WO 2012/132067 | 10/2012 |
| WO | WO 2012/133782 | 10/2012 |
| WO | WO-2012145417 A1 | 10/2012 |
| WO | WO-2012151481 A1 | 11/2012 |
| WO | WO-2012162067 A2 | 11/2012 |
| WO | WO-2012177653 A2 | 12/2012 |
| WO | WO 2013/004842 | 1/2013 |
| WO | WO 2013/012733 | 1/2013 |
| WO | WO 2013/046704 | 4/2013 |
| WO | WO 2013/046722 | 4/2013 |
| WO | WO 2013/047748 | 4/2013 |
| WO | WO 2013/047752 | 4/2013 |
| WO | WO 2013/081143 | 6/2013 |
| WO | WO 2013/125667 | 8/2013 |
| WO | WO 2013/138680 | 9/2013 |
| WO | WO-2013138400 A1 | 9/2013 |
| WO | WO 2013/152001 | 10/2013 |
| WO | WO-2013149111 A2 | 10/2013 |
| WO | WO 2013/166099 | 11/2013 |
| WO | WO 2013/186719 | 12/2013 |
| WO | WO-2013180200 A1 | 12/2013 |
| WO | WO 2014/006217 | 1/2014 |
| WO | WO 2014/028354 | 2/2014 |
| WO | WO 2014/030728 | 2/2014 |
| WO | WO 2014/047500 | 3/2014 |
| WO | WO-2014043344 A1 | 3/2014 |
| WO | WO 2014/074532 | 5/2014 |
| WO | WO-2014100689 A1 | 6/2014 |
| WO | WO 2014/114651 | 7/2014 |
| WO | WO 2014/119969 | 8/2014 |
| WO | WO 2014/144080 | 9/2014 |
| WO | WO 2014/144575 | 9/2014 |
| WO | WO 2014/144903 | 9/2014 |
| WO | WO 2014/145159 | 9/2014 |
| WO | WO 2014/145806 | 9/2014 |
| WO | WO 2014/160958 | 10/2014 |
| WO | WO 2014/163101 | 10/2014 |
| WO | WO 2014/182676 | 11/2014 |
| WO | WO 2014/184384 | 11/2014 |
| WO | WO 2014/190441 | 12/2014 |
| WO | WO 2015/022658 | 2/2015 |
| WO | WO 2015/023972 | 2/2015 |
| WO | WO2015034000 A1 | 3/2015 |
| WO | WO2015091738 A1 | 6/2015 |
| WO | WO 2015/111008 | 7/2015 |
| WO | WO 2015/127134 | 8/2015 |
| WO | WO 2015/134894 | 9/2015 |
| WO | WO 2015/162590 | 10/2015 |
| WO | WO-2016000813 A1 | 1/2016 |
| WO | WO 2016/073906 | 3/2016 |
| WO | WO 2016/073853 | 5/2016 |
| WO | WO 2016/073879 | 5/2016 |
| WO | WO 2016/092439 | 6/2016 |
| WO | WO 2016/098356 | 6/2016 |
| WO | WO 2016/098357 | 6/2016 |
| WO | WO-2016117346 A1 | 7/2016 |
| WO | WO 2016/125495 | 8/2016 |
| WO | WO 2016/136933 | 9/2016 |
| WO | WO 2016/160756 | 10/2016 |
| WO | WO 2016/168613 | 10/2016 |
| WO | WO 2016178980 A1 | 11/2016 |
| WO | WO 2016209956 A1 | 12/2016 |
| WO | WO 2017/046994 | 3/2017 |
| WO | WO 2017/049011 | 3/2017 |
| WO | WO 2017064615 A1 | 4/2017 |
| WO | WO 2017/104779 | 6/2017 |
| WO | WO 2017/104783 | 6/2017 |
| WO | WO-2017104779 A1 | 6/2017 |
| WO | WO-2017110981 A1 | 6/2017 |
| WO | WO 2017/120523 | 7/2017 |
| WO | WO 2017123636 A1 | 7/2017 |
| WO | WO-2017217524 A1 | 12/2017 |
| WO | WO-2017217525 A1 | 12/2017 |
| WO | WO-2017218515 A1 | 12/2017 |
| WO | WO-2017218592 A1 | 12/2017 |
| WO | WO-2018025982 A1 | 2/2018 |
| WO | WO-2018139623 A1 | 8/2018 |
| WO | WO 2018143266 A1 | 8/2018 |
| WO | WO-2018167322 A1 | 9/2018 |
| WO | WO-2018169993 A1 | 9/2018 |
| WO | WO-2018184739 A1 | 10/2018 |
| WO | WO-2019084438 A1 | 5/2019 |
| WO | WO-2019112984 A1 | 6/2019 |
| WO | WO-2020027279 A1 | 2/2020 |
| WO | WO2020209318 A1 | 10/2020 |

OTHER PUBLICATIONS

Office Action dated Mar. 15, 2018 in U.S. Appl. No. 15/210,360, Igawa, T., et al., filed Jul. 14, 2016.
Final Office Action dated Dec. 1, 2017 in U.S. Appl. No. 15/210,353, Igawa, T., et al., filed Jul. 14, 2016.
Office Action dated Dec. 29, 2017 in U.S. Appl. No. 15/495,026, Igawa, T., et al., filed Apr. 24, 2017.
Final Office Action dated Jul. 19, 2018, in U.S. Appl. No. 15/495,026, Igawa, T., et al., filed Apr. 24, 2017.
Interview Summary dated Jul. 5, 2018, in U.S. Appl. No. 14/347,187, Igawa, T., et al., filed Jul. 25, 2014.
Interview Summary dated Jul. 10, 2018, in U.S. Appl. No. 14/520,423, Igawa, T., et al., filed Oct. 22, 2014.
Office Action dated Apr. 2, 2018, in U.S. Appl. No. 14/007,947, Igawa, T., et al., filed Dec. 30, 2013.
Office Action dated Mar. 9, 2018, in U.S. Appl. No. 14/520,423, Igawa, T., et al., filed Oct. 22, 2014.
Office Action dated Jul. 27, 2017, in U.S. Appl. No. 14/520,423, Igawa, T., et al., filed Oct. 22, 2014.
Office Action dated Jun. 20, 2018, in U.S. Appl. No. 15/210,353, Igawa, T., et al., filed Jul. 14, 2016.
Advisory Action dated Jun. 28, 2018, in U.S. Appl. No. 14/404,051, Igawa, T., et al., filed Nov. 26, 2014.
Advisory Action dated Aug. 30, 2018, in U.S. Appl. No. 14/404,051, Igawa, T., et al., filed Nov. 26, 2014.
Final Office Action dated Feb. 12, 2016, in U.S. Appl. No. 13/595,139, Igawa T. et al., filed Aug. 27, 2012.
Final Office Action dated Dec. 17, 2015, in U.S. Appl. No. 13/889,512, Igawa T. et al., filed May 8, 2013.
Final Office Action dated May 2, 2017, in U.S. Appl. No. 13/990,158, Igawa, T. et al., filed Mar. 28, 2014.
Final Office Action dated Dec. 10, 2018, in U.S. Appl. No. 14/007,947, Igawa, T., et al., filed Dec. 13, 2018.

(56) References Cited

OTHER PUBLICATIONS

Final Office Action dated Jul. 24, 2017, in U.S. Appl. No. 14/361,013, Igawa, T. et al., filed May 28, 2014.
Final Office Action dated Apr. 2, 2018, in U.S. Appl. No. 14/379,825, Igawa, T. et al., filed Aug. 20, 2014.
Final Office Action dated Oct. 18, 2017, in U.S. Appl. No. 14/404,051, Igawa, T. et al., filed Nov. 26, 2014.
Final Office Action dated Jul. 25, 2017, in U.S. Appl. No. 15/210,360, Igawa, T. et al., filed Jul. 14, 2016.
Final Office Action dated Dec. 5, 2018, in U.S. Appl. No. 15/210,360, Igawa, T., et al., filed Jul. 14, 2016.
Office Action dated Aug. 3, 2015, in U.S. Appl. No. 13/595,139, Igawa T. et al., filed Aug. 27, 2012.
Office Action dated Sep. 26, 2018, in U.S. Appl. No. 13/595,139, Igawa T. et al., filed Aug. 27, 2012.
Office Action dated Nov. 14, 2012, in U.S. Appl. No. 13/595,139, Igawa T. et al., filed Aug. 27, 2012.
Office Action dated Nov. 23, 2016, in U.S. Appl. No. 13/595,139, Igawa T. et al., filed Aug. 27, 2012.
Office Action dated Mar. 26, 2015, in U.S. Appl. No. 13/889,512, Igawa T. et al., filed May 8, 2013.
Office Action dated Aug. 4, 2015, in U.S. Appl. No. 13/889,512, Igawa T. et al., filed May 8, 2013.
Office Action dated Nov. 28, 2016, in U.S. Appl. No. 13/889,512, Igawa T. et al., filed May 8, 2013.
Office Action dated Aug. 19, 2016, in U.S. Appl. No. 13/990,158, Igawa, T., et al., filed Mar. 28, 2014.
Office Action dated Jan. 8, 2018, in U.S. Appl. No. 14/347,034, Igawa, T., et al., filed Mar. 25, 2014.
Office Action dated Sep. 4, 2018, in U.S. Appl. No. 14/347,187, Igawa, T., et al., filed Jul. 25, 2014.
Office Action dated Oct. 28, 2016, in U.S. Appl. No. 14/361,013, in U.S. Appl. No. 14/361,013, Igawa, T., et al., filed May 28, 2014.
Office Action dated Jul. 20, 2017, in U.S. Appl. No. 14/379,825, Igawa T., et al., filed Aug. 20, 2014.
Office Action dated Nov. 1, 2018, in U.S. Appl. No. 14/379,825, Igawa T., et al., filed Aug. 20, 2014.
Office Action dated Dec. 6, 2016, in U.S. Appl. No. 14/404,051, Igawa T., et al., filed Nov. 26, 2014.
Office Action dated Aug. 27, 2018, in U.S. Appl. No. 14/781,069, Mimoto, F., filed Sep. 29, 2015.
Office Action dated Jan. 8, 2018, in U.S. Appl. No. 15/230,904, Igawa, T., et al., filed Aug. 8, 2016.
Office Action dated May 25, 2017, in U.S. Appl. No. 15/230,904, Igawa, T., et al., filed Aug. 8, 2016.
Office Action dated Sep. 20, 2018, in U.S. Appl. No. 15/952,945, Igawa, T., et al., filed Apr. 13, 2018.
Restriction Requirement dated Jan. 6, 2016, in U.S. Appl. No. 13/990,158, Igawa, T., et al., filed Mar. 28, 2014.
Restriction Requirement dated Mar. 16, 2016, in U.S. Appl. No. 14/361,013, Igawa, T., et al., filed May 28, 2014.
Restriction Requirement dated Dec. 22, 2016, in U.S. Appl. No. 14/379,825, Igawa, T., et al., filed Aug. 20, 2014.
Restriction Requirement dated Apr. 4, 2016, in U.S. Appl. No. 14/404,051, Igawa, T., et al., filed Nov. 26, 2014.
Restriction Requirement dated Jun. 28, 2018, in U.S. Appl. No. 15/050,145, Igawa, T., et al., filed Feb. 22, 2016.
Interview Summary dated Feb. 26, 2019, in U.S. Appl. No. 14/781,069, Mimoto, F., filed Sep. 29, 2015.
Notice of Allowance dated Jan. 7, 2019, in U.S. Appl. No. 14/347,187, Igawa T., et al., filed Jul. 25, 2014.
Office Action dated Feb. 5, 2019, in U.S. Appl. No. 15/495,026, Igawa, T., et al., filed Apr. 24, 2017.
Restriction Requirement dated Dec. 7, 2017, in U.S. Appl. No. 14/781,069, filed Sep. 29, 2015.
Interview Summary dated Dec. 3, 2018, in U.S. Appl. No. 15/952,945, Igawa, T., et al., filed Apr. 13, 2018.
Interview Summary dated Feb. 8, 2019, in U.S. Appl. No. 15/952,945, Igawa, T., et al., filed Apr. 13, 2018.

U.S. Appl. No. 15/952,945, filed Apr. 13, 2018, Igawa, et al., (U.S. Pat. No. 10,472,623; U.S. Publication No. 20180282718A1).
U.S. Appl. No. 15/988,348, filed May 24, 2018, Igawa, et al. (U.S. Publication No. 20180258161A1).
U.S. Appl. No. 15/976,288, filed May 10, 2018, Igawa, et al. (U.S. Pat. No. 10,519,229; U.S. Publication No. 20180258163A1).
U.S. Appl. No. 15/963,449, filed Apr. 26, 2018, Ruike, et al. (U.S. Pat. No. 10,738,111; U.S. Publication No. 20180319876A1).
U.S. Appl. No. 15/963,455, filed Apr. 26, 2018, Ruike, et al. (U.S. Publication No. 20180319877A1).
U.S. Appl. No. 16/065,192, international filing date, Dec. 22, 2016, Ruike, et al. (U.S. Publication No. 20190002548A1).
U.S. Appl. No. 13/524,528, filed Jun. 15, 2012, Igawa, et al. (now abandoned) (U.S. Publication No. 20120253016A1).
U.S. Appl. No. 15/379,597, filed Dec. 15, 2016, Wisconsin Alumni Research Foundation. (U.S. Pat. No. 10,233,252; U.S. Publication 20170174778A1).
U.S. Appl. No. 14/520,423, filed Oct. 22, 2014, Igawa, et al. (U.S. Pat. No. 10,662,245; U.S. Publication No. 20150166666A1).
U.S. Appl. No. 13/959,489, filed Aug. 5, 2013, Igawa, et al. (now abandoned) (U.S. Publication No. 20130317203A1).
U.S. Appl. No. 15/263,617, filed Sep. 13, 2016, Igawa, et al. (now abandoned) (U.S. Publication No. 20170121412A1).
U.S. Appl. No. 12/680,112, filed Jun. 23, 2010, Igawa, et al. (now abandoned) (U.S. Publication No. 20110245473A1).
U.S. Appl. No. 13/889,484, filed May 8, 2013, Igawa, et al. (U.S. Pat. No. 9,868,948; U.S. Publication No. 20130303396A1).
U.S. Appl. No. 13/889,512, filed May 8, 2013, Igawa, et al. (U.S. Pat. No. 9,890,377; U.S. Publication No. 20130336963A1).
U.S. Appl. No. 12/936,587, filed Jan. 3, 2011, Igawa, et al. (now abandoned) (U.S. Publication No. 20110111406A1).
U.S. Appl. No. 14/347,034, filed Mar. 25, 2014, Igawa, et al. (now abandoned) (U.S. Publication No. 20150050269A1).
U.S. Appl. No. 14/347,187, filed Mar. 25, 2014, Igawa, et al. (U.S. Pat. No. 10,253,100; U.S. Publication No. 20140363428A1).
U.S. Appl. No. 15/050,145, filed Feb. 22, 2016, Igawa, et al. (U.S. Publication No. 20160244526A1).
U.S. Appl. No. 15/495,026, filed Apr. 24, 2017, Igawa, et al. (U.S. Publication No. 20170226206A1).
U.S. Appl. No. 15/544,930, filed Jul. 20, 2017, Murata, et al. (U.S. Publication No. 20180016327A1).
U.S. Appl. No. 14/974,350, filed Dec. 18, 2015, Ruike, et al. (U.S. Pat. No. 9,765,135; U.S. Publication No. 20160176954A1).
U.S. Appl. No. 14/974,488, filed Dec. 18, 2015, Ruike, et al. (U.S. Pat. No. 10,000,560; U.S. Publication No. 20160200807A1).
U.S. Appl. No. 15/015,287, filed Feb. 4, 2016, Igawa, et al. (U.S. Pat. No. 9,969,800; U.S. Publication No. 20160229908A1).
U.S. Appl. No. 12/295,039, filed Sep. 11, 2012, Igawa, et al. (U.S. Publication No. 20090324589A1).
U.S. Appl. No. 12/679,922, filed Oct. 1, 2010, Igawa et al. (U.S. Pat. No. 9,096,651; U.S. Publication No. 20110076275A1).
U.S. Appl. No. 13/518,861, filed Oct. 4, 2012, Igawa, et al. (now abandoned) (U.S. Publication No. 20130018174A1).
U.S. Appl. No. 16/019,752, filed Jun. 27, 2018, Ruike, Y., et al. (U.S. Pat. No. 10,385,122; U.S. Publication No. 20190062413A1).
U.S. Appl. No.16/028,140, filed Jul. 5, 2018, Igawa, T., et al. (U.S. Publication No. 20190185557A1).
U.S. Appl. No. 16/041,976, filed Jul. 23, 2018, Igawa, T., et al. (U.S. Publication No. 20190085085A1).
U.S. Appl. No. 61/313,102, filed Mar. 11, 2010.
U.S. Appl. No. 139,504, filed Dec. 30, 1987, Ngo, T. T.(U.S. Pat. No. 4,801,687).
U.S. Appl. No. 12/311,768, 371(c) date Oct. 11, 2007, Lasters. I. J. I., et al. (U.S. Publication No. 20100216187A1).
U.S. Appl. No. 12/780,006, filed May 14, 2010, Radin, A., et al. (US. Publication No. 20100316636A1).
U.S. Appl. No. 13/595,139, filed Aug. 27, 2012, Igawa, T. (U.S. Publication No. 20130011866A1).
U.S. Appl. No. 15/553,609, 371(c) date Feb. 26, 2016, Chugai Seiyaku Kabushiki Kaisha (U.S. Publication No. 20180148509A1).
U.S. Appl. No. 10/576,372, 371(0) date Nov. 4, 2004, Rossi, M., et al. (U.S. Pat. No. 7,820,800; U.S. Publication No. 20070037734A1).

(56) References Cited

OTHER PUBLICATIONS

U.S. Appl. No. 11/155,909, filed Jun. 17, 2005, Cho, H. S., et al. (U.S. Pat. No. 7,632,924; U.S. Publication No. 20060153860A1).
U.S. Appl. No. 11/557,466, filed Nov. 7, 2006, Dennis, M. S., et al. (U.S. Pat. No. 8,679,490; U.S. Publication No. 20070160598A1).
U.S. Appl. No. 12/066,838, 371(c) date Oct. 5, 2006, Davies, J. D., et al. (U.S. Pat. No. 7632499; U.S. Publication No. 20090131638A1).
U.S. Appl. No. 12/262,712, filed Oct. 31, 2008, La Vallie, E. R., et al. (U.S. Pat. No. 8,415,459; U.S. Publication No. 20090148436A1).
U.S. Appl. No. 12/990,137, 371(c) date Apr. 28, 2009, Foltz, I., et al. (U.S. Pat. No. 9,315,577; U.S. Publication No. 20110150888A1).
U.S. Appl. No. 13/816,894, 371(c) date Aug. 15, 2011, Han, H., et al. (U.S. Pat. No. 8,999,343; U.S. Publication No. 20130209489A1).
U.S. Appl. No. 12/680,087, filed Jan. 3, 2011, Igawa, T., et al. (U.S. Pat. No. 8,562,991; U.S. Publication No. 2011098450A1).
U.S. Appl. No. 15/688,004, filed Aug. 28, 2017, Ruike, Y., et al. (U.S. Publication No. 20180002415A1).
U.S. Appl. No. 12/660,528, filed Feb. 26, 2010, Sabbadini, R. A., et al. (U.S. Publication No. 20100292443A1).
U.S. Appl. No. 13/637,415, filed Feb. 4, 2013, Igawa, T., et al. (U.S. Publication No. 20130131319A1).
U.S. Appl. No. 13/990,158, filed Mar. 28, 2014, Igawa, T., et al. (now abandoned) (U.S. Publication No. 20140234340A1).
U.S. Appl. No. 14/007,947, filed Dec. 30, 2013, Igawa, T., et al. (U.S. Pat. No. 10,618,965; U.S. Publication No. 20140105889A1).
U.S. Appl. No. 15/210,353, filed Jul. 14, 2016, Igawa, T., et al. (U.S. Publication No. 20170002066A1).
U.S. Appl. No. 15/210,360, filed Jul. 14, 2016, Igawa, T., et al. (U.S. Publication No. 20170002080A1).
U.S. Appl. No. 15/230,904, filed Aug. 8, 2016, Igawa, T., et al. (now abandoned) (U.S. Publication No. 20170022270A1).
U.S. Appl. No. 16/264,735, filed Feb. 1, 2019, Chugai Seiyaku Kabushiki Kaisha. (U.S. Publication No. 20190233525A1).
U.S. Appl. No. 16/323,142, 371(c) filed Feb. 4, 2019, Chugai Seiyaku Kabushiki Kaisha et al.
Araujo et al., "Increased rheumatoid factor interference observed during immunogenicity assessment of an Fc-engineered therapeutic antibody," J Pharm BiomedAnal., Jul. 15, 2011;55(5):1041-9. doi: 10.1016/j.jpba.2011.03.008. Epub Mar. 11, 2011.
Hironiwa et al., "Calcium-dependent antigen binding as a novel modality for antibody recycling by endosomal antigen dissociation," MAbs. Jan. 2016;8(1):65-73. doi: 10.1080/19420862.2015.1110660. Epub Oct. 23, 2015.
Maier et al., "Assessment of fully automated antibody homology modeling protocols in molecular operating envirorment," *Proteins*. Aug. 2014;82(8):1599-610. doi: 10.1002/prot.24576. Epub Apr. 23, 2014.
Fish & Richardson P.C., Reply to Office Action dated Oct. 18, 2016, in U.S. Appl. No. 14/741,786, filed Jan. 17, 2017, 28 pages.
USPTO Non-Final Office Action in U.S. Appl. No. 14/741,786, dated Feb. 7, 2017, 9 pages.
USPTO Restriction Requirement in U.S. Appl. No. 14/347,187, dated Jan. 26, 2017, 8 pages.
Mazda et al., "Regulation of Muscle Homeostasis and Metabolism by the TGF-β Superfamily Cytokine, Myostatin/growth Differentiation Factor 8 (GDF8)," Journal of Kyoto prefectural university of medicine. 2013;122(3):133-41.
Fish & Richardson P.C., Reply to Restriction Requirement dated Jan. 26, 2017 in U.S. Appl. No. 14/347,187, dated Mar. 27, 2017, 2 pages.
Igawa et al., "pH-dependent antigen-binding antibodies as a novel therapeutic modality," Biochim Biophys Acta., Nov. 30, 2014;1844(11):1943-1950.
Ober et al., "Visualizing the Site and Dynamics of IgG Salvage by the MHC Class I-Related Receptor, FcRn," J Immunol., Feb. 15, 2004;172(4):2021-9.
U.S. Appl. No. 15/553,609, filed Aug. 25, 2017, Takahiro.
U.S. Appl. No. 15/688,004, filed Aug. 28, 2017, Ruike et al.
Akira et al., "Interleukin-6 in Biology and Medicine," Adv Immunol., Dec. 1993; 54: 1-78.

Annual Report 2012 (Integrated Edition Including CSR Report) Mar. 27, 2013, 154 pages.
Araki et al., "Clinical improvement in a patient with neuromyelitis optica following therapy with the anti-IL-6 receptor monoclonal antibody tocilizumab," Mod Rheumatol. Jul. 2013 ;23(4) :827-31, doi: 10. 1007/s10165-012-0715-9. Epub Jul. 11, 2012.
Aricha et al., "Blocking of IL-6 suppresses experimental autoimmune myasthenia gravis," J Autoimmun. Mar. 2011;36(2) :135-41. doi: 10. 1016/j.jaut. 2010. 12. 001. Epub Dec. 30, 2010.
Borrok et al., "pH-dependent Binding Engineering Reveals an FcRn Affinity Threshold That Governs IgG Recycling," J Biol Chem. Feb. 13, 2015;290(7):4282-90. doi: 10. 1074/ jbc. M114. 603712. Epub Dec. 23, 2014.
Chen et al., "Enhancement and destruction of antibody function by somatic mutation: unequal occurrence is controlled by V gene combinatorial associations." EMBO J. Jun. 15, 1995;14(12):2784-94.
Colman et al., "Effects of amino acid sequence changes on antibody-antigen interactions," Res Immunol. Jan. 1994;145(1):33-6.
Cooper et al., "Variable donain-identical antibodies exhibit IgG subclass-related differences in affinity and kinetic constants as detemined by surface plasmon resonance," Mol Immunol. Jun. 1994; 31(8): 577-84.
Fiedler et al., "An engineered IN-1 Fab fragment with improved affinity for the Nogo-A axonal growth inhibitor permits immunochemical detection and shows enhanced neutraliziug activity," Protein Eng. Nov. 2002:15(11):931-41.
Foote et al., "Antibody framework residues affecting the conformation of the hypervatiable loops," J Mol Biol. Mar. 20, 1992;224(2):487-99.
Fukuzwa et al., "Long lasting neutralization of C5 bgy SKY59, a novel recycling antibody, is a potential therapy for compliment-mediated diseases," Sci. Rep. Apr. 24, 2017; 7(1):1080. doi:10.1038/x41598-017-01087-7.
Gera et al., "Design of pH Sensitive Binding Proteins from the Hypenthermophilic Sso7d Scaffold," PLoS One, 2012:7(11):e48928. doi: 10.1371/journal.pone.0048928. Epub Nov. 7, 2012.
Glick et al., Molecular Biotechnology: Principles and Applications of Recombinant DNA, 3rd Edition, Chemical Industry Press, Mar. 2003, p. 168 (English Translation).
Hirano et al., "Complementary DNA for a novel human interleukin (BSF-2) that induces B lymphocytes to produce immunoglobulin," Nature, 324: 73-76 (Nov. 1986).
Hirata et al., "Characterization of IL-6 Receptor Expression by Monoclonal and Polyclonal Antibodies," J Immunol, Nov. 1, 1989;143(9) :2900-6.
Hoogenboom, "Selecting and screening recombinant antibody libraries," Nat Biotechnol., Sep. 2005;23(9):1105-16.
Huang et al., "A Monoclonal Auti-Human IL-6 Receptor Antibody Inhibits the Proliferation of Human Myeloma Cells," Hybridoma, Oct. 1993:12(5) :621-30.
Iwabe et al., "Pathogenetic significance of increased levels of interleukin-a in the peritoneal fluid of patients with endometriosis," Fertil Steril. May 1998:69(5):924-30.
Knappik et al., "Fully Synthetic Human Combinatorial Antibody Libraries (HuCAL) Based on Modular Consensus Frameworks and CDRs Randomized with Trinucleotides," J Mol Biol., Feb. 11, 2000;296(1):57-86.
Krieckaert et al., "Immunogenicity of biologic therapies—we need tolerance," Nat Rev Rheumatol. Oct. 2010;6(10) :558-9, doi: 10. 1038/nrrbeum. 2010. 153.
Kussie et al., "A single engineered amino acid substitution changes antibody fine specificity," J Immunol. Jan. 1, 1994;152(1):146-52.
Lederman et al., "A single amino acid substitution in a common African allele of the CD4 molecule ablates binding of the monoclonal antibody, OKT4," Mol Immunol. Nov. 1991;28(11):1171-81.
Li et al., "beta-Endorphin omission analogs: dissociation of immunoreactivity from other biological activities," Proc Natl Acad Sci U S A. Jun. 1980;77(6):3211-4.
Lin et al., "Preclinical Pharmacokinetics, Interspecies Scaling, and Tissue Distribution of a Humanized Monoclonal Antibody against Vascular Endothelial Growth Factor." J Pharmacol Exp Ther. Jan. 1999;288(1):371-8.

(56) References Cited

OTHER PUBLICATIONS

Lotz et al., "B Cell Stimulating Factor 2/Intereukin 6 is a Costimulant for Human Thymocytes and T Lymphocytes," J. Exp. Med., Mar. 1, 1988; 167(3): 1253-1258.
Muller et al., "VEGF and the Fab fragment of a humanized neutralizing antibody: crystal structure of the complex at 2.4 Å resolution and mutational analysis of the interface," Structure, Sep. 6, 1998;(9):1153-67.
Novick et al., "Monoclonal Antibodies to the Soluble Human IL-6 Receptor: Affinity Purification, ELISA, and Inhibition of Ligand Binding," Hybridoma. Feb. 1991:10(1) :137-46.
Okabe, Proprietary Innovative Antibody Engineering Technologies in Chugai Pharmaceutical: Dec. 18, 2012, 78 pages.
Osbourn et al., "Generation of a panel of related human scFv antibodies with high affinities for human CEA," Immunotechnology. Sep. 1996:2(3):181-96.
Pancook et al., In Vitro Affinity Maturation of Human IgM Antibodies Reactive with Tumor-Associated Antigens, Hybrid Hybridomics. 2001:20(5-6):383-96.
Reichert, "Antibodies to watch in 2014," mAbs, 6(4): 799-802 (Jul./Aug. 2014).
Schier et al., "Isolation of Picomolar Affinity Anti-c-erbB-2 Single-chain Fv by Molecular Evolution of the Complementarity Determining Regions in the Center of the Antibody Binding Site." J Mol Biol. Nov. 8, 1996:263(4):551-67.
Taga et al., "Interleukin-6 Triggers the Association of Its Receptor with a Possible Signal Transducer, gp130," Cell. Aug. 11, 1989; 58(3): 873-581.
Taga et al., "Receptors for B Cell Stimulatory Factor 2," J. Exp. Med. Oct. 1, 1987; 166(4): 967-981.
Vidarsson et al., "IgG subclasses and allotypes: from structre to effector functions," Front Immunol. Oct. 20, 2014;5:520, doi: 10.3389/fimmu.2014.00520. eCollection 2014.
Wu et al., "Stepwise in vitro affinity maturation of Vitaxin, an $\alpha v\beta 33$-specific humanized mAb," Proc Natl Acad Sci USA. May 26, 1998 ; 95(11):6037-42.
Yamasaki et al., "Cloning and Expression of the Human Intereukin-6 (BSF-2/IFN$\beta$ 2) Receptor," Science. Aug. 12, 1988:241 (4867) :825-8.
USPTO Final Office Action in U.S. Appl. No. 13/889,512, dated May 31, 2017, 15 pages.
USPTO Restriction Requirement in U.S. Appl. No. 13/637,415, dated Dec. 1, 2016, 8 pages.
USPTO Non-Final Office Action in U.S. Appl. No. 13/637,415, dated May 24, 2017, 27 pages.
USPTO Notice of Allowance in U.S. Appl. No. 14/347,034, dated Sep. 22, 2016, 9 pages.
USPTO Non-Final Office Action in U.S. Appl. No. 14/347,034, dated May 25, 2017, 16 pages.
USPTO Restriction Requirement in U.S. Appl. No. 14/007,947, dated Nov. 30, 2015, 9 pages.
USPTO Non-Final Office Action in U.S. Appl. No. 14/007,947, dated Aug. 22, 2016, 31 pages.
USPTO Final Office Action in U.S. Appl. No. 14/007,947, dated Apr. 21, 2017, 9 pages.
USPTO Notice of Allowance in U.S. Appl. No. 14/741,786, dated Jul. 26, 2017, 9 pages.
USPTO Non-Final Office Action in U.S. Appl. No. 14/347,187, dated Jun. 14, 2017, 23 pages.
Fish & Richardson P.C., Reply to Office Action dated Jun. 14, 2017 in U.S. Appl. No. 14/347,187, dated Oct. 16, 2017, 36 pages.
International Search Report for App. Ser. No. PCT/JP2016/003616, dated Nov. 25, 2016, 4 pages.
USPTO Restriction Requirement in U.S. Appl. No. 15/210,353, dated Oct. 6, 2016, 5 pages.
USPTO Office Action in U.S. Appl. No. 15/210,353, dated Mar. 9, 2017, 16 pages.
USPTO Non-Final Office Action in U.S. Appl. No. 14/974,488, dated Aug. 16, 2017, 18 pages.
USPTO Final Office Action in U.S. Appl. No. 15/210,360, dated Jul. 25, 2017, 23 pages.
Hamers-Casterman et al., "Naturally occurring antibodies devoid of light chains," Nature, Jun. 3, 1993;363(6428):446-8.
Kuroda et al., "Computer-aided antibody design," Protein Eng Des Sel., Oct. 2012;25(10):507-21. Epub Jun. 2, 2012.
Final Office Action dated Jan. 19, 2018 in U.S. Appl. No. 14/347,187, Igawa, T., filed Jul. 25, 2014.
Breitbart, A., et al., "Highly Specific Detection of Myostatin Prodomain by an Immunoradiometric Sandwich Assay in Serum of Healthy Individual Individuals and Patients," PLoS One 8(11):e80454 (2013).
Kim, Y. S., et al., "Production of a Polyclonal Anti-Myostatin Antibody and the Effects on In Ovo Administration of the Antibody of Posthatch Broiler Growth and Muscle Mass," Poultry Science 86:1196-1205 (2007).
Ying, J. and Xue, L., "Large Yellow Croaker MSTN-1 Prodomain Prokaryotic Expression, Polyclonal Antibody Preparation and Antibody Function Identification," Chinese J Cell Biol 36(10):1344-1349 (2014)(Abstract).
Technical Data Sheet: "Polyclonal Antisera: Anti-Human C5," Quidel Online Catalog (2010), 1 page.
Curriculum Vitae of Susannah Davis, cited in European Oppositions of European Patent Application No. 09729337.7/European Patent No. 2275443B1, filed Sep. 1, 2016.
Declaration of Susannah Davis, cited in European Oppositions of European Patent Application No. 09729337.7/European Patent No. 2275443B1, filed Sep. 1, 2016.
U.S. Appl. No. 15/379,597, filed Dec. 15, 2016, applicant, Wisconsin Alumni Research Foundation, related application.
King, D. J., "Applications and Engineering of Monoclonal Antibodies," Celltech Therapeutics 68-71 (1998).
Anderson, C. L., et al., "Perspective—FcRn transports albumin: relevance to immunology and medicine," TRENDS in Immunology 27(7):343-348 (2006).
Smith, B. J., et al., "Prolonged in Vivo Residence Times of Antibody Fragments Associated with Albumin," Bioconjugate Chem 12(5):750-756 (2001).
Birn, H. and Christensen, E., "Renal albumin absorption in physiology and pathology," Kidney International 69:440-449 (2006).
Chaudhury, C., et al., "The Major Histocompatibility Complex-related Fc Receptor for IgG (FcRn) Binds Albumin and Prolongs Its Lifespan," J Exp Med 197(3):315-322 (2003).
Chilukuri, K. P., et al., "Polyethylene glycosylation prolongs the circulatory stability of recombinant human butyrylcholinesterase," Chemico-Biological Interactions 157-158:115-121 (2005).
Chuang, V. T. G., et al., "Pharmaceutical Strategies Utilizing Recombinant Human Serum Albumin," Pharm Res 19(5):569-577 (2002).
Dennis, M. S., et al., "Albumin Binding as a General Strategy for Improving the Pharmacokinetics of Proteins," J Biol Chem 277(38):35035-35043 (2002).
Franks, F., "Conformational Stability of Proteins," Protein Biotechnology 395-436 (1993).
Gekle, M., "Renal Tubule Albumin Transport," Annu Rev Physiol 67:573-594 (2005).
Guasch, A., et al., "Charge Selectivity of the Glomerular Filtration Barrier in Healthy and Nephrotic Humans," J Clin Invest 92:2274-2282 (1993).
Holt, L. J., et al., "Anti-serum albumin domain antibodies extending the half-lives of short lived drugs," Protein Eng Des Sel 21(5):283-288 (2008).
Huang, Y. J., et al., "Recombinant human butyrylcholinesterase from milk of transgenic animals to protect against organophosphate poisoning," PNAS 104(34):13603-13608 (2007).
Kawamoto, M., et al., "Circulatory Stability and Plasma Lidocaine Levels during Continuous and Intermittent Thoracic Epidural Analgesia," J Anesth 5(2):166-171 (1991).
Kim, H. J., and Kim, H-J., "The Glycosylation and Pharmacokinetics of CTLA4Ig Produced in Rice Cells," Biol Pharm Bull 30(10):1913-1917 (2007).
Knudsen, L. B., et al., "Potent Derivatives of Glucagon-like Peptide-1 with Pharmacokinetic Properties Suitable for Once Daily Administration," J Med Chem 43(9):1664-1669 (2000).

(56) References Cited

OTHER PUBLICATIONS

Kratz, F., "Albumin as a drug carrier: Design of prodrugs, drug conjugates and nanoparticles," J Controlled Release 132:171-183 (2008).
Kurtzhals, P., et al., "Albumin Binding and Time Action of Acylated Insulins in Various Species," J Pharma Sci 85(3):304-308 (1996).
Manning, M. C., et al., "Stability of Protein Pharmaceuticals," Pharma Res 6(11):903-918 (1989).
Peters, T., "Ligand Binding by Albumin," Academic Press 76-79 (1996).
Saxena, A., et al., "Role of Oligosaccharides in the Pharmacokinetics of Tissue-Derived and Genetically Engineered Cholinesterases," Mol Pharma 53:112-122 (1998).
Schultze, H. E. and Heremans, J. F., "Turnover of Plasma Proteins," Molecular Biology of Human Proteins with Special Reference to Plasma Proteins, Nature and Metabolism of Extracellular Proteins, Elsevier 1:476-477 (1966).
Stork, R., et al., "A novel tri-functional antibody fusion protein with improved pharmacokinetic properties generated by fusing a bispecific single-chain diabody with an albumin-binding domain from streptococcal protein G," Protein Eng Des Sel 20(11):569-576 (2007).
O'Hear, C. E. and Foote, J., "Antibody buffering of a ligand in vivo," PNAS 102(1):40-44 (2005).
Rehlaender, B. N. and Cho, M. J., "Antibodies as Carrier Proteins," Pharma Res 15(11):1652-1656 (1998).
Bazin, R., et al., "Use of hu-IgG-SCID mice to evaluate the in vivo stability of human monoclonal IgG antibodies," J Immunol Methods 172:209-217 (1994).
Dirnberger, D., et al., "Secretion of biologically active glycoforms of bovine follicle stimulating hormone in plants," Eur J Biochem 268:4570-4579 (2001).
Kurtzhals, P., et al., "Effect of Fatty Acids and Selected Drugs on the Albumin Binding of a Long-Acting, Acylated Insulin Analogue," J Pharma Sci 86(12):1365-1368 (1997).
Makrides, S. C., et al., "Extended in Vivo Half-Life of Human Soluble Complement Receptor Type 1 Fused to a Serum Albumin-Binding Receptor," J Pharmacol Exp Ther 277(1):534-542 (1996).
Inoue, M., et al., "Synthesis of a Superoxide Dismutase Derivative That Circulates Bound to Albumin and Accumulates in Tissues Whose pH is Decreased," Biochem 28:6619-6624 (1989).
Janeway, C. A., et al., Immunobiology $5^{th}$ edition 122 (2001).
Declaration of Roland Kontermann with Curriculum Vitae (Appendix A), dated Nov. 20, 2017, cited in European Oppositions of European Patent Application No. 09729337.7/European Patent No. 2275443B1, filed Sep. 1, 2016.
Declaration of Jan-Terje Andersen, dated Dec. 14, 2017, cited in European Oppositions of European Patent Application No. 09729337.7/European Patent No. 2275443B1, filed Sep. 1, 2016.
Concordance table showing Kabat numbering for antibody Hyb C1.
Concordance table showing Kabat numbering for antibody 300N.
Opposition proceedings and prosecution of European Patent No. 2275443 (4,766 pages).
Information Document Regarding the Oral Proceedings of Feb. 27-28, 2018 dated Feb. 28, 2018.
Horiuchi, T. and Tsukamoto, H., "Complement-targeted therapy: development of C5- and C5a-targeted inhibition," Inflammation and Regeneration 36:11, doi 10.1186/s41232-016-013-6 (2016).
Japanese Patent Office Appeal Decision denying Appeal of Trial Decision to not invalidate Japanese Patent No. 4954326, Appeal No. 2016-800136, dated Nov. 22, 2017.
Japanese Patent Office Appeal Decision denying Appeal of Trial Decision to not invalidate Japanese Patent No. 5503698, Appeal No. 2016-800137, dated Nov. 22, 2017.
Japanese Patent Office Appeal Decision denying Appeal of Trial Decision to not invalidate Japanese Patent No. 5824095, Appeal No. 2016-800138, dated Nov. 22, 2017.
U.S. Appl. No. 15/952,945, filed Apr. 13, 2018, Igawa, et al., unpublished, related application.
U.S. Appl. No. 15/988,348, filed May 24, 2018, Igawa, et al., unpublished, related application.
U.S. Appl. No. 15/976,288, filed May 10, 2018, Igawa, et al., unpublished, related application.
U.S. Appl. No. 15/963,449, filed Apr. 26, 2018, Ruike, et al., unpublished, related application.
U.S. Appl. No. 15/963,455, filed Apr. 26, 2018, Ruike, et al., unpublished, related application.
U.S. Appl. No. 16/065,192, international filing date, Dec. 22, 2016, Ruike, et al., unpublished, related application.
U.S. Appl. No. 13/524,528, filed Jun. 15, 2012, Igawa, et al., related application. (now abandoned).
U.S. Appl. No. 14/520,423, filed Oct. 22, 2014, Igawa, et al., related application.
U.S. Appl. No. 13/959,489, filed Aug. 5, 2013, Igawa, et al., related application. (now abandoned).
U.S. Appl. No. 15/263,617, filed Sep. 13, 2016, Igawa, et al., related application.
U.S. Appl. No. 12/680,112, filed Jun. 23, 2010, Igawa, et al., related application. (now abandoned).
U.S. Appl. No. 13/889,484, filed May 8, 2013, Igawa, et al., related application.
U.S. Appl. No. 13/889,512, filed May 8, 2013, Igawa, et al., related application.
U.S. Appl. No. 12/936,587, filed Jan. 3, 2011, Igawa, et al., related application. (now abandoned).
U.S. Appl. No. 14/347,034, filed Mar. 25, 2014, Igawa, et al., related application.
U.S. Appl. No. 14/347,187, filed Mar. 25, 2014, Igawa, et al., related application.
U.S. Appl. No. 15/050,145, filed Feb. 22, 2016, Igawa, et al., related application.
U.S. Appl. No. 15/495,026, filed Apr. 24, 2017, Igawa, et al., related application.
U.S. Appl. No. 15/544,930, filed Jul. 20, 2017, Murata, et al., related application.
U.S. Appl. No. 14/974,350, filed Dec. 18, 2015, Ruike, et al., related application.
U.S. Appl. No. 14/974,488, filed Dec. 18, 2015, Ruike, et al., related application.
U.S. Appl. No. 15/015,287, filed Feb. 4, 2016, Igawa, et al., related application.
U.S. Appl. No. 12/295,039, filed Sep. 11, 2012, Igawa, et al., related application.
U.S. Appl. No. 12/679,922, filed Oct. 1, 2010, Igawa et al., related application.
U.S. Appl. No. 13/518,861, filed Oct. 4, 2012, Igawa, et al., related application. (now abandoned).
Further Opposition Proceedings and Prosecution submitted Apr. 26 through Jul. 6, 2018 in European Patent Application No. 2275443 (231 pages).
U.S. Appl. No. 16/019,752, filed Jun. 27, 2018, Ruike, Y., et al., related application.
U.S. Appl. No. 16/028,140, filed Jul. 5, 2018, Igawa, T., et al., related application.
U.S. Appl. No. 16/041,976, filed Jul. 23, 2018, Igawa, T., et al., related application.
U.S. Appl. No. 61/313,102, filed Mar. 11, 2010, related application.
Alignment of constant amino acid sequences from WO-2009125825-A1, submitted Feb. 5, 2018 by the opponents in opposition for EP2552955.
Alignment of the amino acid sequences of the Fc regions of the antibodies exemplified in EP2275443, submitted Feb. 2, 2018 by the opponents in opposition for EP2552955.
Alignment of variable heavy and light chain amino acid sequences from WO-2009125825-A1, submitted Feb. 2, 2018 by the opponents in opposition for EP2552955.
Claims as granted for European Publication No. EP2275443, submitted Feb. 2, 2018 by the opponents in opposition for EP2552955.
Priority Japanese Patent Application No. 2010-079667, filed Mar. 30, 2010, submitted Feb. 5, 2018 by the opponents in opposition for EP2552955 (see English translation).
English Translation of Priority Japanese Patent Application No. 2010-079667, filed Mar. 30, 2010, submitted Feb. 5, 2018 by the opponents in opposition for EP2552955.

(56) References Cited

OTHER PUBLICATIONS

Priority Japanese Patent Application No. 2010-250830, filed Nov. 9, 2010, submitted Feb. 5, 2018 by the opponents in opposition for EP2552955 (see English translation).
English Translation of Priority Japanese Patent Application No. 2010-250830, filed Nov. 9, 2010, submitted Feb. 5, 2018 by the opponents in opposition for EP2552955.
Akbarzadeh-Sharbaf, S., et al., In silico design, construction and cloning of Trastuzumab humanized monoclonal antibody: A possible biosimilar for Herceptin, Adv Biomed Res 1:1 (2012), submitted Feb. 2, 2018 by the opponents in opposition for EP2552955.
Atherton, J. C., "Acid-base balance: maintenance of plasma pH," Anaesthesia & Intensive Care Medicine, 10(11):557-561 (2009)(abstract), submitted Feb. 5, 2018 by the opponents in opposition for EP2552955.
Bayry, J., et al., "Immuno affinity purification of foot and mouth disease virus type specific antibodies using recombinant protein adsorbed to polystyrene wells," J Virol Meth 81:21-30 (1999).
Becker, J. M., et al., "Prevention of Postoperative Abdominal Adhesions by a Sodium Hyalurontate-Based Bioresorbable Membrane: A Prospective, Randomized, Double-Blind Multicenter Study," J Am Coll Surg 183:297-306 (1996).
Besada, E., "Potential patient benefit of a subcutaneous formulation of tocilizumab for the treatment of rheumatoid arthritis: a critical review," Patient Preference and Adherance 8:1051-1059 (2014).
Bulun, S. E., "Endometriosis," N Engl J Med 360:268-279 (2009).
Datta-Mannan, A., et al., "Humanized IgG Variants with Differential Binding Properties to the Neonatal Fc Receptor: Relationship to Pharmacokinetics in Mice and Primates," Drug Metab Dispos 35(1):86-94 (2007), submitted Feb. 2, 2018 by the opponents in opposition for EP2552955.
Davydov, L., "Omalizumab (Xolair) for Treatment of Asthma," American Family Physican 71(2):341-342 (2005), submitted Feb. 2, 2018 by the opponents in opposition for EP2552955.
De Felice, F. G., et al., "Formation of amyloid aggregates from human lysozyme and its disease-associated variants using hydrostatic pressure," The FASEB Journal, express article 10.1096/fj.03-1072fje. Published online May 20, 2004.
Donnez, J., et al., "Current Thinking on the Pathogenesis of Endometriosis," Gynecol Obstet Invest 54(supp 1):52-62 (2002).
Ejima, D., et al.,"Effective elution of antibodies by arginine and arginine derivatives in affinity column chromatography," Analytical Biochemistry 345:250-257 (2005).
Giclas, P. C., et al., "Preparation and characterization of monoclonal antibodies against the fifth component of rabbit complement (C5)," J Immunol Meth 105(2):201-209 (1987).
Giudice, L. C. and Kao, L. C "Endometriosis," Lancet 364:1789-1799 (2004).
Goebl, N. A., et al., "Neonatal Fc Receptor Mediates Internalization of Fc in Transfected Human Endothelial Cells," Mol Biol Cell, 19:5490-5505 (2008), submitted Feb. 2, 2018 by the opponents in opposition for EP2552955.
Guo, S., "Recurrence of endometriosis and its control." Human Reproduction Update 15(4):441-461 (2009).
Gurbaxani, B., et al., "Analysis of a family of antibodies with different half-lives in mice fails to find a correlation between affinity for FcRn and serum half-life," Mol Immunol 43:1462-1473 (2006), submitted Feb. 2, 2018 by the opponents in opposition for EP2552955.
Han, H. Q. and Mitch, W. E., "Targeting the Myostatin Signaling Pathway to Treat Muscle Wasting Disease," Curr Opin Support Palliat Care 5(4):334-341 (2011).
Harvey, et al., Lippincott's Illustrated Reviews: Immunology Second Edition Chapter 2 "Antigens and Receptors," 11-23 and Chapter 11 "Lymphocyte Effector Functions," 141-157 (2013).
Hill, J. J., et al., "The Myostatin Propeptide and the Follistatin-related Gene Are Inhibitory Binding Proteins of Myostatin in Normal Serum," J Biol Chem 277(43):40735-40741 (2002).
Hinton, P. R., et al., "Engineered Human IgG Antibodies with Longer Serum Half-lives in Primates," J Biol Chem 279(8):6213-6216 (2004).

Huizinga, T. W. J., et al., "Sarilumab, a fully human monoclonal antibody against IL-6Rα in patients with rheumatoid arthritis and an inadequate response to methotrexate: efficacy and safety results from the randomized SARIL-RA-MOBILITY Part A trial," Ann Rheum Dis 73:1626-1634 (2014).
Irani, V., et al., "Molecular properties of human IgG subclasses and their implications for designing therapeutic monoclonal antibodies against infectious diseases," Mol Immunol 67:171-182 (2015), submitted Feb. 2, 2018 by the opponents in opposition for EP2552955.
Kim, Y. S., et al., "Production of a Monoclonal Anti-Myostatin Antibody and the Effects of In Ovo Administration of the Antibody on Posthatch Broiler Growth and Muscle Mass," Poultry Science 85:1062-1071 (2006).
Molina, M. A., et al., "Trstuzumab (Herceptin), a Humanized Anti-HER2 Receptor Monoclonal Antibody, Inhibits Basal and Activated HER2 Ectodomain Cleavage in Breast Cancer Cells," Cancer Research 61:4744-4749 (2001), submitted Feb. 2, 2018 by the opponents in opposition for EP2552955.
Montero-Julian, F. A., et al., "Pharmacokinetic Study of Anti-Interleukin-6 (IL-6) Therapy With Monoclonal Antibodies: Enhancement of IL-6 Clearance by Cocktails of Anti-IL-6 Antibodies," Blood 85(4):917-924 (1995).
O'Donovan, N. and Crown, J., "EGFR and HER-2 Antagonists in Breast Cancer," Anticancer Res, 27:1285-1294 (2007), submitted Feb. 5, 2018 by the opponents in opposition for EP2552955.
Okiyama, N., et al., "Therapeutic Effects of Interleukin-6 Blockade in a Murine Model Polymyositis That Does Not Require Interleukin-17A," Arth Rheum 60(8):2505-2512 (2009).
Presta, L. G., et al., "Humanization of an Anti-Vascular Endothelial Growth Factor Monoclonal Antibody for the Therapy of Solid Tumors and Other Disorders," Cancer Res, 57:4593-4599 (1997), submitted Feb. 2, 2018 by the opponents in opposition for EP2552955.
Raghavan, M., et al., "Analysis of the pH Dependence of the Neonatal Fc Receptor/Immunoglobulin G Interaction Using Antibody and Receptor Variants," Biochem 34:14649-14657 (1995), submitted Feb. 2, 2018 by the opponents in opposition for EP2552955.
Rojas, J. R., et al., "Formation, Distribution, and Elimination of Infliximab and Anti-Infliximab Immune Complexes in Cynomolgus Monkeys," JPET 313(2):578-585 (2005).
Rother, R. P., et al., "Discovery and development of the complement inhibitor eculizumab for the treatment of paroxysmal nocturnal hemoglobinuria," Nature Biotechnology 25(11):1256-1264 (2007).
Russo, R. C., et al., "The CXCL8/IL-8 chemokine family and its receptors in inflammatory diseases," Expert Rev Clin Immunol 10(5):593-619 (2014).
Tanzi, R. E., et al., "Twenty Years of the Alzheimer's Disease Amyloid Hypothesis: A Genetic Perspective," Cell 120:545-555 (2005).
Vaccaro, C., et al., "Divergent activities of an engineered antibody in murine and human systems have implications for therapeutic antibodies," PNAS 103(49): 18709-18714 (2006), submitted Feb. 2, 2018 by the opponents in opposition for EP2552955.
Vercellini, P., et al., "Postoperative oral contraceptive exposure and risk of endometrioma recurrence," Am J Obstet Gynecol 198:504. e1-504.e5 (2008).
Waelbroeck, M., "The pH Dependence of Insulin Binding," J Biol Chem 257(14):8284-8291 (1982), submitted Feb. 5, 2018 by the opponents in opposition for EP2552955.
Ward, E. S., et al., "Evidence to support the cellular mechanism involved in serum IgG homeostasis in humans," Intl Immunol 15(2):187-195 (2003), submitted Feb. 2, 2018 by the opponents in opposition for EP2552955.
Welch, B., "Adalimumab (Humira) for the Treatment of Rheumatoid Arthritis," American Family Physician 78(12):1406-1408 (2008), submitted Feb. 2, 2018 by the opponents in opposition for EP2552955.
Yada, et al., Lippincott's Illustrated Reviews: Immunology Second Edition, 18, 19, 152,153 (2013).
Yang, D., et al., "Dataset of the binding kinetic rate constants of anti-PCSK9 antibodies obtained using the Biacore T100, ProteOn XPR36, Octet RED384, and IBIS MX96 biosensor platforms," Data in Brief 8:1173-1183 (2016), submitted Feb. 2, 2018 by the opponents in opposition for EP2552955.

(56) References Cited

OTHER PUBLICATIONS

Yang, D., et al., "Maximizing in vivo target clearance by design of pH-dependence target binding antibodies with altered affinity to FcRn," MABS 9(7):1105-1117 (2017), submitted Feb. 2, 2018 by the opponents in opposition for EP2552955.
Yeung, Y. A., et al., "A Therapeutic Anti-VEGF Antibody with Increased Potency Independent of Pharmacokinetic Half-life," Cancer Res 70(8):3269-3277 (2010), submitted Feb. 2, 2018 by the opponents in opposition for EP2552955.
U.S. Appl. No. 139,504, filed Dec. 30, 1987, Ngo, T. T., related application.
U.S. Appl. No. 12/311,768, 371(c) date Oct. 11, 2007, Lasters. I. J. I., et al., related application.
U.S. Appl. No. 12/780,006, filed May 14, 2010, Radin, A., et al., related application.
U.S. Appl. No. 13/595,139, filed Aug. 27, 2012, Igawa, T., related application.
U.S. Appl. No. 15/553,609, 371(c) date Feb. 26, 2016, Chugai Seiyaku Kabushiki Kaisha, related application.
U.S. Appl. No. 10/576,372, 371(c) date Nov. 4, 2004, Rossi, M., et al., related application.
U.S. Appl. No. 11/155,909, filed Jun. 17, 2005, Cho, H. S., et al., related application.
U.S. Appl. No. 11/557,466, filed Nov. 7, 2006, Dennis, M. S., et al., related application.
U.S. Appl. No. 12/066,838, 371(c) date Oct. 5, 2006, Davies, J. D., et al., related application.
U.S. Appl. No. 12/262,712, filed Oct. 31, 2008, La Vallie, E. R et al., related application.
U.S. Appl. No. 12/990,137, 371(c) date Apr. 28, 2009, Foltz, I., et al., related application.
U.S. Appl. No. 13/816,894, 371(c) date Aug. 15, 2011, Han, H., et al., related application.
U.S. Appl. No. 12/680,087, filed Jan. 3, 2011, Igawa, T., et al., related application.
U.S. Appl. No. 15/688,004, filed Aug. 28, 2017, Ruike, Y et al., related application.
U.S. Appl. No. 12/660,528, filed Feb. 26, 2010, Sabbadini, R. A., et al., related application.
Certificate of Analysis, "Rabbit Antibody to Human pro-Myostatin (amino acids 79-92)," Meridian Life Science, Inc., Nov. 13, 2015, XP055478289, Catalog No. K24340R, Lot No. 2K31715.
Data Sheet, "Mouse GDF-8/Myostatin Propeptide Antibody—Antigen Affinity-purified Polyclonal Sheep IgG," R&D Systems, Catalogue No. AF 1539, Feb. 6, 2018, XP055478493.
Data Sheet, "Human Pro-Myostatin (aa 79-92), polyclonal antibody", Immun Diagnostik Antibodies Catalogue No. Ak3004.1/AK3004.2, Jun. 30, 2016.
Antibodies from www.bioinf.org.uk: Dr. Andrew C.R. Martin's Group, Jul. 11, 2018.
EMA product information: Annexes to file of the tocilizumab preparation RoActemra (WC500054890)(2016), submitted Feb. 5, 2018 by the opponents in opposition for EP2552955.
Experimental data characterizing the binding of rituximab to its antigen CD20 and to human FcRn, submitted Feb. 2, 2018 by the opponents in opposition for EP2552955.
Expert Declaration of Madhusudan Natarajan, Ph.D., submitted Feb. 5, 2018 by the opponents in opposition for EP2552955.
International Search Report dated Oct. 31, 2017, in International Application No. PCT/JP2017/028346.
Iwabe, T., et al., "Pathogenic significance of increased levels of interleukin-8 in the peritoneal fluid of patients with endometriosis," Fertility and Sterility 69(5):924-930 (1998).
Result of Consultation mailed Oct. 13, 2016, in European Application No. EP11714860.1, issued during examination of the opposed patent, EP2552955.
Off-rate of Xolair Fab for binding to human IgE at pH7.4 and pH5.5, submitted Feb. 5, 2018 by the opponents in opposition for EP2552955.
Product labeling information of Rituxan (Rituximab)(Nov. 1997), submitted Feb. 5, 2018 by the opponents in opposition for EP2552955.

Supplemental information from opponent, submitted Feb. 2, 2018 by the opponents in opposition for EP2552955.
The Chemical PE Thread, Thunder's Place, blog entry, Jun. 1, 2014, Retrieved from the Internet: URL:https://www.thundersplace.org/male-supplements/the-chemical-pe thread-7.html92.
English Translation of Written Reply for Appeal Case—Patentee filed Mar. 24, 2017, Appeal No. 2016-800136, Trial for Invalidation of Japanese Patent No. 4954326, related case.
English Translation of Written Appeal—Appellant filed Dec. 15, 2016, Appeal No. 2016-800136, Trial for Invalidation of Japanese Patent No. 4954326, related case.
English Translation of Oral Proceedings Statement Brief—Appellant filed Jun. 1, 2017, Appeal No. 2016-800136, Trial for Invalidation of Japanese Patent No. 4954326, related case.
English Translation of Oral Proceedings Statement Brief—Patentee filed Jun. 1, 2017, Appeal No. 2016-800136, Trial for Invalidation of Japanese Patent No. 4954326, related case.
English Translation of Written Statement—Appellant filed Jun. 30, 2017, Appeal No. 2016-800136, Trial for Invalidation of Japanese Patent No. 4954326, related case.
English Translation of Written Statement—Patentee filed Jul. 7, 2017, Appeal No. 2016-800136, Trial for Invalidation of Japanese Patent No. 4954326, related case.
English Translation of Written Statement—Patentee filed Jul. 21, 2017, Appeal No. 2016-800136, Trial for Invalidation of Japanese Patent No. 4954326, related case.
English Translation of Written Reply—Appellant filed Aug. 22, 2017, Appeal No. 2016-800136, Trial for Invalidation of Japanese Patent No. 4954326, related case.
English Translation, "Analysis of the Expression Construct in Cells Used for Production of r-DNA Derived Protein Products," PMSB/ELD Notification No. 3 dated Jan. 6, 1998, Patentee Reference 1 in Appeal No. 2016-800136, Trial for Invalidation of Japanese Patent No. 4954326, related case.
English Translation of Certificate of Experimental Results filed Mar. 21, 2017, Fuji Gotemba Research Labs, Chugai Pharmaceutical Co., Ltd., Patentee's Exhibit 2, Appeal No. 2016-800136, Trial for Invalidation of Japanese Patent No. 4954326, related case.
English Translation of Certificate of Experimental Results filed Mar. 22, 2017, Kamakura Research Labs, Chugai Pharmaceutical Co., Ltd., Patentee's Exhibit 3, Appeal No. 2016-800136, Trial for Invalidation of Japanese Patent No. 4954326, related case.
English Translation of Certificate of Experimental Results filed Mar. 21, 2017, Fuji Gotemba Research Labs, Chugai Pharmaceutical Co., Ltd., Patentee's Exhibit 9, Appeal No. 2016-800136, Trial for Invalidation of Japanese Patent No. 4954326, related case.
English Translation, "Basic Biochemistry Experiments," Nov. 25, 1994, Patentee's Exhibit 11, Appeal No. 2016-800136, Trial for Invalidation of Japanese Patent No. 4954326, related case.
English Translation, "New Biochemistry Experiment Seminars 1, Proteins VII, Protein Engineering," Feb. 15, 1993, Patentee's Exhibit 12, Appeal No. 2016-800136, Trial for Invalidation of Japanese Patent No. 4954326, related case.
English Translation of Appeal Decision dated Nov. 22, 2017, Appeal No. 2016-800136, Trial for Invalidation of Japanese Patent No. 4954326, related case.
English Translation, "Human Heavy Chain Variable Domains," Patentee's Reference 2, Appeal No. 2016-800136, Trial for Invalidation of Japanese Patent No. 4954326, related case.
English Translation, Steipe Lab Molecular Systems Engineering, dated Jul. 20, 2017, Patentee's Reference 2-A, Appeal No. 2016-800136, Trial for Invalidation of Japanese Patent No. 4954326, related case.
English Translation, Steipe Lab Molecular Systems Engineering—Research, dated Jul. 20, 2017, Patentee's Reference 2-B, Appeal No. 2016-800136, Trial for Invalidation of Japanese Patent No. 4954326, related case.
English Translation, Steipe Lab Molecular Systems Engineering—Canonical Sequence Approximation, dated Jul. 20, 2017, Patentee's Reference 2-C, Appeal No. 2016-800136, Trial for Invalidation of Japanese Patent No. 4954326, related case.
English Translation, Steipe Lab Molecular Systems Engineering—Canonical Sequence Approximation, dated Jul. 20, 2017, Patentee's

(56) References Cited

OTHER PUBLICATIONS

Reference 2-D, Appeal No. 2016-800136, Trial for Invalidation of Japanese Patent No. 4954326, related case.
English Translation, Steipe Lab Molecular Systems Engineering—Canonical Sequence Approximation, dated Jul. 20, 2017, Patentee's Reference 2-E, Appeal No. 2016-800136, Trial for Invalidation of Japanese Patent No. 4954326, related case.
English Translation, Steipe Lab Molecular Systems Engineering—Canonical Sequence Approximation, dated Jul. 20, 2017, Patentee's Reference 2-F, Appeal No. 2016-800136, Trial for Invalidation of Japanese Patent No. 4954326, related case.
English Translation, Steipe Lab Molecular Systems Engineering—Canonical Sequence Approximation, dated Jul. 20, 2017, Patentee's Reference 2-G, Appeal No. 2016-800136, Trial for Invalidation of Japanese Patent No. 4954326, related case.
English Translation, Steipe Lab Molecular Systems Engineering—Canonical Sequence Approximation, dated Jul. 20, 2017, Patentee's Reference 2-H, Appeal No. 2016-800136, Trial for Invalidation of Japanese Patent No. 4954326, related case.
Kabat, E. A., et al., "Sequences of Proteins of Immunological Interest," vols. 1-3, $5^{th}$ ed., U.S. Dept. of Health & Human Services (1991), Patentee's Reference 3, Appeal No. 2016-800136, Trial for Invalidation of Japanese Patent No. 4954326, related case.
English Translation of Written Appeal—Appellant filed Dec. 15, 2016, Appeal No. 2016-800137, Trial for Invalidation of Japanese Patent No. 5503698, related case.
English Translation of Written Reply for Appeal Case—Patentee filed Mar. 24, 2017, Appeal No. 2016-800137, Trial for Invalidation of Japanese Patent No. 5503698, related case.
English Translation of Written Reply—Appellant filed Aug. 22, 2017, Appeal No. 2016-800137, Trial for Invalidation of Japanese Patent No. 5503698, related case.
English Translation of Oral Proceedings Statement Brief—Appellant filed Jun. 1, 2017, Appeal No. 2016-800137, Trial for Invalidation of Japanese Patent No. 5503698, related case.
English Translation of Oral Proceedings Statement Brief—Patentee filed Jun. 1, 2017, Appeal No. 2016-800137, Trial for Invalidation of Japanese Patent No. 5503698, related case.
English Translation of Request for Correction—Claims filed Mar. 24, 2017, Appeal No. 2016-800137, Trial for Invalidation of Japanese Patent No. 5503698, related case.
English Translation of Written Statement—Appellant filed Jun. 30, 2017, Appeal No. 2016-800137, Trial for Invalidation of Japanese Patent No. 5503698, related case.
English Translation of Written Statement—Patentee filed Jul. 7, 2017, Appeal No. 2016-800137, Trial for Invalidation of Japanese Patent No. 5503698, related case.
English Translation of Written Statement—Patentee filed Jul. 21, 2017, Appeal No. 2016-800137, Trial for Invalidation of Japanese Patent No. 5503698, related case.
English Translation, "Analysis of the Expression Construct in Cells Used for Production of r-DNA Derived Protein Products," PMSB/ELD Notification No. 3 dated Jan. 6, 1998, Patentee Reference 1 in Appeal No. 2016-800137, Trial for Invalidation of Japanese Patent No. 5503698, related case.
English Translation of Certificate of Experimental Results filed Mar. 21, 2017, Fuji Gotemba Research Labs, Chugai Pharmaceutical Co., Ltd., Patentee's Exhibit 2, Appeal No. 2016-800137, Trial for Invalidation of Japanese Patent No. 5503698, related case.
English Translation of Certificate of Experimental Results filed Mar. 21, 2017, Fuji Gotemba Research Labs, Chugai Pharmaceutical Co., Ltd., Patentee's Exhibit 8, Appeal No. 2016-800137, Trial for Invalidation of Japanese Patent No. 5503698, related case.
English Translation, "Basic Biochemistry Experiments," Nov. 25, 1994, Patentee's Exhibit 10, Appeal No. 2016-800137, Trial for Invalidation of Japanese Patent No. 5503698, related case.
English Translation, "New Biochemistry Experiment Seminars 1, Proteins VII, Protein Engineering," Feb. 15, 1993, Patentee's Exhibit 12, Appeal No. 2016-800137, Trial for Invalidation of Japanese Patent No. 5503698, related case.
English Translation of Corrected Claims filed Mar. 24, 2017, Appeal No. 2016-800137, Trial for Invalidation of Japanese Patent No. 5503698, related case.
English Translation of Appeal Decision dated Nov. 22, 2017, Appeal No. 2016-800137, Trial for Invalidation of Japanese Patent No. 5503698, related case.
English Translation, "Human Heavy Chain Variable Domains," Patentee's Reference 2, Appeal No. 2016-800137, Trial for Invalidation of Japanese Patent No. 5503698, related case.
English Translation, Steipe Lab Molecular Systems Engineering, dated Jul. 20, 2017, Patentee's Reference 2-A, Appeal No. 2016-800137, Trial for Invalidation of Japanese Patent No. 5503698, related case.
English Translation, Steipe Lab Molecular Systems Engineering—Research, dated Jul. 20, 2017, Patentee's Reference 2-B, Appeal No. 2016-800137, Trial for Invalidation of Japanese Patent No. 5503698, related case.
English Translation, Steipe Lab Molecular Systems Engineering—Canonical Sequence Approximation, dated Jul. 20, 2017, Patentee's Reference 2-C, Appeal No. 2016-800137, Trial for Invalidation of Japanese Patent No. 5503698, related case.
English Translation, Steipe Lab Molecular Systems Engineering—Canonical Sequence Approximation, dated Jul. 20, 2017, Patentee's Reference 2-D, Appeal No. 2016-800137, Trial for Invalidation of Japanese Patent No. 5503698, related case.
English Translation, Steipe Lab Molecular Systems Engineering—Canonical Sequence Approximation, dated Jul. 20, 2017, Patentee's Reference 2-E, Appeal No. 2016-800137, Trial for Invalidation of Japanese Patent No. 5503698, related case.
English Translation, Steipe Lab Molecular Systems Engineering—Canonical Sequence Approximation, dated Jul. 20, 2017, Patentee's Reference 2-F, Appeal No. 2016-800137, Trial for Invalidation of Japanese Patent No. 5503698, related case.
English Translation, Steipe Lab Molecular Systems Engineering—Canonical Sequence Approximation, dated Jul. 20, 2017, Patentee's Reference 2-G, Appeal No. 2016-800137, Trial for Invalidation of Japanese Patent No. 5503698, related case.
English Translation, Steipe Lab Molecular Systems Engineering—Canonical Sequence Approximation, dated Jul. 20, 2017, Patentee's Reference 2-H, Appeal No. 2016-800137, Trial for Invalidation of Japanese Patent No. 5503698, related case.
Kabat, E. A., et al., "Sequences of Proteins of Immunological Interest," vols. 1-3, $5^{th}$ ed., U.S. Dept. of Health & Human Services (1991), Patentee's Reference 3, Appeal No. 2016-800137, Trial for Invalidation of Japanese Patent No. 5503698, related case.
English Translation of Written Appeal—Appellant filed Dec. 15, 2016, Appeal No. 2016-800138, Trial for Invalidation of Japanese Patent No. 5824095, related case.
English Translation of Written Reply for Appeal Case—Patentee filed Mar. 24, 2017, Appeal No. 2016-800138, Trial for Invalidation of Japanese Patent No. 5824095, related case.
English Translation of Oral Proceedings Statement Brief—Appellant filed Jun. 1, 2017, Appeal No. 2016-800138, Trial for Invalidation of Japanese Patent No. 5824095, related case.
English Translation of Oral Proceedings Statement Brief—Patentee filed Jun. 1, 2017, Appeal No. 2016-800138, Trial for Invalidation of Japanese Patent No. 5824095, related case.
English Translation of Written Statement—Appellant filed Jun. 30, 2017, Appeal No. 2016-800138, Trial for Invalidation of Japanese Patent No. 5824095, related case.
English Translation of Written Statement—Patentee filed Jul. 7, 2017, Appeal No. 2016-800138, Trial for Invalidation of Japanese Patent No. 5824095, related case.
English Translation of Written Statement—Patentee filed Jul. 21, 2017, Appeal No. 2016-800138, Trial for Invalidation of Japanese Patent No. 5824095, related case.
English Translation of Written Reply—Appellant filed Aug. 22, 2017, Appeal No. 2016-800138, Trial for Invalidation of Japanese Patent No. 5824095, related case.
English Translation, "Analysis of the Expression Construct in Cells Used for Production of r-DNA Derived Protein Products," PMSB/

(56) References Cited

OTHER PUBLICATIONS

ELD Notification No. 3 dated Jan. 6, 1998, Patentee Reference 1 in Appeal No. 2016-800138, Trial for Invalidation of Japanese Patent No. 5824095, related case.

English Translation of Certificate of Experimental Results filed Mar. 21, 2017, Fuji Gotemba Research Labs, Chugai Pharmaceutical Co., Ltd., Patentee's Exhibit 2, Appeal No. 2016-800138, Trial for Invalidation of Japanese Patent No. 5824095, related case.

English Translation of Certificate of Experimental Results filed Mar. 21, 2017, Fuji Gotemba Research Labs, Chugai Pharmaceutical Co., Ltd., Patentee's Exhibit 8, Appeal No. 2016-800138, Trial for Invalidation of Japanese Patent No. 5824095, related case.

English Translation, "Basic Biochemistry Experiments," Nov. 25, 1994, Patentee's Exhibit 10, Appeal No. 2016-800138, Trial for Invalidation of Japanese Patent No. 5824095, related case.

English Translation, "New Biochemistry Experiment Seminars 1, Proteins VII, Protein Engineering," Feb. 15, 1993, Patentee's Exhibit 11, Appeal No. 2016-800138, Trial for Invalidation of Japanese Patent No. 5824095, related case.

English Translation of Appeal Decision dated Nov. 22, 2017, Appeal No. 2016-800138, Trial for Invalidation of Japanese Patent No. 5824095, related case.

English Translation of Japanese Patent Application No. JP2008-104147 filed Apr. 11, 2008, Appellant's Exhibit 7, Appeal No. 2016-800138, Trial for Invalidation of Japanese Patent No. 5824095, related case.

English Translation of Japanese Patent Application No. JP2008-247713 filed Sep. 26, 2008, Appellant's Exhibit 8, Appeal No. 2016-800138, Trial for Invalidation of Japanese Patent No. 5824095, related case.

English Translation of Japanese Patent Application No. JP2009-068744 filed Mar. 19, 2009, Appellant's Exhibit 9, Appeal No. 2016-800138, Trial for Invalidation of Japanese Patent No. 5824095, related case.

English Translation, "Human Heavy Chain Variable Domains," Patentee's Reference 2, Appeal No. 2016-800138, Trial for Invalidation of Japanese Patent No. 5824095, related case.

English Translation, Steipe Lab Molecular Systems Engineering, dated Nov. 20, 2017, Patentee's Reference 2-A, Appeal No. 2016-800138, Trial for Invalidation of Japanese Patent No. 5824095, related case.

English Translation, Steipe Lab Molecular Systems Engineering—Research, dated Jul. 20, 2017, Patentee's Reference 2-B, Appeal No. 2016-800138, Trial for Invalidation of Japanese Patent No. 5824095, related case.

English Translation, Steipe Lab Molecular Systems Engineering—Canonical Sequence Approximation, dated Jul. 20, 2017, Patentee's Reference 2-C, Appeal No. 2016-800138, Trial for Invalidation of Japanese Patent No. 5824095, related case.

English Translation, Steipe Lab Molecular Systems Engineering—Canonical Sequence Approximation, dated Jul. 20, 2017, Patentee's Reference 2-D, Appeal No. 2016-800138, Trial for Invalidation of Japanese Patent No. 5824095, related case.

English Translation, Steipe Lab Molecular Systems Engineering—Canonical Sequence Approximation, dated Jul. 20, 2017, Patentee's Reference 2-E, Appeal No. 2016-800138, Trial for Invalidation of Japanese Patent No. 5824095, related case.

English Translation, Steipe Lab Molecular Systems Engineering—Canonical Sequence Approximation, dated Jul. 20, 2017, Patentee's Reference 2-F, Appeal No. 2016-800138, Trial for Invalidation of Japanese Patent No. 5824095, related case.

English Translation, Steipe Lab Molecular Systems Engineering—Canonical Sequence Approximation, dated Jul. 20, 2017, Patentee's Reference 2-G, Appeal No. 2016-800138, Trial for Invalidation of Japanese Patent No. 5824095, related case.

English Translation, Steipe Lab Molecular Systems Engineering—Canonical Sequence Approximation, dated Jul. 20, 2017, Patentee's Reference 2-H, Appeal No. 2016-800138, Trial for Invalidation of Japanese Patent No. 5824095, related case.

Kabat, E. A., et al., "Sequences of Proteins of Immunological Interest," vols. 1-3, $5^{th}$ ed., U.S. Dept. of Health & Human Services (1991), Patentee's Reference 3, Appeal No. 2016-800138, Trial for Invalidation of Japanese Patent No. 5824095, related case.

Alexion Initiates Simultaneous Registration Trails of ALXN1210 for Patients with Paroxysmal Nocturnal Hemoglobinuria (PNH) and Atypical Hemolytic Uremic Syndrome (aHUS), Alexon Pharmaceuticals, Inc., (2016).

Biacore Sensor Surface Handbook, BR-1005-71; GE Healthcare Bio-Science Aβ, 6-100 (2007).

Biasini, E., et al., "Immunopurification of Pathological Prion Protein Aggregates," vol. 4, Issue 11 (2009).

Chihara, N., et al., "Interleukin 6 signaling promotes anti-aquaporin 4 autoantibody production from plasmablasts in neuromyelitis optica," PNAS, vol. 108; No. 9; 3701-3706 (2011).

Committee for Medicinal Products for Human Use (CHMP): "Soliris eculizumab: EPAR—Scientific Discussion," European Medicines Agency, No. WC500054212, XP002780707, Jun. 22, 2016, pp. 1-41. Retrieved from Internet: URL:http://www.ema.europa.eu/docs/en_GB/document_library/EPAR_-_Scientific_Discussion/human/000791/WC500054212.pdf p. 8.

Feagan, B., et al., "Ustekinumab as Induction and Maintenance Therapy for Crohn's Disease." The New England Journal of Medicine 1943-1960 (2016).

Jaeger, L., "Clinical Immunology and Allergology," (1990).

Kawahata, N., "A Subcutaneously Administered Investigational RNAi Therapeutic (ALN-CC5) Targeting Complement C5 for Treatment of PNH and Complement-Mediated Diseases," Interim Phase 1 Study Results, Alnylam Pharmaceuticals, XP055471916 (May 22, 2016).

King, David J., "Applications and Engineering of Monoclonal Antibodies," Taylor & Francis e-Library:1-246 (2005).

Matsunaga et al., "A pH-dependent conformational transition of Aβ peptide and physicochemical properties of the conformers in the glial cell," Biochem. J., 361, 547-556 (2002).

Mellman, I, "The Importance of Being Acid: The Role of Acidification in Intracellular Membrane Traffic," J. Exp. Biol. 172, 39-45 (1992).

Office Action datd Aug. 19, 2016, in U.S. Appl. No. 13/990,158, Igawa, T., et al., filed Mar. 28, 2014.

OriGene Technologies, Inc. Data Sheet, "Polyclonal Antibody to Myostatin (79-92)—Serum," No. AP02123SU-N, (Mar. 19, 2013).

Popov, S., et al., "The Stoichiometry and Affinity of the Interaction of Murine Fc Fragments With the MHC Class I-Related Receptor, FcRn," Molecular Immunology, vol. 33, No. 6, 521-530 (1996).

Richter W., et al., "Subcutaneous Absorption of Biotherapeutics: Knowns and Unknowns," The American Society for Pharmacology and Experimental Therapeutics, 1881-1889 (2014).

Roitt et al. Immunology, Moscow: Mir, 2000;97-113.

Roitt et al. Immunology, M., Mir, 2000:373-4.

Soliris® (eculizumab) injection, for intravenous use, BLA:125166, Suppl-417, Label (2017).

Yarilin "Osnovy immunologii", M.: Meditsina, 1999:p. 172-4/ Fundamentals of Immunology. M: Medicina, 1999:p. 172-4.

Yarilin "Osnovy immunologii", M.: Meditsina, 1999:p. 175, 182/ Fundamentals of Immunology. M: Medicina, 1999:p. 175, 182.

Zheng, J., et al., "YB-1 immunization combined with regulatory T-cell depletion induces specific T-cell responses that protect against neuroblastoma in the early stage," Acta Biochim Biophys Sin 44: 1006-1014 (2012).

U.S. Appl. No. 16/264,735, filed Feb. 1, 2019, Chugai Seiyaku Kabushiki Kaisha, related application.

U.S. Appl. No. 16/323,142, 371(c) filed Feb. 4, 2019, Chugai Seiyaku Kabushiki Kaisha et al., related application.

Aboud-Pirak, E., et al., "Binding and Endocytosis of a Monoclonal Antibody to a High Molecular Weight Human Milk Fat Globule Membrane-associated Antigen by Cultured MCF-7 Breast Carcinoma Cells," Cancer Res 48:3188-3196 (1988).

Anchin, J. M., et al., "Recognition of Superpotent Sweetener Ligands by a Library of Monoclonal Antibodies," J Mol Recogn 10:235-242 (1997).

(56) References Cited

OTHER PUBLICATIONS

Shire, Experimental data characterizing the binding of rituximab to its antigen CD20 and to human FcRn, submitted Dec. 20, 2018 by the opponents in Opposition.
Cleland, J. L. and Langer, R., "Formulation and Delivery of Proteins and Peptides," American Chemical Society, 6 pages (1994).
Declaration of Madhusudan Natarajan, Ph.D., dated Dec. 19, 2018.
Janssen, D., Merck, E-mail document dated Nov. 6, 2018 establishing the Sigma Product Information Sheet, H-Y Medium was published in 1998.
Hughes-Jones, N.C., et al., "The Effect of pH and Ionic Strength on the Reaction between Anti-D and Erythrocytes," Immunology 7(1):72-81 (1964).
Jain, M., et al., "Engineering antibodies for clinical applications," TRENDS in Biotechnology 25(7):307-316 (2007).
King, D. J., "Applications and Engineering of Monoclonal Antibodies," Celltech Therapeutics, 27-75 (1998).
Kranz, D. M., et al., "Mechanisms of Ligand Binding by Monoclonal Anti-fluorescyl Antibodies," J Biol Chem, 257(12):6987-6995 (1982).
Original claims filed Apr. 10, 2009 in European Patent Application No. 13195713.6 (EP Publication No. 2708558, published Mar. 19, 2014).
Parent Application, European Patent Application No. 09729337.7 filed Apr. 10, 2009 (EP Publication No. 2275443, published Jan. 19, 2011).
Patel, T. V., et al., "A Forgotten Cause of Kidney Injury in Chronic Myelomonocytic Leukemia," Am J Kidney Dis 54(1):159-164 (2009).
Raso, V., et al., "Antibodies Capable of Releasing Diphtheria Toxin in Response to the Low pH Found in Endosomes," J Biol Chem 272(44):27618-27622 (1997).
Raso, V., "Intracellular Targeting Using Bispecific Antibodies," Methods in Molecular Medicine 25:37-50 (2000).
Genentech, Inc., Rituximab biologic license application approval dated Nov. 26, 1997 (License No. 1048), issued by Dept. of Health and Human Services.
IDEC Pharmaceuticals Corporation and Genentech, Inc., Rituximab product label information (G48097-R0 (544)), Nov. 1997.
Sigma, Product Information Sheet, H-Y Medium, Product No. H9014 (1998).
Wang, W., "Instability, stabilization, and formulation of liquid protein pharmaceuticals," Int'l J Pharmaceutics 185:129-188 (1999).
Rituximab definition, accessed via Wikipedia Oct. 24, 2018 (German), with English translation.
Third-Party Submission Under 37 C.F.R. 1.290 submitted Jan. 17, 2019.
Third-Party Submission Under 37 C.F.R. 1.290 submitted Apr. 3, 2019.
Adams et al., "Humanization of a recombinant monoclonal antibody to produce a therapeutic HER dimerization inhibitor, pertuzumab," Cancer Immunol. Immunother., 55:717-727 (2006).
Algonomics—Tripole® applications [online] Retrieved from the Internet on Feb. 29, 2012: http://web.archive.org/web20090221052902/http:/www.algonomics.com/proteinengineering/tripole_applications.php, 2 pages (Feb. 21, 2009).
Allen et al., "Novel mechanism for gonadotropin-releasing hormone neuronal migration involving Gas6/Ark signaling to p38 mitogen-activated protein kinase," Mol. Cell. Biol., 22(2):599-613 (2002).
Almagro et al., "Humanization of antibodies," Front Biosci., 13:1619-33 (2008).
Armour et al., "Recombinant human IgG molecules lacking Fcgamma receptor I binding and monocyte triggering activities," Eur. J. Immunol., 29(8):2613-24 (1999).
Bartelds et al., "Clinical response to adalimumab: relationship to anti-adalimumab antibodies and serum adalimumab concentrations in rheumatoid arthritis," Ann Rheum. Dis., 66:921-926 (2007).
Bellosta et al., "Signaling through the ARK tyrosine kinase receptor protects from apoptosis in the absence of growth stimulation," Oncogene., 15(20):2387-97 (1997).
Bender et al., "Immunogenicity, efficacy and adverse events of adalimumab in RA patients," Rheumatol. Int., 27:269-274 (2007).
Binz et al., "Engineering novel binding proteins from nonimmunoglobulin domains," Nat. Biotechnol., 23:1257-68 (2005).
Bilsborough, "IL-31 is associated with cutaneous lymphocyte antigen-positive skin homing T cells in patients with atopic dermatitis." J. Allergy Clin. Immunol., 117(2):418-25 (2006).
Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," J. Immunol., 157:3250-59 (1996).
Branden and Tooze, "Recognition of Foreign Molecules by the Immune System," Introduction to Protein Structure, 2d Ed., Garland Publishing, pp. 299-323 (1999).
Budagian et al., "A promiscuous liaison between IL-15 receptor and Axl receptor tyrosine kinase in cell death control,"EMBO J., 24(24):4260-70 (2005).
Calbiochem® Buffers, "A guide for the preparation and use of buffers in biological systems," by Chandra Mohan, Ph.D., Copyright© 2003 EMD Biosciences, Inc., an Affiliate of Merck KGaA, Darmstadt, Germany, 37 pages.
Carter. "Bispecific human IgG bv design," J. Immunol. Methods, 248:7-15 (2001).
Chamow et al., "A humanized, bispecific immunoadhesin-antibody that retargets CD3+ effectors to kill HIV-1-infected cells," J. Immunol., 153(9):4268-80 (1994).
Chau et al., "HuM291(Nuvion), a humanized Fc receptor-nonbinding antibody against CD3, anergizes peripheral blood T cells as partial agonist of the T cell receptor," Transplantation., 71(7):941-50 (2001).
Chen et al., "Generation and analysis of random point mutations in an antibody CDR2 sequence: many mutated antibodies lose their ability to bind antigen," J. Exp. Med., 176(3):855-66 (1992).
Chen et al., "Defective secretion of an immunoglobulin caused bv mutations in the heavy chain complementarity determining region 2," J. Exp. Med., 180(2):577-86 (1994).
Chirino et al., "Minimizing the immunogenicity of protein therapeutics," Drug Discov. Today., 9:82-90 (2004).
Chu et al., "Accumulation of succinimide in a recombinant monoclonal antibody in mildly acidic buffers under elevated temperatures," Pharm. Res., 24(6):1145-56 (2007).
Chung et al., "Expression of the proto-oncogene Axl in renal cell carcinoma," DNA Cell Biol., 22(8):533-40 (2003).
Cole et al., "Human IgG2 variants of chimeric anti-CD3 are nonmitogenic to T cells," J. Immunol., 159(7):3613-21 (1997).
Comper and Glasgow. "Charge selectivity in kidney ultrafiltration," Kidney Int., 47:1242-51 (1995).
Cordoba et al., "Non-enzvmatic hinge region fragmentation of antibodies in solution," J. Chromatogr. B. Analyt. Technol. Biomed. Life Sci., 818(2):115-21 (2005).
Couto et al., "Anti-BA46 Monoclonal Antibodv Mc3: Humanization Using a Novel Positional Consensus and in Vivo and in Vitro Characterization," Cancer Res., 55:1717-22 (1995).
Craven et al., "Receptor tyrosine kinases expressed in metastatic colon cancer," Int. J. Cancer, 60(6):791-7 (1995).
Dall'Acqua et al., "Antibody humanization by framework shuffling," Methods, 36(1):43-60 (2005).
Damschroder et al., "Framework shuffling of antibodies to reduce immunogenicity and manipulate functional and biophysical properties," Mol. Immunol., 44(11):3049-60 (2007).
Deen et al., "Structural determinants of glomerular permeability," Am. J. Physiol. Renal. Physiol., 281:F579-F596 (2001).
De Groot et al., "De-immunization of therapeutic proteins by T-cell epitope modification," Dev. Biol. (Basel), 122:171-94 (2005).
Del Rio et al., "An Engineered Penicillin Acylase with Altered Surface Charge is More Stable in Alkaline pH," Ann. NY Acad. Sci., 799:61-64 (1996).
Deng et al., "An Agonist Murine Monoclonal Antibody to the Human c-Mpl Receptor Stimulates Megakaryocytopoiesis," Blood, 92:1981-88 (1998).
Dillon et al., "Interleukin 31, a cytokine produced by activated T cells, induces dermatitis in mice," Nat. Immunol., 5(7):752-760 (2004).

(56) References Cited

OTHER PUBLICATIONS

Dillon et al., "Structural and functional characterization of disulfide isoforms of the human IgG2 subclass," *J. Biol. Chem.*, 283:16206-15 (2008).

Diveu et al., "GPL, a novel cytokine receptor related to GP130 and leukemia inhibitory factor receptor," *J. Biol. Chem.*, 278(50):49850-49859 (2003).

Ewert et al., "Stability improvement of antibodies for extracellular and intracellular applications: CDR grafting to stable frameworks and structure-based framework engineering," *Methods.* 34:184-199 (2004).

Fridell et al., "GAS6 induces Axl-mediated chemotaxis of vascular smooth muscle cells," *J. Biol. Chem.*, 273(12):7123-6 (1998).

Fujii, "Antibody affinity maturation by random mutagenesis," *Methods Mol. Biol.*, 248:345-59 (2004).

Gelderman et al., "The inhibitory effect of CD46, CD55, and CD59 on complement activation after immunotherapeutic treatment of cervical carcinoma cells with monoclonal antibodies or bispecific monoclonal antibodies," *Lab Invest.*, 82(4):483-93 (2002).

Gerstner et al., "Sequence plasticity in the antigen-binding site of a therapeutic anti-HER2 antibody," *J. Mol. Biol.*, 321(5):851-62 (2002).

Gessner et al., "The IgG Fc receptor family," *Ann. Hematol.*, 76:231-248 (1998).

Ghetie et al., "FcRn: the MHC class I-related receptor that is more than an IgG transporter," *Immunol. Today*, 18:592-598 (1997).

Ghetie et al., "Increasing the serum persistence of an IgG fragment by random mutagenesis," *Nat. Biotechnol.*, 15(7):637-40 (1997).

Ghetie et al., "Multiple roles for the major histocompatibility complex class I-related receptor FcRn," *Annu. Rev. Immunol.*, 18:739-766 (2000).

Gobburu et al., "Pharmacokinetics/dynamics of 5c8, a monoclonal antibody to CD154 (CD40 ligand) suppression of an immune response in monkeys," *J. Pharmacol. Exp. Ther.*, 286:925-930 (1998).

Goode et al., "The glomerular basement membrane charge-selectivity barrier: an oversimplified concept?" *Nephrol. Dial. Transplant.*, 11:1714-16 (1996).

Goruppi et al., "Requirement of phosphatidylinositol 3-kinase-dependent pathway and Src for Gas6-Axl mitogenic and survival activities in NIH 3T3 fibroblasts." *Mol. Cell Biol.*, 17(8):4442-53 (1997).

Graves et al., "Molecular modeling and preclinical evaluation of the humanized NR-LU-13 antibody," *Clin. Cancer Res.*, 5:899-908 (1999).

Gupta et al., "Affinity chromatography and co-chromatography of bispecific monoclonal antibody immunoconjugates," J. Biochem. Biophys. Methods, 51:203-216 (2002).

Guyre et al., "Increased potency of Fc-receptor-targeted antigens," *Cancer Immunol. Immunother.*, 45(3-4):146-8 (1997).

Hafizi et al., "Interaction of Axl receptor tyrosine kinase with C1-TEN, a novel C1 domain-containing protein with homology to tensin," *Biochem. Biophys. Res. Commun.*, 299(5):793-800 (2002).

Hafizi et al., "Signalling and functional diversity within the Axl subfamily of receptor tyrosine kinases," *Cytokine Growth Factor Rev.*, 17(4):295-304 (2006).

Hanes et al., "Picomolar affinity antibodies from a fully synthetic naive library selected and evolved by ribosome display," *Nat. Biotechnol.*, 18(12):1287-1292 (2000).

Hanson et al., "Catalytic antibodies and their applications," Curr. Opin. Biotechnol., 16:631-636 (2005).

He et al., "Humanization and pharmacokinetics of a monoclonal antibody with specificity for both E- and P-selectin," *J. Immunol.*, 160:1029-35 (1998).

Hinton et al., "An engineered human IgG1 antibody with longer serum half-life," *J. Immunol.*, 176(1):346-56 (2006).

Hinton et al., "Engineered human IgG antibodies with longer serum half-lives in primates," *J. Biol. Chem.*, 279(8):6213-6 (2004).

Holland et al., "Multiple roles for the receptor tyrosine kinase axl in tumor formation," *Cancer Res.*, 65(20):9294-303.

Hwang et al., "Use of human germline genes in a CDR homology-based approach to antibody humanization," Methods, 36:35-42 (2005).

Igawa et al., "Engineering the variable region of therapeutic IgG antibodies," *MAbs*, 3(3):243-52 (2011).

Igawa et al., "Reduced elimination of IgG antibodies by engineering the variable region," *Protein Eng. Des. Sel.*, 23(5):385-92 (2010).

Igawa et al., "Antibody recycling by engineered pH-dependent antigen binding improves the duration of antigen neutralization," *Nat. Biotechnol.*, 28(11):1203-7 (2010).

Ito et al., "The His-probe method: effects of histidine residues introduced into the complementarity-determining regions of antibodies on antigen-antibody interactions at different pH values," FEBS Lett., 309:85-88 (1992).

Ito et al., "Expression of receptor-type tyrosine kinase, Axl, and its ligand, Gas6, in pediatric thyroid carcinomas around Chernobyl," Thyroid., 12(11):971-5 (2002).

Johnson et al., "Cation exchange-HPLC and mass spectrometry reveal C-terminal amidation of an IgG1 heavy chain," *Anal. Biochem.*, 360:75-83 (2007).

Jones et al., "Identification and removal of a promiscuous CD4+ T cell epitope from the C1 domain of factor VIII," *Thromb. Haemost.*, 3:991-1000 (2005).

Kashmiri et al., "Generation, characterization, and in vivo studies of humanized anticarcinoma antibody CC49," *Hybridoma*, 14:461-473 (1995).

Katayose et al., "MUC1-specific targeting immunotherapy with bispecific antibodies: inhibition of xenografted human bile duct carcinoma growth," *Cancer Res.*, 56(18):4205-12 (1996).

Khawli et al., "Improved tumor localization and radioimaging with chemically modified monoclonal antibodies," *Cancer Biother. Radiopharm.*, 11:203-215 (1996).

Kim et al., "Antibody Engineering for the Development of Therapeutic Antibodies," Mol. Cells, 20:17-29(2005).

Kim et al., "Chemical modification to reduce renal uptake of disulfide-bonded variable region fragment of anti-tac monoclonal antibody labeled with 99$^m$Tc." Bioconjugate Chem., 10:447-453 (1999).

Kim et al., "Lowering of pI by acylation improves the renal uptake of 99mTc-labeled anti-Tac dsFv: effect of different acylating reagents," Nucl. Med. Biol., 29:795-801 (2002).

Kobayashi et al., "The pharmacokinetic characteristics of glycolated humanized anti-Tac Fabs are determined by their isoelectric points," Cancer Res., 59:422-430 (1999).

Komissarov et al., "Site-specific mutagenesis of a recombinant anti-single-stranded DNA Fab. Role of heavy chain complementarity-determining region 3 residues in antigen interaction," *J. Biol. Chem.*, 272(43):26864-70 (1997).

Kreutz et al., "Efficient bispecific monoclonal antibody purification using gradient thiophilic affinity chromatography," J. Chromalogr. B, 714:161-170 (1998).

Kurfis et al., "Role of Arg182 in the second extracellular loop of angiotensin II receptor AT2 in ligand binding," *Biochem. Biophys. Res. Commun.*, 263:816-819 (1999).

Leong et al., "Adapting pharmacokinetic properties of a humanized anti-interleukin-8 antibody for therapeutic applications using site-specific pegylation," *Cytokine*, 16(3):106-19 (2001).

Levin et al., "Optimizing the affinity and specificity of proteins with molecular display," *Mol. Biosyst.*, 2(1):49-57 (2006) (Epub Nov. 8, 2005).

Lindhofer et al., "Preferential Species-Restricted Heavy/Light Chain Pairing in Rat/Mouse Quadromas," J. Immunol., 155:219-225 (1995).

Liu et al., "Heterogeneity of monoclonal antibodies," *J. Pharm. Sci.*, 97(7):2426-47 (2008).

Lobo et al., "Antibody pharmacokinetics and pharmacodynamics," *J. Pharm. Sci.*, 93:2645-68 (2004).

Lund et al., "Expression and characterization of truncated forms of humanized L243 IgG1. Architectural features can influence synthesis of its oligosaccharide chains and affect superoxide production triggered through human Fcgamma receptor I," Eur. J. Biochem., 267:7246-57 (2000).

(56) References Cited

OTHER PUBLICATIONS

Maeda et al., "pH-dependent receptor/ligand dissociation as a determining factor for intracellular sorting of ligands for epidermal growth factor receptors in rat hepatocytes," *J. Control Release*, 82(1):71-82 (2002).
Maini et al., "Double-blind randomized controlled clinical trial of the interleukin-6 receptor antagonist, tocilizumab, in European patients with rheumatoid arthritis who had an incomplete response to methotrexate," Arthritis Rheum., 54:2817-29 (2006).
Manzke et al., "Single-step purification of bispecific monoclonal antibodies for immunotherapeutic use by hydrophobic interaction chromatography," J. Immunol. Methods, 208:65-73 (1997).
Martin et al., "Crystal structure at 2.8 A of an FcRn/heterodimeric Fc complex: mechanism of pH-dependent binding," Mol. Cell, 7:867-877 (2001).
Martinez et al., "Disulfide connectivity of human immunoglobulin G2 structural isoforms," *Biochemistry*, 47(28):7496-7508 (2008).
Marvin et al., "Recombinant approaches to IgG-like bispecific antibodies," Acta. Pharmacol. Sin., 26:649-658 (2005).
Marvin et al., "Redesigning an antibody fragment for faster association with its antigen," Biochemistry, 42:7077-83 (2003).
Maxfield et al., "Endocytic recycling," *Nat. Rev. Mol. Cell Biol.*, 5(2):121-32 (2004).
McCloskey et al., "GAS6 mediates adhesion of cells expressing the receptor tyrosine kinase Ax1," *J. Biol. Chem.*, 272(37):23285-91 (1997).
Merchant et al., "An efficient route to human bispecific IgG," Nat. Biotechnol., 16:677-681 (1998).
Meric et al., "Expression profile of tyrosine kinases in breast cancer," *Clin. Cancer Res.*, 8(2):361-7 (2002).
Murtaugh et al., "A combinatorial histidine scanning library approach to engineer highly pH-dependent protein switches," *Protein Sci.*, 20(9):1619-31 doi:10.1002/pro 696 (2011).
Nakano et al., "Vascular smooth muscle cell-derived, Gla-containing growth-potentiating factor for Ca(2+)-mobilizing growth factors," *J. Biol. Chem.*, 270(11):5702-5 (1995).
Nakano et al., "Prevention of growth arrest-induced cell death of vascular smooth muscle cells by a product of growth arrest-specific gene, gas6," *FEBS Lett.*, 387(1):78-80 (1996).
Neis et al., "Enhanced expression levels of IL-31 correlate with IL-4 and IL-13 in atopic and allergic contact dermatitis," *J. Allergy Clin. Immunol.*, 118(4):930-937 (2006).
Neubauer et al., "Expression of ax1, a transforming receptor tyrosine kinase, in normal and malignant hematopoiesis," *Blood*, 84(6):1931-41 (1994).
Nesterova et al., "Glypican-3 as a novel target for an antibody-drug conjugate," AACR Abstract No. 656, Los Angeles, CA (Apr. 4-18, 2007).
Nishimoto et al.. "Humanized anti-interleukin-6 receptor antibody treatment of multicentric Castleman disease," *Blood*, 106:2627-32 (2005).
Nishimoto et al., "Interleukin 6: from bench to bedside." *Nat. Clin. Pract. Rheumatol.*, 2:619-626 (2006).
O'Bryan et al., "ax1, a transforming gene isolated from primary human myeloid leukemia cells, encodes a novel receptor tyrosine kinase," *Mol. Cell Biol.*, 11(10):5016-31 (1991).
Ohsugi et al., Pharm. Stage, 7:13-18 (2007).
Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).
Ono et al., "The humanized anti-HM1.24 antibody effectively kills multiple myeloma cells by human effector cell-mediated cytotoxicity," *Mol. Immunol.*, 36(6):387-95 (1999).
Panka et al., "Variable region framework differences result in decreased or increased affinity of variant anti-digoxin antibodies," *Proc. Natl. Acad. Sci. U.S.A.*, 85(9):3080-4 (1988).
Pardridge et al., "Enhanced endocytosis in cultured human breast carcinoma cells and in vivo biodistribution in rats of a humanized monoclonal antibody after cationization of the protein," *J. Pharmacol. Exp. Ther.*, 286(1):548-54 (1998).
Pavlaki et al., "Matrix metalloproteinase inhibitors (MMPIs): the beginning of phase I or the termination of phase III clinical trials," *Cancer Metastasis Rev.*, 22(2-3):177-203 (2003).
Pavlinkova et al., "Charge-modified single chain antibody constructs of monoclonal antibody CC49: Generation, characterization, pharmacokinetics, and biodistribution analysis," Nucl. Med. Biol., 26:27-34 (1999).
Pavlou et al., "The therapeutic antibodies market to 2008," *Eur. J. Pharm. Biopharm.*, 59:389-396 (2005).
Poduslo et al., "Polyamine modification increases the permeability of proteins at the blood-nerve and blood-brain barriers," *J. Neurochem.*, 66:1599-1609 (1996).
Pons et al., "Energetic analysis of an antigen/antibody interface: alanine scanning mutagenesis and double mutant cycles on the HyHEL-10/lysozyme interaction," *Protein Sci.*, 8(5):958-68 (1999).
Presta, "Engineering of therapeutic antibodies to minimize immunogenicity and optimize function," *Adv. Drug Deliv. Rev.*, 58(5-6):640-56 (2006).
Queen et al., "A humanized antibody that binds to the interleukin 2 receptor," *Proc. Natl. Acad. Sci. U.S.A.*, 86(24):10029-10033 (1989).
R&D Systems (R&D Systems, Anti-human IL-31 RA Antibody, Catalog #AF2769, Oct. 2008), 1 page.
Raap et al., "Correlation of IL-31 serum levels with severity of atopic dermatitis," *J. Allergy Clin. Immunol.*, 122(2):421-423 (2008).
Raffen et al., "Reengineering immunoglobulin domain interactions by introduction of charged residues," *Protein Eng.*, 11:303-309 (1998).
Rajpal et al., A general method for greatly improving the affinity of antibodies by using combinatorial libraries, Proc. Natl. Acad. Sci. USA, 102:8466-71 (2005).
Rathanaswami et al., "Demonstration of an in vivo generated sub-picomolar affinity fully human monoclonal antibody to interleukin-8," Biochem. Biophys. Res. Commun., 334:1004-13 (2005).
Reddy et al., "Elimination of Fc receptor-dependent effector functions of a modified IgG4 monoclonal antibody to human CD4," *J. Immunol.*, 164(4): 1925-33 (2000).
Reichert et al., "Monoclonal antibody successes in the clinic," *Nat. Biotechnol.*, 23:1073-78 (2005).
Reichert et al., "Development Pends for monoclonal antibody cancer therapeutics," *Nat. Rev. Drug Discov.*, 6(5):349-56 (2007).
Rothe et al., "Ribosome display for improved biotherapeutic molecules," *Expert Opin. Biol. Ther.*, 6:177-187 (2006).
Sainaghi et al., "Gas6 induces proliferation in prostate carcinoma cell lines expressing the Ax1 receptor," *J. Cell. Physiol.*, 204(1):36-44 (2005).
Salfeld et al., "Isotype selection in antibody engineering," *Nat. Biotechnol.*, 25:1369-72 (2007).
Sal-Man et al., "Arginine mutations within a transmembrane domain of Tar, an *Escherichia coli* aspartate receptor, can drive homodimer dissociation and heterodimer association in vivo," Biochem. J., 385:29-36 (2005).
Sato et al., "Reshaping a human antibody to inhibit the interleukin 6-dependent tumor cell growth," *Cancer Res.*, 53:851-856 (1993).
Sawabu et al., "Growth arrest-specific gene 6 and Ax1 signaling enhances gastric cancer cell survival via Akt pathway," *Mol. Carcinog.*, 46(2):155-64 (2007).
Schaeffer et al., "The Rat Glomerular Filtration Barrier Does Not Show Negative Charge Selectivity," *Microcirculation*, 9:329-342 (2002).
Schmidt et al., *Human Physiology*, Moscow, 2:431-436 (1996), and English translation: Schmidt et al., "Hemostatis and Coagulation," *Human Physiology*, R.F. Schmidt, G. Thews (Eds.), Second, Completely Revised Edition, 418-423 [translated by Marguerite A. Biederman-Thorson], Springer-Verlag, 1989.
Schmidt et al., *Human Physiology*, Moscow, 3:764 (1996), and English translation: Schmidt et al., "Enzymes of the pancreatic juice," *Human Physiology*, R.F. Schmidt, G. Thews (Eds.), Second, Completely Revised Edition, 716 [translated by Marguerite A. Biederman-Thorson], Springer-Verlag, 1989.
Schmitz et al., "Phage display: a molecular tool for the generation of antibodies—a review," *Placenta.*, 21 Suppl A:S106-12 (2000).

(56) References Cited

OTHER PUBLICATIONS

Segal et al., "Bispecific antibodies in cancer therapy," Curr. Opin. Immunol., 11:558-562 (1999).
Shaul, "Exploring the charge space of protein-protein association: a proteomic study," Proteins, 60:341-352 (2005).
Shieh et al., "Expression of ax1 in lung adenocarcinoma and correlation with tumor progression," Neoplasia., 7(12):1058-64 (2005).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (2001) (Epub Nov. 28, 2000).
Shire et al., "Challenges in the development of high protein concentration formulations," J. Pharm. Sci., 93:1390-1402 (2004).
Sinha et al., "Electrostatics in protein binding and function," Curr. Protein Pept. Sci., 3(6):601-14 (2002).
Sonkoly et al., "IL-31: a new link between T cells and pruritus in atopic skin inflammation," J. Allergy Clin. Immunol., 117:411-417 (2006).
Strand et al., "Biologic therapies in rheumatology: lessons learned, future directions," Nat. Rev. Drug Discov., 6:75-92 (2007).
Stenhoff et al., "Vitamin K-dependent Gas6 activates ERK kinase and stimulates growth of cardiac fibroblasts," Biochem. Biophys. Res. Commun., 319(3):871-8 (2004).
Sun et al., "Coexpression of Gas6/Ax1 in human ovarian cancers," Oncology, 66(6):450-7 (2004).
Tan et al., "Engineering the isoelectric point of a renal cell carcinoma targeting antibody greatly enhances scFv solubility," Immunotechnology, 4(2):107-114 (1998).
Tarditi et al., "Selective high-performance liquid chromatographic purification of bispecific monoclonal antibodies," J. Chromatogr., 599:13-20 (1992).
Teeling et al., "The biological activity of human CD20 monoclonal antibodies is linked to unique epitopes on CD20," J. Immunol., 177(1):362-71 (2006).
Ten Kate et al., "Effect of isoelectric point on biodistribution and inflammation: imaging with indium-111-labelled IgG," Eur. J. Nucl. Med., 17:305-309 (1990).
Tsuchiya, Credit Suisse Seminar, "Therapeutic Antibody," at Fuji-Gotemba Laboratories, p. 21 (2006).
Tsurushita et al., "Design of humanized antibodies: From anti-Tac to Zenapax," Methods, 36:69-83 (2005).
Vaisitti et al., "Cationization of monoclonal antibodies: another step towards the "magic bullet"?," J. Biol. Regul. Homeost. Agents., 19(3-4):105-12 (2005).
Vajdos et al., "Comprehensive functional maps of the antigen-binding site of an anti-ErbB2 antibody obtained with shotgun scanning mutagenesis," J. Mol. Biol., 320(2):415-28 (2002).
Vajkoczy et al., "Dominant-negative inhibition of the Ax1 receptor tyrosine kinase suppresses brain tumor cell growth and invasion and prolongs survival," Proc. Natl. Acad. Sci. U.S.A., 103(15):5799-804 (2006).
Van Walle et al., Immunogenicity screening in protein drug development, Expert Opin. Biol. Ther., 7:405-418 (2007).
Varnum et al., "Ax1 receptor tyrosine kinase stimulated by the vitamin K-dependent protein encoded by growth-arrest-specific gene 6," Nature, 373(6515):623-6 (1995).
Wang et al., "Polyethylene Glycol-modified Chimeric Toxin Composed of Transforming Growth Factor alpha Pseudomonas Exotoxin," Cancer. Res., 53:4588-4594 (1993).
Wiens et al., "Somatic mutation in VH complementarity-determining region 2 and framework region 2: differential effects on antigen binding and Ig secretion," J. Immunol., 159(3):1293-302 (1997).
Wiens et al., "Mutation of a single conserved residue in VH complementarity-determining region 2 results in a severe Ig secretion defect," J. Immunol., 167(4):2179-86 (2001).
Wu et al., "Development of motavizumab, an ultra-potent antibody for the prevention of respiratory syncytial virus infection in the upper and lower respiratory tract," J. Mol. Biol., 368:652-665 (2007).
Wypych et al., "Human IgG2 antibodies display disulfide-mediated structural isoforms," J. Biol. Chem., 283(23):16194-16205 (2008).
Xiang et al., "Study of B72.3 combining sites by molecular modeling and site-directed mutagenesis," Protein Eng., 13(5):339-44 (2000).
Yagi et al., "Interleukin-31 stimulates production of inflammatory mediators from human colonic subepithelial myofibroblasts," Int. J. Mol. Med., 19(6):941-946 (2007).
Yamagata et al., "Synaptic adhesion molecules," Curr. Opin. Cell Biol., 15(5):621-32 (2003).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., 301:467-477 (2002).
Yang et al., "Tailoring structure-function and pharmacokinetic properties of single-chain Fv proteins by site-specific PEGylation," Protein Eng., 16:761-770 (2003).
Zuckier et al., "Chimeric human-mouse IgG antibodies with shuffled constant region exons demonstrate that multiple domains contribute to in vivo half-life," Cancer Res., 58:3905-08 (1998).
Zwick et al., "The long third complementarity-determining region of the heavy chain is important in the activity of the broadly neutralizing anti-human immunodeficiency virus type 1 antibody 2F5," J. Virol., 78(6):3155-61 (2004).
International Search Report for App. Ser. No. PCT/JP2008/067534, dated Oct. 21, 2008, 4 pages.
International Preliminary Report on Patentability for App. Ser. No. PCT/JP2008/067534, dated Apr. 7, 2010, 7 pages.
International Search Report for App. Ser. No. PCT/JP2009/066590, dated Oct. 20, 2009, 2 pages.
International Preliminary Report on Patentability for App. Ser. No. PCT/JP2008/067499, dated Apr. 7, 2010, 6 pages.
USPTO Restriction Requirement in U.S. Appl. No. 12/680,112, dated Oct. 7, 2011, 6 pages.
Fish & Richardson P.C., Amendment and Response to Species Election Requirement dated Oct. 7, 2011 in U.S. Appl. No. 12/680,112, filed Dec. 6, 2011, 15 pages.
USPTO Non Final Office Action in U.S. Appl. No. 12/680,112, dated Feb. 29, 2012, 8 pages.
USPTO Restriction Requirement in U.S. Appl. No. 12/295,039, dated Oct. 12, 2010, 9 pages.
Fish & Richardson P.C., Response to Restriction Requirement dated Oct. 12, 2010 in U.S. Appl. No. 12/295,039, filed Apr. 11, 2011, 9 pages.
USPTO Non-Final Office Action in U.S. Appl. No. 12/295,039, dated Jun. 28, 2011, 9 pages.
Fish & Richardson P.C., Amendment in Reply to Action dated Jun. 28, 2011 in U.S. Appl. No. 12/295,039, filed Dec. 27, 2011, 14 pages.
USPTO Final Office Action in U.S. Appl. No. 12/295,039, dated Apr. 12, 2012, 8 pages.
International Preliminary Report on Patentability for App. Ser. No. PCT/JP2007/057036, dated Oct. 21, 2008, 6 pages.
International Search Report for App. Ser. No. PCT/JP2007/057036, dated May 1, 2007, 2 pages.
European Search Report for App. Ser. No. 07 74 0494, dated Sep. 3, 2009, 3 pages.
USPTO Restriction Requirement in U.S. Appl. No. 12/936,587, dated Dec. 6, 2011, 7 pages.
Fish & Richardson P.C., Third Preliminary Amendment and Response to Restriction Requirement dated Dec. 6, 2011 in U.S. Appl. No. 12/936,587, filed Jun. 5, 2012, 7 pages.
USPTO Restriction Requirement in U.S. Appl. No. 12/936,587, dated Jun. 25, 2012, 5 pages.
Fish & Richardson P.C., Response to Species Election Requirement dated Jun. 25, 2012 in U.S. Appl. No. 12/936,587, filed Jul. 25, 2012, 1 page.

(56) References Cited

OTHER PUBLICATIONS

International Search Report for App. Ser. No. PCT/JP2009/057309, dated Jul. 7, 2009, 8 pages.
International Preliminary Report on Patentability for App. Ser. No. PCT/JP2009/057309, dated Nov. 30, 2010, 7 pages.
European Search Report for App. Ser. No. EP 09 72 9337, dated Nov. 3, 2011, 3 pages.
International Preliminary Report on Patentability for App. Ser. No. PCT/JP2007/057058, dated Oct. 21, 2008, 11 pages.
International Search Report App. Ser. No. PCT/JP2007/057058, dated May 7, 2001, 2 pages.
European Search Report for App. Ser. No. 07 74 0474, dated Mar. 16, 2009, 5 pages.
Fish & Richardson P.C., Amendment and Response to Restriction Requirement dated Nov. 18, 2009 in U.S. Appl. No. 10/575,905, filed Apr. 16, 2010, 12 pages.
Fish & Richardson P.C., Amendment in Reply to Action dated Jun. 23, 2010 in U.S. Appl. No. 10/575,905, filed Dec. 22, 2010, 10 pages.
USPTO Final Office Action in U.S. Appl. No. 10/575,905, dated Feb. 24, 2011, 7 pages.
Fish & Richardson P.C., Amendment in Reply to Action dated Jun. 23, 2010 in U.S. Appl. No. 10/575,193, filed Dec. 22, 2010, 13 pages.
USPTO Notice of Allowance in U.S. Appl. No. 10/575,193, dated Mar. 18, 2011, 11 pages.
Fish & Richardson P.C., Amendment in U.S. Appl. No. 10/575,193, filed Jun. 17, 2011, 15 pages.
USPTO Notice of Allowance in U.S. Appl. No. 10/575,193, dated Jul. 13, 2011, 8 pages.
USPTO Restriction Requirement in U.S. Appl. No. 12/295,075, dated Feb. 22, 2011, 9 pages.
Fish & Richardson P.C., Response to Restriction Requirement dated Feb. 22, 2011 in U.S. Appl. No. 12/295,075, filed Aug. 18, 2011, 2 pages.
USPTO Non-Final Office Action in U.S. Appl. No. 12/295,075, dated Nov. 4, 2011, 14 pages.
Fish & Richardson P.C., Amendment in Reply to Action dated Nov. 4, 2011 in U.S. Appl. No. 12/295,075, filed May 3, 2012, 12 pages.
USPTO Final Office Action in U.S. Appl. No. 12/295,075, dated Jul. 19, 2012, 12 pages.
USPTO Restriction Requirement in U.S. Appl. No. 11/910,836, dated Mar. 18, 2011, 7 pages.
Fish & Richardson P.C., Response to Restriction Requirement dated Mar. 18, 2011 in U.S. Appl. No. 11/910,836, filed Sep. 6, 2011, 1 page.
USPTO Non-Final Office Action in U.S. Appl. No. 11/910,836, dated Sep. 30, 2011, 21 pages.
USPTO Restriction Requirement in U.S. Appl. No. 11/910,128, dated Jun. 9, 2011, 10 pages.
USPTO Non-Final Office Action in U.S. Appl. No. 11/910,128, dated Apr. 25, 2012, 21 pages.
Fish & Richardson P.C., Response to Restriction Requirement dated Jun. 9, 2011 in U.S. Appl. No. 11/910,128, filed Dec. 2, 2011, 1 page.
International Preliminary Report on Patentability for App. Ser. No. PCT/JP2009/066590, dated May 10, 2011, 6 pages.
International Preliminary Report on Patentability for App. Ser. No. PCT/JP2009/070376, dated Jul. 5, 2011, 11 pages.
USPTO Non-Final Office Action U.S. Appl. No. 12/680,087, dated Oct. 27, 2011, 6 pages.
Fish & Richardson P.C., Amendment and Reply to Action dated Oct. 27, 2011 in U.S. Appl. No. 12/680,087, filed Jan. 26, 2012, 6 pages.
USPTO Notice of Allowance in U.S. Appl. No. 12/680,087, dated Feb. 24, 2012, 5 pages.
USPTO Notice of Allowance in U.S. Appl. No. 12/680,087, dated Jun. 25, 2012, 11 pages.
International Preliminary Report on Patentability for App. Ser. No. PCT/JP2010/058166, dated Dec. 16, 2011, 15 pages.
USPTO Restriction Requirement in U.S. Appl. No. 12/680,082, dated Jun. 6, 2012, 12 pages.
Fish & Richardson P.C., Fourth Preliminary Amendment and Response to Restriction Requirement dated Jun. 6, 2012 in U.S. Appl. No. 12/680,082, filed Jun. 29, 2012, 13 pages.
International Search Report for App. Ser. No. PCT/JP2010/066490, dated Nov. 9, 2010, 5 pages.
International Preliminary Report on Patentability for App. Ser. No. PCT/JP2010/066490, dated Apr. 11, 2012, 6 pages.
USPTO Restriction Requirement in U.S. Appl. No. 13/434,643, dated Jul. 27, 2012, 6 pages.
USPTO Restriction Requirement in U.S. Appl. No. 12/745,781, dated Jul. 30, 2012, 9 pages.
Chien et al., "Significant structural and functional change of an antigen-binding site by a distant amino acid substitution: proposal of a structural mechanism," *Proc. Natl. Acad. Sci. U.S.A.*, 86(14):5532-6 (1989).
Davies et al., "Affinity improvement of single antibody VH domains: residues in all three hypervariable regions affect antigen binding," *Immunotechnology*, 2(3):169-79 (1996).
De Pascalis et al., "Grafting of "abbreviated" complementarity-determining regions containing specificity-determining residues essential for ligand contact to engineer a less immunogenic humanized monoclonal antibody," *J. Immunol.*, 169(6):3076-84 (2002).
Holt et al., "Domain antibodies: proteins for therapy," *Trends Bioteclmol.*, 21(11):484-90 (2003).
Maynard et al., "Antibody engineering," *Annu. Rev. Biomed. Eng.*, 2:339-76 (2000).
Pini et al., "Design and use of a phage display library. Human antibodies with subnanomolar affinity against a marker of angiogenesis eluted from a two-dimensional gel," *J. Biol. Chem.*, 273(34):21769-76 (1998).
Rudikoff et al., "Single amino acid substitution altering antigen-binding specificity," *Proc. Natl. Acad. Sci. U.S.A.*, 79(6):1979-83 (1982).
Wu et al.., "Humanization of a murine monoclonal antibody by simultaneous optimization of framework and CDR residues," *J. Mol. Biol.*, 294(1):151-62 (1999).
Fish & Richardson P.C., Amendment in Reply to Action dated Apr. 12, 2012 in U.S. Appl. No. 12/295,039, filed Sep. 11, 2012, 12 pages.
USPTO Restriction Requirement in U.S. Appl. No. 12/680,082, dated Sep. 14, 2012, 6 pages.
USPTO Restriction Requirement in U.S. Appl. No. 12/745,781, dated Sep. 4, 2012, 10 pages.
Fish & Richardson P.C., Amendment in Reply to Action of Feb. 29, 2012 in U.S. Appl. No. 12/680,112, filed Aug. 27, 2012, 12 pages.
Burges et al., "Effective relief of malignant ascites in patients with advanced ovarian cancer by a trifunctional anti-EpCAM x anti-CD3 antibody: a phase I/II study," *Clin. Cancer Res.*, 13(13):3899-905 (2007).
Dall'Acqua et al., "Modulation of the effector functions of a human IgG1 through engineering of its hinge region," *J. Immunol.*, 177(2);1129-38 (2006).
Elliott et al., "Activation of the erythropoietin (EPO) receptor by bivalent anti-EPO receptor antibodies," *J. Biol. Chem.*, 271(40):24691-7 (1996).
Kai et al., "Switching constant domains enhances agonist activities of antibodies to a thrombopoietin receptor," *Nat. Biotechnol.*, 26(2):209-11 (2008).
Kim et al., "Mapping the site on human IgG for binding of the MHC class I-related receptor, FcRn," *Eur. J. Immunol.*, 29(9):2819-25 (1999).
Kobayashi et al., "A monoclonal antibody specific for a distinct region of hen egg-white lysozyme," *Mol. Immunol.*, 19:619-30 (1982).
Morell et al., "Metabolic properties of IgG subclasses in man," *J. Clin. Invest.*, 49(4):673-80 (1970).
Ruf et al., "Pharmacokinetics and in vivo stability of intraperitoneally administered therapeutic antibody catummaxomab," *J. Clin. Oncol.*, 26 (May 20 suppl) (2008), abstr 14006.
USPTO Restriction Requirement in U.S. Appl. No. 12/679,922, dated Oct. 2, 2012, 9 pages.

(56) References Cited

OTHER PUBLICATIONS

Fish & Richardson P.C., Response to Restriction Requirement dated Sep. 4, 2012 in U.S. Appl. No. 12/745,781, filed Sep. 21, 2012, 176 pages.
USPTO Restriction Requirement in U.S. Appl. No. 12/680,112, dated Sep. 19, 2012, 6 pages.
Ruf et al., "Pharmacokinetics and in vivo stability of intraperitoneally administered therapeutic antibody catumaxomab," *J. Clin, Oncol.*, 26 (May 20 suppl) (2008), abstr 14006.
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell. Biol.*, 111:2129-2138 (1990).
Lazar et al., "Transforming growth factor alpha: mutation of aspartic acid 47 and leucine 48 results in different biological activities," *Mol. Cell. Biol.*, 8:1247-1252 (1988).
Ohno et al., "Antigen-binding specificities of antibodies are primarily determined by seven residues of VH," *Proc. Natl. Acad. Sci. U.S.A.*, 82(9):2945-9 (1985).
Ozhegov et al., Tolkovyi Slovar Russkogo iazyka: 2004, p. 292 (with an English translation of the corresponding part only).
Padlan et al., "Identification of specificity-determining residues in antibodies," *FASEB J.*, 9:133-139(1995).
R&D Systems (R&D Systems, Biotinylated Anti-human IL-31 RA Antibody, Catalog #BAF2769, Nov. 2005), 1 page.
USPTO Non-Final Office Action in U.S. Appl. No. 12/745,781, dated Oct. 18, 2012, 21 pages.
Fish & Richardson P.C., Amendment and Reply to Restriction Requirement dated Sep. 19, 2012 in U.S. Appl. No. 12/680,112, filed Oct. 17, 2012, 13 pages.
Fish & Richardson P.C., Response to Restriction Requirement dated Oct. 2, 2012 in U.S. Appl. No. 12/679,922, filed Nov. 1, 2012, 2 pages.
USPTO Non-Final Office Action in U.S. Appl. No. 12/936,587, dated Nov. 7, 2012, 13 pages.
Fish & Richardson P.C., Amendment in Reply to Office Action dated Apr. 25, 2012 in U.S. Appl. No. 11/910,128, filed Oct. 25, 2012, 32 pages.
Fish & Richardson P.C., Amendment and Response to Election Requirement dated Sep. 14, 2012 in U.S. Appl. No. 12/680,082, filed Nov. 8, 2012, 14 pages.
International Preliminary Report on Patentability for App. No. PCT/JP2010/073361, dated Aug. 14, 2012, 7 pages.
U.S. Appl. No. 13/582,073, filed Aug. 31, 2012, Kuramochi et al.
U.S. Appl. No. 13/637,415, filed Sep. 26, 2012, Igawa et al.
Amersham Biosciences, "Affinity Chromatography: Principles and Methods," Edition AD, pp. 16-18, 137(2002).
Brown et al., "Tolerance of single, but not multiple, amino acid replacements in antibody $V_H$ CDR2: a means of minimizing B cell wastage from somatic hypermutation?," *J. Immunol.*, 156(9):3285-91 (1996).
Dall'Acqua et al., "Increasing the affinity of a human IgG1 for the neonatal Fc receptor: biological consequences," *J. Immunol.*, 169(9):5171-80 (2002).
Jefferis et al., "Recognition sites on human IgG for Fc gamma receptors: the role of glycosylation," *Immunol. Lett.*, 44(2-3):111-7 (1995).
Lay et al., "Sulfasalazine suppresses drug resistance and invasiveness of lung adenocarcinoma cells expressing AXL," *Cancer Res.*, 67(8):3878-87 (2007).
MacCallum et al., "Antibody-antigen interactions: contact analysis and binding site topography," *J. Mol. Biol.*, 262:732-45 (1996).
Sarmay et al., "Mapping and comparison of the interaction sites on the Fc region of IgG responsible for triggering antibody dependent cellular cytotoxicity (ADCC) through different types of human Fc gamma receptor," *Mol. Immunol.*, 29(5):633-9 (1992).
Yeung et al., "Engineering human IgG1 affinity to human neonatal Fc receptor: impact of affinity improvement on pharmacokinetics in primates," *J. Immunol.*, 182(12):7663-71 (2009).
Zhu et al., "MHC class I-related neonatal Fc receptor for IgG is functionally expressed in monocytes, intestinal macrophages, and dendritic cells," *J. Immunol.*, 166(5):3266-76 (2001).
USPTO Non-Final Office Action in U.S. Appl. No. 12/679,922, dated Jan. 3, 2013, 25 pages.
Fish & Richardson P.C., Supplemental Amendment in U.S. Appl. No. 11/910,128, filed Nov. 14, 2012, 20 pages.
USPTO Notice of Allowance in U.S. Appl. No. 12/680,087, dated Nov. 26, 2012, 7 pages.
International Search Report for App. Ser. No. PCT/JP2011/055101, dated May 10, 2011, 4 pages.
International Preliminary Report on Patentability for App. Ser. No. PCT/JP2011/055101, dated Oct. 2, 2012, 6 pages.
USPTO Restriction Requirement in U.S. Appl. No. 13/497,269, dated Dec. 6, 2012, 9 pages.
USPTO Restriction Requirement in U.S. Appl. No. 12/809,138, dated Dec. 13, 2012, 8 pages.
USPTO Restriction Requirement in U.S. Appl. No. 13/320,317, dated Dec. 18, 2012, 13 pages.
International Search Report for App. Ser. No. PCT/JP2011/001888, dated Nov. 2, 2011, 7 pages.
Fish & Richardson P.C., Amendment in Replv to Action dated Jul. 19, 2012 in U.S. Appl. No. 12/295,075, filed Jan. 17, 2013, 113 pages.
Fish & Richardson P.C., Response to Restriction Requirement dated Dec. 18, 2012 in U.S. Appl. No. 13/320,317, filed Jan. 18, 2013, 3 pages.
Fish & Richardson P.C., Response to Restriction Requirement dated Jul. 27, 2012 and Preliminary Amendment in U.S. Appl. No. 13/434,643, filed Jan. 24, 2013, 10 pages.
Abe et al., "Purification of monoclonal antibodies with light-chain heterogeneity produced by mouse hybridomas raised with NS-1 myelomas: application of hydrophobic interaction high-performance liquid chromatography," *J. Biochem. Biophys. Methods*, 27:215-227 (1993).
Amersham Biosciences, "Protein Purification Handbook," Edition AC, 98 pages (2001).
Hamilton, "Molecular engineering: applications to the clinical laboratory," *Clin. Chem.*, 39(9):1988-97 (1993).
Kranenborg et al., "Development and characterization of anti-renal cell carcinoma x antichelate bispecific monoclonal antibodies for two-phase targeting of renal cell carcinoma," *Cancer Res.*, 55:5864s-5867s(1995).
Krauss et al., "Impact of antibody framework residue VH-71 on the stability of a humanised anti-MUC1 scFv and derived immunoenzyme," *Br. J. Cancer*, 90:1863-70 (2004).
Lansdorp et al., "Purification and analysis of bispecific tetrameric antibody complexes," *Mol. Immunol.*, 27:659-666 (1990).
Marks et al., "By-passing immunization: building high affinity human antibodies by chain shuffling," *Biotechnology (N.Y.)*, 10(7):779-83 (1992).
Mihara et al., "Tocilizumab inhibits signal transduction mediated by both mIL-6R and sIL-6R, but not by the receptors of other members of IL-6 cytokine family," *Int. Immunopharmacol.*, 5(12):1731-40 (2005).
Morimoto et al., "Single-step purification of F(ab')2 fragments of mouse monoclonal antibodies (immunoglobulins G1) by hydrophobic interaction high performance liquid chromatography using TSKgel Phenyl-5PW," *J. Biochem. Biophys. Methods*, 24:107-117 (1992).
Presta et al., "Molecular engineering and design of therapeutic antibodies," *Curr. Opin. Immunol.*, 20(4):460-70, doi: 10.1016/j.coi.2008.06.012 (2008).
Roitt et al., *Immunology, M., Mir*, (2000), pp. 110, 150, and 537-9 (in Russian, with what is believed to be a published English equivalent of those pages).
Singer et al., Genes & Genomes 1:63 (1998) (in Russian, with English translation).
Suresh et al., "Bispecific monoclonal antibodies from hybrid hybridomas," Methods Enzymol., 121:210-228(1986).
Suzuki et al., "Importance of neonatal FcR in regulating the serum half-life of therapeutic proteins containing the Fc domain of human

(56) References Cited

OTHER PUBLICATIONS

IgG1: a comparative study of the affinity of monoclonal antibodies and Fc-fusion proteins to human neonatal FcR," *J. Immunol.*, 184(4):1968-76 (2010).
Warnaar et al., "Purification of bispecific F(ab')2 from murine trinoma OC/TR with specificity for CD3 and ovarian cancer," *Hybridoma*, 13:519-526 (1994).
Yang et al., "CDR walking mutagenesis for the affinity maturation of a potent human anti-HIV-1 antibody into the picomolar range," *J. Mol. Biol.*, 254(3):392-403 (1995).
Zalevsky et al., "Enhanced antibody half-life improves in vivo activity," *Nat. Biotechnol.*, 28(2):157-9 (2010).
USPTO Non-Final Office Action in U.S. Appl. No. 13/434,643, dated Feb. 12, 2013, 17 pages.
USPTO Non Final Office Action in U.S. Appl. No. 12/680,112, dated Feb. 4, 2013, 9 pages.
USPTO Non-Final Office Action U.S. Appl. No. 12/680,082, dated Feb. 14, 2013, 12 pages.
USPTO Restriction Requirement in U.S. Appl. No. 13/257,145, dated Mar. 20, 2013, 11 pages.
USPTO Restriction Requirement in U.S. Appl. No. 13/524.528, dated Mar. 21, 2013, 7 pages.
USPTO Notice of Allowance in U.S. Appl. No. 12/680,087, dated Apr. 15, 2013, 9 pages.
Rich et al., "Grading the commercial optical biosensor literature—Class of 2008: 'The Mighty Binders'," *J. Mol. Recognit.*, 23(1):1-64 (2010). doi: 10.1002/jmr.1004.
U.S. Appl. No. 13/990,158, filed May 29, 2013, Igawa et al.
Igawa et al., "Antibody optimization technologies for developing next generation antibody therapeutics," *Bio Industry*, 28(7):15-21 (2011) (with English translation).
Ishii et al., "FcRn, a critical regulator of antibody pharmacokinetics," *Folia Pharmacol. Jpn.*, 136(5):280-284 (2010) (with English translation).
Sigma-Aldrich, "Product Information: Monoclonal Anti-Flag ® M1, Clone M1 produced in mouse, purified immunoglobulin," Sigma-Aldrich.com, Catalog No. F3040. Retrieved from the Internet on Nov. 5, 2003 at: http://www.sigmaaldrich.com/content/dam/sigma-aldrich/does/Sigma/Datasheet/f3040dat.pdf.
Wojciak et al., "The crystal structure of sphingosine-1-phosphate in complex with a Fab fragment reveals metal bridging of an antibody and its antigen," *Proc Natl Acad Sci U S A.*, 106(42):17717-22 (2009).
Zhou et al., "Interfacial metal and antibody recognition," *Proc Natl Acad Sci U S A.*, 102(41):14575-80 (2005).
International Search Report for App. Ser. No. PCT/JP2011/077619, dated Feb. 28, 2012, 4 pages.
International Preliminary Report on Patentability for App. Ser. No. PCT/JP2012/058603, dated Oct. 8, 2013, 11 pages.
Padlan et al., "Structure of an antibody-antigen complex: crystal structure of the HyHEL-10 Fab-lysozyme complex," *Proc. Natl. Acad. Sci. USA*, 86:5938-5942 (1989).
International Preliminary Report on Patentability for App. Ser. No. PCT/JP2011/077619, dated Jun. 4, 2013, 8 pages.
Fish & Richardson P.C., Reply to Restriction Requirement dated Mar. 21, 2013 in U.S. Appl. No. 13/524,528, filed Sep. 13, 2013, 1 page.
USPTO Non-Final Office Action in U.S. Appl. No. 13/524,528, dated Sep. 30, 2013, 9 pages.
U.S. Appl. No. 14/007,947, filed Dec. 30, 2013, Igawa et al.
Beck et al., "Strategies and challenges for the next generation of therapeutic antibodies," *Nat Rev Immunol.*, 10(5):345-52 (2010).
Chaparro-Riggers et al., "Increasing serum half-life and extending cholesterol lowering in vivo by engineering antibody with pH-sensitive binding to PCSK9," *J Biol Chem.*, 287(14):11090-7 (2012).
Devanaboyina et al., "The effect of pH dependence of antibody-antigen interactions on subcellular trafficking dynamics," *MAbs*, 5(6):851-9 (2013).

Feinberg et al., "Mechanism of pH-dependent N-acetylgalactosamine binding by a functional mimic of the hepatocyte asialoglycoprotein receptor," *J Biol Chem.*, 275(45):35176-84 (2000).
Finkelman et al., "Anti-cytokine antibodies as carrier proteins. Prolongation of in vivo effects of exogenous cytokines by injection of cytokine-anti-cytokine antibody complexes," *J Immunol.*, 151(3):1235-44(1993).
Igawa et al., "Engineered monoclonal antibody with novel antigen-sweeping activity in vivo," *PLoS One*, 8(5):e63236 (2013).
Tabrizi et al., "Elimination mechanisms of therapeutic monoclonal antibodies," *Drug Discov Today*, 11(1-2):81-8 (2006).
Vaughn et al., "Structural basis of pH-dependent antibody binding by the neonatal Fc receptor," *Structure*, 6(1):63-73 (1998).
Yamamoto et al., "Molecular studies of pH-dependent ligand interactions with the low-density lipoprotein receptor," *Biochemistry*, 47(44):11647-52 (2008).
Lee et al., "High-affinity human antibodies from phage-displayed synthetic Fab libraries with a single framework scaffold," *J Mol Biol.*, 340(5):1073-93 (2004).
Sarkar et al., "Rational cytokine design for increased lifetime and enhanced potency using pH-activated histidine switching," *Nat Biotechnol.*, 20(9):908-13 (2002).
Amigorena et al., "Cytoplasmic domain heterogeneity and functions of IgG Fc receptors in B lymphocytes," *Science*, 256(5065):1808-12 (1992).
Amigorena et al., "Fc gamma RII expression in resting and activated B lymphocytes," *Eur J Immunol.*, (8):1379-85 (1989).
Armour et al., "Differential binding to human FcgammaRIIa and FcgammaRIIb receptors by human IgG wildtype and mutant antibodies," *Mol Immunol.*, 40(9):585-93 (2003).
Blank et al., Decreased transcription of the human FCGR2B gene mediated by the −343 G/C promoter polymorphism and association with systemic lupus erythematosus. *Hum Genet.*, 117(2-3):220-7 (2005).
Boruchov et al., "Activating and inhibitory IgG Fc receptors on human DCs mediate opposing functions," *J Clin Invest.*, 115(10):2914-23 (2005).
Boumpas et al., "A short course of BG9588 (anti-CD40 ligand antibody) improves serologic activity and decreases hematuria in patients with proliferative lupus glomerulonephritis," *Arthritis Rheum.*, (2003).
Bruhns et al., Specificity and affinity of human Fcgamma receptors and their polymorphic variants for human IgG subclasses, *Blood*, 113(16):3716-25 (2009).
Cemerski et al., "Suppression of mast cell degranulation through a dual-targeting tandem IgE-IgG Fc domain biologic engineered to bind with high affinity to FcγRIIb," *Immunol Lett.*, 143(1):34-43 (2012).
Chen et al., "Association of a transmembrane polymorphism of Fcgamma receptor IIb (FCGR2B) with systemic lupus erythematosus in Taiwanese patients," *Arthritis Rheum.*, 54(12):3908-17 (2006).
Chu et al., "Inhibition of B cell receptor-mediated activation of primary human B cells by coengagement of CD19 and FcgammaRIIb with Fc-engineered antibodies," *Mol Immunol.*, 45(15):3926-33 (2008).
Chu et al., "Reduction of total IgE by targeted coengagement of IgE B-cell receptor and FcγRIIb with Fc-engineered antibody," *J Allergy Clin Immunol.*, 129(4):1102-15 (2012).
Chuntharapai et al., "Isotype-dependent inhibition of tumor growth in vivo by monoclonal antibodies to death receptor 4," *J Immunol.*, 166(8):4891-8 (2001).
Clark, "IgG effector mechanisms," *Chem Immunol.*, 65:88-110 (1997).
Dall'Acqua et al., "Properties of human IgG1s engineered for enhanced binding to the neonatal Fc receptor (FcRn)" *J Biol Chem.*, 281(33):23514-24 (2006).
Datta-Mannan et al., "Monoclonal antibody clearance. Impact of modulating the interaction of IgG with the neonatal Fc receptor," *J Biol Chem.*, Jan. 19, 2007;282(3):1709-17, Epub Nov. 29, 2006.
Dhodapkar et al., "Selective blockade of inhibitory Fcgamma receptor enables human dendritic cell maturation with IL-12p70

(56) References Cited

OTHER PUBLICATIONS production and immunity to antibody-coated tumor cells," *Proc Natl Acad Sci USA*, 102(8):2910-5 (2005).
Duffau et al., "Platelet CD154 potentiates interferon-alpha secretion by plasmacytoid dendritic cells in systemic lupus erythematosus," *Sci Transl Med.*, 2(47):47ra63 (2010).
Floto et al., "Loss of function of a lupus-associated FcgammaRIIb polymorphism through exclusion from lipid rafts," *Nat Med.*, 11(10):1056-8 (2005).
Fournier et al., "Activation of human peripheral IgM+ B cells is transiently inhibited by BCR-independent aggregation of Fc gammaRIIB." *J Immunol.*, 181(8):5350-9 (2008).
Greenwood et al., "Structural motifs involved in human IgG antibody effector functions," *Eur J Immunol.*, 23(5):1098-104 (1993).
Heyman, "Feedback regulation by IgG antibodies," *Immunol Lett.*, 88(2):157-61 (2003).
Jefferis et al., "Interaction sites on human IgG-Fc for FcgammaR: current Models," *Immunol Lett.*, 82(1-2):57-65 (2002).
Kohrt et al., "Stimulation of natural killer cells with a CD137-specific antibody enhances trastuzumab efficacy in xenotransplant models of breast cancer," *J Clin Invest.*, 122(3):1066-75 (2012).
Li et al., "CD72 down-modulates BCR-induced signal transduction and diminishes survival in primary mature B lymphocytes," *J Immunol.*, 176(9):5321-8 (2006).
Li et al., "Inhibitory Fcγ receptor engagement drives adjuvant and anti-tumor activities of agonistic CD40 antibodies," *Science*, 333(6045):1030-4 (2011).
Liang et al., "Immunity against a therapeutic xenoprotein/Fc construct delivered by gene transfer is reduced through binding to the inhibitory receptor FcγRIIb," *J Gene Med.*, 13(9):470-7 (2011).
Mackay et al., "Selective dysregulation of the FcgammaIIB receptor on memory B cells in SLE," *J Exp Med.*, 203(9):2157-64 (2006).
Manger et al., "Fcgamma receptor IIa polymorphism in Caucasian patients with systemic lupus erythematosus: association with clinical symptoms," *Arthritis Rheum.*, 41(7):1181-9 (1998).
Meyer et al., "Bevacizumab immune complexes activate platelets and induce thrombosis in FCGR2A transgenic mice," *J Thromb Haemost.*, Jan. 2009;7(1):171-81. Epub Oct. 30, 2008.
Mi et al., "Targeting the neonatal fc receptor for antigen delivery using engineered fc fragments," *J Immunol.*, 181(11):7550-61 (2008).
Morgan et al., "The N-terminal end of the CH2 domain of chimeric human IgG1 anti-HLA-DR is necessary for C1q, Fc gamma RI and Fc gamma RIII binding," *Immunology.*, 86(2):319-24 (1995).
Muta et al., "A 13-amino-acid motif in the cytoplasmic domain of Fc gamma RIIB modulates B-cell receptor signaling," *Nature*,368(6466):70-3 (1994).
Nakamura et al., "Fcgamma receptor IIB-deficient mice develop Goodpasture's syndrome upon immunization with type IV collagen: a novel murine model for autoimmune glomerular basement membrane disease," *J Exp Med.*, 191(5):899-906 (2000).
Nicholas et al., "Regulation of the immune response. I. Reduction in ability of specific antibody to inhibit long-lasting IgG immunological priming after removal of the Fc fragment," *J Exp Med.*, 129(6):1183-201 (1969).
Niebecker et al., "Safety of therapeutic monoclonal antibodies," *Curr Drug Saf.*, 5(4):275-86 (2010).
Nimmerjahn et al., "Fcgamma receptors as regulators of immune responses," *Nat Rev Immunol.*, 8(1):34-47 (2008).
Olferiev et al., "The role of activating protein 1 in the transcriptional regulation of the human FCGR2B promoter mediated by the −343 G -> C polymorphism associated with systemic lupus erythematosus," *J Biol Chem.*, 282(3):1738-46 (2007).
Qiao et al., "Dependence of antibody-mediated presentation of antigen on FcRn," *Proc Natl Acad Sci USA*, 105(27):9337-42 (2008).
Radaev et al., "The role of Fc glycosylation and the binding of peptide inhibitors," *J Biol Chem.*, 276(19):16478-83 (2001).
Ravetch et al., "Immune inhibitory receptors," *Science*, 290(5489):84-9 (2000).

Richards et al., "Optimization of antibody binding to FcgammaRIIa enhances macrophage phagocytosis of tumor cells," *Mol Cancer Ther.*, 7(8):2517-27 (2008).
Robles-Carrillo et al., "Anti-CD40L immune complexes potently activate platelets in vitro and cause thrombosis in FCGR2A transgenic mice," *J Immunol.*, 185(3):1577-83 (2010).
Salmon et al., "Fc gamma RIIA alleles are heritable risk factors for lupus nephritis in African Americans," *J Clin Invest.*, 97(5):1348-54 (1996).
Scappaticci et al., "Arterial thromboembolic events in patients with metastatic carcinoma treated with chemotherapy and bevacizumab," *J Natl Cancer Inst.*, 100(2):156 (2008).
Smith et al., "FcgammaRIIB in autoimmunity and infection: evolutionary and therapeutic implications," *Nat Rev Immunol.*, May;10(5):328-43 (2010).
Su et al., Expression profile of FcgammaRIIb on leukocytes and its dysregulation in systemic lupus erythematosus, *J Immunol.*, 178(5):3272-80 (2007).
Veri et al., "Therapeutic control of B cell activation via recruitment of Fcgamma receptor IIb (CD32B) inhibitory function with a novel bispecific antibody scaffold," *Arthritis Rheum.*, 62(7):1933-43 (2010).
Veri et al., "Monoclonal antibodies capable of discriminating the human inhibitory Fcgamma-receptor IIB (CD32B) from the activating Fcgamma-receptor IIA (CD32A): biochemical, biological and functional characterization," *Immunology*, 121(3):392-404 (2007).
Warmerdam et al., Molecular basis for a polymorphism of human Fc gamma receptor II (CD32), *J Exp Med.*, 172(1):19-25 (1990).
Wernersson et al., "IgG-mediated enhancement of antibody responses is low in Fc receptor gamma chain-deficient mice and increased in Fc gamma RII-deficient mice," *J Immunol.*, 163(2):618-22 (1999).
Wilson et al., "An Fcγ receptor-dependent mechanism drives antibody-mediated target-receptor signaling in cancer cells," *Cancer Cell*, 19(1):101-13 (2011).
Xu et al., "Fc gamma Rs modulate cytotoxicity of anti-Fas antibodies: implications for agonistic antibody-based therapeutics," *J Immunol.*, 171(2):562-8 (2003).
Yuasa et al., "Deletion of fcgamma receptor IIB renders H-2(b) mice susceptible to collagen-induced arthritis," *J Exp Med.*, 189(1):187-94(1999).
Zhang et al., "Effective therapy for a murine model of human anaplastic large-cell lymphoma with the anti-CD30 monoclonal antibody, HeFi-1,does not require activating Fc receptors," *Blood*, 108(2):705-10 (2006).
Scappaticci et al., "Arterial thromboembolic events in patients with metastatic carcinoma treated with chemotherapy and bevacizumab," *J Natl Cancer Inst.*, 99(16):1232-9 (2007).
Stewart et al., "Site-directed mutagenesis of a catalytic antibody: an arginine and a histidine residue play key roles," *Biochemistry*, 33(8):1994-2003 (1994).
International Search Report for App. Ser. No. PCT/JP2012/058603, dated May 29, 2012, 2 pages.
Sims et al., "HMGB1 and RAGE in inflammation and cancer," *Annu Rev Immunol.*, 28:367-88 (2010).
Wang et al., "HMG-1 as a late mediator of endotoxin lethality in mice," *Science*, 285(5425):248-51 (1999).
International Search Report for App. Ser. No. PCT/JP2012/075083, dated Oct. 23, 2012, 2 pages.
International Preliminary Report on Patentability for App. Ser. No. PCT/JP2012/075083, dated Apr. 1, 2014, 8 pages.
Drake et al., "Chapter 5: Biophysical Considerations for Development of Antibody-Based Therapeutics," *Biophysical Considerations for Development of Antibody-Based Therapeutics*, Springer Springer Science+Business Media New York, 95-7 (2012).
Clark, "An alignment of IgG sequences from Human, Mouse and Rat," Part II Immunoglobulin lectures (v4), pp. 5(i)-5(ii) [retrieved on Jul. 25, 2014], Retrieved from the Internet: http://www.path.cam.ac.uk/~mrc7/lecturenotes/handout1a.pdf.
Sebba et al., "Tocilizumab: the first interleukin-6-receptor inhibitor," *Am J Health Syst Pharm.*, Aug. 1, 2008;65(15):1413-8. doi: 10.2146/ajhp070449.
Takkinen et al., "Affinity and Specificity Maturation by CDR Walking," Antibody Engineering, Springer Lab Manuals, pp. 540-545 (2001).

(56) References Cited

OTHER PUBLICATIONS

Alley et al., "Antibody-drug conjugates: targeted drug delivery for cancer," *Curr Opin Chem Biol.*, Aug. 2010; 14(4):529-37. doi: 10.1016/j.cbpa.2016.06.170. Epub Jul. 17, 2010.

Baeuerle et al., "BiTE: Teaching antibodies to engage T-cells for cancer therapy," *Curr Opin Mol Ther.*, 11(1):22-30 (2009).

Davda et al., "Properties of a general PK/PD model of antibody-ligand interactions for therapeutic antibodies that bind to soluble endogenous targets," *MAbs*, Sep.-Oct. 2010; 2(5):576-88. doi: 10.4161/mabs.2.5.12833, Epub Sep. 1, 2016.

De Bono et al., "ING-1, a monoclonal antibody targeting Ep-CAM in patients with advanced adenocarcinomas," *Clin Cancer Res.*, 10(22):7555-65 (2004).

Deng et al., "Pharmacokinetics of humanized monoclonal anti-tumor necrosis factor-{alpha} antibody and its neonatal Fc receptor variants in mice and cynomolgus monkeys," *Drug Metab Dispos.*, Apr. 2010;38(4):600-5. doi: 10.1124/dmd.109.031310. Epub Jan. 13, 2010.

Desjarlais et al., "Optimizing engagement of the immune system by anti-tumor antibodies: an engineer's perspective," *Drug Discov Today*, Nov. 2007; 12(21-22):898-910. Epub Oct. 22, 2007.

Haringman et al., "A randomized controlled trial with an anti-CCL2 (anti-monocyte chemotactic protein 1) monoclonal antibody in patients with rheumatoid arthritis," *Arthritis Rheum.*, 54(8):2387-92 (2006).

Juszczak et al., "Ipilimumab: a novel immunomodulating therapy causing autoimmune hypophysitis: a case report and review," *Eur J Endocrinol.*, Jul. 2012; 167(1):1-5. doi: 10.1530/EJE-12-0167. Epub Apr. 10, 2012.

Lewis et al., "Differential responses of human tumor cell lines to anti-p185HER2 monoclonal antibodies," *Cancer Immunol Immunother.*, 37(4):255-63 (1993).

Lutterbuese et al., "T cell-engaging BiTE antibodies specific for EGFR potently eliminate KRAS- and BRAF-mutated colorectal cancer cells," *Proc Natl Acad Sci USA.*, Jul. 13, 2010; 107(28):12605-10. doi: 10.1073/pnas.1000976107. Epub Jun. 28, 2010.

Martin et al., "Preclinical safety and immune-modulatng effects of therapeutic monoclonal antibodies to interleukin-6 and tumor necrosis factor-α in cynomolgus macaques," *J Immunotoxicol.*, Jul. 1, 2004;1(3):131-9. doi:10.1080/15476910490894904.

Nam et al., "Current evidence for the management of rheumatoid arthritis with biological disease-modifying antirheumatic drugs: a systematic literature review informing the EULAR recommendations for the management of RA," *Ann Rheum Dis.*, Jun. 2010; 69(6):976-86. doi: 10.1136/ard.2009.126573. Epub May 6, 2010.

Nishimoto et al., "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease," *Blood*, Nov. 15, 2008;112(10):3959-64. doi: 10.1182/blood-2008-05-155846. Epub Sep. 10, 2008.

Petkova et al., "Enhanced half-life of genetically engineered human IgG1 antibodies in a humanized FcRn mouse model: potential application in humorally mediated autoimmune disease," *Int Immunol.*, 18(12):1759-69 (2006).

Reverberi et al., "Factors affecting the antigen-antibody reaction," *Blood Transfus.*, Nov. 2007;5(4):227-40. doi: 10.2450/2007.0047-07.

Riechelmann et al., "Phase I trial with the CD44v6-targeting immunoconjugate bivatuzumab mertansine in head and neck squamous cell carcinoma," *Oral Oncol.*, Sep. 2008; 44(9):823-9. doi: 10.1016/j.oraloncology.2007.10.009. Epub Jan. 18, 2008.

Roopenian et al. "FcRn: the neonatal Fc receptor comes of age," *Nat Rev Immunol.*, 7(9):715-25 (2007).

Satoh et al., "Non-fucosylated therapeutic antibodies as next-generation therapeutic antibodies," *Expert Opin Biol Ther.*, 6(11):1161-73 (2006).

Takeuchi et al., "The Japanese experience with biologic therapies for rheumatoid arthritis," *Nat Rev Rheumatol.*, Nov. 2010; 6(11):644-52. doi: 10.1038/nrrheum.2010.154. Epub Sep. 28, 2010.

Trinh et al., "Ipilimumab in the treatment of melanoma," *Expert Opin Biol Ther.*, Jun. 2012; 12(6):773-82. doi: 10.1517/14712598.2012.675325. Epub Apr. 14, 2012.

Vaccaro et al., "Engineering the Fc region of immunoglobulin G to modulate in vivo antibody levels," *Nat Biotechnol.*, 23(10):1283-8 (2005).

Weiner et al., "Monoclonal antibodies: versatile platforms for cancer immunotherapy," *Nat Rev Immunol.*, May 2010; 10(5):317-27. doi: 10.1038/nri2744.

Xiao et al., "Pharmacokinetics of anti-hepcidin monoclonal antibody Ab 12B9m and hepcidin in cynomolgus monkeys," *AAPS J.*, Dec. 2010;12(4):646-57. doi: 10.1208/s12248-010-9222-0. Epub Aug. 25, 2010.

Zheng et al., "Translational pharmacokinetics and pharmacodynamics of an FcRn-variant anti-CD4 monoclonal antibody from preclinical model to phase I study," *Clin Pharmacol Ther.*, Feb. 2011; 89(2):283-90. doi: 10.1038/clpt.2010.311. Epub Dec. 29, 2010.

International Search Report for App. Ser. No. PCT/JP2012/006218, dated Mar. 26, 2013, 11 pages.

Schuster et al., "Signaling of human ciliary neurotrophic factor (CNTF) revisited. The interleukin-6 receptor can serve as an alpha-receptor for CTNF," *J Biol Chem.*, Mar. 14, 2003;278(11):9528-35.

Seda et al., "B-cell receptor signalling and its crosstalk with other pathways in normal and malignant cells," *Eur J Haematol.*, Aug. 1, 2014. doi: 10.1111/ejh.12427.

Janeway et al., Immunobiology, The Immune System in Health and Disease, 3rd Edition, 1997 Garland Publishing Inc., pp. 3:1-3:11.

Nordlund et al., "Introduction of histidine residues into avidin subunit interfaces allows pH-dependent regulation of quaternary structure and biotin binding," *FEBS Lett.*, Dec. 18, 2003;555(3):449-54.

Patton et al., "An acid dissociation bridging ELISA for detection of antibodies directed against therapeutic proteins in the presence of antigen," *J Immunol Methods*, Sep. 2005;304(1-2):189-95.

Stearns et al., "The interaction of a Ca2+-dependent monoclonal antibody with the protein C activation peptide region. Evidence for obligatory Ca2+ binding to both antigen and antibody," *J Biol Chem.*, Jan. 15, 1988;263(2):826-32.

Ward et al., "A calcium-binding monoclonal antibody that recognizes a non-calcium-binding epitope in the short consensus repeat units (SCRs) of complement C1r," *Mol Immunol.*, Jan. 1992;29(1):83-93.

USPTO Restriction Requirement in U.S. Appl. No. 13/637,415, dated Dec. 31, 2014, 8 pages.

Fish & Richardson P.C., Reply to Restriction Requirement dated Dec. 31, 2014 in U.S. Appl. No. 13/637,415, filed Feb. 25, 2015, 1 page.

USPTO Restriction Requirement in U.S. Appl. No. 14/347,034, dated Dec. 18, 2014, 9 pages.

Fish & Richardson P.C., Reply to Restriction Requirement dated Dec. 18, 2014 in U.S. Appl. No. 14/347,034, filed Mar. 18, 2015, 2 pages.

USPTO Non-Final Office Action in U.S. Appl. No. 14/347,034, dated Apr. 16, 2015, 9 pages.

USPTO Non-Final Office Action in U.S. Appl. No. 13/637,415, dated May 13, 2015, 24 pages.

Lazar et al., "Engineered antibody Fc variants with enhanced effector function," *Proc Natl Acad Sci USA*, Mar. 1, 20064;103(11):4005-10. Epub Mar. 6, 2006.

Amersham Biosciences, "Antibody Purification Handbook," Edition 18-1037-46 [online], [retrieved on Nov. 5, 2015], Retrieved from the Internet: http://www.promix.ru/manuf/ge/chrom/lit/Antibody_Purification.pdf.

Cuatrecasas et al., "Affinity Chromatography," *Methods Enzymol.*, 1971;12:345-78.

Durkee et al., "Immunoaffinity chromatographic purification of Russell's viper venom factor X activator using elution in high concentrations of magnesium chloride," *Protein Expr Purif.*, Oct. 1993;4(5);405-11.

GE Healthcare. Application note 28-9277-92 AA. "High-throughput screening of elution pH for monoclonal antibodies on MabSelect SuRe using PreDictor plates" [online], [retrieved on Nov. 5, 2015], Retrieved from the Internet: https://www.gelifesciences.com/gehcls_

(56) References Cited

OTHER PUBLICATIONS images/GELS/Related%20Content/Files/1314787424814/litdoc28927792AA_20110831131840.pdf.
Singer et al., "Genes & Genomes," Moscow, "Mir," 1998;1:63-64.
Wikipedia, "Chaotropic agent" [online], [retrieved on Nov. 2, 2015], Retrieved from the Internet: https://en.wikipedia.org/wiki/Chaotropic_agent.
USPTO Interview Summary in U.S. Appl. No. 14/347,034, dated Aug. 17, 2015, 3 pages.
Fish & Richardson P.C., Reply to Non-Final Office Action dated May 13, 2015 in U.S. Appl. No. 13/637,415, filed Aug. 13, 2015, 21 pages.
USPTO Final Office Action in U.S. Appl. No. 13/637,415, dated Nov. 13, 2015, 20 pages.
Fish & Richardson P.C., Reply to Non-Final Office Action dated Apr. 16, 2015 in U.S. Appl. No. 14/347,034, filed Sep. 16, 2015, 28 pages.
USPTO Final Office Action in U.S. Appl. No. 14/347,034, dated Oct. 16, 2015, 5 pages.
Balint et al., "Antibody engineering by parsimonious mutagenesis," Gene., 137(1):109-18 (1993).
U.S. Appl. No. 15/210,360, filed Jul. 14, 2016, Igawa et al.
U.S. Appl. No. 15/210,353, filed Jul. 14, 2016, Igawa et al.
Beringhelli et al., "pH and ionic strength dependence of protein (un)folding and ligand binding to bovine beta-lactoglobulins A and B," Biochemistry, Dec. 24, 2002;41(51):15415-22.
Bogdanovich et al., "Functional improvement of dystrophic muscle by myostatin blockade," Nature, Nov. 28, 2002;420(6914):418-21.
Burmeister et al., "Crystal structure of the complex of rat neonatal Fc receptor with Fc," Nature, Nov. 24, 1994;372(6504):379-83.
Desai et al., "Fc gamma receptor IIB on dendritic cells enforces peripheral tolerance by inhibiting effector T cell responses," J Immunol., May 15, 2007;178(10):6217-26.
Epstein, "Non-randomness of amino-acid changes in the evolution of homologous proteins," Nature, Jul. 22, 1967;215(5099):355-9.
Fillipovich, Biochemical basis of human life, VLADOS, 2005:49-50 (with English translation).
Hoodless et al., "Mechanism and function of signaling by the TGF beta superfamily," Curr Top Microbiol Immunol., 1998;228:235-72.
Kamei et al., "Quantitative methods for developing Fc mutants with extended half-lives," Biotechnol Bioeng., Dec. 20, 2005;92(6):748-60.
Kingsley et al., "The TGF-beta superfamily: new members, new receptors, and new genetic tests of function in different organisms," Genes Dev., Jan. 1994;8(2):133-46.
Lee et al., "Genetic analysis of the role of proteolysis in the activation of latent myostatin," PLoS One, Feb. 20, 2008;3(2):e1628.
Lee et al., "Regulation of myostatin activity and muscle growth," Proc Natl Acad Sci U S A., Jul. 31, 2001;98(16):9306-11.
Li et al., "Apoptotic and antitumor activity of death receptor antibodies require inhibitory Fcγ receptor engagement," Proc Natl Acad Sci U S A., Jul. 3, 2012;109(27):10966-71.
Luttrell et al., "Reaction coupling of chelation and antigen binding in the calcium ion-dependent antibody binding of cyclic AMP," J Biol Chem., Nov. 15, 1991;266(32):21626-30.
Malbec et al., "Antibodies against growth factor receptors can inhibit the proliferation of transformed cells via a cis-interaction with inhibitory FcR," Immunol Lett., Mar. 30, 2012;143(1):28-33.
McCroskery et al., "Improved muscle healing through enhanced regeneration and reduced fibrosis in myostatin-null mice," J Cell Sci., Aug. 1, 2005;118(Pt 15):3531-41.
McPherron et al., "Regulation of skeletal muscle mass in mice by a new TGF-beta superfamily member," Nature, May 1, 1997;387(6628):83-90.
McPherron et al., "Double muscling in cattle due to mutations in the myostatin gene," Proc Natl Acad Sci U S A., Nov. 11, 1997;94(23):12457-61.
Palladino et al., "Anti-TNF-alpha therapies: the next generation," Nat Rev Drug Discov., Sep. 2003;2(9):736-46.

Pakula et al., "Genetic analysis of protein stability and function," Annu Rev Genet., 1989;23:289-310.
Schroter et al., "A generic approach to engineer antibody pH-switches using combinatorial histidine scanning libraries and yeast display," MAbs., 2015;7(1):138-51. doi: 10.4161/19420862.2014.985993.
Singer et al., Genes & Genomes, 1991;67-69.
Szlama et al., "Latent myostatin has significant activity and this activity is controlled more efficiently by WFIKKN1 than by WFIKKN2," FEBS J., Aug. 2013;280(16):3822-39. doi: 10.1111/febs.12377, Epub Jul. 5, 2013.
Wagner et al., "Loss of myostatin attenuates severity of muscular dystrophy in mdx mice," Ann Neurol., Dec. 2002;52(6):832-6.
Wenink et al., "The inhibitory Fc gamma IIb receptor dampens TLR4-mediated immune responses and is selectively up-regulated on dendritic cells from rheumatoid arthritis patients with quiescent disease," J Immunol., Oct. 1, 2009;183(7):4509-20.
Whittemore et al., "Inhibition of myostatin in adult mice increases skeletal muscle mass and strength," Biochem Biophys Res Commun., Jan. 24, 2003;300(4):965-71.
Zhang et al., "Immune complex/Ig negatively regulate TLR4-triggered inflammatory response in macrophages through Fc gamma RIIb-dependent PGE2 production," J Immunol., Jan. 1, 2009;182(1):554-62.
Zimmers et al., "Induction of cachexia in mice by systemically administered myostatin," Science, May 24, 2002;296(5572):1486-8.
Fish & Richardson P.C., Reply to Final Office Action dated Oct. 16, 2015 in U.S. Appl. No. 14/347,034, filed Jan. 13, 2016, 28 pages.
USPTO Notice of Allowance in U.S. Appl. No. 14/347,034, dated Feb. 17, 2016, 6 pages.
Reply to Final Office Action dated Nov. 13, 2015 in U.S. Appl. No. 13/637,415, filed May 12, 2016.
USPTO Notice of Allowance in U.S. Appl. No. 14/347,034, dated Jun. 3, 2016, 5 pages.
USPTO Non-Final Office Action in U.S. Appl. No. 14/741,786, dated Jun. 10, 2016, 19 pages.
U.S. Appl. No. 15/263,617, filed Sep. 13, 2016, Igawa et al.
Brown et al., "A study of the interactions between an IgG-binding domain based on the B domain of staphylococcal protein A and rabbit IgG," Mol Biotechnol., Aug. 1998;10(1):9-16.
Chen et al., "Selection and analysis of an optimized anti-VEGF antibody: crystal structure of an affinity-matured Fab in complex with antigen," J Mol Biol., Nov. 5, 1999:293(4):865-81.
Declaration of Nimish Gera, Ph.D., CV and Exhibits, dated Sep. 1, 2016, 24 pages.
Junghans et al., "The protection receptor for IgG catabolism is the beta2-microglobulin-containing neonatal intestinal transport receptor," Proc Natl Acad Sci U S A., May 28, 1996;93(11):5512-6.
Laitinen et al., "Brave new (strept)avidins in biotechnology," Trends Biotechnol, Jun. 2007;25(6):269-77. Epub Apr. 12, 2007.
Linder et al., "Design of a pH-dependent cellulose-binding domain," FEBS Lett., Mar. 19, 1999;447(1):13-6.
Marshall et al., "Rational design and engineering of therapeutic proteins," Drug Discov Today., Mar. 1, 2003;8(5):212-21.
Schroeder et al., "Similarity and divergence in the development and expression of the mouse and human antibody repertoires," Dev Comp Immunol., 2006:30(1-2):119-35.
Fish & Richardson P.C., Reply to Office Action dated Jun. 10, 2016, in U.S. Appl. No. 14/741,786, filed Sep. 9, 2016 37 pages.
USPTO Final Office Action in U.S. Appl. No. 14/741,786, dated Oct. 18, 2016, 11 pages.
U.S. Appl. No. 15/230,904, filed Sep. 13, 2016, Igawa et al.
Clynes et al., "Fc receptors are required in passive and active immunity to melanoma," Proc Natl Acad Sci U.S.A., Jan. 20, 1998;95(2):652-6.
Clynes et al., "Inhibitory Fc receptors modulate in vivo cytotoxicity against tumor targets," Nat Med., Apr. 2000;6(4):443-6.
De Groot et al., "Reducing risk, improving outcomes: bioengineering less immunogenic protein therapeutics," Clin Immunol., May 2009;131(2):189-201. doi: 10.1016/j.clim.2009.01.009. Epub Mar. 6, 2009.

(56) References Cited

OTHER PUBLICATIONS

Dmytrijuk et al., "FDA report: eculizumab (Soliris) for the treatment of patients with paroxysmal nocturnal hemoglobinuria," Oncologist, Sep. 2008;13(9):993-1000. doi: 10.1634/theoncologist.2008-0086. Epub Sep. 10, 2008.
Dufner et al., "Harnessing phage and ribosome display for antibody optimization," Trends Biotechnol., Nov. 2006;24(11):523-9. Epub Sep. 26, 2006.
Haviland et al., "Complete cDNA sequence of human complement pro-C5. Evidence of truncated transcripts derived from a single copy gene," J Immunol., Jan. 1, 1991;146(1):362-368.
Holash et al., "VEGF-Trap: a VEGF blocker with potent antitumor effects," Proc Natl Acad Sci U.S.A, Aug. 20, 2002;99(17):11393-8. Epub Aug. 12, 2002.
Holers, "The spectrum of complement alternative pathway-mediated diseases," Immunol Rev., Jun. 2008;223:300-16. doi: 10.1111/j.1600-065X.2008.00641.x.
Mollnes et al., "Identification of a human C5 beta-chain epitope exposed in the native complement component but concealed in the SC5b-9 complex," Scand J Immunol., Sep. 1988:28(3):307-312.
Nishimura et al., "Genetic variants in C5 and poor response to eculizumab," N Engl J Med., Feb. 13, 2014;370(7):632-9. doi: 10.1056/NEJMoa1311084.
Russo et al., "The CXCL8/IL-8 chemokine family and its receptors in inflammatory diseases," Expert Rev Clin Immunol., May 2014;10(5):593-619. doi: 10.1586/1744666X.2014.894886. Epub Mar. 29, 2014.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., Jan. 31, 2003:278(5):3466-73. Epub Nov. 8, 2002.
Strohl, "Optimization of Fc-mediated effector functions of monoclonal antibodies," Curr Opin Biotechnol., Dec. 2009;20(6):685-91. doi: 10.1016/j.copbio.2009.10.011. Epub Nov. 4, 2009.
Wu et al., "Structure-based engineering of a monoclonal antibody for improved solubility," Protein Eng Des Sel., Aug. 2010;23(8):643-51. doi: 10.1093/protein/gzq037. Epub Jun. 11, 2010.
Advisory Action dated Aug. 19, 2019, in U.S. Appl. No. 15/952,951, Igawa, et al., filed Apr. 13, 2018, 2 pages.
Advisory Action dated Jan. 7, 2016, in U.S. Appl. No. 13/889,484, Igawa, et al., filed May 8, 2013, 3 pages.
Final Office Action dated Aug. 1, 2013 for U.S. Appl. No. 13/595,139, Igawa, et al., filed Aug. 27, 2012.
Final Office Action dated Apr. 6, 2015, in U.S. Appl. No. 13/889,484, Igawa, et al., filed May 8, 2013, 11 pages.
Final Office Action dated Apr. 2, 2019, in U.S. Appl. No. 15/210,353, Igawa, et al., filed Jul. 14, 2016, 27 pages.
Final Office Action dated Aug. 4, 2015, in U.S. Appl. No. 13/889,484, Igawa, et al., filed May 8, 2013, 11 pages.
Final Office Action dated Aug. 16, 2017, in U.S. Appl. No. 13/889,484, Igawa, et al., filed May 8, 2013, 14 pages.
Final Office Action dated Feb. 4, 2020, in U.S. Appl. No. 15/210,360, Southwell, J.E., filed Apr. 5, 2018, 20 pages.
Final Office Action dated Jan. 26, 2021, in U.S. Appl. No. 15/210,360, Southwell, J.E., filed Apr. 5, 2018, 25 pages.
Final Office Action dated Jun. 14, 2019, in U.S. Appl. No. 14/379,825, Igawa, et al., filed Aug. 20, 2014, 23 pages.
Final Office Action dated Jun. 3, 2019, in U.S. Appl. No. 15/952,945, Igawa, et al., filed Apr. 13, 2018, 17 pages.
Final Office Action dated Jun. 3, 2019, in U.S. Appl. No. 15/952,951, Igawa, et al., filed Apr. 13, 2018, 20 pages.
Final Office Action dated Mar. 3, 2020, in U.S. Appl. No. 13/637,415, Igawa, et al., filed Feb. 4, 2013, 26 pages.
Final Office Action dated May 30, 2017, in U.S. Appl. No. 13/595,139, Igawa, et al., filed Aug. 27, 2012, 15 pages.
Final Office Action dated Nov. 26, 2019, in U.S. Appl. No. 15/050,145, Igawa, et al., filed Feb. 22, 2016, 21 pages.
Office Action dated Feb. 15, 2019, in U.S. Appl. No. 15/050,145, Igawa, et al., filed Feb. 22, 2016, 19 pages.
Office Action dated Jan. 28, 2021, for U.S. Appl. No. 17/020,543, Igawa, et al.
Office Action dated Jul. 14, 2020, in U.S. Appl. No. 14/404,051, Igawa, et al., filed Nov. 26, 2014, 30 pages.
Office Action dated Jun. 10, 2019, in U.S. Appl. No. 13/637,415, Igawa, et al., filed Feb. 4, 2013, 26 pages.
Office Action dated Jun. 27, 2019, in U.S. Appl. No. 15/210,360, Southwell, J.E., filed Apr. 5, 2018, 27 pages.
Office Action dated Mar. 10, 2017, in U.S. Appl. No. 15/210,360, Southwell, J.E., filed Apr. 5, 2018, 18 pages.
Office Action dated Mar. 13, 2015, in U.S. Appl. No. 13/595,139, Igawa, et al., filed Aug. 27, 2012, 11 pages.
Office Action dated Nov. 25, 2016, in U.S. Appl. No. 13/889,484, Igawa, et al., filed May 8, 2013, 11 pages.
Office Action dated Nov. 4, 2020, in U.S. Appl. No. 14/379,825, Igawa, et al., filed Aug. 20, 2014, 31 pages.
Office Action dated Oct. 1, 2018, in U.S. Appl. No. 15/952,951, Igawa, et al., filed Apr. 13, 2018, 11 pages.
Office Action dated Oct. 11, 2019, in U.S. Appl. No. 14/404,051, Igawa, et al., filed Nov. 26, 2014, 19 pages.
Office Action dated Oct. 5, 2020, in U.S. Appl. No. 15/050,145, Igawa, et al., filed Feb. 22, 2016, 27 pages.
Reply to Final Office Action dated Jul. 11, 2016, in U.S. Appl. No. 13/595,139, Igawa, et al., filed Aug. 27, 2012, 4 pages.
Reply to Final Office Action dated Jul. 15, 2016, in U.S. Appl. No. 13/889,512, Igawa, et al., filed May 8, 2013, 4 pages.
Reply to Office Action dated Dec. 2, 2015, in U.S. Appl. No. 13/595,139, Igawa, et al., filed Aug. 27, 2012, 28 pages.
Reply to Office Action dated Dec. 2, 2015, in U.S. Appl. No. 13/889,484, Igawa, et al., filed May 8, 2013, 9 pages.
Reply to Office Action dated Jul. 6, 2015, in U.S. Appl. No. 13/889,484, Igawa, et al., filed May 8, 2013, 14 pages.
Reply to Office Action dated Jun. 11, 2015, in U.S. Appl. No. 13/595,139, Igawa, et al., filed Aug. 27, 2012, 19 pages.
Reply to Office Action dated Jun. 25, 2015, in U.S. Appl. No. 13/889,512, Igawa, et al., filed May 8, 2013, 10 pages.
Reply to Office Action dated Nov. 2, 2015, in U.S. Appl. No. 13/889,512, Igawa, et al., filed May 8, 2013, 13 pages.
Reply to Office Action filed May 14, 2013 in U.S. Appl. No. 13/595,139, Igawa, et al., filed Aug. 27, 2012, 19 pages.
Reply to Restriction Requirement dated Apr. 26, 2016, in U.S. Appl. No. 14/007,947, Igawa, et al., filed Dec. 30, 2013, 2 pages.
Restriction Requirement dated Nov. 19, 2020, in U.S. Appl. No. 16/697,310, Igawa, et al., filed Nov. 27, 2019, 12 pages.
Restriction Requirement dated Oct. 19, 2016, in U.S. Appl. No. 15/210,360, Igawa, et al., filed Jul. 14, 2016, 5 pages.
U.S. Appl. No. 15/952,951 inventors Igawa, T., et al., filed Apr. 13, 2018.
U.S. Appl. No. 16/361,498 inventors Igawa, T., et al., filed Mar. 22, 2019.
U.S. Appl. No. 16/480,047 inventors Shinomiya, K., et al., filed Jul. 23, 2019.
U.S. Appl. No. 16/480,765 inventors Sampei, Z., et al., filed Jul. 25, 2019.
U.S. Appl. No. 16/514,467 inventors Ruike, Y., et al., filed Jul. 17, 2019.
U.S. Appl. No. 16/697,310, inventors Igawa, T., et al., filed Nov. 27, 2019.
U.S. Appl. No. 16/806,027 inventors Igawa, T., et al., filed Feb. 3, 2020.
U.S. Appl. No. 16/838,415 inventors Igawa, T., et al., filed Feb. 4, 2020.
U.S. Appl. No. 16/889,066 inventors Ruike, Y., filed Jun. 1, 2020.
U.S. Appl. No. 16/928,129 inventors Shinomiya, K., et al., filed Jul. 14, 2020.
U.S. Appl. No. 16/983,115 inventors Kakehi, T., et al., filed Mar. 8, 2020.
U.S. Appl. No. 17/097,298 inventors Igawa, T., et al., filed Nov. 13, 2020.
U.S. Appl. No. 17/020,543, inventors Igawa, T., et al., filed Sep. 14, 2020.
U.S. Appl. No. 17/263,691, inventors Shinomiya, K., et al., 371(c) date Jan. 27, 2021.

(56) References Cited

OTHER PUBLICATIONS

U.S. Appl. No. 17/333,256, inventors Kakiuchi, A., et al., filed May 28, 2021.
Abe, T., et al., "Effect of $\beta_2$-microglobulin adsorption column on dialysis-related amyloidosis," Kidney Int'l, 64:1522-1528 (2003).
Abelev, G.I., "Monoclonal Antibodies," Sorosovkii Educational Journal, 1:16-20 (1998).
Actemra (tocilizumab), Highlights of Prescribing Information, as revised in Aug. 2017 (1 page).
Aleshin, A.E., et al., "Crystal Structure of C5b-6 Suggests Structural Basis for Priming Assembly of the Membrane Attack Complex," The Journal of Biological Chemistry 287(23):19642-19652, American Society for Biochemistry and Molecular Biology, United States (Jun. 2012).
Alignment Sequence 1047 and 30 dated Jan. 26, 2021, cited in corresponding European application Office Action dated Feb. 2, 2021.
Alignment Sequence 472 and 24 dated Jan. 26, 2021, cited in corresponding European application Office Action dated Feb. 2, 2021.
Alignment of SEQ ID Nos. 28-32 from WO2009125825, cited in Opposition in EP2698431 on Jun. 23, 2021.
Almagro, J.C., et al., "Design and Validation of a Synthetic VH Repertoire with Tailored Diversity for Protein Recognition," Journal of Molecular Recognition 19(5):413-422, John Wiley & Sons, England (Sep.-Oct. 2006).
Altshuler, D.V., et al., "Production of Recombinant Antibodies and Methods to Increase Their Affinity," Advances in Biological Chemistry (Uspekhi biologitsheskoy khimii), 50:203-4, 215, 219-28 (2010).
Altshuler, D.V., et al., "Production of Recombinant Antibodies and Methods to Increase Their Affinity," Advances in Biological Chemistry (Uspekhi biologitsheskoy khimii), 50:207 (2010).
Ando, K, et al., "Tocilizumab, a Proposed Therapy for the Cachexia of Interleukin6-Expressing Lung Cancer," PLoS One, 9(7):e102436, Public Library of Science, United States (Jul. 2014).
Annex 1 accompanying Response to Appeal of Opponent 2 dated Sep. 16, 2020 in Opposition against EP2552955.
Annotated amino acid sequence of the variable heavy (VH) and variable light (VL) domains of the monoclonal antibodies bevacizumab/Avastin, adalimumab/Humira, omalizumab/Xolair, and rituximab/Mabthera, cited in EP Opposition of EP255295 on Sep. 6, 2019.
Anonymous, "Interleukin 6," Wikipedia, Feb. 22, 2019, XP055598802, retrieved from https://en.wikipedia.org/wiki/Interleukin_6, Jun. 24, 2019, 20 pages.
European Patent Application No. 12/764,620 as filed Mar. 30, 2012 (now EP2698431), cited in Opposition in EP2698431 on Jun. 23, 2021.
Arduin, E., et al., "Highly reduced binding to high and low affinity mouse Fc gamma receptors by L234A/L235A and N297A Fc mutations engineered into mouse IgG2a," Mol Immunol., 63:456-463 (2015).
Arici, A., et al., "Local Cytokines in Endometrial Tissue: The Role of Interleukin-8 in the Pathogenesis of Endometriosis," Annals of the New York Academy of Sciences 955:101-9; discussion 118, 396-406, New York Academy of Sciences; Blackwell, United States (Mar. 2002).
Avsian-Kretchmer, O. and Hsueh, A. J. W., "Comparative Genomic Analysis of Eight-Membered Ring Cystine Knot-Containing Bone Morphogenetic Protein Antagonists," Molecular Endocrinology, 18(1):1-12, Endocrine Society, United States (Jan. 2004).
Balemans, W., et al., "Increased Bone Density in Sclerosteosis is Due to the Deficiency of a Novel Secreted Protein (SOST)," Human Molecular Genetics, 10(5):537-543, Oxford, England (Mar. 2001).
Bork, P., "Powers and Pitfalls in Sequence Analysis: the 70% Hurdle," Genome Research, 10(4): 398-400, United States, Cold Spring Harbor Laboratory Press, c1995 (Apr. 2000).
Borrok, M.J., et al., "pH-Dependent Binding Engineering Reveals an FcRn Affinity Threshold That Governs IgG Recycling," J Biol Chem. 290(7):4282-4290 (2015).
Bowie, J.U., et al., "Deciphering the Message in Protein Sequences: Tolerance to Amino Acid Substitutions," Science 247(4948):1306-1310, American Association for the Advancement of Science, United States (Mar. 1990).
Brunkow, M. E., et al., "Bone Dysplasia Sclerosteosis Results from Loss of the SOST Gene Product, a Novel Cystine Knot-Containing Protein," American Journal of Human Genetics 68(3):577-589, Cell Press, United States (Mar. 2001).
Buckler, D. R., et al., "Antibody Drug Discovery" edited by Wood, C. R. London: Imperial College Press, Section 2.4. Library Selection, p. 49-57 (2012).
Burmester, G.R., et al., "Efficacy and Safety of Subcutaneous Tocilizumab Versus Intravenous Tocilizumab in Combination with Traditional DMARDs in Patients with RA at Week 97 (SUMMACTA)," Annals of the Rheumatic Diseases 75(1):68-74, BMJ, England (Jan. 2016).
Chang, B.S. and Shenson, S., "Practical Approaches to Protein Formulation Development," Pharmaceutical Biotechnology 13:1-25, Plenum Press, United States (2002).
Chugai NMO Clinical Trial Webinar, Sakura Star Study, Dec. 12, 2014, accessed at https://s3.amazonaws.com/gjcf-wp-uploads/wp-content/uploads/2016/05/16162202/12_12_14_Chugai_Webinar_PPT_Complete_Deck_FINAL.pdf, accessed on Sep. 5, 2019, 18 pages.
Chugai Pharmaceutical, A Phase I, Multiple-dose Study of SA237, Study JapicCTI—No. 121786; submitted to Clinicaltrials.jp on Jan. 31, 2014; downloaded from clinicaltrials.jp archive on Sep. 5, 2019 as https://www.clinicaltrials.jp/cti -user/trial/Show.jsp, 5 pages.
Chugai Pharmaceutical, A phase I, multiple-dose study of SA237, Study JapicCTI—No. 121786; submitted to Clinicaltrials.jp on Jun. 19, 2012; downloaded from clinicaltrials.jp archive on Sep. 5, 2019 as https://www.clinicaltrials.jp/ctiuser/trial/Show.jsp, 5 pages.
Chugai Pharmaceutical, A phase I, Multiple-Dose Study of SA237, Study JapicCTI—No. 121786; Submitted to Clinicaltrials.jp on Mar. 19, 2012; downloaded from clinicaltrials.jp archive on Sep. 5, 2019 as https://www.clinicaltrials.jp/cti-user/trial/Show.jsp, 5 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, Version 1, ClinicalTrials.gov, Jan. 6, 2014, accessed at https://clinicaltrials.gov/ct2/history/NCT02028884?V1=View#StudyPageTop, accessed on Sep. 4, 2019, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 2; submitted to ClinicalTrials.gov on Feb. 25, 2014; downloaded from ClinicalTrials.gov archive on Sep. 4, 2019 as https://clinicaltrials.gov/ct2/history/NCT02028884?V2=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 3; submitted to ClinicalTrials.gov on Sep. 4, 2015; downloaded from ClinicalTrials.gov archive on Sep. 4, 2019 as https://clinicaltrials.gov/ct2/history/NCT02028884?V3=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 4, Submitted to ClinicalTrials.gov on Dec. 8, 2015; Downloaded from ClinicalTrials.gov archive on Sep. 4, 2019 as https://clinicaltrials.gov/ct2/history/NCT02028884?V4=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 1, ClinicalTrials.gov, Feb. 25, 2014, accessed at https://clinicaltrials.gov/ct2/history/NCT02073279?V1=View#StudyPageTop, accessed on Sep. 4, 2019, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 10; submitted to ClinicalTrials.gov

(56) References Cited

OTHER PUBLICATIONS on Jul. 7, 2015; downloaded from ClinicalTrials.gov archive on Sep. 5, 2019 as https://clinicaltrials.gov/ct2/history/NCT02073279?V10=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 11; submitted to ClinicalTrials.gov on Aug. 3, 2015; downloaded from ClinicalTrials.gov archive on Sep. 5, 2019 as https://clinicaltrials.gov/ct2/history/NCT02073279?V11=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 12; submitted to ClinicalTrials.gov on Septembers, 2015; downloaded from ClinicalTrials.gov archive on Sep. 5, 2019 as https://clinicaltrials.gov/ct2/history/NCT02073279?V12=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 13, ClinicalTrials.gov, Oct. 5, 2015, acccessed at https://clinicaltrials.gov/ct2/history/NCT02073279?V13=View#StudyPageTop, accessed on Sep. 5, 2019, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 14; submitted to ClinicalTrials.gov on Dec. 8, 2015; downloaded from ClinicalTrials.gov archive on Sep. 5, 2019 as https://clinicaltrials.gov/ct2/history/NCT02073279?V14=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 2; submitted to ClinicalTrials.gov on Jul. 22, 2014; downloaded from ClinicalTrials.gov archive on Sep. 5, 2019 as https://clinicaltrials.gov /ct2/history/NCT02073279?V2= View#StudyPageTop, 6 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 3; submitted to ClinicalTrials.gov on Dec. 15, 2014; downloaded from ClinicalTrials.gov archive on Sep. 5, 2019 as https://clinicaltrials.gov /ct2/history/NCT02073279?V3=View#StudyPageTop, 7 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 4; Submitted to ClinicalTrials.gov on Feb. 5, 2015; downloaded from ClinicalTrials.gov archive on Sep. 5, 2019 as https://clinicaltrials.gov/ct2/history/NCTO2073279?V4=View#StudyPageTop, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 5, ClinicalTrials.gov, Feb. 6, 2015, accessed at https://clinicaltrials.gov/ct2/history/NCT02073279?V5=View#StudyPageTop, accessed on Sep. 5, 2019, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 6; submitted to ClinicalTrials.gov on Mar. 4, 2015; downloaded from ClinicalTrials.gov archive on Sep. 5, 2019 as https://clinicaltrials.gov/ct2/history/NCT02073279?V6=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 7; submitted to ClinicalTrials.gov on Apr. 1, 2015; downloaded from ClinicalTrials.gov archive on Sep. 5, 2019 as https://clinicaltrials.gov/ct2/history/NCT02073279?V7=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 8; submitted to ClinicalTrials.gov on May 7, 2015; downloaded from ClinicalTrials.gov archive on Sep. 5, 2019 as https://clinicaltrials.gov/ct2/history/NCT02073279?V8=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 9, ClinicalTrials.gov, Jun. 5, 2015, accessed at https://clinicaltrials.gov/ct2/history/NCT02073279?V9=View#StudyPageTop, accessed on Sep. 5, 2019, 9 pages.

Coico, R., et al., "Academy" Immunology Manual, 61-62, Publishing Center (Immunologia: utshebnoe posobie. Moscow, Akademia) (2008).

Coloma, M. J., et al., "Design and Production of Novel Tetravalent Bispecific Antibodies," Nature Biotechnology 15(2):159-163, Nature America Publishing, United States (Feb. 1997).

Costa, L., et al., "Efficacy of Tocilizumab in a Patient with Refractory Psoriatic Arthritis," Clinical Rheumatology 33(9):1355-1357, Springer, Germany (Sep. 2014).

Cunningham, B. A., et al., "The Covalent Structure of a Human γG-Immunoglobulin. VII. Amino Acid Sequence of Heavy-Chain Cyanogen Bromide Fragments $H^1$-H4," Biochemistry, 9(16):3161-3170 (1970).

Curtiss, F.R., "Selectivity and Specificity are the Keys to Cost-Effective Use of Omalizumab for Allergic Asthma," Journal of Managed Care Pharmacy, 11(9):774-776, United States, Academy of Managed Care Pharmacy (Nov. 2005).

D'Angelo, S., et al., "Many Routes to an Antibody Heavy-Chain CDR3: Necessary, Yet Insufficient, for Specific Binding," Frontiers in Immunology 9:395, Frontiers Research Foundation, Switzerland (Mar. 2018).

Dagbay, K. B., "Structural basis of specific inhibition of extracellular activation of pro- or latent myostatin by the monoclonal antibody SRK-015," J Biol Chem., 295(16):5404-5418 (2020).

Datta-Mannan, A., et al., "FcRn affinity—pharmacokinetic relationship of five human IgG4 antibodies engineered for improved in vitro FcRn binding properties in cynomolgus monkeys," Drug Metab Dispos., 40(8):1545-1555 (2012).

Decision from Appeal Court, decided Feb. 23, 2011 in *Centocor Ortho Biotech. Inc., et al.* v. *Abbott Laboratories et al.* 636 F. 3d 1341 (Fed. Cir. 2011 )(2010-1144).

Decision of the Opposition Division dated Dec. 19, 2019 in EP2552955.

Decision of the Opposition Division for EP Application No. EP2275443, dated Apr. 26, 2018.

Decision of the Intellectual Property High Court dated Jun. 26, 2019, Case No. 2018 (gyo ke) 10043, Case of Demand for Revocation of Trial Decision.

Decision of the Intellectual Property High Court dated Jun. 26, 2019, Case No. 2018 (gyo ke) 10044, Case of Demand for Revocation of Trial Decision.

Decision of the Intellectual Property High Court dated Jun. 26, 2019, Case No. 2018 (gyo ke) 10045, Case of Demand for Revocation of Trial Decision.

Declaration of J. Boucneau dated Sep. 6, 2019, cited in EP Opposition in EP2552955.

Declaration of M. Hiroyasu dated Oct. 21, 2020, cited in the corresponding European application Office Action on Feb. 2, 2021. Originally filed description of European Patent Application No. EP13195713.6, filed Apr. 10, 2009 (EP Publication No. 2708558).

Diamond, B. and Scharff, M. D., "Somatic Mutation of the T15 Heavy Chain Gives Rise to an Antibody With Autoantibody Specificity," Proceedings of the National Academy of Sciences of the United States of America, 81(18):5841-5844, United States, National Academy of Sciences (Sep. 1984).

Edwards, B.M., et al., "The Remarkable Flexibility of the Human Antibody Repertoire; Isolation of Over One Thousand Different

(56) References Cited

OTHER PUBLICATIONS

Antibodies to a Single Protein, BLyS," Journal of Molecular Biology 334(1):103-118, Elsevier, England (Nov. 2003).
English translation of Japanese Patent Application No. 2010-079667, cited in Opposition in EP2698431 on Jun. 23, 2021.
English translation of Japanese Patent Application No. 2010-250830, cited in Opposition in EP2698431 on Jun. 23, 2021.
English translation of PCT/JP2011/072550, cited in Opposition in EP2698431 on Jun. 23, 2021.
English translation of PCT/JP2012/054624, cited in Opposition in EP2698431 on Jun. 23, 2021.
English translation of PCT/JP2011/001888, cited in Opposition in EP2698431 on Jun. 23, 2021.
EUTM register extract—Biocore, cited in EP Opposition in EP2552955 on Sep. 15, 2020.
Evidence for publication date of "D10" (Zalevsky 2010), cited in Opposition of EP2552955 on Sep. 6, 2019.
Example antibody family tree, attached to the written submission for Opposition against EP 2708559 on Mar. 12, 2020.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Germany; submitted to clinicaltrialsregister.eu on Dec. 20, 2013; downloaded from clinicaltrialsregister.eu archive on Sep. 5, 2019 as https://www.clinicaltrialsregister.eu/ctr-search!trial/2013-003752-21/DE, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 5, 2019 ashttps://www.clinicaltrialsregister.eu/ctr-search/trial/2013-003752-21/HU, 6 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Italy; submitted to clinicaltrialsregister.eu on Feb. 6, 2014; downloaded from clinicaltrialsregister.eu archive on Sep. 5, 2019 as https://www.clinicaltrialsregister.eu/ctr-search!trial/2013-003752-21/IT, 5 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Spain; submitted to clinicaltrialsregister.eu on Mar. 11, 2015; downloaded from clinicaltrialsregister.eu archive on Sep. 5, 2019 as https://www.clinicaltrialsregister.eu/ctr-search/trial/2013-003752-21/ES, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in the United Kingdom; submitted to clinicaltrialsregister.eu on Oct. 15, 2013; downloaded from clinicaltrialsregister.eu archive on Sep. 5, 2019 ashttps://www.clinicaltrialsregister.eu/ctr-search/trial/2013-003752-21/GB, 6 pages.
F. Hoffmann-La Roche Ltd., A Multicenter, Randomized, Addition to Baseline Treatment, Double-blind, Placebo-controlled, Phase 3 Study to Evaluate the Efficacy and Safety of Satralizumab (SA237) in Patients With Neuromyelitis Optica (NMO) and NMO Spectrum Disorder (NMOSD), Study EudraCT 2013-003752-21, Poland, clinicaltrialsregister.eu, Oct. 15, 2013, accessed at https://www.clinicaltrialsregister.eu/ctr-search/trial/2013-003752-21/GB, accessed on Sep. 5, 2019, 7 pages.
F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD), Study EudraCT 2015-005431-41 in Croatia; submitted to clinicaltrialsregister.eu on Dec. 15, 2016; downloaded from clinicaltrialsregister.eu archive on Sep. 5, 2019 as https://www.clinicaltrialsregister.eu/ctr-search?trial/2015-005431-41/HR, 6 pages.
F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD), Study EudraCT 2015-005431-41 in Poland; submitted to clinicaltrialsregister.eu on Apr. 7, 2016; downloaded from clinicaltrialsregister.eu archive on Sep. 5, 2019 as https://www.clinicaltrialsregister.eu/ctr-search/trial/2015-005431-41/PL, 6 pages.
Fakhouri, F., et al., "C3 glomerulopathy: a new classification," Nature Reviews Nephrology 6(8):494-499, London Nature Pub. Group, England (Aug. 2010).
Ferl, G. Z., et al., "A Predictive Model of Therapeutic Monoclonal Antibody Dynamics and Regulation by the Neonatal Fc Receptor (FcRn)," Ann Biomed Eng. Nov. 2005;33(11):1640-52(Erratum in: Ann Biomed Eng. Oct. 2011;39(10):2668).
Finlay, W.J., et al., "Affinity Maturation of a Humanized Rat Antibody for Anti-RAGE Therapy: Comprehensive Mutagenesis Reveals a High Level of Mutational Plasticity Both Inside and Outside the Complementarity-Determining Regions," Journal of Molecular Biology 388(3):541-558, Elsevier, England (May 2009).
Fischer, N. and Leger, O., "Bispecific Antibodies: Molecules That Enable Novel Therapeutic Strategies," Pathobiology 74(1):3-14, Basel, Switzerland (2007).
Fisher, P.A and Smith, D.E., "Affinity Purification of Antibodies Using Antigens Immobilized on Solid Supports," Biochemical Society Transactions, 16(2):134-138, Portland Press on the Behalf of the Biochemical Society, England (Apr. 1988).
Furuya, Y., et al., "Interleukin-6 as a Potential Therapeutic Target for Pulmonary Arterial Hypertension," International Journal of Rheumatology 2010:720305, Hindawi Pub. Corp., United States (Aug. 2010).
GenBank, "Complement Component C5 [*Homo sapiens*]," Accession No. AAA51925.1, accessed at https://www.ncbi.nlm.nih.goV/protein/AAA51925.1, Oct. 31, 1994, 3 pages.
Goel, M., et al., "Plasticity within the Antigen-Combining Site May Manifest as Molecular Mimicry in the Humoral Immune Response," Journal of Immunology 173(12):7358-7367, American Association of Immunologists, United States (Dec. 2004).
Gonzalez, E.M., et al., "BMP-1/Tolloid-like metalloproteases process endorepellin, the angiostatic C-terminal fragment of perlecan," The Journal of Biological Chemistry, 280(8):7080-7087, American Society for Biochemistry and Molecular Biology, United States (Feb. 2005).
Guidance on the use of International Nonproprietary Names (INNs) for Pharmaceutical Substances, World Health Organisation, 2017.
Han, C. and Zhou, H., "Monoclonal antibodies: interspecies scaling with minimal preclinical information," Ther Deliv., 2(3):359-368 (2011) , cited in Opposition in EP2698431 on Jun. 23, 2011.
Hashizume, M., et al., "Tocilizumab, a Humanized Anti-interleukin-6 Receptor Antibody, Improved Anemia in Monkey Arthritis by Suppressing IL-6-induced Hepcidin Production," Rheumatology International, 30(7):917-923, Springer International, Germany (May 2010).
Honda, S., et al., "Marginal Zone B Cells Exacerbate Endotoxic Shock via Interleukin-6 Secretion Induced by Fcα/μR-coupled TLR4 Signalling," Nature Communications 7:11498, Nature Pub. Group, England (May 2016).
Hughes, J. B., et al., "Report of the Use of Drug Sensitivity Tests in General Practice," Med J Aust., 1:72-74 (1964).
Huse, K., et al., "Purification of Antibodies by Affinity Chromatography," Journal of Biochemical and Biophysical Methods 51(3):217-231, (May 2002).
Igawa, T., et al., "Sweeping Antibody as a Novel Therapeutic Antibody Modality Capable of Eliminating Soluble Antigens From Circulation," Immunological Reviews, 270(1):132-151, Blackwell, England (Mar. 2016).

(56) References Cited

OTHER PUBLICATIONS

Iijima, T., et al., "Tocilizumab Improves Systemic Rheumatoid Vasculitis With Necrotizing Crescentic Glomerulonephritis," Modern Rheumatology 25:138-142, Taylor & Francis, United States (Jan. 2015).

Ishii-Watabe, A., et al., "Molecular Design of Therapeutic Monoclonal Antibodies," Journal of Pharmaceutical Science and Technology 74(1):4-11, The Academy of Pharmaceutical Science and Technology, Japan (2014).

Jung, S. T., et al., "Aglycosylated IgG variants expressed in bacteria that selectively bind FcγRI potentiate tumor cell killing by monocyte-dendritic cells," PNAS, 107(2):604-609 (2010).

Kabat, et al., "Sequences of proteins of immunological interest (1987)," National Institute of Health 91(3242): 103, 310, Bethesda (1991).

Kakita, M., et al., "Isolation of a Human Monoclonal Antibody With Strong Neutralizing Activity Against Diphtheria Toxin", Infection and Immunity, 74:3682-3683, American Society for Microbiology, United States (Jun. 2006).

Kamata, N., et al., "Comparison of Ph and Ionic Strength Dependence of Interactions Between Monoclonal Antibodies and Bovine Beta-lactoglobulin," Bioscience, Biotechnology, and Biochemistry, 60(1):25-29, Taylor & Francis, England (Jan. 1996).

Kanyavuz, A., et al., "Breaking the Law: Unconventional Strategies for Antibody Diversification," Nature Reviews, Immunology 19(6):355-368, Nature Pub. Group, England (Jun. 2019).

Keller, H. and Kneissel, M., "SOST is a Target Gene for PTH in Bone," Bone 37(2):148-158, Elsevier Science, United States (Aug. 2005).

Khosla, S. and Riggs, B.L., "Concise Review for Primary-Care Physicians," Mayo Clinic Proceedings, 70:978-982 (1995).

Kipriyanov, S.M., et al., "Generation of Recombinant Antibodies," Molecular Biotechnology 12(2):173-201, Humana Press, United States (Sep. 1999).

Kishimoto, T., "Interleukin-6 and its Receptor in Autoimmunity," Journal of Autoimmunity 5(A):123-132, Elsevier, London (Apr. 1992).

Kondo, M., et al., "A Case of Overlap Syndrome Successfully Treated with Tocilizumab: A Hopeful Treatment Strategy for Refractory Dermatomyositis?", Rheumatology 53:1907-1908, Oxford University Press, England (Oct. 2014).

Kontermann, R. and Dübel, S., editors, "Antibody Engineering," 1:47-62, 415-427 (2010).

Krieg, C., et al., "Functional analysis of B and T lymphocyte attenuator engagement on CD4+ and CD8+ T cells," Journal of Immunology, 175(10):6420-6427, American Association of Immunologists, United States (Nov. 2005).

Kroetsch, A., et al., "Engineered pH-dependent recycling antibodies enhance elimination of Staphylococcal enterotoxin B superantigen in mice," MABS, 11(2):411-421 (2019).

Kurki, P., et al., "Desmin Antibodies in Acute Infectious Myopericarditis," APMIS: Acta Pathologica, Microbiologica, et Immunologica Scandinavica 97(6):527-532, Munksgaard, Denmark (Jun. 1989).

Lloyd, C., et al., "Modelling the Human Immune Response: Performance of a 1011 Human Antibody Repertoire Against a Broad Panel of Therapeutically Relevant Antigens," Protein Engineering, Design & Selection 22(3):159-168, Oxford University Press, England (Mar. 2009).

MacCallum, R. M., et al., "Antibody-antigen Interactions: Contact Analysis and Binding Site Topography," J Mol Biol 262:732-745 (1996).

Makarova, T.P., et al., "Experience of Using Eculizumab in a Child with Atypical Hemolytic Uremic Syndrome," Nephrology 18(3):84-88, 2014.

Mariuzza, R.A., et al., "The Structural Basis of Antigen-Antibody Recognition," Annual Review of Biophysics and Biophysical Chemistry 16:139-159, (Jun. 1987).

Mayilyan, K.R., "Complement Genetics, Deficiencies, and Disease Associations," Protein & Cell 3(7):487-496, Springer; Higher Education Press, Germany (Jul. 2012).

Mease, P.M., et al., "Secukinumab Inhibition of Interleukin-17A in Patients with Psoriatic Arthritis," The New England Journal of Medicine 373(14):1329-1339, Massachusetts Medical Society, United States (Oct. 2015).

Medesan, C., et al., "Comparative Studies of Rat IgG to Further Delineate the Fc:FcRn Interaction Site," European Journal of Immunology 28(7):2092-2100, Wiley-VCH, Germany (Jul. 1998).

Mihara, M., et al., "Anti-interleukin 6 Receptor Antibody Inhibits Murine Aa-amyloidosis," The Journal of Rheumatology, 31 (6):1132-1138, Journal of Rheumatology Publishing Co, Canada (Jun. 2004).

Mimoto, F., et al., "Engineered antibody Fc variant with selectively enhanced FcγRIIb binding over both FcγRIIa$^{R131}$ and FcγRIIa$^{H131}$," Protein Eng Des Sel., 26(10):589-598 (2013), cited in Opposition in EP2698431 on Jun. 23, 2021.

Moore, G. L., et al., "Engineered Fc variant antibodies with enhanced ability to recruit complement and mediate effector functions," mAbs, 2(2):181-189 (2010).

Mori, K., et al., "Novel Models of Cancer-related Anemia in Mice Inoculated With Il-6-producing Tumor Cells," Biomedical Research, 30(1):47-51, Biomedical Research Foundation, Japan (Feb. 2009).

Morris, G.E., "Epitope Mapping of Protein Antigens by Competition ELISA," in the Protein Protocols Handbook, Springer Protocols Handbooks, pp. 595-600, Humana Press. New Jersey (1996).

Motozawa, N., et al., "Unique Circumferential Peripheral Keratitis in Relapsing Polychondritis: A Case Report," Medicine 96(41):e7951, Lippincott Williams & Wilkins, United States (Oct. 2017).

Muller, D. and Kontermann, E., "Bispecific Antibodies. In: Handbook of Therapeutic Antibodies" (ed. by S. Dübel), 2:345-378, WILEY-VCH, Weinheim (2007).

Muramatsu, H., "Latent Myostatin Specific Elimination by Sweeping Antibody® is a Novel Therapeutic Approach to Improve Muscle Strength," Neuromuscular Disorders, 29(1):S86, Elsevier Inc. (Oct. 2019).

Murray, P., et al., "Human Biochemistry, Moscow, Mir," 1:34 (1993).

Narazaki, M., et al., "Therapeutic Effect of Tocilizumab on Two Patients with Polymyositis," Rheumatology, 50(7):1344-1346, Oxford University Press, England (Jul. 2011).

Narhi, L. O., et al., "Effect of Three Elution Buffers on the Recovery and Structure of Monoclonal Antibodies," Analytical Biochemistry 253(2):236-245, Elsevier, United States (Nov. 1997).

Nishimura, J., et al., "An Optimized Crovalimab Dose and Regimen Reduced the Formation of Drug-Target-Drug Complexes in Patients with Paroxysmal Nocturnal Hemoglobinuria from the Phase I/II COMPOSER Trial," Blood, 136 (Supp 1):2-3 (2020).

Ohno, S., et al., "Antigen-binding specificities of antibodies are primarily determined by seven residues of VH," Proc Natl Acad Sci., 82:2945-2949 (1985).

Opposition Statement of Opponent 1, dated Feb. 2, 2018 in EP 2552955.

Opposition Statement of Opponent 2, dated Feb. 2, 2018 in EP 2552955.

Opposition Statement of Opponent 5, dated Feb. 5, 2018 in EP 2552955.

Padlan, E. A., "Review: Anatomy of the Antibody Molecule," Mol Immunol., 31(3):169-217 (1994).

Patentee's explanation in the submission of Apr. 28, 2020 in Annex A made in the appeal case for EP 2552955.

Patentee's response to Article 94(3) EPC communication on EP 3521311 filed on Oct. 20, 2020.

Perng, et al., "Desmin Aggregate Formation by R120G alphaB-crystallin is Caused by Altered Filament Interactions and is Dependent Upon Network Status in Cells," Molecular Biology of the Cell 15(5):2335-2346, American Society for Cell Biology, United States (May 2004).

Piche-Nicholas, N.M., et al., "Changes in Complementarity-determining Regions Significantly Alter IgG Binding to the Neonatal Fc Receptor (FcRn) and Pharmacokinetics," mAbs 10(1):81-94, Taylor & Francis, United States (Jan. 2018).

(56) References Cited

OTHER PUBLICATIONS

Pirruccello-Straub, M., et al., "Blocking Extracellular Activation of Myostatin as a Strategy for Treating Muscle Wasting," Scientific Reports, 8(1):2292, England, Nature Publishing Group (Feb. 2018).
Presta, L. G., et al., "Engineering therapeutic antibodies for improved function," Biochem Soc Trans., 30(4):487-490 (2002).
Product Information Sheet from SIGMA-H-Y Medium (1998) and document establishing that it was published in 1998, 4 pages (submitted by the Opponent during EP opposition procedure for EP2708558 and posted by EPO on Jan. 15, 2019).
Promega Protocols and Applications Guide, 1991, 2nd Edition (submitted by the Opponent during EP opposition procedure for EP2708558 and posted by EPO on Jan. 14, 2019), 3 pages.
PTAB Final Written Decision, *Butamax TM Advanced Biofuels LLC v. Gevo, Inc.*, Case IPR2013-00539, Paper 33 (PTAB Mar. 3, 2015)(U.S. Pat. No. 8,723,565 B2).
Rachner, T.D., et al., "Osteoporosis: Now and the Future," Lancet 377(9773):1276-1287, Elsevier, London (Apr. 2011).
Raso, V., et al., "Intracellular Targeting with Low pH-Triggered Bispecific Antibodies," The Journal of Biological Chemistry 272(44):27623-27628, American Society for Biochemistry and Molecular Biology, United States (Oct. 1997).
Reply to Final Office Action dated Dec. 2, 2015, in U.S. Appl. No. 13/889,484, Igawa, et al., filed May 8, 2013, 9 pages.
Reply to Restriction Requirement dated Jul. 1, 2016, in U.S. Appl. No. 13/990,158, Igawa, et al., filed Mar. 28, 2014, 7 pages.
Rich, R.L., et al., "A global benchmark study using affinity-based biosensors," Analytical Biochemistry, 386(2):194-216, Elsevier, United States (Mar. 2009).
Roche Media Release (retrieved from https://www.roche.com/media/releases/med-cor-2011-01-05.htm.
Roitt, A., et al., Extract from Chapter 6, Immunology (2000), Moscow, "Mir", pp. 110-111 and English translation of section bridging pp. 110-111.
Roitt, et al., Immunology, 5th edition pp. 80-81 (1998).
Roitt, et al., Immunology, Moscow, Mir, 110-111, 151 (2000), with English translation, Immunology, 62-68 (2006).
Roth, A., et al., "The Complement C5 Inhibitor Crovalimab in Paroxysmal Nocturnal Hemoglobinuria," Blood 135(12):912-920, Elsevier, United States (Mar. 2020).
Sada, E., et al., "Effect of Histidine Residues in Antigenic Sites on pH Dependence of Immuno-Adsorption Equilibrium," Applied Microbiology and Biotechnology 27:528-532, Springer (Feb. 1988).
Salfeld, J.G., "Isotype Selection in Antibody Engineering," Nature Biotechnology 25(12):1369-1372, Nature America Publishing, United States (2007).
Sampei, Z., et al., "Identification and Multidimensional Optimization of an Asymmetric Bispecific Igg Antibody Mimicking the Function of Factor Vili Cofactor Activity," PLoS One, 8(2):e57479, Public Library of Science, United States (2013).
Schrama, D., et al., "Antibody Targeted Drugs as Cancer Therapeutics," Nature Reviews Drug Discovery, 5(2):147-159, England, Nature Pub. Group (2006).
Serada, S., et al., "IL-6 Blockade Inhibits the Induction of Myelin Antigen-Specific Th17 Cells and Th1 Cells in Experimental Autoimmune Encephalomyelitis," Proceedings of the National Academy of Sciences 105:9041 -9046, National Academy of Sciences, United States (Jul. 2008).
Shadduck, R.K., et al., "Fractionation of Antibodies to L-cell Colony-Stimulating Factor by Affinity Chromatography," Blood 53(6):1182-1190, American Society of Hematology, United States (Jun. 1979).
Shima, Y., et al., "Tocilizumab, a Humanized Anti-Interleukin-6 Receptor Antibody, Ameliorated Clinical Symptoms and MRI Findings of a Patient with Ankylosing Spondylitis," Modern Rheumatology, 21(4):436-439, Taylor & Francis, United States (Aug. 2011).
Shimizu, H., et al., "Successful Treatment with Tocilizumab for Refractory Scleritis Associated with Relapsing Polychondritis," Scandinavian Journal of Rheumatology 46:418-419, Informa Healthcare, England (Sep. 2017).
Sibéril, S., et al., "Molecular aspects of human FcγR interactions with IgG: Functional and therapeutic consequences," Immunol Lett., 106:111-118 (2006).
Sigma product information for ACES buffer, cited in EP Opposition in EP2552955 on Sep. 6, 2019.
Sikkink, L. A., et al., "Biochemical and aggregation analysis of Bence Jones proteins from difference light chain diseases," Amyloid, 15(1):29-39 (2008).
Silpa-Archa et al., "Outcome of Tocilizumab Treatment in Refractory Ocular Inflammatory Diseases," Acta Ophthalmol., 94:e400-e406 (2016).
Sondermann, P., et al., "The 3.2-A crystal structure of the human IgG1 Fc fragment-Fc gammaRIII complex," Nature, 406(6793):267-273, Nature Publishing Group, England (Jul. 2000).
Stavenhagen, J. B., et al., "Enhancing the potency of therapeutic monoclonal antibodies via Fc optimization," Advan Enzyme Regul., 48:152-164 (2008).
Submission of Opponent 1, dated Sep. 6, 2019 in EP 2552955.
Submission of Opponent 2, dated Sep. 6, 2019 in EP 2552955.
Submission of Opponent 5, dated Sep. 6, 2019 in EP 2552955.
Submission of Proprietor (Chugai Seiyaku) in the opposition-appeal case to EP2275443 (based on D7), dated Feb. 20, 2017.
Submission of Proprietor's (Chugai Seiyaku) Submission dated Sep. 5, 2016 in EP11714860.1 (EP2552955).
Submission of Proprietor's (Chugai Seiyaku) Submission dated Sep. 19, 2016 in EP11714860.1 (EP2552955).
Supplementary data provided by opponent on Feb. 2, 2018 for EP2552955 (EP Application No. 11714860.1).
Suzuki, H., et al., "Anti-Murine IL-6 Receptor Antibody Inhibits IL-6 Effects in Vivo," Immunology Letters 30(1):17-21, Elsevier/North-Holland Biomedical Press, Netherlands (Sep. 1991).
Table summarizing lack of novelty over "D6"(= WO 2009/086320, A;Jul. 9, 2009), cited in EP Opposition of EP2552955 on Sep. 6, 2019.
Tarantul, V. Z., Explanatory biotechnological dictionary of Russian-English. Moscow, Languages of Slavic cultures, 72 (2009).
Tarantul, V. Z., Explanatory biotechnological dictionary of Russian-English (Tolkovyj biotechnologicheshkiy slovar, Moscow, Languages of Slavic cultures, 228, (2009).
Tawfik, D.S., et al., "pH On-Off Switching of Antibody-Hapten Binding by Site-Specific Chemical Modification of Tyrosine," Protein Engineering 7(3):431-434, Oxford University Press, England (Mar. 1994).
Van Assche, G., et al., "Adalimumab in Crohn's disease," Biologies Target and Therapy, 1(4):355-365, Dove Medical Press, New Zealand (Dec. 2007).
Venturi, M., et al., "The Monoclonal Antibody 1f6 Identifies a pH-dependent Conformational Change in the Hydrophilic NH(2) terminus of NhaA Na(+)/H(+) Antiporter of *Escherichia coli*," The Journal of Biological Chemistry 275(7):4734-4742, American Society for Biochemistry and Molecular Biology, United States (Feb. 2000).
Wang, Y. and Lv, L., Chinese Journal of Clinical Pharmacology and Therapeutics, 20(4):455-459 (2015).
Wang, H.-h., et al., "Complement C5a, C5a receptor and their antagonists: research advance," International Journal of Pharmaceutical Research, 37(3):181-186 (2010).
Wang, W., et al., "Monoclonal Antibodies With Identical Fc Sequences Can Bind to FcRn Differentially With Pharmacokinetic Consequences," Drug Metabolism and Disposition the Biological Fate of Chemicals, 39(9):1469-1477, United States, American Society for Pharmacology and Experimental Therapeutics (Sep. 2011).
Watts, J.K. and Corey, D.R., "Silencing Disease Genes in the Laboratory and the Clinic," The Journal of Pathology 226(2):365-379, John Wiley and Sons, England (Jan. 2012).
Who Drug Information, 32(2):283, 303, 304, International Nonproprietary Names (2018).
Wolfman, N., et al., "Activation of Latent Myostatin by the Bmp-1/tolloid Family of Metalloproteinases," Proceedings of the National Academy of Sciences of the United States of America, 100(26):15842-15846, National Academy of Sciences, United States (Dec. 2003).

(56) References Cited

OTHER PUBLICATIONS

Wong, E. K. S. and Kavanagh, D., "Anticomplement C5 therapy with eculizumab for the treatment of paroxysmal nocturnal hemoglobinuria and atypical hemolytic uremic syndrome," Transl Res., 165(2):306-320 (2015).
Yang, D., et al., "Comparison of Biosensor Platforms in the Evaluation of High Affinity Antibody-antigen Binding Kinetics," Analytical Biochemistry 508:78-96, Elsevier, United States (Sep. 2016).
Yang, M., et al., "Effect of anti CD20 antibody Fab' fragment on apoptosis of B lymphoma cells and intracellular calcium," Tumor, 26(2):116-119 (2006).
Yarilin, "Osnovy immunologii," M.Meditsina, 1999, pp. 181-184.
Yoon, S.O., et al., "Construction, Affinity Maturation, and Biological Characterization of an Anti-tumor-associated Glycoprotein-72 Humanized Antibody," The Journal of Biological Chemistry 281(11):6985-6992, Elsevier, United States (Mar. 2006).
Yu, X., et al., "Development and Validation of a Cell-Based Fluorescent Method for Measuring Antibody Affinity," Journal of Immunological Methods, 442:49-53, Netherlands, Elsevier (Mar. 2017).
Zhang, Q., et al., "Monoclonal Antibodies as Therapeutic Agents in Oncology and Antibody Gene Therapy," Cell Research, 17(2):89-99, England, Nature Publishing Group (Feb. 2007).
Zheng, Y., et al., "Minipig as a Potential Translatable Model for Monoclonal Antibody Pharmacokinetics After Intravenous and Subcutaneous Administration," mAbs 4(2):243-255 Taylor & Francis, United States (Mar.-Apr. 2012).
Japanese Patent Application No. 2014-257647, filed on Dec. 19, 2014, cited in European Search Opinion dated Dec. 10, 2019 in EP3472316.
Memorandum Order, C.A. No. 18-1802 (MN) dated Apr. 15, 2020.
U.S. Appl. No. 06/534,658 inventors Insel, R. A., filed Sep. 22, 1983.
U.S. Appl. No. 07/730,040 inventors Esmon, C. T., filed Jul. 12, 1991.
U.S. Appl. No. 08/472,523 inventors Raso, V. A., filed Jun. 7, 1995.
U.S. Appl. No. 08/477,728 inventors Queen, C. L., filed Jun. 7, 1995.
U.S. Appl. No. 09/027,449 inventors Gonzalez, T. N., et al., filed Feb. 20, 1998.
U.S. Appl. No. 09/121,952 inventors Hsei, V., et al., filed Jul. 24, 1998.
U.S. Appl. No. 09/730,857 inventors Matsushima K., et al., filed Jul. 12, 2000.
U.S. Appl. No. 10/257,864, inventors Fukishima, N., et al., filed Jun. 24, 2003.
U.S. Appl. No. 10/822,300 inventors Hinton, P. R., filed Apr. 9, 2004.
U.S. Appl. No. 11/483,250 inventors Lazar; G. A., filed Jul. 7, 2006.
U.S. Appl. No. 11/572,634 inventors Allan, B., filed Jan. 25, 2007.
U.S. Appl. No. 11/725,970 inventors Glaser, S., et al., filed Mar. 19, 2007.
U.S. Appl. No. 11/764,001 inventors Lazar, G. A., filed Jun. 15, 2007.
U.S. Appl. No. 12/532,261 inventors Guild, B. C., et al., filed Sep. 21, 2009.
U.S. Appl. No. 12/611,090 inventors Kim, M., filed Nov. 2, 2009.
U.S. Appl. No. 12/673,599 inventors Clegg, S. J., filed Aug. 15, 2008.
U.S. Appl. No. 12/792,810 inventors Bohrmann, B., filed Jun. 3, 2010.
U.S. Appl. No. 12/820,654 inventors Tamburini. P.P., et al., filed Jun. 22, 2010.
U.S. Appl. No. 12/913,145 inventors Finney, H. M., filed Oct. 27, 2010.
U.S. Appl. No. 13/322,760 inventors Agnetti, G., et al., filed Nov. 28, 2011.
U.S. Appl. No. 13/388,270 inventors Schebye, X. M., filed Aug. 31, 2010.
U.S. Appl. No. 13/458,730 inventors Zhang, Y., filed Apr. 27, 2012.
U.S. Appl. No. 13/480,356 inventors Walker, W. L., filed May 24, 2012.
U.S. Appl. No. 13/509,237 inventors Weaver, D., et al., filed Aug. 23, 2012.
U.S. Appl. No. 13/557,562 inventors Diefenbach-Streiber, B., et al., filed Jul. 25, 2012.
U.S. Appl. No. 13/791,312 inventors Grabstein, K., filed Mar. 8, 2013.
U.S. Appl. No. 13/795,674 inventors Feldhaus, A. L., filed Mar. 12, 2013.
U.S. Appl. No. 14/021,777 inventors Flanagan, K., filed Sep. 9, 2013.
U.S. Appl. No. 14/212,189 inventors Dutzar, B. H., filed Mar. 14, 2014.
U.S. Appl. No. 14/340,872 inventors Lowman, H. B., filed Jul. 25, 2014.
U.S. Appl. No. 14/422,207 inventors Igawa, T., filed Aug. 23, 2013.
U.S. Appl. No. 14/423,269 inventors Katada, H., filed Aug. 23, 2013.
U.S. Appl. No. 14/789,329 inventors Andrien, B. A., et al., filed Jan. 7, 2015.
U.S. Appl. No. 15/952,951 inventors Igawa, T., et al., filed Apr. 13, 2018, related application.
U.S. Appl. No. 16/072,696 inventors Natarajan, M., et al., filed Aug. 3, 2019.
U.S. Appl. No. 16/361,498 inventors Igawa, T., et al., filed Mar. 22, 2019, related application.
U.S. Appl. No. 16/480,047 inventors Shinomiya, K., et al., filed Jul. 23, 2019, related application.
U.S. Appl. No. 16/480,765 inventors Sampei, Z., et al., filed Jul. 25, 2019, related application.
U.S. Appl. No. 16/514,467 inventors Ruike, Y., et al., filed Jul. 17, 2019, related application.
U.S. Appl. No. 16/697,310, inventors Igawa, T., et al., filed Nov. 27, 2019, related application.
U.S. Appl. No. 16/806,027 inventors Igawa, T., et al., filed Feb. 3, 2020, related application.
U.S. Appl. No. 16/838,415 inventors Igawa, T., et al., filed Feb. 4, 2020, related application.
U.S. Appl. No. 16/889,066 inventors Ruike, Y., filed Jun. 1, 2020, related application.
U.S. Appl. No. 16/928,129 inventors Shinomiya, K., et al., filed Jul. 14, 2020, related application.
U.S. Appl. No. 16/983,115 inventors Kakehi, T., et al., filed Mar. 8, 2020, related application.
U.S. Appl. No. 17/097,298 inventors Igawa, T., et al., filed Nov. 13, 2020, related application.
U.S. Appl. No. 17/020,543, inventors Igawa, T., et al., filed Sep. 14, 2020, related application.
U.S. Appl. No. 17/263,691, inventors Shinomiya, K., et al., 371 (c) date Jan. 27, 2021, related application.
U.S. Appl. No. 17/333,256, inventors Kakiuchi, A., et al., filed May 28, 2021, related application.
U.S. Appl. No. 15/393,380, inventors Svensson, C., et al., filed Dec. 29, 2016.
U.S. Appl. No. 11/436,266, inventors Chamberlain, A. K., et al., filed May 17, 2006.
U.S. Appl. No. 16/108,897, inventors Igawa, T., et al., filed Aug. 22, 2018.
Declaration of Meiri Kawazoe dated Mar. 21, 2017, submitted by Patentee to European Patent Office on Oct. 13, 2021 in Opposition against EP2708558.
Zwolak, A., et al., "Rapid Purification of Human Bispecific Antibodies via Selective Modulation of Protein A Binding," Scientific Reports, 7:15521 (2017).
Xu, J., ed., Chinese Medicated Bath Encyclopedia—"Take Medicated Bath Without Getting Sick," Golden Shield Press, p. 177 (2013).
Clinical Trial NCT03157635, "Study to Assess Safety, Efficacy, Pharmacokinetics, and Pharmacodynamics of Crovalimab in Healthy Volunteers and Participants With Paroxysmal Nocturnal Hemoglobinuria," Last update posted: Jul. 7, 2021, retrieved Sep. 24, 2021.

(56) References Cited

OTHER PUBLICATIONS

Gershoni, J. M., et al., "Epitope Mapping—The First Step in Developing Epitope-Based Vaccines," Biodrugs, 21(3):145-156 (2007).
Jakubke, et al., "Physicochemical properties," Amino Acids, Peptides and Proteins, Moscow, Mir, 356-363 (1985).
Kharkevich, D. A., Pharmacology (Farmakologia), Moscow, GEOTAR—Media, textbook, $9^{th}$ edition, pp. 39, 63, 568 (2006).
Ramos, I., et al., "Evaluation of CA-125 and soluble CD-23 in patients with pelvic endometriosis: a case-control study," Rev Assoc Med Bras., 58(1):26-32 (1992).
U.S. Appl. No. 17/494,199, filed Oct. 5, 2021, Igawa et al., related application.
U.S. Appl. No. 17/509,128, filed Oct. 28, 2021, Igawa et al., related application.
U.S. Appl. No. 17/602,196, 371 (c) date Oct. 7, 2021, Wakabayashi et al., related application.
U.S. Application No. 17/494,199, filed Oct. 5, 2021, Igawa et al.
U.S. Application No. 17/509,128, filed Oct. 28, 2021, Igawa et al.
U.S. Application No. 17/602,196, 371(c) date Oct. 7, 2021, Wakabayashi et al.

\* cited by examiner

HEAVY CHAIN

```
VH1 : QVQLQESGPGLVKPSETLSLTCAVSGYSIS  HDHAWS  WVRQPPGEGLEWIG  HISYSGITNYNPHLQD
VH2 : QVQLQESGPGLVKPSETLSLTCAVSGYSIS  HDHAWS  WVRQPPGEGLEWIG  HISYSGITNYNPHLQD
VH3 : QVQLQESGPGLVKPSETLSLTCAVSGHSIS  HDHAWS  WVRQPPGEGLEWIG  FISYSGITNYNPSLQG
VH4 : QVQLQESGPGLVKPSETLSLTCAVSGHSIS  HDHAWS  WVRQPPGEGLEWIG  FISYSGITNYNPTLQG
                                *
         FR1                   CDR1      FR2             CDR2
```

```
VH1 : RVTISRDTSKNQFSLKLSSVTAADTAAYYCAR  FLARITANDH  WGEGTLVTVSS
VH2 : RVTISRDTSKNQFSLKLSSVTAADTAVYYCAR  FLARITANDH  WGEGTLVTVSS
VH3 : RVTISRDNSKNTLYLQMNSLRAEDTAVYYCAR  SLARTTANDY  WGEGTLVTVSS
VH4 : RVTISRDNSKNTLYLQMNSLRAEDTAVYYCAR  SLARTTANDY  WGEGTLVTVSS
          *  *** *** ** *  *           *  *  *
         FR3                          CDR3         FR4
```

LIGHT CHAIN

```
VL1 : DIQMTQSPSSLSASVGDSVTITC  QASRDISSHLN  WYQQKPGKAPELLIY  YGSHLLS  GVPSRFSGSGSGTDFTFTISSLEAEDAATYYC  QQGNRLPYT  FGQGTKVEIE
VL2 : DIQMTQSPSSLSASVGDSVTITC  QASRDISSHLN  WYQQKPGKAPELLIY  YGSHLES  GVPSRFSGSGSGTDFTFTISSLEAEDAATYYC  QQGNRLPYT  FGQGTKVEIE
VL3 : DIQMTQSPSSLSASVGDSVTITC  QASTDISSHLN  WYQQKPGKAPELLIY  YGSHLLS  GVPSRFSGSGSGTDFTFTISSLEAEDAATYYC  QQGNRLPYT  FGQGTKVEIE
                                   *                           *
        FR1                   CDR1          FR2           CDR2          FR3                          CDR3        FR4
```

FIG. 25

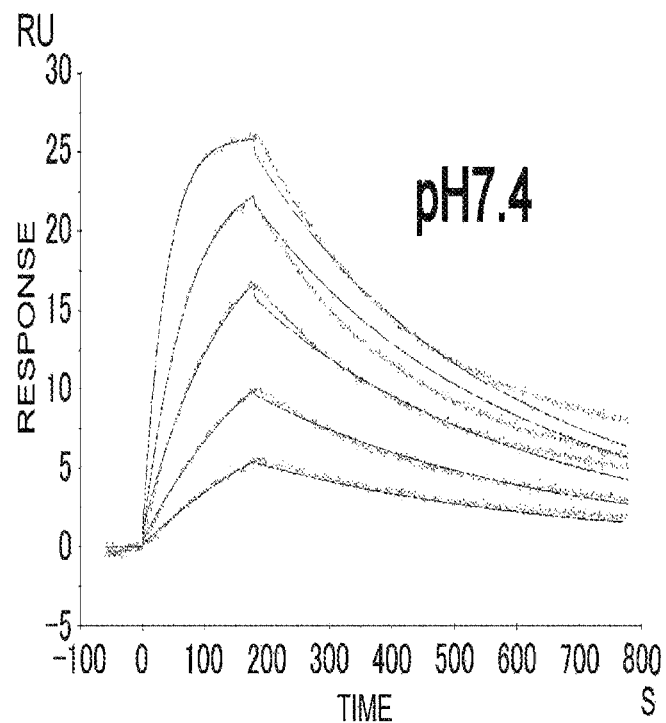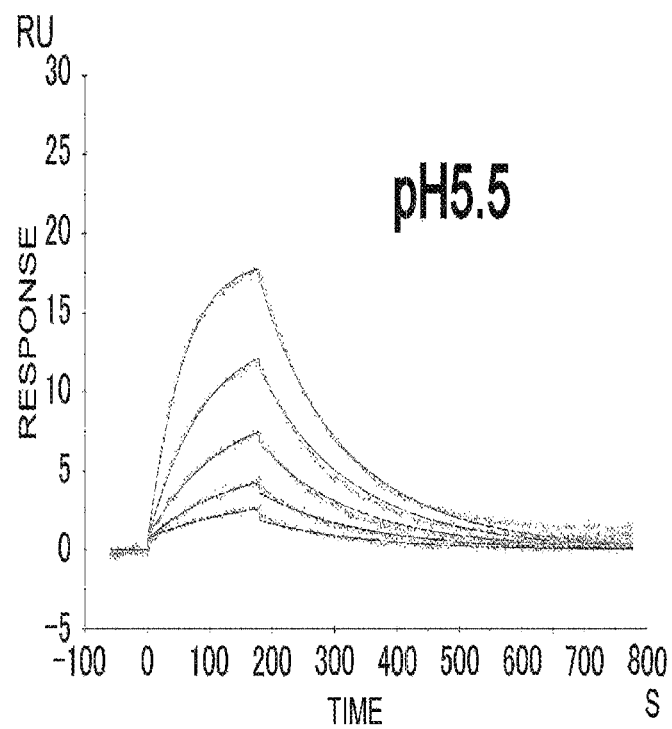
FIG. 26

ANTIGEN-BINDING MOLECULE CAPABLE OF BINDING TWO OR MORE ANTIGEN MOLECULES REPEATEDLY

CROSS-REFERENCE TO RELATED APPLICATIONS

This application is a continuation of U.S. application Ser. No. 15/952,951, filed on Apr. 13, 2018, which is a divisional of U.S. application Ser. No. 13/595,139, filed on Aug. 27, 2012, which is a continuation of U.S. application Ser. No. 12/936,587, having a 371(c) date of Jan. 3, 2011, which is the National Stage of International Application Serial No. PCT/JP2009/057309, filed on Apr. 10, 2009, which claims priority to Japanese Application Nos. 2008-104147, filed on Apr. 11, 2008; 2008-247713, filed on Sep. 26, 2008; and 2009-068744, filed on Mar. 19, 2009, each of which is incorporated herein by reference.

REFERENCE TO SEQUENCE LISTING SUBMITTED ELECTRONICALLY

The content of the electronically submitted sequence listing (Name: 6663_0150_Sequence_Listing.txt; Size: 117 bytes; and Date of Creation: Sep. 11, 2020) filed with the application is incorporated herein by reference in its entirety.

TECHNICAL FIELD

The present invention relates to methods for improving the pharmacokinetics of antigen-binding molecules and methods for increasing the number of times of antigen-binding of antigen-binding molecules, as well as antigen-binding molecules having improved pharmacokinetics, antigen-binding molecules having increased number of times of antigen-binding, and methods for producing such molecules.

BACKGROUND ART

Antibodies are drawing attention as pharmaceuticals as they are highly stable in plasma and have few adverse effects. At present, a number of IgG-type antibody pharmaceuticals are available on the market and many more antibody pharmaceuticals are currently under development (Non-Patent Documents 1 and 2). Meanwhile, various technologies applicable to second-generation antibody pharmaceuticals have been developed, including those that enhance effector function, antigen-binding ability, pharmacokinetics, and stability, and those that reduce the risk of immunogenicity (Non-Patent Document 3). In general, the requisite dose of an antibody pharmaceutical is very high. This, in turn, has led to problems, such as high production cost, as well as the difficulty in producing subcutaneous formulations. In theory, the dose of an antibody pharmaceutical may be reduced by improving antibody pharmacokinetics or improving the affinity between antibodies and antigens.

The literature has reported methods for improving antibody pharmacokinetics using artificial substitution of amino acids in constant regions (Non-Patent Documents 4 and 5). Similarly, affinity maturation has been reported as a technology for enhancing antigen-binding ability or antigen-neutralizing activity (Non-Patent Document 6). This technology enables enhancement of antigen-binding activity by introduction of amino acid mutations into the CDR region of a variable region or such. The enhancement of antigen-binding ability enables improvement of in vitro biological activity or reduction of dosage, and further enables improvement of in vivo efficacy (Non-Patent Document 7).

The antigen-neutralizing capacity of a single antibody molecule depends on its affinity. By increasing the affinity, an antigen can be neutralized by smaller amount of an antibody. Various methods can be used to enhance the antibody affinity. Furthermore, if the affinity could be made infinite by covalently binding the antibody to the antigen, a single antibody molecule could neutralize one antigen molecule (a divalent antibody can neutralize two antigen molecules). However, the stoichiometric neutralization of one antibody against one antigen (one divalent antibody against two antigens) is the limit of pre-existing methods, and thus it is impossible to completely neutralize antigen with the smaller amount of antibody than the amount of antigen. In other words, the affinity enhancing effect has a limit (Non-Patent Document 9). To prolong the neutralization effect of a neutralizing antibody for a certain period, the antibody must be administered at a dose higher than the amount of antigen produced in the body during the same period. With the improvement of antibody pharmacokinetics or affinity maturation technology alone described above, there is thus a limitation in the reduction of the required antibody dose.

Accordingly, in order to sustain antibody's antigen-neutralizing effect for a target period with smaller amount of the antibody than the amount of antigen, a single antibody must neutralize multiple antigens. Methods for neutralizing multiple antigens with a single antibody include antigen inactivation using catalytic antibodies, which are antibodies conferred with a catalytic function. When the antigen is a protein, it can be inactivated by hydrolyzing its peptide bonds. An antibody can repeatedly neutralize antigens by catalyzing such hydrolysis (Non-Patent Document 8). There are many previous reports published on catalytic antibodies and technologies for producing them. However, there have been no reports of catalytic antibodies having sufficient catalytic activity as a pharmaceutical agent. Specifically, in an antibody in vivo study for a certain antigen, there has been no publication of catalytic antibodies which can produce a comparable or stronger effect even at low doses or produce a more prolonged effect even at a same dose as compared to an ordinary non-catalytic neutralizing antibody.

As described above, there have been no reports of antibodies that can produce a more superior in vivo effect than ordinary neutralizing antibodies through a single antibody neutralizing multiple antigen molecules. Thus, from the viewpoint of dose reduction and prolongation of the durability, there is a need for new technologies that permit the production of novel antibody molecules having a stronger in vivo effect than ordinary neutralizing antibodies by individually neutralizing multiple antigen molecules.

Prior art documents related to the present invention are shown below:

PRIOR ART DOCUMENTS

Non-Patent Documents

Non-Patent Document 1: Monoclonal antibody successes in the clinic. Janice M Reichert, Clark J Rosensweig, Laura B Faden & Matthew C Dewitz, Nature Biotechnology 23, 1073-1078 (2005)

Non-Patent Document 2: Pavlou A K, Belsey M J. The therapeutic antibodies market to 2008. Eur J Pharm Biopharm. 2005 April; 59(3):389-96

Non-Patent Document 3: Kim S J, Park Y, Hong H J. Antibody engineering for the development of therapeutic antibodies. Mol Cells. 2005 Aug. 31; 20(1):17-29. Review Non-Patent Document 4: Hinton P R, Xiong J M, Johlfs M G, Tang M T, Keller S, Tsurushita N. An engineered human IgG1 antibody with longer serum half-life. J Immunol. 2006 Jan. 1; 176(1):346-56

Non-Patent Document 5: Ghetie V, Popov S, Borvak J, Radu C, Matesoi D, Medesan C, Ober R J, Ward E S. Increasing the serum persistence of an IgG fragment by random mutagenesis. Nat Biotechnol. 1997 July; 15(7):637-40

Non-Patent Document 6: Rajpal A, Beyaz N, Haber L, Cappuccilli G, Yee H, Bhatt R R, Takeuchi T, Lerner R A, Crea R. A general method for greatly improving the affinity of antibodies by using combinatorial libraries. Proc Natl Acad Sci USA. 2005 Jun. 14; 102(24):8466-71. Epub 2005 Jun. 6

Non-Patent Document 7: Wu H, Pfarr D S, Johnson S, Brewah Y A, Woods R M, Patel N K, White W I, Young J F, Kiener P A. Development of Motavizumab, an Ultra-potent Antibody for the Prevention of Respiratory Syncytial Virus Infection in the Upper and Lower Respiratory Tract. J Mol Biol. 2007, 368, 652-665

Non-Patent Document 8: Hanson C V, Nishiyama Y, Paul S. Catalytic antibodies and their applications. Curr Opin Biotechnol. 2005 December; 16(6):631-6

Non-Patent Document 9: Rathanaswami P, Roalstad S, Roskos L, Su Q J, Lackie S, Babcook J. Demonstration of an in vivo generated sub-picomolar affinity fully human monoclonal antibody to interleukin-8. Biochem Biophys Res Commun. 2005 Sep. 9; 334(4):1004-13

SUMMARY OF THE INVENTION

Problems to be Solved by the Invention

The above noted circumstances led to the discoveries of the present invention. Accordingly, an objective of the present invention is to provide methods for binding antigen-binding molecules to the antigens multiple times and methods for improving the pharmacokinetics of antigen-binding molecules, as well as antigen-binding molecules that are capable of binding to the antigens multiple times, antigen-binding molecules having improved pharmacokinetics, pharmaceutical compositions containing such antigen-binding molecules, and methods for producing such molecules and compositions.

Means for Solving the Problems

Dedicated studies on methods for binding polypeptides having antigen-binding ability, such as antigen-binding molecules, to the antigens multiple times, and methods for improving the half-lives of such molecules in plasma (blood) (improving their pharmacokinetics) were conducted herein. As a result, it was discovered that if the antigen-binding activity of an antigen-binding molecule at the early endosomal pH is lower than its antigen-binding activity at the pH of plasma (blood), it would be able to bind to antigens multiple times and have a longer half-life in plasma.

Accordingly, the present invention relates to methods for binding antigen-binding molecules to antigens multiple times, methods for improving the pharmacokinetics of antigen-binding molecules, and methods for producing antigen-binding molecules with improved pharmacokinetics; the present invention also relates to antigen-binding molecules that are capable of binding to antigens multiple times and antigen-binding molecules with improved pharmacokinetics. More specifically, the present invention provides:

[1] an antigen-binding molecule having a KD(pH5.8)/KD(pH7.4) value, defined as the ratio of KD for the antigen at pH 5.8 and KD for the antigen at pH 7.4, of 2 or higher;

[2] the antigen-binding molecule of [1], wherein the KD(pH5.8)/KD(pH7.4) value is 10 or higher;

[3] the antigen-binding molecule of [1], wherein the KD(pH5.8)/KD(pH7.4) value is 40 or higher;

[4] the antigen-binding molecule of any one of [1] to [3], wherein at least one amino acid of the antigen-binding molecule has been substituted with histidine, or at least one histidine has been inserted into the antigen-binding molecule;

[5] the antigen-binding molecule of any one of [1] to [4], wherein the antigen-binding molecule has an antagonistic activity;

[6] the antigen-binding molecule of any one of [1] to [5], wherein the antigen-binding molecule binds to a membrane antigen or a soluble antigen;

[7] the antigen-binding molecule of any one of [1] to [6], wherein the antigen-binding molecule is an antibody;

[8] a pharmaceutical composition comprising the antigen-binding molecule of any one of [1] to [7];

[9] a method for improving the pharmacokinetics of an antigen-binding molecule by impairing the antigen-binding activity of the antigen-binding molecule at pH 5.8 as compared to that at pH 7.4;

[10] a method for increasing the number of times of antigen-binding for an antigen-binding molecule by impairing the antigen-binding activity of the antigen-binding molecule at pH 5.8 as compared to that at pH 7.4;

[11] a method for increasing the number of antigens that can be bound by an antigen-binding molecule by impairing the antigen-binding activity of the antigen-binding molecule at pH 5.8 as compared to that at pH 7.4;

[12] a method for dissociating within a cell an antigen from an extracellularly-bound antigen-binding molecule by impairing the antigen-binding activity of the antigen-binding molecule at pH 5.8 as compared to that at pH 7.4;

[13] a method for releasing an antigen-binding molecule, which has been bound to an antigen and internalized into a cell, in an antigen-free form to the outside of the cell by impairing the antigen-binding activity of the antigen-binding molecule at pH 5.8 as compared to that at pH 7.4;

[14] a method for increasing the ability of an antigen-binding molecule to eliminate an antigen in plasma by impairing the antigen-binding activity of the antigen-binding molecule at pH 5.8 as compared to that at pH 7.4;

[15] the method of any one of [9] to [14], wherein the KD(pH5.8)/KD(pH7.4) value, defined as the ratio of KD for the antigen at pH 5.8 and KD for the antigen at pH 7.4, is 2 or higher;

[16] the method of any one of [9] to [14], wherein the KD(pH5.8)/KD(pH7.4) value is 10 or higher;

[17] the method of any one of [9] to [14], wherein the KD(pH5.8)/KD(pH7.4) value is 40 or higher;

[18] a method for improving the pharmacokinetics of an antigen-binding molecule by substituting at least one amino acid of the antigen-binding molecule with histidine, or inserting at least one histidine into the antigen-binding molecule;

[19] a method for increasing the number of times of antigen-binding for an antigen-binding molecule by substituting at least one amino acid of the antigen-binding molecule with histidine, or inserting at least one histidine into the antigen-binding molecule;

[20] a method for increasing the number of antigens that can be bound by an antigen-binding molecule by substituting at least one amino acid of the antigen-binding molecule with histidine, or inserting at least one histidine into the antigen-binding molecule;

[21] a method for dissociating within a cell an antigen from an extracellularly-bound antigen-binding molecule by substituting at least one amino acid of the antigen-binding molecule with histidine, or inserting at least one histidine into the antigen-binding molecule;

[22] a method for releasing an antigen-binding molecule, which has been bound to an antigen and internalized into a cell, in an antigen-free form to the outside of the cell, by substituting at least one amino acid of the antigen-binding molecule with histidine, or inserting at least one histidine into the antigen-binding molecule;

[23] a method for increasing the ability of an antigen-binding molecule to eliminate an antigen in plasma by substituting at least one amino acid of the antigen-binding molecule with histidine, or inserting at least one histidine into the antigen-binding molecule;

[24] the method of any one of [18] to [23], wherein the histidine substitution or insertion increases the KD(pH5.8)/KD(pH7.4) value, defined as the ratio of the antigen-binding activity at pH 5.8 and the antigen-binding activity at pH 7.4, as compared to the KD(pH5.8)/KD(pH7.4) value before the histidine substitution or insertion;

[25] the method of any one of [9] to [24], wherein the antigen-binding molecule has an antagonistic activity;

[26] the method of any one of [9] to [25], wherein the antigen-binding molecule binds to a membrane antigen or a soluble antigen;

[27] the method of any one of [9] to [26], wherein the antigen-binding molecule is an antibody;

[28] a method of screening for an antigen-binding molecule, which comprises the steps of:
  (a) determining the antigen-binding activity of an antigen-binding molecule at pH 6.7 to pH 10.0;
  (b) determining the antigen-binding activity of the antigen-binding molecule at pH 4.0 to pH 6.5; and
  (c) selecting an antigen-binding molecule whose antigen-binding activity at pH 6.7 to pH 10.0 is greater than the antigen-binding activity at pH 4.0 to pH 6.5;

[29] the screening method of [28], which comprises the step of selecting an antibody whose antigen-binding activity at pH 6.7 to pH 10.0 is twice or higher that of the antigen-binding activity at pH 4.0 to pH 6.5;

[30] a method of screening for an antigen-binding molecule, which comprises the steps of:
  (a) binding an antigen-binding molecule to an antigen under a condition of pH 6.7 to pH 10.0;
  (b) placing the antigen-binding molecule that bound to the antigen of (a) under a condition of pH 4.0 to pH 6.5; and
  (c) obtaining an antigen-binding molecule that dissociated under the condition of pH 4.0 to pH 6.5;

[31] a method of screening for an antigen-binding molecule whose binding activity at a first pH is greater than that at a second pH, which comprises the steps of:
  (a) binding an antigen-binding molecule to an antigen-immobilized column under the condition of a first pH;
  (b) eluting the antigen-binding molecule that had bound to the column at the first pH from the column under the condition of a second pH; and
  (c) collecting the eluted antigen-binding molecule;

[32] a method of screening for an antigen-binding molecule whose binding activity at a first pH is greater than that at a second pH, which comprises the steps of:
  (a) binding an antigen-binding molecule library to an antigen-immobilized column under the condition of a first pH;
  (b) eluting the antigen-binding molecule from the column under the condition of a second pH;
  (c) amplifying the gene encoding the eluted antigen-binding molecule; and
  (d) obtaining the eluted antigen-binding molecule.

[33] the screening method of [31] or [32], wherein the first pH is 6.7 to 10.0 and the second pH is 4.0 to 6.5;

[34] the screening method of any one of [28] to [33], wherein at least one or more amino acids of the antigen-binding molecule has been substituted with histidine, or at least one histidine has been inserted into the antigen-binding molecule;

[35] the screening method of any one of [28] to [33], for obtaining an antigen-binding molecule that is superior in retention in the plasma;

[36] the screening method of any one of [28] to [33], for obtaining an antigen-binding molecule that is capable of binding to an antigen two or more times;

[37] the screening method of any one of [28] to [33], for obtaining an antigen-binding molecule that is capable of binding to more antigens as compared to the number of its antigen-binding sites;

[38] the screening method of any one of [28] to [33], for obtaining an antigen-binding molecule that dissociates an extracellularly-bound antigen within a cell.

[39] the screening method of any one of [28] to [33], for obtaining an antigen-binding molecule that is bound to an antigen and internalized into a cell, and released to the outside of the cell in an antigen-free form;

[40] the screening method of any one of [28] to [33], for obtaining an antigen-binding molecule that has increased ability to eliminate an antigen in plasma;

[41] the screening method of any one of [28] to [40], wherein the antigen-binding molecule is used as a pharmaceutical composition;

[42] the screening method of any one of [28] to [41], wherein the antigen-binding molecule is an antibody;

[43] a method for producing an antigen-binding molecule, which comprises the steps of:
  (a) determining the antigen-binding activity of an antigen-binding molecule at pH 6.7 to pH 10.0;
  (b) determining the antigen-binding activity of the antigen-binding molecule at pH 4.0 to pH 6.5;
  (c) selecting the antigen-binding molecule whose antigen-binding activity at pH 6.7 to pH 10.0 is greater than that at pH 4.0 to pH 6.5;
  (d) obtaining the gene encoding the antigen-binding molecule selected in (c); and
  (e) producing the antigen-binding molecule using the gene obtained in (d);

[44] a method for producing an antigen-binding molecule, which comprises the steps of:
  (a) binding an antigen-binding molecule to an antigen under a condition of pH 6.7 to pH 10.0;
  (b) allowing the antigen-binding molecule bound to the antigen of (a) to stand under a condition of pH 4.0 to pH 6.5;
  (c) collecting the antigen-binding molecule that dissociated under the condition of pH 4.0 to pH 6.5;
  (d) obtaining the gene encoding the antigen-binding molecule obtained in (c); and
  (e) producing the antigen-binding molecule using the gene obtained in (d);
[45] a method for producing an antigen-binding molecule whose binding activity at a first pH is greater than that at a second pH, which comprises the steps of:
  (a) binding an antigen-binding molecule to an antigen-immobilized column under the first pH condition;
  (b) eluting the antigen-binding molecule, which is bound to the column at the first pH, from the column under a second pH condition;
  (c) collecting the eluted antigen-binding molecule;
  (d) obtaining the gene encoding the antigen-binding molecule obtained in (c); and
  (e) producing the antigen-binding molecule using the gene obtained in (d);
[46] a method for producing an antigen-binding molecule whose binding activity at a first pH is greater than that at a second pH, which comprises the steps of:
  (a) binding an antigen-binding molecule library to an antigen-immobilized column under the first pH condition;
  (b) eluting the antigen-binding molecule from the column under the second pH condition;
  (c) amplifying the gene encoding the eluted antigen-binding molecule;
  (d) collecting the eluted antigen-binding molecule;
  (e) obtaining the gene encoding the antigen-binding molecule collected in (d); and
  (f) producing the antigen-binding molecule using the gene obtained in (e);
[47] the production method of [45] or [46], wherein the first pH is 6.7 to 10.0 and the second pH is 4.0 to 6.5.
[48] the production method of any one of [43] to [47], which further comprises the step of substituting at least one amino acid of the antigen-binding molecule with histidine, or inserting at least one histidine into the antigen-binding molecule;
[49] the production method of any one of [43] to [48], wherein the antigen-binding molecule is an antibody;
[50] a pharmaceutical composition comprising an antigen-binding molecule produced by the production method of any one of [43] to [49].

Effects of the Invention

The present invention provides methods for making single antigen-binding molecules to repeatedly bind to multiple antigen molecules. When an antigen-binding molecule binds to multiple antigen molecules, the pharmacokinetics of the antigen-binding molecule can be improved and such molecule can exert more superior in vivo effects than those of ordinary antigen-binding molecules.

BRIEF DESCRIPTION OF THE DRAWINGS

FIG. 25 is a diagram depicting FR1, FR2, FR3, and FR4 along with CDR1, CDR2, and CDR3 of heavy chains (VH1, VH2, VH3, VH4) and light chains (VL1, VL2, VL3). Asterisks indicate locations where amino acid mutations exist in the aligned sequences.

FIG. 26 presents Biacore™ sensorgrams depicting the pH-dependent binding of an anti-IL-6 antibody, Anti-IL6 clone 2, to IL-6 at pH 7.4 and pH 5.5. The curves in the sensorgram at pH 7.4 correspond to 100, 50, 25, 12.5, and 6.25 ng/mL IL-6, from above.

MODE FOR CARRYING OUT THE INVENTION

Figure 1:
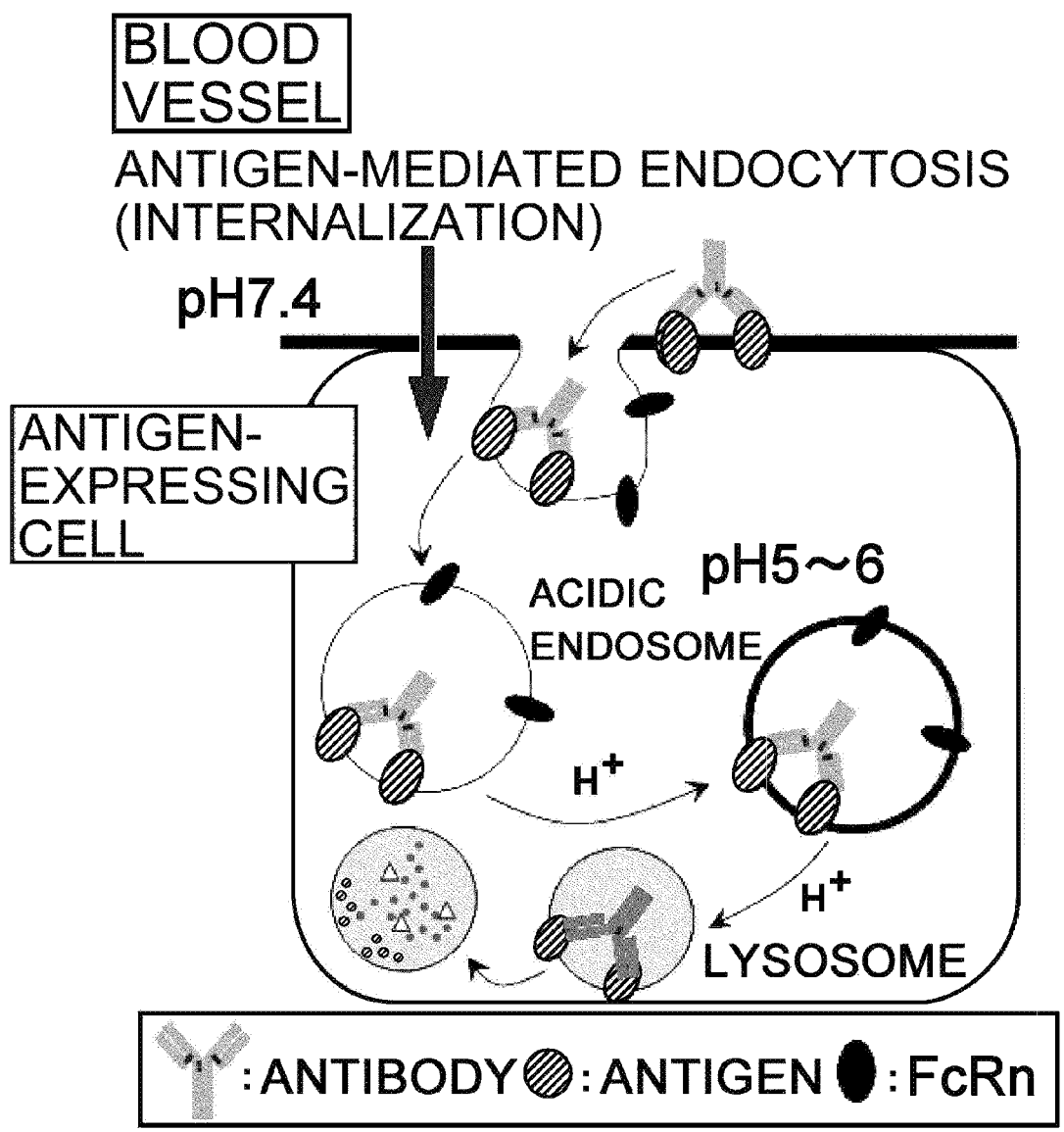
FIG. 1 is a diagram depicting a degradation pathway of antibodies bound to membrane-bound antigen.

The present invention provides methods for increasing the number of times of antigen-binding in antigen-binding molecules. More specifically, the present invention provides methods for increasing the number of times of antigen-binding in antigen-binding molecules by impairing the antigen-binding ability of the antigen-binding molecules at acidic pH as compared to that at neutral pH. Furthermore, the present invention provides methods for increasing the number of times of antigen-binding in antigen-binding molecules by substituting histidine for at least one amino acid in the antigen-binding molecules or inserting at least one histidine into the antigen-binding molecules. In addition, the present invention provides methods for increasing the number of times of antigen-binding in antigen-binding molecules by substituting, deleting, adding, and/or inserting amino acids in the antibody constant region of antigen-binding molecules.

The present invention also provides methods for increasing the number of antigens that can be bound by an antigen-binding molecule. More specifically, the present invention provides methods for increasing the number of antigens that can be bound by an antigen-binding molecule by impairing the antigen-binding ability at acidic pH as compared to that at neutral pH. Furthermore, the present invention provides methods for increasing the number of antigens that can be bound by an antigen-binding molecule by substituting histidine for at least one amino acid in the antigen-binding molecules or inserting at least one histidine into the antigen-binding molecules. In addition, the present invention provides methods for increasing the number of antigens that can be bound by an antigen-binding molecule through substituting, deleting, adding, and/or inserting amino acids in the antibody constant region of antigen-binding molecules.

The present invention also provides methods for dissociating within a cell an antigen from an extracellularly-bound antigen-binding molecule. More specifically, the present invention provides methods for dissociating within a cell an antigen from an extracellularly-bound antigen-binding molecule by impairing the antigen-binding ability at acidic pH as compared to that at neutral pH. Furthermore, the present invention provides methods for dissociating within a cell an antigen from an extracellularly-bound antigen-binding molecule by substituting histidine for at least one amino acid in the antigen-binding molecule or inserting at least one histidine into the antigen-binding molecule. In addition, the present invention provides methods for dissociating within a cell an antigen from an extracellularly-bound antigen-binding molecule through substituting, deleting, adding, and/or inserting amino acids in the antibody constant region of antigen-binding molecule.

The present invention also provides methods for releasing an antigen-binding molecule, which has been bound to an antigen and internalized into a cell, in an antigen-free form to the outside of the cell. More specifically, the present invention provides methods for releasing an antigen-binding molecule, which has been bound to an antigen and internalized into a cell, in an antigen-free form to the outside of the cell, by impairing the antigen-binding ability at acidic pH as compared to that at neutral pH. Furthermore, the present invention provides methods for releasing an antigen-binding molecule, which has been bound to an antigen and internalized into a cell, in an antigen-free form to the outside of the cell, by substituting histidine for at least one amino acid in the antigen-binding molecule or inserting at least one histidine into the antigen-binding molecule. In addition, the present invention provides methods for releasing an antigen-binding molecule, which has been bound to an antigen and internalized into a cell, in an antigen-free form to the outside of the cell, through substituting, deleting, adding, and/or inserting amino acids in the antibody constant region of antigen-binding molecule.

The present invention also provides methods for increasing the ability of an antigen-binding molecule to eliminate antigens in plasma. More specifically, the present invention provides methods for increasing the ability of an antigen-binding molecule to eliminate antigens in plasma by impairing the antigen-binding ability at acidic pH as compared to that at neutral pH. Furthermore, the present invention provides methods for increasing the ability of an antigen-binding molecule to eliminate antigens in plasma by substituting histidine for at least one amino acid in the antigen-binding molecules or inserting at least one histidine into the antigen-binding molecules. In addition, the present invention provides methods for increasing the ability of an antigen-binding molecule to eliminate antigens in plasma through substituting, deleting, adding, and/or inserting amino acids in the antibody constant region of antigen-binding molecule.

The present invention also provides methods for improving the pharmacokinetics of antigen-binding molecules. More specifically, the present invention provides methods for improving the pharmacokinetics of antigen-binding molecules (prolonging the retention in plasma) by impairing the antigen-binding ability at acidic pH as compared to that at neutral pH. Furthermore, the present invention provides methods for improving the pharmacokinetics of antigen-binding molecules by substituting histidine for at least one amino acid in the antigen-binding molecules or inserting at least one histidine into the antigen-binding molecules. In addition, the present invention provides methods for improving the pharmacokinetics of antigen-binding molecules by substituting, deleting, adding, and/or inserting amino acids in the antibody constant region of antigen-binding molecules.

Further, the present invention provides methods for increasing the ability of the antigen-binding molecules to eliminate antigens in plasma. More specifically, the present invention provides methods for increasing the ability of the antigen-binding molecules to eliminate antigens in plasma by impairing the antigen-binding ability of the antigen-binding molecules at acidic pH as compared to that at neutral pH. Furthermore, the present invention provides methods for increasing the ability of the antigen-binding molecules to eliminate antigens in plasma by substituting at least one amino acid in the antigen-binding molecules with histidine or inserting at least one histidine into the antigen-binding molecules. In addition, the present invention provides methods for increasing the ability of the antigen-binding molecules to eliminate antigens in plasma by substituting, deleting, adding, and/or inserting amino acids in the antibody constant region of antigen-binding molecules.

Herein, "improvement of the pharmacokinetics", "amelioration of the pharmacokinetics", "superior pharmacokinetics" are interchangeable with "improvement of the retention in plasma (blood)", "amelioration of the retention in plasma (blood)", and "superior retention in plasma (blood)", respectively, and these phrases are synonymous.

Herein, impairing the antigen-binding activity at acidic pH as compared to that at neutral pH means that the antigen-binding ability of an antigen-binding molecule at pH 4.0 to pH 6.5 is impaired as compared to that at pH 6.7 to pH 10.0, preferably that the antigen-binding activity of an antigen-binding molecule at pH 5.5 to pH 6.5 is impaired as compared to that at pH 7.0 to pH 8.0, and more preferably that the antigen-binding activity of an antigen-binding molecule at pH 5.8 is impaired as compared to that at pH 7.4. Accordingly, in the present invention, acidic pH is typically pH 4.0 to pH 6.5, preferably pH 5.5 to pH 6.5, and more preferably pH 5.8. Alternatively, in the present invention, neutral pH is typically pH 6.7 to pH 10.0, preferably pH 7.0 to pH 8.0, and more preferably pH 7.4.

Herein, the phrase "impairing the antigen-binding ability of an antigen-binding molecule at acidic pH as compared to that at neutral pH" is interchangeable with the phrase "increasing the antigen-binding ability of an antigen-binding molecule at neutral pH as compared to that at acidic pH". In other words, in the present invention, the difference in the antigen-binding ability of an antigen-binding molecule should be increased between acidic and neutral pHs. For example, the value of KD(pH5.8)/KD(pH7.4) should be increased, as described below. The difference in the antigen-binding ability of an antigen-binding molecule between acidic and neutral pHs may be increased, for example, by either or both, impairing the antigen-binding ability at acidic pH and increasing the antigen-binding ability at neutral pH.

Conditions other than the pH for determining the antigen-binding activity can be selected appropriately by those skilled in the art, and the conditions are not particularly limited. The antigen-binding activity can be determined, for example, under conditions of MES buffer and 37° C. as described in the Examples herein. Furthermore, the antigen-binding activity of an antigen-binding molecule can be determined by methods known to those skilled in the art, for example, using a Biacore™ surface plasmon resonance system (GE Healthcare) or the like, as described in the Examples herein. When the antigen is a soluble antigen, the activity of binding to the soluble antigen can be assessed by injecting the antigen as an analyte onto a chip immobilized with the antigen-binding molecule. Alternatively, when the antigen is a membrane antigen, the activity of binding to the membrane antigen can be assessed by injecting the antigen-binding molecule as an analyte onto an antigen-immobilized chip.

In the present invention, the difference in the antigen-binding activity between acidic and neutral pHs is not particularly limited as long as the antigen-binding activity at acidic pH is lower than that at neutral pH. However, the value of KD(pH5.8)/KD(pH7.4), which is a ratio of dissociation constant (KD) against an antigen at pH 5.8 and that at pH 7.4, is preferably 2 or greater, more preferably 10 or greater, and still more preferably 40 or greater. The upper limit of KD(pH5.8)/KD(pH7.4) value is not particularly limited, and may be any value, for example, 400, 1,000, or 10,000, as long as the molecule can be produced by technologies of those skilled in the art. When the antigen is a soluble antigen, the antigen-binding activity can be presented in terms of the dissociation constant (KD). Alternatively, when the antigen is a membrane antigen, the antigen-binding activity can be presented in terms of the apparent dissociation constant. The dissociation constant (KD) and apparent dissociation constant (apparent KD) can be determined by methods known to those skilled in the art, for example, using a Biacore™ surface plasmon resonance system (GE Healthcare), Scatchard plot, or FACS.

Alternatively, it is possible to use, for example, kd, a dissociation rate constant, as an indicator for the difference in the antigen-binding activity between acidic and neutral pHs. When the dissociation rate constant (kd) is used as an indicator for the difference in the binding activity instead of the dissociation constant (KD), the value of kd(pH5.8)/kd(pH7.4), which is a ratio of dissociation rate constant (kd) against an antigen at pH 5.8 and that at pH 7.4, is preferably 2 or greater, more preferably 5 or greater, even more preferably 10 or greater, and still more preferably 30 or greater. The upper limit of kd(pH5.8)/kd(pH7.4) value is not particularly limited, and may be any value, for example, 50, 100, or 200, as long as the molecule can be produced by technologies common to those skilled in the art.

When the antigen is a soluble antigen, the antigen-binding activity can be presented in terms of the dissociation rate constant (kd). Alternatively, when the antigen is a membrane antigen, the antigen-binding activity can be presented in terms of the apparent dissociation rate constant. The dissociation rate constant (kd) and apparent dissociation rate constant (apparent kd) can be determined by methods known to those skilled in the art, for example, using a Biacore™ surface plasmon resonance system (GE Healthcare) or FACS.

In the present invention, when the antigen-binding activity of an antigen-binding molecule is determined at different pHs, it is preferred that the measurement conditions except for pH are constant.

The methods for impairing the antigen-binding activity of an antigen-binding molecule at pH 5.8 as compared to that at pH 7.4 (methods for conferring the pH-dependent binding ability) are not particularly limited and may be any methods. Such methods include, for example, methods for impairing the antigen-binding activity at pH 5.8 as compared to that at pH 7.4 by substituting histidine for amino acids in the antigen-binding molecule or inserting histidine into the antigen-binding molecule. It is already known that an antibody can be conferred with a pH-dependent antigen-binding activity by substituting histidine for amino acids in the antibody (FEBS Letter, 309(1), 8588 (1992)). Such histidine mutation (substitution) or insertion sites are not particularly limited, and any site is acceptable as long as the antigen-binding activity at pH 5.8 is lowered than that at pH 7.4 (the value of KD(pH5.8)/KD(pH7.4) gets greater) as compared to before mutation or insertion. When the antigen-binding molecule is an antibody, such sites include, for example, sites within an antibody variable region. The appropriate number of histidine mutation or insertion sites can be appropriately determined by those skilled in the art. Histidine may be substituted or inserted at a single site, or two or more sites. It is also possible to introduce non-histidine mutation (mutation with amino acids other than histidine) at the same time. Furthermore, histidine mutation may be introduced simultaneously with histidine insertion. It is possible to substitute or insert histidine at random using a method such as histidine scanning, which uses histidine instead of alanine in alanine scanning known to those skilled in the art. Alternatively, antigen-binding molecules whose KD(pH5.8)/KD(pH7.4) is increased as compared to before mutation can be selected from an antigen-binding molecule library with random histidine mutation or insertion.

When histidine is substituted for amino acids of an antigen-binding molecule or inserted between amino acids of the molecule, it is preferred, but not required, that the antigen-binding activity of the antigen-binding molecule at pH 7.4 after histidine substitution or insertion is comparable to that at pH 7.4 before histidine substitution or insertion. The "antigen-binding activity of the antigen-binding molecule at pH 7.4 after histidine substitution or insertion is comparable to that at pH 7.4 before histidine substitution or insertion" means that even after histidine substitution or insertion, the antigen-binding molecule retains 10% or more, preferably 50% or more, more preferably 80% or more, and still more preferably 90% or more of the antigen-binding activity of before histidine substitution or insertion. When the antigen-binding activity of the antigen-binding molecule has been impaired due to histidine substitution or insertion, the antigen-binding activity may be adjusted by introducing substitution, deletion, addition, and/or insertion of one or more amino acids into the antigen-binding molecule so that the antigen-binding activity becomes comparable to that before histidine substitution or insertion. The present invention also includes such antigen-binding molecules having a comparable binding activity as a result of substitution, deletion, addition, and/or insertion of one or more amino acids after histidine substitution or insertion.

Alternative methods for impairing the antigen-binding activity of an antigen-binding molecule at pH 5.8 as compared to that at pH 7.4 include methods of substituting non-natural amino acids for amino acids in an antigen-binding molecule or inserting non-natural amino acids into amino acids of an antigen-binding molecule. It is known that the pKa can be artificially controlled using non-natural amino acids (Angew. Chem. Int. Ed. 2005, 44, 34; Chem Soc Rev. 2004 Sep. 10; 33(7):422-30; Amino Acids. 1999; 16(3-4):345-79). Thus, in the present invention, non-natural amino acids can be used instead of histidine described above. Such non-natural amino acid substitution and/or insertion may be introduced simultaneously with the histidine substitution and/or insertion described above. Any non-natural amino acids may be used in the present invention. It is possible to use non-natural amino acids known to those skilled in the art.

Furthermore, when the antigen-binding molecule is a substance having an antibody constant region, alternative methods for impairing the antigen-binding activity of the antigen-binding molecule at pH 5.8 as compared to that at pH 7.4 include methods for modifying the antibody constant region contained in the antigen-binding molecule. Such methods for modifying the antibody constant region include, for example, methods for substituting a constant region described in the Examples herein.

Alternative methods for modifying the antibody constant region include, for example, methods to assess various constant region isotypes (IgG1, IgG2, IgG3, and IgG4) and select an isotype that impairs the antigen-binding activity at pH 5.8 (increases the dissociation rate at pH 5.8). Alternatively, methods include those for impairing the antigen-binding activity at pH 5.8 (increasing the dissociation rate at pH 5.8) by substituting amino acids in the amino acid sequence of a wild-type isotype (the amino acid sequence of wild type IgG1, IgG2, IgG3, or IgG4). The sequence of the hinge region of an antibody constant region is considerably different among isotypes (IgG1, IgG2, IgG3, and IgG4), and the difference in the hinge region amino acid sequence has a great impact on the antigen-binding activity. Thus, it is possible to select an appropriate isotype to impair the antigen-binding activity at pH 5.8 (to increase the dissociation rate at pH 5.8) by considering the type of antigen or epitope. Furthermore, since the difference in the hinge region amino acid sequence has a significant influence on the antigen-binding activity, preferred amino acid substitution sites in the amino acid sequence of a wild type isotype are assumed to be within the hinge region.

When the antigen-binding activity of the antigen-binding substance at pH 5.8 is weakened compared to that at pH 7.4 (when KD(pH5.8)/KD(pH7.4) value is increased) by the above described methods and such, it is generally preferable that the KD(pH5.8)/KD(pH7.4) value be two times or more, more preferably five times or more, and even more preferably ten times or more as compared to that of the original antibody, although the invention is not particularly limited thereto.

Herein, the "improvement of the pharmacokinetics" means prolongation of the time required for the elimination of the antigen-binding molecule from plasma (for example, reaching the state where the antigen-binding molecule cannot return to the plasma due to degradation in cells, or other reasons) after administration to an animal such as human, mouse, rat, monkey, rabbit, or dog, as well as prolongation of the plasma retention time of the antigen-binding molecule being in a form capable of binding to antigens (for example, being in an antigen-free form) during the period until it is eliminated from the plasma after administration. Even if an antigen-binding molecule is circulated in plasma, it cannot bind to an antigen when it already binds to another antigen. Accordingly, the period where the antigen-binding molecule can newly binds to another antigen is prolonged (the chance to bind another antigen increases) by prolonging the period where the antigen-binding molecule is in an antigen-free form. This makes it possible to shorten the period where the antigen is free from antigen-binding molecules in vivo (in other words, to prolong the period where the antigen is bound by an antigen-binding molecule). For example, the ratio of antigens bound to antigen-binding molecules against the antigens in the body in plasma (total of antigen molecules bound to and free from the antigen-binding molecules) generally decreases in a certain period of time after the administration of the antigen-binding molecules. However, such decrease can be suppressed (for example, the degree of decrease can be made smaller) by prolonging the retention time of the antigen-binding molecules in a form capable of binding to antigens. This results in an increase in the ratio of antigens bound to antigen-binding molecules against the antigens in the body in a certain period of time after antibody administration.

Specifically, in the present invention, the "improvement of the pharmacokinetics" does not necessarily mean the prolongation (extension) of the time required for the elimination of the antigen-binding molecule after administration. Even if the time required for the elimination of the antigen-binding molecule after administration remains unchanged, the pharmacokinetics can be said "improved" in the present invention if the plasma retention time of the antigen-binding molecule being in a form capable of binding to an antigen (for example, the antigen-binding molecule being in an antigen-free form) is prolonged;
the period where the antigen is free from an antigen-binding molecule in the body is shortened (in other words, the period where the antigen-binding molecule is bound to an antigen is prolonged); and the ratio of antigens bound to antigen-binding molecules against the antigens in the body is increased. Thus, in the present invention, the "improvement of the pharmacokinetics" encompasses at least:

(1) prolongation of the time required for the elimination of the antigen-binding molecule from plasma after administration of the antigen-binding molecule;
(2) prolongation of the plasma retention time of the antigen-binding molecule in a form capable of binding to an antigen after administration of the antigen-binding molecule;
(3) shortening of the period where the antigen is free from an antigen-binding molecule in the body after administration of the antigen-binding molecule (prolongation of the period where the antigen-binding molecule is bound to an antigen in the body); and
(4) increase in the ratio of antigens bound to antigen-binding molecules to the antigen in the body.

When the antigen is a soluble antigen present in plasma, even if the pharmacokinetics of the antigen-binding molecule (rate of elimination from plasma) is equivalent, there are cases where elimination of antigen bound to the antigen-binding molecule is accelerated. Reducing the pharmacokinetics of the antigen (accelerating elimination from plasma) results in the relative improvement of the pharmacokinetics of the antigen-binding molecule, and thus, leads to the prolongation of the time of the antigen-binding molecule present in plasma in a form capable of binding to antigens. Thus, in one embodiment, the "improvement of the pharmacokinetics" of antigen-binding molecules of the present invention includes increasing the rate of eliminating soluble antigens from plasma after administration of the antigen-binding molecules (the ability of the antigen-binding molecule to eliminate antigens from plasma).

In the present invention, when the antigen is a membrane antigen, whether a single antigen-binding molecule binds to multiple antigens can be assessed by testing whether the pharmacokinetics of the antigen-binding molecule is improved. Whether the "pharmacokinetics is improved" can be assessed by the following method. For example, whether the time required for the elimination of an antigen-binding molecule after administration is prolonged can be assessed by determining any one of parameters for the antigen-binding molecule, such as half-life in plasma, mean plasma retention time, and clearance in plasma ("Pharmacokinetics: Enshu-niyoru Rikai (Understanding through practice)" Nanzando). For example, when the half-life in plasma or mean plasma retention time of an antigen-binding molecule administered to mice, rats, monkeys, rabbits, dogs, humans, or other animals is prolonged, the pharmacokinetics of the antigen-binding molecule is judged to be improved. These parameters can be determined by methods known to those skilled in the art. For example, the parameters can be appropriately assessed by noncompartmental analysis using pharmacokinetics analysis software WinNonlin (Pharsight) according to the appended instruction manual.

Alternatively, whether the plasma retention time of an antigen-binding molecule in a form capable of binding to antigens after administration of the antigen-binding molecule is prolonged can be assessed by measuring the plasma concentration of the antigen-free antigen-binding molecule and determining any one of parameters for the antigen-free antigen-binding molecule, such as half-life in plasma, mean plasma retention time, and clearance in plasma. The concentration of the antigen-free antigen-binding molecule in plasma can be measured by methods known to those skilled in the art. For example, such measurements are described in Clin Pharmacol. 2008 April; 48(4):406-17.

Furthermore, whether the period where an antigen is free from the antigen-binding molecules in the body after administration of the antigen-binding molecules is shortened (the period where the antigen-binding molecule is bound to an antigen in the body is prolonged) can be assessed by determining the plasma concentration of the unbound antigen that is free from antigen-binding molecules, and considering the period where the concentration of free antigen in plasm or the amount ratio of free antigen against the total antigen remains low. The plasma concentration of the free antigen or amount ratio of free antigen against total antigen can be determined by methods known to those skilled in the art. For example, such measurements are described in Pharm Res. 2006 January; 23(1):95-103. Alternatively, when the antigen exerts some function in vivo, whether the antigen is bound by an antigen-binding molecule that neutralizes the antigen's function (antagonistic molecule) can be assessed by testing whether the function of the antigen is neutralized. Whether the function of the antigen is neutralized can be assessed by assaying an in vivo marker that reflects the function of the antigen. Whether the antigen is bound by an antigen-binding molecule that activates the function of the antigen (agonistic molecule) can be assessed by assaying an in vivo marker that reflects the function of the antigen.

There is no particular limitation on the determination of the plasma concentration of free antigen and amount ratio of free antigen against total antigen, and in vivo marker assay, but the determination is preferably carried out after a certain period following administration of an antigen-binding substance. In the present invention, such a period following administration of an antigen-binding substance is not particularly limited, and an appropriate period can be determined by those skilled in the art depending on the properties of the administered antigen-binding substance and the like. Examples of the period are: one day after administration of an antigen-binding substance; three days after administration of an antigen-binding substance, seven days after administration of an antigen-binding substance, 14 days after administration of an antigen-binding substance, and 28 days after administration of an antigen-binding substance.

In the present invention, it is preferred to improve the pharmacokinetics in human. Even when the plasma retention in human is difficult to determine, it can be predicted based on the plasma retention in mice (for example, normal mice, human antigen-expressing transgenic mice, and human FcRn-expressing transgenic mice) or monkeys (for example, cynomolgus monkeys).

Methods for determining the retention in plasma are not particularly limited. The determination can be carried out, for example, according to the methods described in the Examples herein.

Whether an antigen-binding molecule is capable of binding to antigens multiple times can be assessed by testing whether the antigen bound to an antigen-binding molecule under the same neutral condition as plasma dissociates under the same acidic condition as endosome and how many antigens the antigen-binding molecule can rebind to under the neutral condition. Specifically, the assessment can be carried out by allowing the antigen-binding molecule and antigen to form a complex under the neutral condition, exposing the complex to an acidic condition for a predetermined period, and then testing whether the antigen-binding molecule can rebind to an antigen under the neutral condition, using a device for assaying antigen-binding molecule-antigen reactions, such as a Biacore™ surface plasmon resonance system. When the antigen-binding capacity of the antigen-binding molecule conferred with the pH-dependent binding ability has been improved to twice that of the antigen-binding molecule before modification, the number of times of binding of the antigen-binding molecule conferred with the pH-dependent binding ability can be judged to be increased to twice that of the antigen-binding molecule before modification. Alternatively, when the antigen is a membrane antigen and thus the antigen-binding molecule is eliminated from plasma through antigen-mediated uptake and degradation in a lysosome, whether the number of times of binding of the antigen-binding molecule conferred with the pH-dependent binding ability is increased as compared to that before modification can be assessed by comparing the pharmacokinetics or duration of antigen binding between the antigen-binding molecule conferred with the pH-dependent binding ability and the antigen-binding molecule before modification. For example, when the antigen-binding duration of the antigen-binding molecule conferred with the pH-dependent binding ability is prolonged twice that of the antigen-binding molecule before modification, the number of times of binding of the antigen-binding molecule conferred with the pH-dependent binding ability is judged to be increased to twice that of the antigen-binding molecule before modification. Alternatively, when the plasma concentration of an unbound antigen, which is free from the antigen-binding molecule, is determined and the period where the plasma concentration of the free antigen or the amount ratio of the free antigen against the total antigen remains low is prolonged to twice, the number of times of binding of the antigen-binding molecule conferred with the pH-dependent binding ability is judged to be increased to twice that of the antigen-binding molecule before modification.

When the antigen is a soluble antigen, if the antigen bound to an antigen-binding molecule under the neutral condition in plasma dissociates in an endosome, and the antigen-binding molecule returns to the plasma, the antigen-binding molecule can again bind to an antigen under the neutral condition in plasma. Thus, an antigen-binding molecule that has the characteristics to dissociate with an antigen in acidic condition of an endosome is capable of binding to antigens multiple times. Compared to when the antigen bound to an antigen-binding molecule does not dissociate in an endosome (the antigen remains bound to the antigen-binding molecule when returning to plasma), when the antigen bound to an antigen-binding molecule dissociates in endosomes, the antigen is delivered to a lysosome and then degraded, and thus, the rate of elimination of the antigen from plasma increases. That is, it is also possible to determine whether the antigen-binding molecule is capable of binding to antigens multiple times using the rate of elimination of antigen from plasma as an index. The rate of elimination of the antigen from plasma can be determined, for example, by administering the antigens (e.g., membrane antigen) and antigen-binding molecules in vivo, and then measuring the concentration of antigens in plasma. When an antigen (e.g., membrane antigen) is produced or secreted in vivo, the plasma antigen concentration is reduced if the rate of elimination of the antigen from plasma is increased. Thus, it is also possible to determine whether the antigen-binding molecule is capable of binding to antigens multiple times using the plasma antigen concentration as an index.

Herein, "increasing the number of times of antigen-binding of the antigen-binding molecule" means that the number of cycles is increased when taking as one cycle the process where an antigen-binding molecule administered to human, mouse, monkey, or such binds to an antigen and is internalized into a cell. Specifically, herein, "the antigen-binding molecule binds twice to an antigen" means that the antigen-binding molecule bound by an antigen is internalized into a cell and released in an antigen-free form to the outside of the cell, and the released antigen-binding molecule rebinds to another antigen and is internalized into a cell again.

When the antigen-binding molecule is internalized into a cell, it may be in a form bound by a single antigen, or two or more antigens.

Herein, "the number of times of antigen-binding of an antigen-binding molecule is increased" does not necessarily mean that the number of times of antigen-binding increases in every antigen-binding molecules. For example, among antigen-binding molecules in an antigen-binding-molecule composition, the proportion of antigen-binding molecules that bind to antigens twice or more times may increase, or the average number of binding events of antigen-binding molecules in an antigen-binding-molecule composition may increase.

In the present invention, it is preferred that the number of times of antigen-binding of an antigen-binding molecule increases when the molecule is administered to a human. However, when it is difficult to determine the number of times of antigen-binding in human, the number in human may be predicted based on the results obtained by in vitro assay or measurement using mice (for example, antigen-expressing transgenic mice and human FcRn-expressing transgenic mice) or monkeys (for example, cynomolgus monkeys).

In the present invention, it is preferred that an antigen-binding molecule binds to antigens twice or more times. For example, it is preferred that, of the antigen-binding molecules in an antigen-binding-molecule composition, at least 10% or more, preferably 30% or more, more preferably 50% or more, and still more preferably 80% or more (for example, 90% or more, 95% or more, and so on) bind to antigens twice or more times.

Herein, "increasing the number of antigens that can be bound by an antigen-binding molecule" means increasing the number of antigens that can be bound by an antigen-binding molecule during the period until the antigen-binding molecule is degraded in a lysosome of a cell after administration of the antigen-binding molecule to an animal such as human, mouse, or monkey.

In general, antibodies such as IgG have two binding domains, and thus a single antibody binds to a maximum of two antigens. An antibody bound to antigen(s) is internalized into a cell, and the antibody and antigen(s) are degraded in a lysosome. In general, antibodies such as IgG can bind to a maximum of two antigens. When the antigen-binding activity of an antigen-binding molecule such as an antibody at the endosomal pH is impaired as compared to that at the plasma pH by the methods of the present invention, the antigen-binding molecule such as an antibody internalized into a cell dissociates the antigen and is released to the outside of the cell, and thus can bind to another antigen again. In other words, the methods of the present invention enable for an antigen-binding molecule to bind to more antigens than the number of its antigen-binding sites. Specifically, by using the methods of the present invention, for example, IgG having two antigen-binding sites can bind to three or more antigens, preferably four or more antigens, during a period until the antibody is degraded after administration. For example, when the antibody is a neutralizing antibody, "increasing the number of antigens that can be bound by an antigen-binding molecule" is interchangeable with "increasing the number of antigens that the antigen-binding molecule can neutralize". Thus, "bind" can be replaced with "neutralize" when the antibody is a neutralizing antibody.

In the present invention, "increasing the number of antigens that can be bound by an antigen-binding molecule" does not necessarily mean increasing the number of antigens that can be bound by every antigen-binding molecule. For example, the average number of antigens that can be bound by an antigen-binding molecule in an antigen-binding-molecule composition may increase, or the proportion of antigen-binding molecules that can bind to more antigens than the number of their antigen-binding sites may increase.

In the present invention, it is preferred that the number of antigens that can be bound by an antigen-binding molecule increases when the molecule is administered to a human. However, when it is difficult to determine the number in human, it may be predicted based on the results obtained by in vitro assay or measurement using mice (for example, antigen-expressing transgenic mice and human FcRn-expressing transgenic mice) or monkeys (for example, cynomolgus monkeys). When the antibody is a neutralizing antibody, the above-described number of times of antigen-binding of the antigen-binding molecule is generally assumed to correlates with the number of antigens which can be neutralized by an antigen-binding molecule. Thus, the number of antigens which can be neutralized by an antigen-binding molecule can be determined by the same methods described above for determining the number of times of binding of an antigen-binding molecule.

Furthermore, the present invention provides methods for binding an antigen-binding molecule to antigens twice or more times in the body, by administering an antigen-binding molecule whose antigen-binding activity at acidic pH is lower than that at neutral pH.

The present invention also relates to methods for neutralizing antigens that are greater in number than the number of antigen-binding sites of an antigen-binding molecule having the neutralizing activity, by administering the antigen-binding molecule whose antigen-binding activity at acidic pH is lower than that at neutral pH. Preferably, the present invention relates to methods for neutralizing three or more antigens, preferably four or more antigens by administering IgG whose antigen-binding activity at acidic pH is lower than that at neutral pH.

The present invention also relates to methods for dissociating within a cell an antigen from an extracellularly-bound antigen-binding molecule by impairing the antigen-binding ability of the antigen-binding molecule at acidic pH as compared to that at neutral pH. In the present invention, the antigen may be dissociated from the antigen-binding molecule anywhere within a cell; however, it is preferred that the antigen is dissociated within an early endosome. In the present invention, "an antigen is dissociated within a cell from an extracellularly-bound antigen-binding molecule" does not necessarily mean that every antigen internalized into a cell via binding to the antigen-binding molecule is dissociated from the antigen-binding molecule within the cell. It is acceptable that the proportion of antigen that is dissociated from the antigen-binding molecule within a cell increases when compared to before impairing the antigen-binding ability of the antigen-binding molecule at acidic pH as compared to that at neutral pH.

Furthermore, the present invention relates to methods for enhancing the intracellular binding of an antigen-binding molecule free from an antigen to FcRn by impairing the antigen-binding ability of the antigen-binding molecule at acidic pH as compared to that at neutral pH. In general, FcRn binds to an antigen-binding molecule within an endosome. However, an antigen-binding molecule bound to a membrane antigen is assumed not to bind to FcRn. Thus, in a preferred embodiment, when the antigen is a membrane-bound antigen, the present invention includes methods for enhancing the endosomal dissociation of antigens from antigen-binding molecules and thus enhancing the FcRn binding of the antigen-binding molecules, by impairing the antigen-binding ability of an antigen-binding molecule at the endosomal pH (acidic pH) as compared to that at the plasma pH (neutral pH). When the antigen is a soluble antigen, the antigen-binding molecule can bind to FcRn in the presence or absence of the antigen. If dissociation of the antigen from the antigen-binding molecule within endosomes can be promoted by impairing the antigen-binding ability of the antigen-binding molecule at intraendosomal (acidic) pH as compared to that at plasma (neutral) pH, the FcRn binding of the antigen-binding molecule that is "free from an antigen" can be enhanced by the methods of the present invention.

Regardless of whether an antigen is membrane-bound or soluble, if an antigen-binding molecule free from an antigen can return to plasma with FcRn, the antigen-binding molecule can bind to the antigen again. By repeating this process, the antigen-binding molecule can bind to the antigen multiple times. In the present invention, "enhancing the FcRn binding of an antigen-binding molecule within a cell" does not necessarily mean that every antigen-binding molecule binds to FcRn. It is acceptable that the proportion of an antigen-binding molecule free from an antigen that binds to FcRn within a cell increases when compared to before impairing the antigen-binding ability of the antigen-binding molecule at the endosomal pH as compared to that at the plasma pH. Preferred antigen-binding molecules in the methods of the present invention for enhancing the intracellular binding between the antigen-binding molecule and FcRn include, for example, antigen-binding molecules that bind to membrane-bound antigens (membrane antigens) such as membrane proteins. Other preferable antigen-binding molecules include antigen-binding molecules that bind to soluble antigens such as soluble proteins.

The methods of enhancing the binding of an antigen-binding molecule and FcRn within a cell are alternatively expressed as the methods of promoting the FcRn binding of an antigen-binding molecule within a cell, for example, within endosomes.

Furthermore, the present invention relates to methods for releasing an antigen-binding molecule, which has been bound to an antigen and internalized into a cell, in an antigen-free form to the outside of the cell, by impairing the antigen-binding ability of the antigen-binding molecule at acidic pH as compared that at neutral pH. In the present invention, "releasing an antigen-binding molecule, which has been bound to an antigen and internalized into a cell, in an antigen-free form to the outside of the cell" does not necessarily mean that every antigen-binding molecule, which has been bound to an antigen and internalized into a cell, is released in an antigen-free form to the outside of the cell. It is acceptable that the proportion of antigen-binding molecules that are released to the outside of the cell increases when compared to before impairing the antigen-binding ability of the antigen-binding molecule at acidic pH as compared to that at neutral pH. It is preferred that the antigen-binding molecule released to the outside of a cell retains the antigen-binding ability. Furthermore, the method of releasing an antigen-binding molecule, which has been bound to an antigen and internalized into a cell, in an antigen-free form to the outside of the cell can also be referred to as a method of conferring to the antigen-binding molecule a property that the antigen-binding molecule becomes more easily released to the outside of the cell in an antigen-free form when the antigen-binding molecule is bound to an antigen and internalized into a cell.

Furthermore, the present invention relates to methods for increasing the ability of the antigen-binding molecules to eliminate antigens in plasma by impairing the antigen-binding ability of the antigen-binding molecules at acidic pH as compared to that at neutral pH. In the present invention "the ability to eliminate antigens in plasma" refers to the ability to eliminate from plasma antigens that are present in plasma, when the antigen-binding molecules are administered in vivo or are secreted in vivo. Thus, in the present invention, "increasing the ability of the antigen-binding molecule to eliminate antigen in plasma" means that the rate of elimination of antigens from plasma when the antigen-binding molecules are administered in vivo is accelerated as compared to that before lowering the antigen-binding ability of the antigen-binding molecules at acidic pH as compared to that at neutral pH. Whether the ability of the antigen-binding molecule to eliminate antigens in plasma is increased can be determined by, for example, administering soluble antigens and antigen-binding molecules in vivo, and then measuring the concentration of soluble antigens in plasma. When the concentration of soluble antigens in plasma after the administration of soluble antigens and antigen-binding molecules is reduced by lowering the antigen-binding ability of the antigen-binding molecule at acidic pH than that at neutral pH, it can be determined that the ability of the antigen-binding molecule to eliminate antigens in plasma is increased.

The present invention also relates to methods for improving the pharmacokinetics of an antigen-binding molecule by substituting histidine or non-natural amino acid for at least one amino acid in the antigen-binding molecule or inserting histidine or non-natural amino acid into the molecule.

Furthermore, the present invention provides methods for increasing the number of times of antigen-binding of an antigen-binding molecule by substituting histidine or non-natural amino acid for at least one amino acid in the antigen-binding molecule or inserting histidine or non-natural amino acid into the molecule.

In addition, the present invention relates to methods for increasing the number of antigens that can be bound by an antigen-binding molecule by substituting histidine or non-natural amino acid for at least one amino acid in the antigen-binding molecule or inserting histidine or non-natural amino acid into the molecule.

The present invention also provides methods for dissociating an antigen within a cell from an extracellularly-bound antigen-binding molecule by substituting at least one amino acid in the antigen-binding molecule with histidine or non-natural amino acid, or inserting histidine or non-natural amino acid into the molecule.

The present invention also provides methods for releasing an antigen-binding molecule, which has been bound to an antigen and internalized into a cell, in an antigen-free form to the outside of the cell by substituting at least one amino acid in the antigen-binding molecule with histidine or non-natural amino acid, or inserting histidine or non-natural amino acid into the molecule.

The present invention also provides methods for increasing the ability of the antigen-binding molecule to eliminate antigens in plasma by substituting at least one amino acid in the antigen-binding molecule with histidine or non-natural amino acid, or inserting histidine or non-natural amino acid into the molecule.

The site of histidine or non-natural amino acid mutation (substitution, insertion, etc.) is not particularly limited. A histidine or non-natural amino acid may be substituted or inserted at any site. Preferred sites of histidine or non-natural amino acid substitution or insertion include, for example, sites within a region that has an impact on the antigen-binding ability of the antigen-binding molecule. For example, when the antigen-binding molecule is an antibody, such sites include an antibody variable region or CDR. The number of histidine or non-natural amino acid mutations is not particularly limited. Histidine or non-natural amino acid may be substituted or inserted at a single site, or at two or more sites. Furthermore, a deletion, addition, insertion, and/or substitution of other amino acids may be introduced simultaneously with the histidine or non-natural amino acid substitution or insertion.

In the present invention, when the antigen-binding molecule is an antibody, possible sites of histidine or non-natural amino acid substitution include, for example, sites within the CDR sequence or sequence responsible for the CDR structure of an antibody. Such sites include, for example, the sites listed below. The amino acid positions are numbered based on the Kabat numbering (Kabat E A et al., (1991) Sequences of Proteins of Immunological Interest, NIH).

Heavy chain: H27, H31, H32, H33, H35, H50, H58, H59, H61, H62, H63, H64, H65, H99, H100b, and H102

Light chain: L24, L27, L28, L32, L53, L54, L56, L90, L92, and L94

Among the above sites, H32, H61, L53, L90, and L94 could be universal modification sites.

When the antigen is the IL-6 receptor (e.g., human IL-6 receptor), preferable modification sites include the following. However, the modification sites are not particularly limited thereto.

Heavy chain: H27, H31, H32, H35, H50, H58, H61, H62, H63, H64, H65, H100b, and H102

Light chain: L24, L27, L28, L32, L53, L56, L90, L92, and L94

When histidine or non-natural amino acid is substituted at multiple sites, preferred combinations of substitution sites include, for example, the combination of H27, H31, and H35; combination of H27, H31, H32, H35, H58, H62, and H102; combination of L32 and L53; and combination of L28, L32, and L53. In addition, preferred combinations of substitution sites of heavy and light chains include the combination of H27, H31, L32, and L53.

When the antigen is IL-6 (e.g., human IL-6), preferable modification sites include the following. However, the modification sites are not particularly limited thereto.

Heavy chain: H32, H59, H61, and H99

Light chain: L53, L54, L90, and L94

When the antigen is the IL-31 receptor (e.g., human IL-31 receptor), preferable modification sites include H33. However, the modification sites are not particularly limited thereto.

Regarding the above sites, only one site may be substituted with histidine or non-natural amino acid. Alternatively, multiple sites may be substituted with histidine or non-natural amino acid.

The methods of the present invention are applicable to any antigen-binding molecules, regardless of the type of target antigen.

The antigen-binding molecules of the present invention are not particularly limited as long as they have the specific binding activity to an antigen of interest. Preferred antigen-binding molecules of the present invention include, for example, substances having an antigen-binding domain of an antibody. The antigen-binding domain of an antibody includes, for example, CDR and variable region. When the antigen-binding domain of an antibody is CDR, the antigen-binding molecule may include all of the six CDRs of a whole antibody, or one, or two or more of them. Alternatively, when an antigen-binding molecule includes CDR as a binding domain of an antibody, the CDR may include amino acid deletion, substitution, addition, and/or insertion, or may be a partial CDR.

Furthermore, when the antigen-binding molecule includes an antibody constant region, the present invention relates to methods for improving the pharmacokinetics of antigen-binding molecules by modification (for example, amino acid substitution, deletion, addition, and/or insertion) of the antibody constant region in the antigen-binding molecule.

In addition, when the antigen-binding molecule includes an antibody constant region, the present invention provides methods for increasing the number of times of antigen-binding of an antigen-binding molecule by modification (for example, amino acid substitution, deletion, addition, and/or insertion) of the antibody constant region in the antigen-binding molecule.

Furthermore, when the antigen-binding molecule includes an antibody constant region, the present invention relates to methods for increasing the number of antigens that can be bound by an antigen-binding molecule by modification (for example, amino acid substitution, deletion, addition, and/or insertion) of the antibody constant region in the antigen-binding molecule.

Furthermore, when the antigen-binding molecule includes an antibody constant region, the present invention relates to methods for dissociating within a cell an antigen from an extracellularly-bound antigen-binding molecule by modification (for example, amino acid substitution, deletion, addition, and/or insertion) of the antibody constant region in the antigen-binding molecule.

Furthermore, when the antigen-binding molecule includes an antibody constant region, the present invention relates to methods for releasing an antigen-binding molecule, which has been bound to an antigen and internalized into a cell, in an antigen-free form to the outside of the cell, by modification (for example, amino acid substitution, deletion, addition, and/or insertion) of the antibody constant region in the antigen-binding molecule.

Furthermore, when the antigen-binding molecule includes an antibody constant region, the present invention relates to methods for increasing the ability of an antigen-binding molecule to eliminate antigens in plasma by modification (for example, amino acid substitution, deletion, addition, and/or insertion) of the antibody constant region in the antigen-binding molecule.

In a preferred embodiment, the antigen-binding substance of the present invention includes antigen-binding substances including an FcRn-binding region. After internalized into cells, antigen-binding substances including an FcRn-binding region can return to the plasma by the FcRn salvage pathway. The FcRn-binding region is preferably a domain that directly binds to FcRn. Preferred FcRn-binding region includes, for example, antibody Fc regions. However, the FcRn-binding region of the present invention may be a region that can bind to a polypeptide having the ability to bind to FcRn such as albumin or IgG, since such region that can bind to the polypeptide having FcRn-binding ability can binds indirectly to FcRn via albumin, IgG, etc.

Antigens recognized by antigen-binding molecules such as antibodies of interest in the methods of the present invention are not particularly limited. Such antibodies of interest may recognize any antigen. Antibodies whose pharmacokinetics is to be improved by the methods of the present invention include, for example, antibodies that recognize membrane antigens such as receptor proteins (membrane-bound receptors and soluble receptors) and cell surface markers, and antibodies that recognize soluble antigens such as cytokines. Preferred examples of membrane antigens of the present invention include membrane proteins. Examples of soluble antigens of the present invention include soluble proteins. Antigens recognized by antibodies whose pharmacokinetics is to be improved by the methods of the present invention include, for example, IL-1, IL-2, IL-3, IL-4, IL-5, IL-6, IL-7, IL-8, IL-9, IL-10, IL-11, IL-12, IL-15, IL-31, IL-23, IL-2 receptor, IL-6 receptor, OSM receptor, gp130, IL-5 receptor, CD40, CD4, Fas, osteopontin, CRTH2, CD26, PDGF-D, CD20, monocyte chemotactic factor, CD23, TNF-α, HMGB-1, α4 integrin, ICAM-1, CCR2, CD11a, CD3, IFNγ, BLyS, HLA-DR, TGF-β, CD52, and IL-31 receptor. Particularly preferred antigens include IL-6 receptor.

Furthermore, the antigen-binding molecule of interest in the methods of the present invention includes antigen-binding molecules having an antagonistic activity (antagonistic antigen-binding molecules) and antigen-binding molecules having an agonistic activity (agonistic antigen-binding molecules). In a preferred embodiment, the antigen-binding molecule includes antagonistic antigen-binding molecules, in particular, antagonistic antigen-binding molecules that recognize membrane antigens such as receptors, or soluble antigens such as cytokines. For example, an antagonistic antigen-binding molecule that recognizes a receptor inhibits the ligand-receptor binding by binding to the receptor, and thus inhibits the signaling mediated via the receptor.

In the present invention, the antigen-binding molecule of interest is not particularly limited, and may be any antigen-binding molecules. The antigen-binding molecule of the present invention preferably includes both antigen-binding activity (antigen-binding region) and FcRn-binding region. In particular, preferred antigen-binding molecule of the present invention includes a region that binds to human FcRn. The antigen-binding molecule including both antigen-binding activity and FcRn-binding region includes, for example, antibodies. The antibodies preferred in the context of the present invention include, for example, IgG antibodies. When the antibody to be used is an IgG antibody, the type of IgG is not limited; the IgG belonging to any isotype (subclass) such as IgG1, IgG2, IgG3, or IgG4 can be used. Furthermore, amino acid mutations (e.g., M73) may be introduced into the constant region of any of these IgG isotypes. Amino acid mutations to be introduced include, for example, those potentiate or impair the binding to Fc☐ receptor (Proc Natl Acad Sci USA. 2006 Mar. 14; 103(11): 4005-10) and those potentiate or impair the binding to FcRn (J Biol Chem. 2001 Mar. 2; 276(9):6591-604), but are not limited to these examples. Alternatively, it is also possible to alter the pH-dependent binding by selecting an appropriate constant region such as of IgG2.

When the antigen-binding molecule of interest of the present invention is an antibody, it may be an antibody derived from any animal, such as a mouse antibody, human antibody, rat antibody, rabbit antibody, goat antibody, or camel antibody. Furthermore, the antibody may be a modified antibody, for example, a chimeric antibody, and in particular, a modified antibody including amino acid substitution in the sequence of a humanized antibody, etc. The antibodies also include bispecific antibodies, antibody modification products linked with various molecules, and polypeptides including antibody fragments.

"Chimeric antibodies" are antibodies prepared by combining sequences derived from different animals. Specifically, the chimeric antibody includes, for example, antibodies having heavy and light chain variable (V) regions from a mouse antibody and heavy and light chain constant (C) regions from a human antibody.

"Humanized antibodies", also referred to as reshaped human antibodies, are antibodies in which complementarity determining regions (CDRs) of an antibody derived from a nonhuman mammal, for example, a mouse, are transplanted into the CDRs of a human antibody. Methods for identifying CDRs are known (Kabat et al., Sequence of Proteins of Immunological Interest (1987), National Institute of Health, Bethesda, Md.; Chothia et al., Nature (1989) 342:877). General genetic recombination technologies suitable for this purpose are also known (see European Patent Application EP 125023; and WO 96/02576).

Bispecific antibody refers to an antibody that has, in the same antibody molecule, variable regions that recognize different epitopes. A bispecific antibody may be an antibody that recognizes two or more different antigens, or an antibody that recognizes two or more different epitopes on a same antigen.

Furthermore, polypeptides including antibody fragments include, for example, Fab fragments, F(ab')2 fragments, scFv (Nat Biotechnol. 2005 September; 23(9):1126-36), domain antibodies (dAb) (WO 2004/058821, WO 2003/002609), scFv-Fc (WO 2005/037989), dAb-Fc, and Fc fusion proteins. Of these, molecules including an Fc domain have the activity of binding to FcRn, and are therefore suitable for use in the methods discovered in the present invention.

Further, the antigen-binding molecules that are applicable to the present invention may be antibody-like molecules. An antibody-like molecule is a molecule that can exhibit functions by binding to a target molecule (Current Opinion in Biotechnology 2006, 17:653-658; Current Opinion in Biotechnology 2007, 18:1-10; Current Opinion in Structural Biology 1997, 7:463-469; Protein Science 2006, 15:14-27), and includes, for example, DARPins (WO 2002/020565), Affibody (WO 1995/001937), Avimer (WO 2004/044011; WO 2005/040229), and Adnectin (WO 2002/032925). If these antibody-like molecules can bind to target molecules in a pH-dependent manner, it is possible for a single molecule to bind multiple target molecules.

Furthermore, the antigen-binding molecule may be a receptor protein or a receptor-Fc fusion protein that binds to a target, including, for example, TNFR-Fc fusion protein, IL1R-Fc fusion protein, VEGFR-Fc fusion protein, and CTLA4-Fc fusion protein (Nat Med. 2003 January; 9(1):47-52; BioDrugs. 2006; 20(3):151-60). If such receptor proteins and receptor-Fc fusion proteins can bind to target molecules in a pH-dependent manner, it is possible for a single molecule to bind multiple target molecules.

Moreover, the antigen-binding molecule may be an artificial ligand protein or artificial ligand fusion protein that binds to a target and has the neutralizing effect, and includes, for example, mutant IL-6 (EMBO J. 1994 Dec. 15; 13(24): 5863-70). If such artificial ligand proteins and artificial ligand fusion proteins can bind to target molecules in a pH-dependent manner, it is possible for a single molecule to bind multiple target molecules.

Furthermore, the antibodies of the present invention may include modified sugar chains. Antibodies with modified sugar chains include, for example, antibodies with modified glycosylation (WO 99/54342), antibodies that are deficient in fucose that is added to the sugar chain (WO 00/61739; WO 02/31140; WO 2006/067847; WO2 006/067913), and antibodies having sugar chains with bisecting GlcNAc (WO 02/79255).

Although the methods of the present invention are not limited to any specific theory, the relationship between making the antigen-binding ability at acidic pH weaker as compared to that at neutral pH, the improvement of the pharmacokinetics, and the multiple-time binding to the antigen can be explained as follows, for instance.

For example, when the antibody is an antibody that binds to a membrane antigen, the antibody administered into the body binds to the antigen and then is taken up via internalization into endosomes in the cells together with the antigen and while the antibody is kept bound to the antigen. Then, the antibody translocates to lysosomes while the antibody is kept bound to the antigen, and the antibody is degraded by the lysosome together with the antigen. The internalization-mediated elimination from the plasma is called antigen-dependent elimination, and such elimination has been reported with numerous antibody molecules (Drug Discov Today. 2006 January; 11(1-2):81-8). When a single molecule of IgG antibody binds to antigens in a divalent manner, the single antibody molecule is internalized while the antibody is kept bound to the two antigen molecules, and degraded in the lysosome. Accordingly, in the case of typical antibodies, one molecule of IgG antibody cannot bind to three or more molecules of antigen. For example, a single IgG antibody molecule having a neutralizing activity cannot neutralize three or more antigen molecules.

The relatively prolonged retention (slow elimination) of IgG molecules in the plasma is due to the function of FcRn which is known as a salvage receptor of IgG molecules. When taken up into endosomes via pinocytosis, IgG molecules bind to FcRn expressed in the endosomes under the acidic condition in the endosomes. While IgG molecules that did not bind to FcRn transfer to lysosomes where they are degraded, IgG molecules that bound to FcRn translocate to the cell surface and return again in the plasma by dissociating from FcRn under the neutral condition in the plasma.

Alternatively, when the antigen is an antigen that binds to a soluble antigen, the antibody administered into the body binds to the antigen and then is taken up into cells while the antibody is kept bound to the antigen. Many antibodies taken up into cells are released to the outside of cells via FcRn. However, since the antibodies are released to the outside of cells, with the antibodies kept bound to antigens, the antibodies cannot bind to antigens again. Thus, similar to antibodies that bind to membrane antigens, in the case of typical antibodies, one molecule of IgG antibody cannot bind to three or more antigen molecules.

The present inventors reasoned that, when antibodies that bound to antigens such as membrane antigens are taken up into endosomes by internalization, while the antibodies that are kept bound to the antigens translocate to lysosomes and are degraded, the IgG antibodies whose antigens dissociated in the endosomes could bind to FcRn that are expressed in the endosomes. Specifically, the present inventors discovered that an antibody that strongly binds to an antigen in the plasma but weakly binds to the antigen within the endosome can bind to an antigen in plasma and be taken up while kept forming a complex with the antigen into endosomes in the cells via internalization; dissociate from the antigen in the endosome; then bind to FcRn and translocate to the cell surface; and return again in the plasma in a state not bound to antigens to neutralize multiple membrane-bound antigens. Furthermore, the present inventors discovered that an antibody having the property of strongly binding to antigens in the plasma but weakly binding to antigens in the endosome can dissociate from the antigens in the endosome even when the antibody had bound to antigens such as soluble antigens; therefore, they are released again into the plasma in a state not bound to antigens and can neutralize multiple soluble antigens.

In particular, the present inventors noted that the pH in the plasma was different from the pH in the endosomes, and thus discovered that antibodies that strongly bind to antigens under plasma pH condition but that weakly bind to antigens under endosomal pH condition were superior in retention in the plasma, because one antibody molecule could bind to multiple antigens.

The endosomes, which are membrane vesicles, form networks in the cytoplasm of eukaryotic cells and are responsible for the metabolism of macromolecules in the process from the cell membrane to the lysosomes. The pH in the endosomes has been reported be generally an acidic pH of 5.5 to 6.0 (Nat Rev Mol Cell Biol. 2004 February; 5(2):121-32). Meanwhile, the pH in the plasma is known to be almost neutral (normally, pH 7.4).

Accordingly, an antigen-binding molecule whose antigen-binding activity at acidic pH is weaker than the antigen-binding activity at neutral pH binds to the antigen in the plasma which have a neutral pH, is taken up into cells, and then dissociates from the antigen in the endosomes which have an acidic pH. The antigen-binding molecule that dissociated from the antigen binds to FcRn, translocates to the cell surface, and returns again in the plasma in a state not bound to antigens. As a result, the antigen-binding molecule can bind to antigens multiple times, and the pharmacokinetics is improved.

<Antigen-Binding Molecule Substances>

Furthermore, the present invention provides antigen-binding molecules whose antigen-binding activity at pH 4.0 to pH 6.5 is lower than that at pH 6.7 to pH 10.0, preferably antigen-binding molecules whose antigen-binding activity at pH 5.0 to pH 6.0 is lower than that at pH 7.0 to 8.0. Specifically, antigen-binding molecules whose antigen-binding activity at pH 4.0 to pH 6.5 is lower than that at pH 6.7 to pH 10.0 include, for example, antigen-binding molecules whose antigen-binding activity at pH 5.8 is lower than that at pH 7.4. Antigen-binding molecules whose antigen-binding activity at pH 5.8 is lower than that at pH 7.4 can also be expressed as antigen-binding molecules whose antigen-binding activity at pH 7.4 is higher than that at pH 5.8.

As for the antigen-binding molecules of the present invention whose antigen-binding activity at pH 5.8 is lower than that at pH 7.4, so long as the antigen-binding activity at pH 5.8 is lower than the binding at pH 7.4, there is no limitation on the difference in binding activity, and the antigen-binding activity at pH 5.8 only need to be lower, even slightly.

A preferred embodiment of an antigen-binding molecule of the present invention whose antigen-binding activity at pH 5.8 is lower than that at pH 7.4 includes antigen-binding molecules whose antigen-binding activity at pH 7.4 is twice or greater than that at pH 5.8. A more preferred embodiment of the antigen-binding molecule includes antigen-binding molecules whose antigen-binding activity at pH 7.4 is ten times or greater than that at pH 5.8. A still more preferred embodiment of the antigen-binding molecule includes antigen-binding molecules whose antigen-binding activity at pH 7.4 is 40 times or greater than that at pH 5.8.

Specifically, in a preferred embodiment, the antigen-binding molecule of the present invention has antigen-binding activity at pH 5.8 that is lower than that at pH 7.4, wherein the value of KD(pH5.8)/KD(pH7.4), which is a ratio of KD for the antigen at pH 5.8 and that at pH 7.4, is preferably 2 or greater, more preferably 10 or greater, and still more preferably 40 or greater. The upper limit of the KD(pH5.8)/KD(pH7.4) value is not particularly limited, and may be any value, for example, 400, 1000, or 10000, as long as production is possible using the technologies of those skilled in the art.

In another preferred embodiment, the antigen-binding molecule of the present invention whose antigen-binding activity at pH 5.8 is lower than that at pH 7.4, has a value of kd(pH5.8)/kd(pH7.4), which is a ratio of the kd for the antigen at pH 5.8 and the kd for the antigen at pH 7.4, that is 2 or greater, more preferably 5 or greater, even more preferably 10 or greater, and still more preferably 30 or greater. The upper limit of the kd(pH5.8)/kd(pH7.4) value is not particularly limited, and may be any value, for example, 50, 100, or 200, as long as production is possible using the technologies of those skilled in the art.

Conditions other than the pH at which the antigen-binding activity is measured can be appropriately selected by those skilled in the art, and the conditions are not particularly limited; however, the measurements can be carried out, for example, under conditions of MES buffer and 37° C., as described in the Examples. Furthermore, the antigen-binding activity of an antigen-binding molecule can be determined by methods known to those skilled in the art, for example, using a Biacore™ T100 surface plasmon resonance system (GE Healthcare) or the like, as described in the Examples.

It is presumed that such an antigen-binding molecule, which weakly binds to an antigen at acidic pH, easily dissociates from the antigen under the endosomal acidic condition, and that after internalization into cells, it binds to FcRn and is easily released to the outside of the cells. The antigen-binding molecule released to the outside of the cells without being degraded inside the cells can bind again to other antigens. Accordingly, when the antigen-binding molecule is, for example, an antigen-binding neutralizing molecule, the antigen-binding molecule that easily dissociates from the antigen under the endosomal acidic condition can bind and neutralize antigens multiple times. As a result, antigen-binding molecules whose antigen-binding activity at pH 4.0 to pH 6.5 is lower than that at pH 6.7 to pH 10.0 are superior in retention in the plasma.

In a preferred embodiment, the antigen-binding molecule whose antigen-binding activity at pH 5.8 is lower than that at pH 7.4 includes antigen-binding molecules in which at least one amino acid in the antigen-binding molecule is substituted with histidine or a non-natural amino acid, or in which at least one histidine or a non-natural amino acid has been inserted. The site into which the histidine or non-natural amino acid mutation is introduced is not particularly limited and may be any site, as long as the antigen-binding activity at pH 5.8 is weaker than that at pH 7.4 (the KD(pH5.8)/KD(pH7.4) value is greater or the kd(pH5.8)/kd(pH7.4) value is greater) as compared to before substitution. Examples include variable regions and CDRs of an antibody in the case the antigen-binding molecule is an antibody. The number of amino acids to be substituted with histidine or non-natural amino acid and the number of amino acids to be inserted can be appropriately determined by those skilled in the art. One amino acid may be substituted with histidine or non-natural amino acid, or one amino acid may be inserted, or two or more amino acids may be substituted with histidine or non-natural amino acids, or two or more amino acids may be inserted. Moreover, apart from the substitutions to histidine or to non-natural amino acid or insertion of histidine or of non-natural amino acid, deletion, addition, insertion, and/or substitution and such of other amino acids may also be simultaneously carried out. Substitutions to histidine or to non-natural amino acid or insertion of histidine or of non-natural amino acid may be carried out at random using a method such as histidine scanning, which uses histidine instead of alanine in alanine scanning which is known to those skilled in the art. Antigen-binding molecules whose KD(pH5.8)/KD(pH7.4) or kd(pH5.8)/kd (pH7.4) is increased as compared to before mutation can be selected from antigen-binding molecules into which histidine or non-natural amino acid mutation has been introduced at random.

Preferred antigen-binding molecules with mutation to histidine or to non-natural amino acid and whose antigen-binding activity at pH 5.8 is lower than that at pH 7.4 include, for example, antigen-binding molecules whose antigen-binding activity at pH 7.4 after the mutation to histidine or to non-natural amino acid is equivalent to the antigen-binding activity at pH 7.4 before the mutation to histidine or to non-natural amino acid. In the present invention, "an antigen-binding molecule after histidine or non-natural amino acid mutation has an antigen-binding activity that is equivalent to that of the antigen-binding molecule before histidine or non-natural amino acid mutation" means that, when the antigen-binding activity of an antigen-binding molecule before histidine or non-natural amino acid mutation is set as 100%, the antigen-binding activity of the antigen-binding molecule after histidine or non-natural amino acid mutation is at least 10% or more, preferably 50% or more, more preferably 80% or more, and still more preferably 90% or more. The antigen-binding activity at pH 7.4 after histidine or non-natural amino acid mutation may be greater than the antigen-binding activity at pH 7.4 before histidine or non-natural amino acid mutation. When the antigen-binding activity of the antigen-binding molecule is decreased due to substitution or insertion of histidine or non-natural amino acid, the antigen-binding activity may be adjusted by introducing substitution, deletion, addition, and/or insertion and such of one or more amino acids into the antigen-binding molecule so that the antigen-binding activity becomes equivalent to that before histidine substitution or insertion. The present invention also includes such antigen-binding molecules whose binding activity has been made equivalent as a result of substitution, deletion, addition, and/or insertion of one or more amino acids after histidine substitution or insertion.

Further, when the antigen-binding molecule is a substance including an antibody constant region, in another preferred embodiment of the antigen-binding molecule whose antigen-binding activity at pH 5.8 is lower than that at pH 7.4, the present invention includes methods for modifying antibody constant regions contained in the antigen-binding molecules. Specific examples of antibody constant regions after modification include the constant regions described in the Examples.

When the antigen-binding activity of the antigen-binding substance at pH 5.8 is weakened compared to that at pH 7.4 (when KD(pH5.8)/KD(pH7.4) value is increased) by the above described methods and such, it is generally preferable that the KD(pH5.8)/KD(pH7.4) value is two times or more, more preferably five times or more, and even more preferably ten times or more as compared to that of the original antibody, but is not particularly limited thereto.

The antigen-binding molecules of the present invention may further have any other property, as long as their antigen-binding activity at pH 4.0 to pH 6.5 is lower than that at pH 6.7 to pH 10.0. For example, the antigen-binding molecules may be agonistic or antagonistic antigen-binding molecules. Preferred antigen-binding molecules of the present invention include, for example, antagonistic antigen-binding molecules. In general, an antagonistic antigen-binding molecule inhibits receptor-mediated intracellular signaling by inhibiting the binding between a ligand (agonist) and the receptor.

Furthermore, the present invention provides antibodies in which amino acid on at least one site indicated below is substituted with histidine or non-natural amino acid. Amino acid positions are indicated based on the Kabat numbering (Kabat E A et al., (1991) Sequences of Proteins of Immunological Interest, NIH).

Heavy chain: H27, H31, H32, H33, H35, H50, H58, H59, H61, H62, H63, H64, H65, H99, H100b, and H102

Light chain: L24, L27, L28, L32, L53, L54, L56, L90, L92, and L94

Among the above sites, H32, H61, L53, L90, and L94 could be universal modification sites.

When the antigen is the IL-6 receptor (e.g., human IL-6 receptor), preferable modification sites include the following. However, the modification sites are not particularly limited thereto.

Heavy chain: H27, H31, H32, H35, H50, H58, H61, H62, H63, H64, H65, H100b, and H102

Light chain: L24, L27, L28, L32, L53, L56, L90, L92, and L94

When histidine or non-natural amino acid is substituted at multiple sites, preferred combinations of substitution sites include, for example, the combination of H27, H31, and H35; combination of H27, H31, H32, H35, H58, H62, and H102; combination of L32 and L53; and combination of L28, L32, and L53. In addition, preferred combinations of substitution sites of heavy and light chains include the combination of H27, H31, L32, and L53.

When the antigen is IL-6 (e.g., human IL-6), preferable modification sites include the following. However, the modification sites are not particularly limited thereto.

Heavy chain: H32, H59, H61, and H99

Light chain: L53, L54, L90, and L94

When the antigen is the IL-31 receptor (e.g., human IL-31 receptor), preferable modification sites include H33. However, the modification sites are not particularly limited thereto.

The antigen-binding molecules of the present invention may recognize any antigen. Antigens recognized by antibodies of the present invention specifically include the above-mentioned receptor proteins (membrane-bound receptors or soluble receptors), membrane antigens such as cell surface markers, and soluble antigens such as cytokines, for example, IL-1, IL-2, IL-3, IL-4, IL-5, IL-6, IL-7, IL-8, IL-9, IL-10, IL-11, IL-12, IL-15, IL-31, IL-23, IL-2 receptor, IL-6 receptor, OSM receptor, gp130, IL-5 receptor, CD40, CD4, Fas, osteopontin, CRTH2, CD26, PDGF-D, CD20, monocyte chemoattractant factor, CD23, TNF-α, HMGB-1, α4 integrin, ICAM-1, CCR2, CD11a, CD3, IFNγ, BLyS, HLA-DR, TGF-β, CD52, and IL-31 receptor.

Particularly preferred antigens include the IL-6 receptor.

The antigen-binding molecules of the present invention are described above.

In a preferred embodiment of the present invention, the antigen-binding molecules include antibodies. Antibodies having antigen-binding activity and FcRn-binding region include, for example, IgG antibodies. When the antibody used is an IgG antibody, there is no limitation as to its type. It is possible to use IgG1, IgG2, IgG3, IgG4, and such.

The origin of antibody of the present invention is not particularly limited, and may be of any origin. It is possible to use, for example, mouse antibodies, human antibodies, rat antibodies, rabbit antibodies, goat antibodies, camel antibodies, and others. Furthermore, the antibodies may be, for example, the above-described chimeric antibodies, and in particular, modified antibodies with amino acid sequence substitutions, such as humanized antibodies. The antibodies may also be the above-described bispecific antibodies, antibody modification products to which various molecules have been linked, polypeptides including antibody fragments, and antibodies with modified sugar chains.

Generation of chimeric antibodies is known. In the case of a human-mouse chimeric antibody, for example, a DNA encoding an antibody V region may be linked to a DNA encoding a human antibody C region; this can be inserted into an expression vector and introduced into a host to produce the chimeric antibody.

"Humanized antibodies" are also referred to as reshaped human antibodies, and are antibodies in which the complementarity determining region (CDR) of a nonhuman mammal, for example a mouse, is transplanted to the CDR of a human antibody. Methods for identifying CDRs are known (Kabat et al., Sequence of Proteins of Immunological Interest (1987), National Institute of Health, Bethesda, Md.; Chothia et al., Nature (1989) 342:877). General genetic recombination technologies suitable for this purpose are also known (see European Patent Application EP 125023; and WO 96/02576). Humanized antibodies can be produced by known methods, for example, the CDR of a mouse antibody can be determined, and a DNA encoding an antibody in which the CDR is linked to the framework region (FR) of a human antibody is obtained. Humanized antibodies can then be produced using a system that uses conventional expression vectors. Such DNAs can be synthesized by PCR, using as primers several oligonucleotides prepared to have portions that overlap with the end regions of both the CDR and FR (see the method described in WO 98/13388). Human antibody FRs linked via CDRs are selected such that the CDRs form a suitable antigen binding site. If required, amino acids in the FRs of an antibody variable region may be substituted so that the CDRs of the reshaped human antibody can form a suitable antigen binding site (Sato, K. et al., Cancer Res. (1993) 53:10.01-6). Amino acid residues in the FRs that can be modified include portions that directly bind to an antigen via non-covalent bonds (Amit et al., Science (1986) 233: 747-53), portions that influence or have an effect on the CDR structure (Chothia et al., J. Mol. Biol. (1987) 196: 901-17), and portions involved in VH-VL interactions (EP 239400).

When the antibodies of the present invention are chimeric antibodies or humanized antibodies, the C regions of these antibodies are preferably derived from human antibodies. For example, Cγ1, Cγ2, Cγ3, and Cγ4 can be used for the H chain, while Cκ and Cλ can be used for the L chain. Moreover, if required, amino acid mutations may be introduced into the human antibody C region to enhance or lower the binding to Fcγ receptor or FcRn or to improve antibody stability or productivity. A chimeric antibody of the present invention preferably includes a variable region of an antibody derived from a nonhuman mammal and a constant region derived from a human antibody. Meanwhile, a humanized antibody preferably includes CDRs of an antibody derived from a nonhuman mammal and FRs and C regions derived from a human antibody. The constant regions derived from human antibodies preferably include an FcRn-binding region. Such antibodies include, for example, IgGs (IgG1, IgG2, IgG3, and IgG4). The constant regions used for the humanized antibodies of the present invention may be constant regions of antibodies of any isotype. A constant region of human IgG is preferably used, though it is not limited thereto. The FRs derived from a human antibody, which are used for the humanized antibodies, are not particularly limited either, and may be derived from an antibody of any isotype.

The variable and constant regions of chimeric and humanized antibodies of the present invention may be modified by deletion, substitution, insertion, and/or addition, and such, so long as the binding specificity of the original antibodies is exhibited.

Since the immunogenicity in the human body is lowered, chimeric and humanized antibodies using human-derived sequences are thought to be useful when administered to humans for therapeutic purposes or such.

The antibodies of the present invention may be prepared by any method. For example, antibodies whose antigen-binding activity at pH 5.8 is originally greater than or comparable to that at pH 7.4 may be artificially modified through histidine substitution described above or the like so that their antigen-binding activity at pH 5.8 becomes lower than that at pH 7.4. Alternatively, antibodies whose antigen-binding activity at pH 5.8 is lower than that at pH 7.4 may be selected by screening a number of antibodies obtained from an antibody library or hybridomas as described below.

When histidine is substituted for amino acids in an antibody, known sequences may be used for the H chain or L chain amino acid sequence of the antibody before introduction of histidine mutations, or amino acid sequences of antibodies newly obtained by methods known to those skilled in the art can also be used. For example, the antibodies may be obtained from an antibody library, or they may be obtained by cloning genes encoding antibodies from hybridomas producing monoclonal antibodies.

Regarding antibody libraries, many antibody libraries are already known, and methods for producing antibody libraries are also known; therefore, those skilled in the art can appropriately obtain antibody libraries. For example, regarding antibody phage libraries, one can refer to the literature such as Clackson et al., Nature 1991, 352: 624-8; Marks et al., J. Mol. Biol. 1991, 222: 581-97; Waterhouses et al., Nucleic Acids Res. 1993, 21: 2265-6; Griffiths et al., EMBO J. 1994, 13: 324.0-60; Vaughan et al., Nature Biotechnology 1996, 14: 309-14; and Japanese Patent Kohyo Publication No. (JP-A) H20-504970 (unexamined Japanese national phase publication corresponding to a non-Japanese international publication). In addition, it is possible to use known methods, such as methods using eukaryotic cells as libraries (WO 95/15393) and ribosome display methods. Furthermore, technologies to obtain human antibodies by panning using human antibody libraries are also known. For example, variable regions of human antibodies can be expressed on the surface of phages as single chain antibodies (scFvs) using phage display methods, and phages that bind to antigens can be selected. Genetic analysis of the selected phages can determine the DNA sequences encoding the variable regions of human antibodies that bind to the antigens. Once the DNA sequences of scFvs that bind to the antigens is revealed, suitable expression vectors can be produced based on these sequences to obtain human antibodies. These methods are already well known, and one can refer to WO 92/01047, WO 92/20791, WO 93/06213, WO 93/11236, WO 93/19172, WO 95/01438, and WO 95/15388.

As for methods for obtaining genes encoding antibodies from hybridomas, known technologies may be basically used, which involve the use of desired antigens or cells expressing the desired antigens as sensitizing antigens, using these to perform immunizations according to conventional immunization methods, fusing the resulting immune cells with known parent cells by conventional cell fusion methods, screening monoclonal antibody producing cells (hybridomas) by conventional screening methods, synthesizing cDNAs of antibody variable regions (V regions) from mRNAs of the obtained hybridomas using reverse transcriptase, and linking them with DNAs encoding the desired antibody constant regions (C regions).

More specifically, sensitizing antigens to obtain the above-described antibody genes encoding the H chains and L chains include both complete antigens with immunogenicity and incomplete antigens including haptens and the like with no antigenicity; however they are not limited to these examples. For example, it is possible to use whole proteins and partial peptides of proteins of interest. In addition, it is known that substances comprising polysaccharides, nucleic acids, lipids, and such can be antigens. Thus, the antigens of the antibodies of the present invention are not particularly limited. The antigens can be prepared by methods known to those skilled in the art, for example, by baculovirus-based methods (for example, WO 98/46777) and such. Hybridomas can be produced, for example, by the method of Milstein et al. (G. Kohler and C. Milstein, Methods Enzymol. 1981, 73: 3-46) and such. When the immunogenicity of an antigen is low, immunization may be performed after linking the antigen with a macromolecule having immunogenicity, such as albumin. Alternatively, if necessary, antigens may be converted into soluble antigens by linking them with other molecules. When transmembrane molecules such as membrane antigens (for example, receptors) are used as antigens, portions of the extracellular regions of the membrane antigens can be used as a fragment, or cells expressing transmembrane molecules on their cell surface may be used as immunogens.

Antibody-producing cells can be obtained by immunizing animals using appropriate sensitizing antigens described above. Alternatively, antibody-producing cells can be prepared by in vitro immunization of lymphocytes that can produce antibodies. Various mammals can be used for immunization; such commonly used animals include rodents, lagomorphs, and primates. Such animals include, for example, rodents such as mice, rats, and hamsters; lagomorphs such as rabbits; and primates including monkeys such as cynomolgus monkeys, rhesus monkeys, baboons, and chimpanzees. In addition, transgenic animals carrying human antibody gene repertoires are also known, and human antibodies can be obtained by using these animals (see WO 96/34096; Mendez et al., Nat. Genet. 1997, 15: 146-56). Instead of using such transgenic animals, for example, desired human antibodies having binding activity against antigens can be obtained by in vitro sensitization of human lymphocytes with desired antigens or cells expressing the desired antigens, and then fusing the sensitized lymphocytes with human myeloma cells such as U266 (see Japanese Patent Application Kokoku Publication No. (JP-B) H01-59878 (examined, approved Japanese patent application published for opposition)). Furthermore, desired human antibodies can be obtained by immunizing transgenic animals carrying a complete repertoire of human antibody genes, with desired antigens (see WO 93/12227, WO 92/03918, WO 94/02602, WO 96/34096, and WO 96/33735).

Animal immunization can be carried out by appropriately diluting and suspending a sensitizing antigen in phosphate buffered saline (PBS), physiological saline, or such, and mixing it with an adjuvant to emulsify, if necessary. This is then intraperitoneally or subcutaneously injected into animals. Then, the sensitizing antigen mixed with Freund's incomplete adjuvant is preferably administered several times every four to 21 days. Antibody production can be confirmed by measuring the titer of the antibody of interest in animal sera using conventional methods.

Antibody-producing cells obtained from lymphocytes or animals immunized with a desired antigen can be fused with myeloma cells to generate hybridomas using conventional fusing agents (for example, polyethylene glycol) (Goding, Monoclonal Antibodies: Principles and Practice, Academic Press, 1986, 59-103). When required, hybridoma cells can be cultured and grown, and the binding specificity of the antibody produced from these hybridomas can be measured using known analysis methods, such as immunoprecipitation, radioimmunoassay (RIA), and enzyme-linked immunosorbent assay (ELISA). Thereafter, hybridomas producing antibodies of interest whose specificity, affinity, or activity has been determined can be subcloned by methods such as limiting dilution.

Next, genes encoding the selected antibodies can be cloned from hybridomas or antibody-producing cells (sensitized lymphocytes, and such) using probes that can specifically bind to the antibodies (for example, oligonucleotides complementary to sequences encoding the antibody constant regions). It is also possible to clone the genes from mRNA using RT-PCR. Immunoglobulins are classified into five different classes, IgA, IgD, IgE, IgG, and IgM. These classes are further divided into several subclasses (isotypes) (for example, IgG-1, IgG-2, IgG-3, and IgG-4; IgA-1 and IgA-2; and such). H chains and L chains used in the present invention to produce antibodies are not particularly limited and may originate from antibodies belonging to any of these classes or subclasses; however, IgG is particularly preferred.

Herein, it is possible to modify H-chain-encoding genes and L-chain-encoding genes using genetic engineering technologies. Genetically modified antibodies, such as chimeric antibodies and humanized antibodies, which have been artificially modified for the purpose of decreasing heterologous immunogenicity and such against humans, can be appropriately produced for antibodies such as mouse antibodies, rat antibodies, rabbit antibodies, hamster antibodies, sheep antibodies, and camel antibodies. Chimeric antibodies are antibodies including H chain and L chain variable regions of nonhuman mammal antibody, such as mouse antibody, and the H chain and L chain constant regions of human antibody. Chimeric antibodies can be obtained by ligating a DNA encoding a variable region of a mouse antibody to a DNA encoding a constant region of a human antibody, inserting this into an expression vector, and introducing the vector into a host to produce the antibody. A humanized antibody, which is also called a reshaped human antibody, can be synthesized by PCR using several oligonucleotides produced so that they have overlapping portions at the ends of DNA sequences designed to link the complementarity determining regions (CDRs) of an antibody of a nonhuman mammal such as a mouse. The resulting DNA can be ligated to a DNA encoding a human antibody constant region. The ligated DNA can be inserted into an expression vector, and the vector can be introduced into a host to produce the antibody (see EP 239400 and WO 96/02576). Human antibody FRs that are ligated via the CDR are selected when the CDR forms a favorable antigen-binding site. If necessary, amino acids in the framework region of an antibody variable region may be substituted such that the CDR of the reshaped human antibody forms an appropriate antigen-binding site (K. Sato et al., Cancer Res. 1993, 53: 10.01-10.06).

In addition to the humanization described above, antibodies may be modified to improve their biological properties, for example, the binding to the antigen. In the present invention, such modifications can be achieved by methods such as site-directed mutagenesis (see for example, Kunkel (1910.0) Proc. Natl. Acad. Sci. USA 82: 488), PCR mutagenesis, and cassette mutagenesis. In general, mutant antibodies whose biological properties have been improved show amino acid sequence homology and/or similarity of 70% or higher, more preferably 80% or higher, and even more preferably 90% or higher (for example, 95% or higher, 97%, 98%, or 99%), when compared to the amino acid sequence of the original antibody variable region. Herein, sequence homology and/or similarity is defined as the ratio of amino acid residues that are homologous (same residue) or similar (amino acid residues classified into the same group based on the general properties of amino acid side chains) to the original antibody residues, after the sequence homology value has been maximized by sequence alignment and gap introduction, if necessary. In general, natural amino acid residues are classified into groups based on the characteristics of their side chains as follows:

(1) hydrophobic: alanine, isoleucine, valine, methionine, and leucine;
(2) neutral hydrophilic: asparagine, glutamine, cysteine, threonine, and serine;
(3) acidic: aspartic acid and glutamic acid;
(4) basic: arginine, histidine, and lysine;
(5) residues that affect the orientation of the chain: glycine, and proline; and
(6) aromatic: tyrosine, tryptophan, and phenylalanine.

In general, a total of six complementarity determining regions (CDRs; hypervariable regions) present on the H chain and L chain variable regions interact with each other to form an antigen-binding site of an antibody. A variable region alone is also known to be capable of recognizing and binding to an antigen, although its affinity is lower than the affinity of the whole binding site. Thus, antibody genes encoding the H chain and L chain of the present invention may encode fragments each including the H chain or L chain antigen-binding site, as long as the polypeptide encoded by the gene retains the activity of binding to the desired antigen.

As described above, the heavy chain variable region is in general constituted by three CDRs and four FRs. In a preferred embodiment of the present invention, amino acid residues to be "modified" can be appropriately selected from amino acid residues, for example, in a CDR or FR. In general, modifications of amino acid residues in the CDRs may reduce the antigen-binding ability. Thus, appropriate amino acid residues to be "modified" in the present invention are preferably selected from amino acid residues in the FRs, but are not limited thereto. It is possible to select amino acids in a CDR as long as the modification has been confirmed not to reduce the binding ability. Alternatively, by using public databases or such, those skilled in the art can obtain appropriate sequences that can be used as an FR of antibody variable region of an organism such as human or mouse.

Furthermore, the present invention provides genes encoding the antibodies of the present invention. The genes encoding the antibodies of the present invention may be any genes, and may be DNAs, RNAs, nucleic acid analogs, or the like.

Furthermore, the present invention also provides host cells carrying the genes described above. The host cells are not particularly limited and include, for example, *E. coli* and various animal cells. The host cells may be used, for example, as a production system to produce and express the antibodies of the present invention. In vitro and in vivo production systems are available for polypeptide production systems. Such in vitro production systems include, for example, production systems using eukaryotic cells or prokaryotic cells.

Eukaryotic cells that can be used as host cells include, for example, animal cells, plant cells, and fungal cells. Animal cells include: mammalian cells, for example, CHO (J. Exp. Med. (1995) 108: 94.0), COS, HEK293, 3T3, myeloma, BHK (baby hamster kidney), HeLa, and Vero; amphibian cells such as *Xenopus laevis* oocytes (Valle el al., Nature (1981) 291: 338-340); and insect cells such as Sf9, Sf21, and Tn5. CHO-DG44, CHO-DX11B, COS7 cells, HEK293 cells, and BHK cells are preferably used to express the antibodies of the present invention. Among animal cells, CHO cells are particularly preferable for large-scale expression. Vectors can be introduced into host cells, for example, by calcium phosphate methods, DEAE-dextran methods, methods using cationic liposome DOTAP (Boehringer-Mannheim), electroporation methods, and lipofection methods.

Regarding plant cells, for example, *Nicotiana tabacum*-derived cells and duckweed (*Lemna minor*) are known as a protein production system. Calluses can be cultured from these cells to produce the antibodies of the present invention. Regarding fungal cells, known protein expression systems are those using yeast cells, for example, cells of genus *Saccharomyces* (such as *Saccharomyces cerevisiae* and *Saccharomyces pombe*); and cells of filamentous fungi, for example, genus *Aspergillus* (such as *Aspergillus niger*). These cells can be used as a host to produce the antibodies of the present invention.

Bacterial cells can be used in the prokaryotic production systems. Regarding bacterial cells, production systems using *Bacillus subtilis* are known in addition to the production systems using *E. coli* described above. Such systems can be used in producing the antibodies of the present invention.

<Screening Methods>

The present invention provides methods of screening for antigen-binding molecules whose antigen-binding activity at acidic pH is lower than that at neutral pH. The present invention also provides methods of screening for antigen-binding molecules which can individually bind to multiple antigens. The present invention also provides methods of screening for antigen-binding molecules which are superior in the retention in plasma. The present invention also provides methods of screening for an antigen-binding molecule that dissociates within a cell from an extracellularly-bound antigen. The present invention also provides methods of screening for an antigen-binding molecule that is bound to an antigen and internalized into a cell, and released to the outside of the cell in an antigen-free form. The present invention also provides methods of screening for an antigen-binding molecule that has increased ability to eliminate antigens in plasma. Furthermore, the present invention also provides methods of screening for antigen-binding molecules which are particularly useful when used as pharmaceutical compositions.

Specifically, the present invention provides methods of screening for antigen-binding molecules, which comprise the steps of:
(a) determining the antigen-binding activity of an antigen-binding molecule at pH 6.7 to pH 10.0;
(b) determining the antigen-binding activity of the antigen-binding molecule at pH 4.0 to pH 6.5; and
(c) selecting an antigen-binding molecule whose antigen-binding activity at pH 6.7 to pH 10.0 is greater than the antigen-binding activity at pH 4.0 to pH 6.5.

In the screening methods of the present invention, the antigen-binding activity of the antigen-binding molecule at pH 6.7 to pH 10.0 is not particularly limited, as long as it is an antigen-binding activity at a pH between pH 6.7 and pH 10.0. However, for example, a preferred antigen-binding activity is an antigen-binding activity at a pH between pH 7.0 and pH 8.0, and a more preferred antigen-binding activity is an antigen-binding activity at pH 7.4. Further, the antigen-binding activity of the antigen-binding molecule at pH 4.0 to pH 6.5 is not particularly limited, as long as it is an antigen-binding activity at a pH between pH 4.0 and pH 6.5. However, for example, a preferred antigen-binding activity is an antigen-binding activity at a pH between pH 5.5 to pH 6.5, and a more preferred antigen-binding activity is an antigen-binding activity at pH 5.8 or pH 5.5.

The antigen-binding activity of an antigen-binding molecule can be determined by methods known to those skilled in the art. Conditions other than the pH can be appropriately determined by those skilled in the art. The antigen-binding activity of an antigen-binding molecule can be assessed as dissociation constant (KD), apparent dissociation constant (apparent KD), dissociation rate ($k_d$), apparent dissociation rate (apparent $k_d$), or such. These constants can be determined by methods known to those skilled in the art, for example, using a Biacore™ surface plasmon resonance system (GE Healthcare), Scatchard plot, or FACS.

Herein, "the step of selecting an antigen-binding molecule whose antigen-binding activity at pH 6.7 to pH 10.0 is greater than that at pH 4.0 to pH 6.5" has a same meaning as "the step of selecting an antigen-binding molecule whose antigen-binding activity at pH 4.0 to pH 6.5 is lower than that at pH 6.7 to pH 10.0".

The difference between the antigen-binding activity at pH 6.7 to pH 10.0 and that at pH 4.0 to pH 6.5 is not particularly limited as long as the antigen-binding activity at pH 6.7 to pH 10.0 is greater than that at pH 4.0 to pH 6.5. However, the antigen-binding activity at pH 6.7 to pH 10.0 is preferably twice or greater, more preferably ten times or greater, and still more preferably 40 times or greater than the antigen-binding activity at pH 4.0 to pH 6.5.

Furthermore, the present invention also provides methods of screening for antigen-binding molecules, which comprise the steps of:
(a) binding an antigen-binding molecule to an antigen under a condition of pH 6.7 to pH 10.0;
(b) placing the antigen-binding molecule that bound to the antigen of (a) under a condition of pH 4.0 to pH 6.5; and
(c) obtaining the antigen-binding molecule that dissociated under the condition of pH 4.0 to pH 6.5.

In addition, the present invention also provides methods of screening for antigen-binding molecules, which comprise the steps of:
(a) selecting an antigen-binding molecule that does not bind to an antigen under a condition of pH 4.0 to pH 6.5;
(b) binding the antigen-binding molecule selected in (a) to an antigen under a condition of pH 6.7 to pH 10.0; and
(c) obtaining the antigen-binding molecule that bound to the antigen under the condition of pH 6.7 to pH 10.0.

Furthermore, the present invention also provides methods of screening for antigen-binding molecules, which comprise the steps of:
(a) binding an antigen-binding molecule to an antigen under a condition of pH 6.7 to pH 10.0;
(b) placing the antigen-binding molecule that bound to the antigen of (a) under a condition of pH 4.0 to pH 6.5;
(c) obtaining the antigen-binding molecule that dissociated under the condition of pH 4.0 to pH 6.5;
(d) amplifying the gene encoding the antigen-binding molecule that dissociated; and
(e) obtaining the eluted antigen-binding molecule.

The steps of (a) to (d) may be repeated twice or more times. Thus, the present invention provides the methods described above further including a step of repeating the steps of (a) to (d) twice or more times. The number for repeating the steps of (a) to (d) is not particularly limited; however, the number is in general ten or less.

Furthermore, the present invention also provides methods of screening for antigen-binding molecules, which comprise the steps of:
(a) selecting an antigen-binding molecule that does not bind to an antigen under a condition of pH 4.0 to pH 6.5;
(b) binding the antigen-binding molecule selected in (a) to an antigen under a condition of pH 6.7 to pH 10.0;
(c) obtaining the antigen-binding molecule that bound to the antigen under the condition of pH 6.7 to pH 10.0;
(d) amplifying the gene encoding the antigen-binding molecule that dissociated; and
(e) collecting the eluted antigen-binding molecule.

The steps of (a) to (d) may be repeated twice or more times. Thus, the present invention provides the methods described above further including a step of repeating the steps of (a) to (d) twice or more times. The number for repeating the steps of (a) to (d) is not particularly limited; however, the number is in general ten or less.

When a phage library or such is used in the screening methods of the present invention, the step of amplifying the gene encoding the antigen-binding molecule can also be a step of amplifying phages.

In the methods of the present invention, binding of the antigen-binding molecule and the antigen may be carried out under any state, without particular limitation. For example, binding of the antigen-binding molecule and the antigen may be carried out by contacting an antigen with an immobilized antigen-binding molecule, or by contacting an antigen-binding molecule with an immobilized antigen. Alternatively, binding of the antigen-binding molecule and the antigen may be carried out by contacting the antigen and antigen-binding molecule in a solution.

Furthermore, the present invention also provides methods of screening for antigen-binding molecules whose binding activity at a first pH is greater than that at a second pH, which comprise the steps of:
(a) binding an antigen-binding molecule to an antigen-immobilized column under the condition of a first pH;
(b) eluting the antigen-binding molecule that had bound to the column at the first pH from the column under the condition of a second pH; and
(c) obtaining the eluted antigen-binding molecule.

Furthermore, the present invention also provides methods of screening for antigen-binding molecules whose binding activity at a first pH is smaller than that at a second pH, which comprise the steps of:
(a) passing an antigen-binding molecule through an antigen-immobilized column under the condition of a first pH;
(b) collecting the antigen-binding molecule that eluted without binding to the column in step (a);
(c) binding the antigen-binding molecule collected in (b) to a column under the condition of a second pH; and
(d) obtaining the antigen-binding molecule that bound to the column in step (c).

Furthermore, the present invention also provides methods of screening for antigen-binding molecules whose binding activity at a first pH is greater than that at a second pH, which comprise the steps of:
(a) binding an antigen-binding molecule library to an antigen-immobilized column under the condition of a first pH;
(b) eluting the antigen-binding molecule from the column under the condition of a second pH;
(c) amplifying the gene encoding the eluted antigen-binding molecule; and
(d) obtaining the eluted antigen-binding molecule.

The steps of (a) to (c) may be repeated twice or more times. Thus, the present invention provides the methods described above further including the step of repeating the steps of (a) to (c) twice or more times. The number for repeating the steps of (a) to (c) is not particularly limited; however, the number is in general ten or less.

In the present invention, each of the first and second pHs may be any pH, as long as they are not identical. In a preferred combination of the first and second pHs, for example, the first pH is between pH 6.7 and pH 10.0, and the second pH is between pH 4.0 and pH 6.5; in a more preferred combination, the first pH is between pH 7.0 and pH 8.0, and the second pH is between pH 5.5 and pH 6.5; and in a still more preferred combination, the first pH is pH 7.4 and the second pH is pH 5.8 or pH5.5.

In another preferred combination of the first and second pHs, for example, the first pH is between pH 4.0 and pH 6.5, and the second pH is between pH 6.7 and pH 10.0; in a more preferred combination, the first pH is between pH 5.5 and pH 6.5, and the second pH is between pH 7.0 and pH 8.0; and in a still more preferred combination, the first pH is pH 5.8 or pH5.5 and the second pH is pH 7.4.

Antigen-binding molecules that are screened by the methods of the present invention may be any antigen-binding molecules. For example, it is possible to use the above-described antigen-binding molecules in the screening of the present invention. For example, it is possible to screen antigen-binding molecules including natural sequences or antigen-binding molecules including amino acid sequences with substitutions. Preferred antigen-binding molecules that are screened in the present invention include, for example, antigen-binding molecules in which at least one amino acid is substituted with histidine or at least one histidine is inserted. The site of introduction of histidine substitution or insertion is not particularly limited, and may be introduced at any site. Furthermore, histidine substitution or insertion may be introduced at one site, or may be introduced at two or more sites. Furthermore, preferred antigen-binding molecules that are screened in the present invention include, for example, antigen-binding molecules including modified antibody constant regions.

Antigen-binding molecules that are screened by the methods of the present invention may be a number of different antigen-binding molecules introduced with histidine substitutions or insertions at different sites, for example, by histidine scanning.

Thus, the screening methods of the present invention may further comprise the step of substituting at least one amino acid in the antigen-binding molecule with histidine or inserting at least one histidine into the antigen-binding molecule.

In the screening methods of the present invention, non-natural amino acids may be used instead of histidine. Therefore, the present invention can also be understood by replacing the above-mentioned histidine with non-natural amino acids.

Moreover, the screening methods of the present invention may further comprise the step of modifying amino acids of antibody constant regions.

Antigen-binding substances that are screened by the screening methods of the present invention may be prepared by any method. For example, it is possible to use pre-existing antibodies, pre-existing libraries (phage libraries and the like), antibodies and libraries that are prepared from hybridomas obtained by immunizing animals or from B cells of immunized animals, antibodies and libraries (libraries with high content of histidine or non-natural amino acid, libraries introduced with histidine or non-natural amino acid at specific sites, and the like) prepared by introducing histidine mutations or non-natural amino acid mutations into the above-described antibodies and libraries, and so on.

Antigen-binding molecules that bind to the antigen multiple times, which are thus superior in the retention in plasma, can be obtained by the screening methods of the present invention. Thus, the screening methods of the present invention can be used as screening methods for obtaining antigen-binding molecules that are superior in the retention in plasma.

Furthermore, antigen-binding molecules that can bind to the antigen two or more times when administered to animals such as humans, mice, or monkeys can be obtained by the screening methods of the present invention. Thus, the screening methods of the present invention can be used as screening methods for obtaining antigen-binding molecules that can bind to the antigen two or more times.

Furthermore, antigen-binding molecules that are capable of binding to more antigens as compared to the number of their antigen-binding sites when administered to animals such as humans, mice, or monkeys can be obtained by the screening methods of the present invention. Thus, the screening methods of the present invention can be used as screening methods for obtaining antigen-binding molecules that are capable of binding to more antigens as compared to the number of their antigen-binding sites. For example, when the antibody is a neutralizing antibody, the screening methods of the present invention can be used as screening methods for obtaining antigen-binding molecules that can neutralize more antigens as compared to the number of the antigen-binding sites of the antigen-binding molecules.

Furthermore, antigen-binding molecules that are capable of dissociating within a cell from an extracellularly-bound antigen when administered to animals such as humans, mice, or monkeys can be obtained by the screening methods of the present invention. Thus, the screening methods of the present invention can be used as screening methods for obtaining antigen-binding molecules that are capable of dissociating within a cell from an extracellularly-bound antigen.

Furthermore, antigen-binding molecules that are bound to an antigen and internalized into a cell, and released to the outside of the cell in an antigen-free form when administered to animals such as humans, mice, or monkeys can be obtained by the screening methods of the present invention. Thus, the screening methods of the present invention can be used as screening methods for obtaining antigen-binding molecules that are bound to an antigen and internalized into a cell, and released to the outside of the cell in an antigen-free form.

Furthermore, antigen-binding molecules that can rapidly eliminate antigens in plasma when administered to animals such as humans, mice, or monkeys can be obtained by the screening methods of the present invention. Thus, the screening methods of the present invention can be used as screening methods for obtaining antigen-binding molecules with increased (high) ability to eliminate antigens in plasma.

Furthermore, such antigen-binding molecules are expected to be especially superior as pharmaceuticals, because the dose and frequency of administration in patients can be reduced and as a result the total dosage can be reduced. Thus, the screening methods of the present invention can be used as methods of screening for antigen-binding molecules for use as pharmaceutical compositions.

In addition, the present invention provides libraries in which the histidine content is increased as compared to the original libraries. Libraries containing antigen-binding molecules with increased histidine content can be used in the screening methods described above and the production methods described hereinafter.

Libraries with increased histidine content can be prepared by methods known to those skilled in the art, which include the following method. 20 types of triplet codons (trinucleotides) encoding 20 types of amino acids can be incorporated at equal frequency when synthesizing nucleic acids to prepare a library by the trinucleotide-method (J Mol Biol. 2008 Feb. 29; 376(4): 1182-200). As a result, the position mutated for the library can be made to contain 20 types of amino acids at equal probability. The frequency of histidine in the position mutated for the library can be increased by increasing the proportion of a histidine-encoding trinucleotide as compared to the remaining amino acids among the 20 types in the synthesis.

<Methods for Producing Antigen-Binding Molecules>

The present invention provides methods for producing antigen-binding molecules whose antigen-binding activity at the endosomal pH is lower than that at the plasma pH. The present invention also provides methods for producing antigen-binding molecules that are superior in the retention in plasma. The present invention also provides methods for producing antigen-binding molecules that are especially useful when used as pharmaceutical compositions.

Specifically, the present invention provides methods for producing antigen-binding molecules, which comprise the steps of:
(a) determining the antigen-binding activity of an antigen-binding molecule at pH 6.7 to pH 10.0;
(b) determining the antigen-binding activity of the antigen-binding molecule at pH 4.0 to pH 6.5;
(c) selecting an antigen-binding molecule whose antigen-binding activity at pH 6.7 to pH 10.0 is greater than that at pH 4.0 to pH 6.5;
(d) obtaining the gene encoding the antigen-binding molecule selected in (c); and
(e) producing the antigen-binding molecule using the gene obtained in (d).

The present invention also provides methods for producing antigen-binding molecules, which comprise the steps of:
(a) binding an antigen-binding molecule to an antigen at pH 6.7 to pH 10.0;
(b) allowing the antigen-binding molecule bound to the antigen of (a) to stand under the condition of pH 4.0 to pH 6.5;
(c) collecting the antigen-binding molecule that dissociated under the condition of pH 4.0 to pH 6.5;
(d) obtaining the gene encoding the antigen-binding molecule obtained in (c); and
(e) producing the antigen-binding molecule using the gene obtained in (d).

Furthermore, the present invention provides methods for producing antigen-binding molecules, which comprise the steps of:
(a) selecting an antigen-binding molecule that does not bind to the antigen under the condition of pH 4.0 to pH 6.5;
(b) binding the antigen under the condition of pH 6.7 to pH 10.0 to the antigen-binding molecule selected in (a);
(c) collecting the antigen-binding molecule that bound to the antigen under the condition of pH 6.7 to pH 10.0;
(d) obtaining the gene encoding the antigen-binding molecule collected in (c); and
(e) producing the antigen-binding molecule using the gene obtained in (d).

In addition, the present invention provides methods for producing antigen-binding molecules, which comprise the steps of:
- (a) binding an antigen-binding molecule to an antigen under the condition of pH 6.7 to 10.0;
- (b) allowing the antigen-binding molecule that bound to the antigen in (a) to stand under the condition of pH 4.0 to pH 6.5;
- (c) collecting the antigen-binding molecule that dissociated under the condition of pH 4.0 to pH 6.5;
- (d) amplifying the gene encoding the dissociated antigen-binding molecule;
- (e) collecting the eluted antigen-binding molecule;
- (f) obtaining the gene encoding the antigen-binding molecule collected in (e); and
- (g) producing the antigen-binding molecule using the gene obtained in (f).

Steps (a) to (d) may be repeated twice or more times. Thus, the present invention provides the methods described above, which further comprise the step of repeating steps (a) to (d) twice or more times. The number of times steps (a) to (d) is repeated is not particularly limited; however, it is generally ten times or less.

Furthermore, the present invention provides methods of screening for antigen-binding molecules, which comprise the steps of:
- (a) selecting an antigen-binding molecule that does not bind to the antigen under the condition of pH 4.0 to pH 6.5;
- (b) binding the antigen under the condition of pH 6.7 to pH 10.0 to the antigen-binding molecule selected in (a);
- (c) collecting the antigen-binding molecule that bound to the antigen under the condition of pH 6.7 to pH 10.0;
- (d) amplifying the gene encoding the dissociated antigen-binding molecule;
- (e) collecting the eluted antigen-binding molecule;
- (f) obtaining the gene encoding the antigen-binding molecule collected in (e); and
- (g) producing the antigen-binding molecule using the gene obtained in (f).

Steps (a) to (d) may be repeated twice or more times. Thus, the present invention provides the methods described above, which further comprise the step of repeating steps (a) to (d) twice or more times. The number of times steps (a) to (d) is repeated is not particularly limited; however, it is generally ten times or less.

Furthermore, the present invention provides methods for producing antigen-binding molecules whose binding activity at a first pH is greater than that at a second pH, which comprise the steps of:
- (a) binding the antigen-binding molecule to a column immobilized with antigen under the first pH condition;
- (b) eluting the antigen-binding molecule, which is bound to the column under the first pH condition from the column under a second pH condition;
- (c) collecting the eluted antigen-binding molecule;
- (d) obtaining the gene encoding the antigen-binding molecule collected in (c); and
- (e) producing the antigen-binding molecule using the gene obtained in (d).

Furthermore, the present invention provides methods for producing antigen-binding molecules whose binding activity at a first pH is greater than that at a second pH, which comprise the steps of:
- (a) binding an antigen-binding molecule library to a column immobilized with antigen under the first pH condition;
- (b) eluting the antigen-binding molecule from the column under the second pH condition;
- (c) amplifying the gene encoding the eluted antigen-binding molecule;
- (d) collecting the eluted antigen-binding molecule;
- (e) obtaining the gene encoding the antigen-binding molecule collected in (d); and
- (f) producing the antigen-binding molecule using the gene obtained in (e).

Steps (a) to (c) may be repeated twice or more times. Thus, the present invention provides the methods described above, which further comprise the step of repeating steps (a) to (c) twice or more times. The number of times steps (a) to (c) is repeated is not particularly limited; however, it is generally ten times or less.

When a phage library or such is used in the production methods of the present invention, the step of amplifying the gene encoding the antigen-binding molecule may be the step of amplifying phages.

Antigen-binding substances that are used in the production methods of the present invention may be prepared by any method. For example, it is possible to use pre-existing antibodies, pre-existing libraries (phage libraries and the like), antibodies and libraries that are prepared from hybridomas obtained by immunizing animals or from B cells of immunized animals, antibodies and libraries (libraries with high content of histidine or non-natural amino acid, libraries introduced with histidine or non-natural amino acid at specific sites, and the like) prepared by introducing histidine mutations or non-natural amino acid mutations into the above-described antibodies and libraries, and so on.

In the above-described production methods, the antigen-binding activity of the antigen-binding molecule at pH 6.7 to pH 10.0 is not particularly limited, as long as the antigen-binding activity is that at a pH between pH 6.7 and pH 10.0. A preferred antigen-binding activity is that at a pH between pH 7.0 and pH 8.0, and a more preferred antigen-binding activity is that at pH 7.4. Alternatively, the antigen-binding activity of the antigen-binding molecule at pH 4.0 to pH 6.5 is not particularly limited, as long as the antigen-binding activity is that at a pH between pH 4.0 and pH 6.5. A preferred antigen-binding activity is that at a pH between pH 5.5 to pH 6.5, and a more preferred antigen-binding activity is that at pH 5.8 or pH 5.5.

The antigen-binding activity of an antigen-binding molecule can be determined by methods known to those skilled in the art. Conditions except for pH can be appropriately determined by those skilled in the art.

The step of selecting antigen-binding molecules whose antigen-binding activity at pH 6.7 to pH 10.0 is greater than that at pH 4.0 to pH 6.5 is synonymous with the step of selecting antigen-binding molecules whose antigen-binding activity at pH 4.0 to pH 6.5 is lower than that at pH 6.7 to pH 10.0.

The difference in the antigen-binding activity at pH 6.7 to pH 10.0 and at pH 4.0 to pH 6.5 is not particularly limited as long as the antigen-binding activity at pH 6.7 to pH 10.0 is greater than that at pH 4.0 to pH 6.5. The antigen-binding activity at pH 6.7 to pH 10.0 is preferably twice or greater, more preferably ten times or greater, and still more preferably 40 times or greater than that at pH 4.0 to pH 6.5.

In the production methods described above, the antigen-binding molecule may be bound to the antigen under any condition, and the condition is not particularly limited. For example, the antigen-binding molecule may be bound to the antigen by contacting the antigen with the immobilized antigen-binding molecule, or by contacting the antigen-binding molecule with the immobilized antigen. Alternatively, the antigen-binding molecule may be bound to the antigen by contacting the antigen and antigen-binding molecule in a solution.

In the production methods described above, each of the first and second pHs may be any pH, as long as they are not identical. In a preferred combination of the first and second pHs, for example, the first pH is between pH 6.7 and pH 10.0, and the second pH is between pH 4.0 and pH 6.5; in a more preferred combination, the first pH is between pH 7.0 and pH 8.0, and the second pH is between pH 5.5 and pH 6.5; and in a still more preferred combination, the first pH is pH 7.4 and the second pH is pH 5.8 or pH 5.5.

In another preferred combination of the first and second pHs, for example, the first pH is between pH 4.0 and pH 6.5, and the second pH is between pH 6.7 and pH 10.0; in a more preferred combination, the first pH is between pH 5.5 and pH 6.5, and the second pH is between pH 7.0 and pH 8.0; and in a still more preferred combination, the first pH is pH 5.8 or pH 5.5 and the second pH is pH 7.4.

Antigen-binding molecules that are produced by the production methods described above may be any antigen-binding molecules. Preferred antigen-binding molecules include, for example, antigen-binding molecules in which at least one amino acid is substituted with histidine or at least one histidine has been inserted. The site where such histidine mutation is introduced is not particularly limited and may be introduced at any site. Furthermore, histidine mutation may be introduced at one site or at two or more sites.

Thus, the production methods of the present invention may further comprise the step of substituting at least one amino acid in an antigen-binding molecule with histidine or inserting at least one histidine into antigen-binding molecules.

In the production methods of the present invention, non-natural amino acids may be used instead of histidine. Therefore, the present invention can also be understood by replacing the above-mentioned histidine with non-natural amino acids.

Furthermore, in another embodiment, the antigen-binding molecules that are produced by the production methods described above include, for example, antigen-binding molecules including modified antibody constant regions. Accordingly, the production methods of the present invention may further comprise the step of modifying the amino acids of antibody constant regions.

The antigen-binding molecules that are produced by the production methods of the present invention are superior in the retention in plasma. Thus, the production methods of the present invention can be used as methods for producing antigen-binding molecules that are superior in the retention in plasma.

Furthermore, antigen-binding molecules produced by the production methods are expected to be capable of binding to the antigen two or more times when administered to animals such as humans, mice, or monkeys. Thus, the production methods of the present invention can be used as methods for producing antigen-binding molecules that are capable of binding to the antigen two or more times.

Furthermore, antigen-binding molecules produced by the production methods of the present invention are expected to be capable of binding to more antigens as compared to the number of their antigen-binding sites when administered to animals such as humans, mice, or monkeys. Thus, the production methods of the present invention can be used as methods for producing antigen-binding molecules that are capable of binding to more antigens as compared to the number of their antigen-binding sites.

Furthermore, antigen-binding molecules produced by the production methods of the present invention are expected to be capable of dissociating within a cell from an extracellularly-bound antigen when administered to animals such as humans, mice, or monkeys. Thus, the production methods of the present invention can be used as methods for producing antigen-binding molecules that are capable of dissociating within a cell from an extracellularly-bound antigen.

Furthermore, antigen-binding molecules produced by the production methods of the present invention are expected to be capable of being bound to an antigen and internalized into a cell as well as being released to the outside of the cell in an antigen-free form, when administered to animals such as humans, mice, or monkeys. Thus, the production methods of the present invention can be used as methods for producing antigen-binding molecules that are capable of being bound to an antigen and internalized into a cell and being released to the outside of the cell in an antigen-free form.

Furthermore, antigen-binding molecules that are produced by the production methods of the present invention are expected to be capable of rapidly eliminating antigens from plasma when administered to animals such as humans, mice, or monkeys. Thus, the production methods of the present invention can be used as method for producing antigen-binding molecules with increased (high) ability to eliminate antigens in plasma.

Furthermore, such antigen-binding molecules can reduce the number of doses in patients and are expected to be especially superior as pharmaceuticals. Thus, the production methods of the present invention can be used as methods for producing antigen-binding molecules for used as pharmaceutical compositions.

Genes obtained by the production methods of the present invention are typically carried by (inserted into) appropriate vectors, and then introduced into host cells. The vectors are not particularly limited as long as they stably retain the inserted nucleic acids. For example, when *Escherichia coli* (*E. coli*) is used as the host, preferred cloning vectors include pBluescript vector (Stratagene); however, various commercially available vectors may be used. When using vectors to produce the antigen-binding molecules of the present invention, expression vectors are particularly useful. The expression vectors are not particularly limited as long as the vectors express the antigen-binding molecules in vitro, in *E. coli*, in culture cells, or in a body of an organism. For example, pBEST vector (Promega) is preferred for in vitro expression; pET vector (Invitrogen) is preferred for *E. coli*; pME18S-FL3 vector (GenBank Accession No. AB009864) is preferred for culture cells; and pME18S vector (Mol Cell Biol. 8:466-472 (1988)) is preferred for bodies of organisms. DNAs of the present invention can be inserted into the vectors by conventional methods, for example, by ligation using restriction enzyme sites (Current protocols in Molecular Biology, edit. Ausubel et al., (1987) Publish. John Wiley & Sons, Section 11.4-11.11).

The above host cells are not particularly limited, and various host cells may be used depending on the purpose. Examples of cells for expressing the antigen-binding molecules include bacterial cells (such as those of *Streptococcus, Staphylococcus, E. coli, Streptomyces,* and *Bacillus subtilis*), eukaryotic cells (such as those of yeast and *Aspergillus*), insect cells (such as *Drosophila* S2 and *Spodoptera* SF9), animal cells (such as CHO, COS, HeLa, C127, 3T3, BHK, HEK293, and Bowes melanoma cells), and plant cells. Vectors can be introduced into a host cell by known methods, for example, calcium phosphate precipitation methods, electroporation methods (Current protocols in Molecular Biology edit. Ausubel et al. (1987) Publish. John Wiley & Sons, Section 9.1-9.9), lipofection methods, and microinjection methods.

The host cells can be cultured by known methods. For example, when using animal cells as a host, DMEM, MEM, RPMI 1640, or IMDM may be used as the culture medium. They may be used with serum supplements such as FBS or fetal calf serum (FCS). The cells may be cultured in serum-free cultures. The preferred pH is about 6 to 8 during the course of culturing. Incubation is carried out typically at 30 to 40° C. for about 15 to 200 hours. Medium is exchanged, aerated, or agitated, as necessary.

Appropriate secretion signals may be incorporated to polypeptides of interest so that the antigen-binding molecules expressed in the host cell are secreted into the lumen of the endoplasmic reticulum, into the periplasmic space, or into the extracellular environment. These signals may be endogenous to the antigen-binding molecules of interest or may be heterologous signals.

On the other hand, for example, production systems using animals or plants may be used as systems for producing polypeptides in vivo. A polynucleotide of interest is introduced into an animal or plant and the polypeptide is produced in the body of the animal or plant, and then collected. The "hosts" of the present invention include such animals and plants.

The production system using animals include those using mammals or insects. It is possible to use mammals such as goats, pigs, sheep, mice, and bovines (Vicki Glaser SPECTRUM Biotechnology Applications (1993)). The mammals may be transgenic animals.

For example, a polynucleotide encoding an antigen-binding molecule of the present invention is prepared as a fusion gene with a gene encoding a polypeptide specifically produced in milk, such as the goat β-casein. Next, goat embryos are injected with polynucleotide fragments containing the fusion gene, and then transplanted to female goats. Desired antigen-binding molecules can be obtained from milk produced by the transgenic goats, which are born from the goats that received the embryos, or from their offspring. Hormones may be administered as appropriate to increase the volume of milk containing the antigen-binding molecule produced by the transgenic goats (Ebert et al., Bio/Technology (1994) 12: 699-702).

Insects such as silkworms may be used to produce the antigen-binding molecules of the present invention. When silkworms are used, baculoviruses carrying a polynucleotide encoding an antigen-binding molecule of interest can be used to infect silkworms, and the antigen-binding molecule of interest can be obtained from their body fluids.

Furthermore, when plants are used to produce the antigen-binding molecules of the present invention, for example, tobacco may be used. When tobacco is used, a polynucleotide encoding an antigen-binding molecule of interest is inserted into a plant expression vector, for example, pMON 530, and then the vector is introduced into bacteria, such as *Agrobacterium tumefaciens*. The bacteria are then allowed to infect tobacco such as *Nicotiana tabacum*, and the desired antigen-binding molecules can be collected from their leaves (Ma et al., Eur. J. Immunol. (1994) 24: 131-138). Alternatively, it is possible to infect duckweed (*Lemna minor*) with similar bacteria. After cloning, the desired antigen-binding molecules can be obtained from the duckweed cells (Cox K M et al., Nat. Biotechnol. 2006 December; 24(12):1591-1597).

The thus obtained antigen-binding molecules may be isolated from the inside or outside (such as the medium and milk) of host cells, and purified as substantially pure and homogenous antigen-binding molecules. The methods for isolating and purifying antigen-binding molecules are not particularly limited, and isolation and purification methods usually used for polypeptide purification can be used. Antigen-binding molecules may be isolated and purified, by appropriately selecting and combining, for example, chromatographic columns, filtration, ultrafiltration, salting out, solvent precipitation, solvent extraction, distillation, immunoprecipitation, SDS-polyacrylamide gel electrophoresis, isoelectric focusing, dialysis, and recrystallization.

Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., (1996) Cold Spring Harbor Laboratory Press). Such chromatographic methods can be conducted using liquid phase chromatography such as HPLC and FPLC. Columns used for affinity chromatography include, protein A columns and protein G columns. Columns using protein A include, for example, Hyper D, POROS, and Sepharose F. F. (Pharmacia).

If needed, an antigen-binding molecule can be modified arbitrarily, and peptides can be partially deleted by allowing an appropriate protein modification enzyme to act before or after purification of the antigen-binding molecule. Such protein modification enzymes include, for example, trypsin, chymotrypsin, lysyl endopeptidases, protein kinases, and glucosidases.

<Anti-IL-6 Receptor Antibodies>

Furthermore, the present invention provides the anti-IL-6 receptor antibodies of (a) to (m) below:

(a) an antibody that includes a heavy chain variable region including an amino acid sequence, in which at least one of Tyr at position 27, Asp at position 31, Asp at position 32, Trp at position 35, Tyr at position 51, Asn at position 59, Ser at position 63, Met at position 106, and Tyr at position 108 in the amino acid sequence of SEQ ID NO: 1 (H53 variable region) has been substituted with His;

(b) an antibody that includes a heavy chain variable region (H3pI) having an amino acid sequence, in which Tyr at position 27, Asp at position 31, and Trp at position 35 in the amino acid sequence of SEQ ID NO: 1 (H53 variable region) have been substituted with His;

(c) an antibody that includes a heavy chain variable region having an amino acid sequence, in which Tyr at position 27, Asp at position 31, Asp at position 32, Trp at position 35, Asn at position 59, Ser at position 63, and Tyr at position 108 in the amino acid sequence of SEQ ID NO: 1 (H53 variable region) have been substituted with His;

(d) an antibody that includes a heavy chain variable region (H170) having an amino acid sequence, in which Tyr at position 27, Asp at position 31, Asp at position 32, Trp at position 35, Asn at position 59, Ser at position 63, and Tyr at position 108 have been substituted with His, and in which Ser at position 99 has been substituted with Val and Thr at position 103 has been substituted with Ile in the amino acid sequence of SEQ ID NO: 1 (H53 variable region);

(e) an antibody that includes a heavy chain variable region having an amino acid sequence, in which Asp at position 31, Tyr at position 51, Ser at position 63, Met at position 106, and Tyr at position 108 in the amino acid sequence of SEQ ID NO: 1 (H53 variable region) have been substituted with His;

(f) an antibody that includes a heavy chain variable region (CLH5) having an amino acid sequence, in which Asp at position 31, Tyr at position 51, Ser at position 63, Met at position 106, and Tyr at position 108 have been substituted with His, and in which Ser at position 99 has been substituted with Phe and Thr at position 103 has been substituted with Ile in the amino acid sequence of SEQ ID NO: 1 (H53 variable region);

(g) an antibody that includes a light chain variable region having an amino acid sequence, in which at least one of Asp at position 28, Tyr at position 32, Glu at position 53, Ser at position 56, and Asn at position 92 in the amino acid sequence of SEQ ID NO: 2 (PF1L variable region) has been substituted with His;

(h) an antibody that includes a light chain variable region (L73) having an amino acid sequence, in which Asp at position 28, Tyr at position 32, and Glu at position 53 in the amino acid sequence of SEQ ID NO: 2 (PF1L variable region) have been substituted with His;

(i) an antibody that includes a light chain variable region (L82) having an amino acid sequence, in which Tyr at position 32 and Glu at position 53 in the amino acid sequence of SEQ ID NO: 1 (H53 variable region) have been substituted with His;

(j) an antibody that includes a light chain variable region (CLL5) having an amino acid sequence, in which Tyr at position 32, Glu at position 53, Ser at position 56, and Asn at position 92 in the amino acid sequence of SEQ ID NO: 2 (PF1L variable region) have been substituted with His;

(k) an antibody that includes the heavy chain variable region of (b) and the light chain variable region of (h);

(l) an antibody that includes the heavy chain variable region of (d) and the light chain variable region of (i); and (m) an antibody that includes the heavy chain variable region of (f) and the light chain variable region of (h).

Specific examples of the heavy chain variable region having an amino acid sequence in which at least one of Tyr at position 27, Asp at position 31, Asp at position 32, Trp at position 35, Tyr at position 51, Asn at position 59, Ser at position 63, Met at position 106, and Tyr at position 108 in the amino acid sequence of SEQ ID NO: 1 (H53 variable region) has been substituted with His include, for example, the following heavy chain variable regions.

a heavy chain variable region having the amino acid sequence of SEQ ID NO: 3 (H3pI)
a heavy chain variable region having the amino acid sequence of SEQ ID NO: 4 (H170)
a heavy chain variable region having the amino acid sequence of SEQ ID NO: 5 (CLH5)

Specific examples of the light chain variable region having an amino acid sequence in which at least one of Asp at position 28, Tyr at position 32, Glu at position 53, Ser at position 56, and Asn at position 92 in the amino acid sequence of SEQ ID NO: 2 (PF1L variable region) has been substituted with His include, for example, the following light chain variable regions.

a light chain variable region having the amino acid sequence of SEQ ID NO: 6 (L73)
a light chain variable region having the amino acid sequence of SEQ ID NO: 7 (L82)
a light chain variable region having the amino acid sequence of SEQ ID NO: 8 (CLL5)

The amino acid positions and substitutions in each of the above-described antibodies H3pI, H170, CLH5, L73, L82, and CLL5 are shown below in Table 1. The amino acid positions are shown based on the Kabat numbering.

TABLE 1

| position | 27 | 31 | 32 | 33 | 35 | 50 | 58 | 61 | 62 | 63 | 64 | 65 | 95 | 99 | 100B | 102 |
|---|---|---|---|---|---|---|---|---|---|---|---|---|---|---|---|---|
| H3pI | H | H |  | H | H |  |  |  |  |  |  |  |  |  |  |  |
| H1 70 | H | H | H | H | H |  | H |  | H |  |  |  | V | I |  | H |
| CLH5 |  | H |  | H |  | H |  |  | H |  |  |  | F | I | H | H |

| position | 24 | 27 | 28 | 32 | 53 | 55 | 56 | 90 | 92 | 94 |
|---|---|---|---|---|---|---|---|---|---|---|
| L73 |  | H | H | H | H |  |  |  |  |  |
| LB2 |  |  |  | H | H | H |  |  |  |  |
| CLL5 |  |  |  | H | H | H | H |  | H |  |

\* In WT, the H chain has histidine at position 33, while the L chain has histidine at position 55.

The present invention provides antibodies comprising at least any one of the amino acid substitutions described above in (a) to (j), and methods for producing the antibodies. Thus, the antibodies of the present invention also include antibodies comprising not only any of the amino acid substitutions described above in (a) to (j) but also amino acid substitution(s) other than those described above in (a) to (j). Amino acid substitutions other than those described above in (a) to (j) include, for example, substitution, deletion, addition, and/or insertion in the amino acid sequence of CDRs and FRs.

Furthermore, the present invention provides the anti-IL-6 receptor antibodies of (1) to (28) below:

(1) an antibody that includes the heavy chain variable region (VH1-IgG1 variable region) having the amino acid sequence from positions 1 to 119 in SEQ ID NO: 21 (VH1-IgG1);

(2) an antibody that includes the heavy chain variable region (VH2-IgG1 variable region) having the amino acid sequence from positions 1 to 119 in SEQ ID NO: 22 (VH2-IgG1);

(3) an antibody that includes the heavy chain variable region (VH3-IgG1 variable region) having the amino acid sequence from positions 1 to 119 in SEQ ID NO: 23 (VH3-IgG1);

(4) an antibody that includes the heavy chain variable region (VH4-IgG1 variable region) having the amino acid sequence from positions 1 to 119 in SEQ ID NO: 24 (VH4-IgG1);

(5) an antibody that includes the light chain variable region (VL1-CK variable region) having the amino acid sequence from positions 1 to 107 in SEQ ID NO: 25 (VL1-CK);

(6) an antibody that includes the light chain variable region (VL2-CK variable region) having the amino acid sequence from positions 1 to 107 in SEQ ID NO: 26 (VL2-CK);
(7) an antibody that includes the light chain variable region (VL3-CK variable region) having the amino acid sequence from positions 1 to 107 in SEQ ID NO: 27 (VL3-CK);
(8) an antibody (Fv1-IgG1) that includes the heavy chain variable region of (2) and the light chain variable region of (6);
(9) an antibody (Fv2-IgG1) that includes the heavy chain variable region of (1) and a light chain variable region having the amino acid sequence of SEQ ID NO: 7 (L82);
(10) an antibody (Fv3-IgG1) that includes the heavy chain variable region of (4) and the light chain variable region of (5);
(11) an antibody (Fv4-IgG1) that includes the heavy chain variable region of (3) and the light chain variable region of (7);
(12) an antibody (VH3-IgG2□GK) that includes a heavy chain having the amino acid sequence of SEQ ID NO: 33;
(13) an antibody (VH3-M58) that includes a heavy chain having the amino acid sequence of SEQ ID NO: 34;
(14) an antibody (VH3-M73) that includes a heavy chain having the amino acid sequence of SEQ ID NO: 35;
(15) an antibody (Fv4-IgG2□GK) that includes the heavy chain of (12) and a light chain having the amino acid sequence of SEQ ID NO: 27 (VL3-CK);
(16) an antibody (Fv4-M58) that includes the heavy chain of (13) and a light chain having the amino acid sequence of SEQ ID NO: 27 (VL3-CK);
(17) an antibody (Fv4-M73) that includes the heavy chain of (14) and a light chain having the amino acid sequence of SEQ ID NO: 27 (VL3-CK);
(18) an antibody (VH2-M71) that includes a heavy chain having the amino acid sequence of SEQ ID NO: 36 (VH2-M71);
(19) an antibody (VH2-M73) that includes a heavy chain having the amino acid sequence of SEQ ID NO: 37 (VH2-M73);
(20) an antibody (VH4-M71) that includes a heavy chain having the amino acid sequence of SEQ ID NO: 38 (VH4-M71);
(21) an antibody (VH4-M73) that includes a heavy chain having the amino acid sequence of SEQ ID NO: 39 (VH4-M73);
(22) an antibody (Fv1-M71) that includes the heavy chain of (18) and a light chain having the amino acid sequence of SEQ ID NO: 26 (VL2-CK);
(23) an antibody (Fv1-M73) that includes the heavy chain of (19) and a light chain having the amino acid sequence of SEQ ID NO: 26 (VL2-CK);
(24) an antibody (Fv3-M71) that includes the heavy chain of (20) and a light chain having the amino acid sequence of SEQ ID NO: 25 (VL1-CK);
(25) an antibody (Fv3-M73) that includes the heavy chain of (21) and a light chain having the amino acid sequence of SEQ ID NO: 25 (VL1-CK);
(26) an antibody that includes a light chain having the amino acid sequence of SEQ ID NO: 25 (VL1-CK);
(27) an antibody that includes a light chain having the amino acid sequence of SEQ ID NO: 26 (VL2-CK); and
(28) an antibody that includes a light chain having the amino acid sequence of SEQ ID NO: 27 (VL3-CK).

Furthermore, the present invention provides the FRs and CDRs of (a) to (v) below:
(a) the heavy chain CDR1 of SEQ ID NO: 40 (VH1, 2, 3, 4);
(b) the heavy chain CDR2 of SEQ ID NO: 41 (VH1, 2);
(c) the heavy chain CDR2 of SEQ ID NO: 42 (VH3);
(d) the heavy chain CDR2 of SEQ ID NO: 43 (VH4);
(e) the heavy chain CDR3 of SEQ ID NO: 44 (VH1, 2);
(f) the heavy chain CDR3 of SEQ ID NO: 45 (VH3, 4);
(g) the heavy chain FR1 of SEQ ID NO: 46 (VH1, 2);
(h) the heavy chain FR1 of SEQ ID NO: 47 (VH3, 4):
(i) the heavy chain FR2 of SEQ ID NO: 48 (VH1, 2, 3, 4);
(j) the heavy chain FR3 of SEQ ID NO: 49 (VH1);
(k) the heavy chain FR3 of SEQ ID NO: 50 (VH2);
(l) the heavy chain FR3 of SEQ ID NO: 51 (VH3, 4);
(m) the heavy chain FR4 of SEQ ID NO: 52 (VH1, 2, 3, 4);
(n) the light chain CDR1 of SEQ ID NO: 53 (VL1, 2);
(o) the light chain CDR1 of SEQ ID NO: 54 (VL3);
(p) the light chain CDR2 of SEQ ID NO: 55 (VL1, VL3);
(q) the light chain CDR2 of SEQ ID NO: 56 (VL2);
(r) the light chain CDR3 of SEQ ID NO: 57 (VL1, 2, 3);
(s) the light chain FR1 of SEQ ID NO: 58 (VL1, 2, 3);
(t) the light chain FR2 of SEQ ID NO: 59 (VL1, 2, 3);
(u) the light chain FR3 of SEQ ID NO: 60 (VL1, 2, 3); and
(v) the light chain FR4 of SEQ ID NO: 61 (VL1, 2, 3).

The respective sequences of the above (a) to (v) are shown in FIG. 25. Furthermore, the present invention provides polypeptides including any one of the FRs and CDRs of the above (a) to (v).

The anti-IL-6 receptor antibodies of the present invention also include fragments and modified products of antibodies including any of the amino acid substitutions described above. Such antibody fragments include, for example, Fab, F(ab')2, Fv, single chain Fv (scFv) in which Fv of H and L chains are linked together via an appropriate linker, single domain H chain and single domain L chain (for example, Nat. Biotechnol. 2005 September; 23(9):1126-36), Unibody (WO 2007059782 A1), and SMIP (WO 2007014278 A2). The origin of antibodies is not particularly limited. The antibodies include human, mouse, rat, and rabbit antibodies. The antibodies of the present invention may also be chimeric, humanized, fully humanized antibodies, or such.

Specifically, such antibody fragments are obtained by treating antibodies with enzymes, for example, papain or pepsin, or by constructing genes that encode such antibody fragments, inserting them into expression vectors, and then expressing them in appropriate host cells (see, for example, Co, M. S. et al., J. Immunol. (1994) 152, 2968-2976; Better, M. & Horwitz, A. H. Methods in Enzymology (1989) 178, 476-496; Plueckthun, A. & Skerra, A. Methods in Enzymology (1989) 178, 497-515; Lamoyi, E., Methods in Enzymology (1989) 121, 652-663; Rousseaux, J. et al., Methods in Enzymology (1989) 121, 663-66; Bird, R. E. et al., TIBTECH (1991) 9, 132-137).

The present invention provides methods of producing (i) a polypeptide of the present invention, or (ii) a polypeptide encoded by a gene encoding the polypeptide of the present invention, wherein the methods comprise the step of culturing a host cell comprising a vector into which a polynucleotide encoding the polypeptide of the present invention is introduced.

More specifically, the present invention provides methods of producing a polypeptide of the present invention, which comprise the steps of:
(a) culturing a host cell comprising a vector into which a gene encoding the polypeptide of the present invention is introduced; and
(b) obtaining the polypeptide encoded by the gene.

scFv is obtained by linking the V regions of antibody H and L chains. In such scFv, the H chain V region is linked to the L chain V region via a linker, preferably a peptide linker (Huston, J. S. et al., Proc. Natl. Acad. Sci. U.S.A. (1988) 10.0, 5879-5883). The H chain and L chain V regions in an scFv may be derived from any of the antibodies described above. The peptide linker to link the V regions includes, for example, arbitrary single chain peptides of 12 to 19 amino acid residues.

When an anti-IL-6 receptor antibody of the present invention includes a constant region, the constant region may be of any type, for example, IgG1, IgG2, or IgG4 may be used. The constant region is preferably a human antibody constant region. Alternatively, the constant region may be a modified form including substitution, deletion, addition, and/or insertion in the amino acid sequence of human IgG1, human IgG2, or human IgG4 constant regions.

Preferred IL-6 receptor to which an anti-IL-6 receptor antibody of the present invention binds is human IL-6 receptor.

The anti-IL-6 receptor antibodies of the present invention are superior in the retention in plasma, and they exist for a prolonged period in the plasma in a form capable of binding to the antigen, i.e., soluble or membrane-associated IL-6 receptors. Thus, the anti-IL-6 receptor antibodies bind in vivo to soluble or membrane-associated IL-6 receptors for a prolonged period. Furthermore, the anti-IL-6 receptor antibodies are capable of binding to IL-6 receptors twice or more times, and thus assumed to be able to neutralize three or more IL-6 receptors.

<Pharmaceutical Compositions>

The present invention also relates to pharmaceutical compositions that include antigen-binding molecules of the present invention, antigen-binding molecules isolated by the screening methods of the present invention, or antigen-binding molecules produced by the production methods of the present invention. The antigen-binding molecules of the present invention and antigen-binding molecules produced by the production methods of the present invention are superior in the retention in plasma, and thus, expected to reduce the administration frequency of the antigen-binding molecules, and are therefore useful as pharmaceutical compositions. The pharmaceutical composition of the present invention may include pharmaceutically acceptable carriers.

In the present invention, pharmaceutical compositions ordinarily refer to agents for treating or preventing, or testing and diagnosing diseases.

The pharmaceutical compositions of the present invention can be formulated by methods known to those skilled in the art. For example, they can be used parenterally, in the form of injections of sterile solutions or suspensions including water or other pharmaceutically acceptable liquid. For example, such compositions may be formulated by mixing in the form of unit dose required in the generally approved medicine manufacturing practice by appropriately combining with pharmaceutically acceptable carriers or media, specifically with sterile water, physiological saline, vegetable oil, emulsifier, suspension, surfactant, stabilizer, flavoring agent, excipient, vehicle, preservative, binder, or such. In such formulations, the amount of active ingredient is adjusted to obtain an appropriate amount in a pre-determined range.

Sterile compositions for injection can be formulated using vehicles such as distilled water for injection, according to standard formulation practice.

Aqueous solutions for injection include, for example, physiological saline and isotonic solutions containing dextrose or other adjuvants (for example, D-sorbitol, D-mannose, D-mannitol, and sodium chloride). It is also possible to use in combination appropriate solubilizers, for example, alcohols (ethanol and such), polyalcohols (propylene glycol, polyethylene glycol, and such), non-ionic surfactants (polysorbate 80™, HCO-50, and such).

Oils include sesame oil and soybean oils. Benzyl benzoate and/or benzyl alcohol can be used in combination as solubilizers. It is also possible to combine buffers (for example, phosphate buffer and sodium acetate buffer), soothing agents (for example, procaine hydrochloride), stabilizers (for example, benzyl alcohol and phenol), and/or antioxidants. Appropriate ampules are filled with the prepared injections.

The pharmaceutical compositions of the present invention are preferably administered parenterally. For example, the compositions may be in the dosage form for injections, transnasal administration, transpulmonary administration, or transdermal administration. For example, they can be administered systemically or locally by intravenous injection, intramuscular injection, intraperitoneal injection, subcutaneous injection, or such.

Administration methods can be appropriately selected in consideration of the patient's age and symptoms. The dose of a pharmaceutical composition containing an antigen-binding molecule may be, for example, from 0.0001 to 1000 mg/kg for each administration. Alternatively, the dose may be, for example, from 0.001 to 100,000 mg per patient. However, the present invention is not limited by the numeric values described above. The doses and administration methods vary depending on the patient's weight, age, symptoms, and such. Those skilled in the art can set appropriate doses and administration methods in consideration of the factors described above.

Amino acids contained in the amino acid sequences of the present invention may be post-translationally modified. For example, the modification of an N-terminal glutamine (Gln) residue into a pyroglutamic acid (pGlu) residue by pyroglutamylation is well-known to those skilled in the art. Naturally, such post-translationally modified amino acids are included in the amino acid sequences in the present invention.

All prior art documents cited in the specification are incorporated herein by reference.

EXAMPLES

Herein below, the present invention will be specifically described with reference to Examples, but it is not to be construed as being limited thereto.

Example 1 Production of Modified Humanized PM1 Antibody

Preparation of Recombinant Soluble Human IL-6 Receptor (SR344)

A recombinant human IL-6 receptor of the human IL-6 receptor, which served an antigen, was prepared as described below. A CHO cell line that constantly expresses a soluble human IL-6 receptor (hereinafter referred to as SR344) (Yamasaki, et al., Science 1988; 241: 825-828 (GenBank #X12830)) consisting of the amino acid sequence from the 1st amino acid to the 344th amino acid on the N-terminal side as reported in J. Biochem., 108, 673-676 (1990), was produced.

SR344 was purified from culture supernatant obtained from the SR344-expressing CHO cells using three column chromatographies: Blue Sepharose 6 FF column chromatography, affinity chromatography using a column in which an antibody specific to SR344 is immobilized, and gel filtration column chromatography. The fraction that eluted as the main peak was used as the final purified product.

Preparation of Recombinant Cynomolgus Monkey Soluble IL-6 Receptor (cIL-6R)

Oligo DNA primers Rhe6Rf1 (SEQ ID NO: 16) and Rhe6Rr2 (SEQ ID NO: 17) were produced based on the publicly-available rhesus monkey IL-6 receptor gene sequence (Birney et al., Ensemble 2006, Nucleic Acids Res., 2006, Jan. 1; 34 (Database issue): D556-61). Using cDNA prepared from cynomolgus pancreas as a template, a DNA fragment encoding the entire length of cynomolgus monkey IL-6 receptor gene was prepared by PCR using primers Rhe6Rf1 and Rhe6Rr2. Using the resulting DNA fragment as a template, a 1131 bp DNA fragment (SEQ ID NO: 20) encoding a protein in which 6×His is added to the C terminal of the soluble region (Met1-Pro363) containing a signal region of cynomolgus monkey IL-6 receptor gene, was amplified by PCR using the oligo DNA primers CynoIL6R N-EcoRI (SEQ ID NO: 18) and CynoIL6R C-NotI-His (SEQ ID NO: 19). The resulting DNA fragment was digested with EcoRI and NotI and inserted into a mammalian cell expression vector, and this was then used to produce a stable expression CHO line (cyno.sIL-6R-producing CHO cells).

A culture medium of cyno.sIL-6R-producing CHO cells was purified with a HisTrap column (GE Healthcare Biosciences), concentrated using Amicon Ultra-15 Ultracel-10 k (Millipore), and further purified with a Superdex 200 pg 16/60 gel filtration column (GE Healthcare Biosciences) to obtain the final purified product of soluble cynomolgus monkey IL-6 receptor (hereinafter referred to as cIL-6R).

Preparation of Recombinant Cynomolgus Monkey IL-6 (cIL-6)

Cynomolgus monkey IL-6 was prepared as follows. A nucleotide sequence encoding the 212 amino acids registered under SWISSPROT Accession No. P79341 was produced, cloned into a mammalian cell expression vector, and introduced into CHO cells to produce a stable expression cell line (cyno.IL-6-producing CHO cells). A culture medium of cyno.IL-6-producing CHO cells was purified with an SP-Sepharose/FF column (GE Healthcare Biosciences), concentrated using Amicon Ultra-15 Ultracel-5 k (Millipore), and then further purified with a Superdex 75 pg 26/60 gel filtration column (GE Healthcare Biosciences). This was concentrated using Amicon Ultra-15 Ultracel-5 k (Millipore) to obtain a final purified product of cynomolgus monkey IL-6 (hereinafter referred to as cIL-6).

Establishment of Human gp130-Expressing BaF3 Cell Line

A BaF3 cell line expressing human gp130 was established as indicated below in order to obtain a cell line exhibiting IL-6-dependent growth.

Full-length human gp130 cDNA (Hibi et al., Cell 1990; 63: 1149-1157 (GenBank #NM_002184)) was amplified by PCR and cloned into the expression vector pCOS2Zeo, which was prepared by removing the DHFR gene expression site from pCHOI (Hirata, et al., FEBS Letter 1994; 356: 244-248) and inserting a Zeocin resistance gene expression site, to construct pCOS2Zeo/gp130. Full-length human IL-6R cDNA was amplified by PCR and cloned into pcDNA3.1(+) (Invitrogen) to construct hIL-6R/pcDNA3.1 (+). 10 µg of pCOS2Zeo/gp130 was mixed into BaF3 cells ($0.8 \times 10^7$ cells) suspended in PBS, and pulsed using a Gene Pulser (Bio-Rad) at a voltage of 0.33 kV and capacitance of 950 µFD. BaF3 cells having undergone gene introduction by electroporation treatment were cultured one whole day and night in RPMI1640 medium (Invitrogen) containing 0.2 ng/mL of mouse interleukin-3 (Peprotech) and 10% fetal bovine serum (hereinafter referred to as FBS, HyClone), and then screened by adding RPMI1640 medium containing 100 ng/mL of human interleukin-6 (R&D Systems), 100 ng/mL of human interleukin-6 soluble receptor (R&D Systems) and 10% FBS to establish a human gp130-expressing BaF3 cell line (hereinafter referred to as BaF3/gp130). Since this BaF3/gp130 proliferates in the presence of human interleukin-6 (R&D Systems) and SR344, it can be used to evaluate the growth inhibitory activity (namely, IL-6 receptor-neutralizing activity) of anti-IL-6 receptor antibody.

Production of Humanized Anti-IL-6 Receptor Antibody

In the context of the instant example and elsewhere herein, the term "wild type" is abbreviated as WT, the term "wild type H chain" is abbreviated as H(WT) (amino acid sequence of SEQ ID NO: 9), and the term "wild type L chain is abbreviated as L(WT) (amino acid sequence: SEQ ID NO. 10). In this context, mutations were introduced into the framework sequence and CDR sequence of humanized mouse PM1 antibody described in Cancer Res. 1993, Feb. 15; 53(4): 851-6, to produce modified H chains H53 (amino acid sequence: SEQ ID NO: 1) and PF1H (amino acid sequence: SEQ ID NO: 11), and modified L chains L28 (amino acid sequence: SEQ ID NO: 12) and PF1L (amino acid sequence: SEQ ID NO: 2). More specifically, the mutants were produced using the QuikChange Site-Directed Mutagenesis Kit (Stratagene) according to the method described in the instructions provided, and the resulting plasmid fragments were inserted into a mammalian cell expression vector to produce the desired H chain expression vectors and L chain expression vectors. The nucleotide sequences of the obtained expression vectors were determined using conventional methodologies known to persons skilled in the art.

Expression and Purification of Humanized Anti-IL-6 Receptor Antibody

The antibodies were expressed by the method described below. Human embryonic kidney cancer-derived HEK293H cell line (Invitrogen) was suspended in DMEM (Invitrogen) supplemented with 10% Fetal Bovine Serum (Invitrogen). The cells were plated at 10 ml per dish in dishes for adherent cells (10 cm in diameter; CORNING) at a cell density of 5 to $6 \times 10^5$ cells/ml and cultured in a $CO_2$ incubator (37° C., 5% $CO_2$) for one whole day and night. Then, the medium was removed by aspiration, and 6.9 ml of CHO-S-SFM-II medium (Invitrogen) was added. The prepared plasmid was introduced into the cells by the lipofection method. The resulting culture supernatants were collected, centrifuged (approximately 2000 g, 5 min, room temperature) to remove cells, and sterilized by filtering through 0.22-µm filter MILLEX®-GV (Millipore) to obtain the supernatants. Antibodies were purified from the obtained culture supernatants by a method known to those skilled in the art using rProtein A Sepharose™ Fast Flow (Amersham Biosciences). To determine the concentration of the purified antibody, absorbance was measured at 280 nm using a spectrophotometer. Antibody concentrations were calculated from the determined values using an absorbance coefficient calculated by the PACE method (Protein Science 1995; 4:2411-2423).

Example 2 Production of pH-Dependently-Binding Antibody H3pI/L73

Method for Creating Antibody Capable of Neutralizing Antigen Multiple Times

Since IgG molecules are divalent, a single IgG molecule can neutralize up to two antigen molecules when the two sites bind to the antigens; however, it cannot neutralize three or more antigen molecules. Therefore, to maintain the neutralizing effect of a neutralizing antibody over a certain period, it is necessary to administer an amount of the antibody equal to or greater than the amount of antigen produced during the period. Thus, there is a limitation on the extent to which the required dose of antibody can be reduced by improving the pharmacokinetics or affinity of antibody. Therefore, if it were possible to neutralize two or more antigen molecules with a single IgG molecule, the same dose could improve the duration of neutralizing effect, or alternatively the dose of antibody required to achieve the same duration could be reduced.

For neutralizing antibodies, there are two types of target antigens: soluble-type antigens, which are present in plasma, and membrane-bound antigens, which are expressed on the surface of cells.

When the antigen is a membrane-bound antigen, an administered antibody binds to the membrane antigen on the cellular surface, and the antibody is subsequently taken up into endosomes within the cell by internalization together with the membrane antigen bound to the antibody. Then, the antibody which is kept bound to the antigen moves to a lysosome where it is degraded by lysosome together with the antigen. The elimination of antibody from the plasma mediated by internalization by membrane antigen is referred to as antigen-dependent elimination, and this has been reported for numerous antibody molecules (Drug Discov. Today, 2006 January; 11(1-2): 81-8). Since a single IgG antibody molecule binds to two antigen molecules when it divalently binds to antigens, and is then internalized and directly degraded by lysosome, a single ordinary IgG antibody cannot neutralize two or more antigen molecules (FIG. 1).

Figure 2:
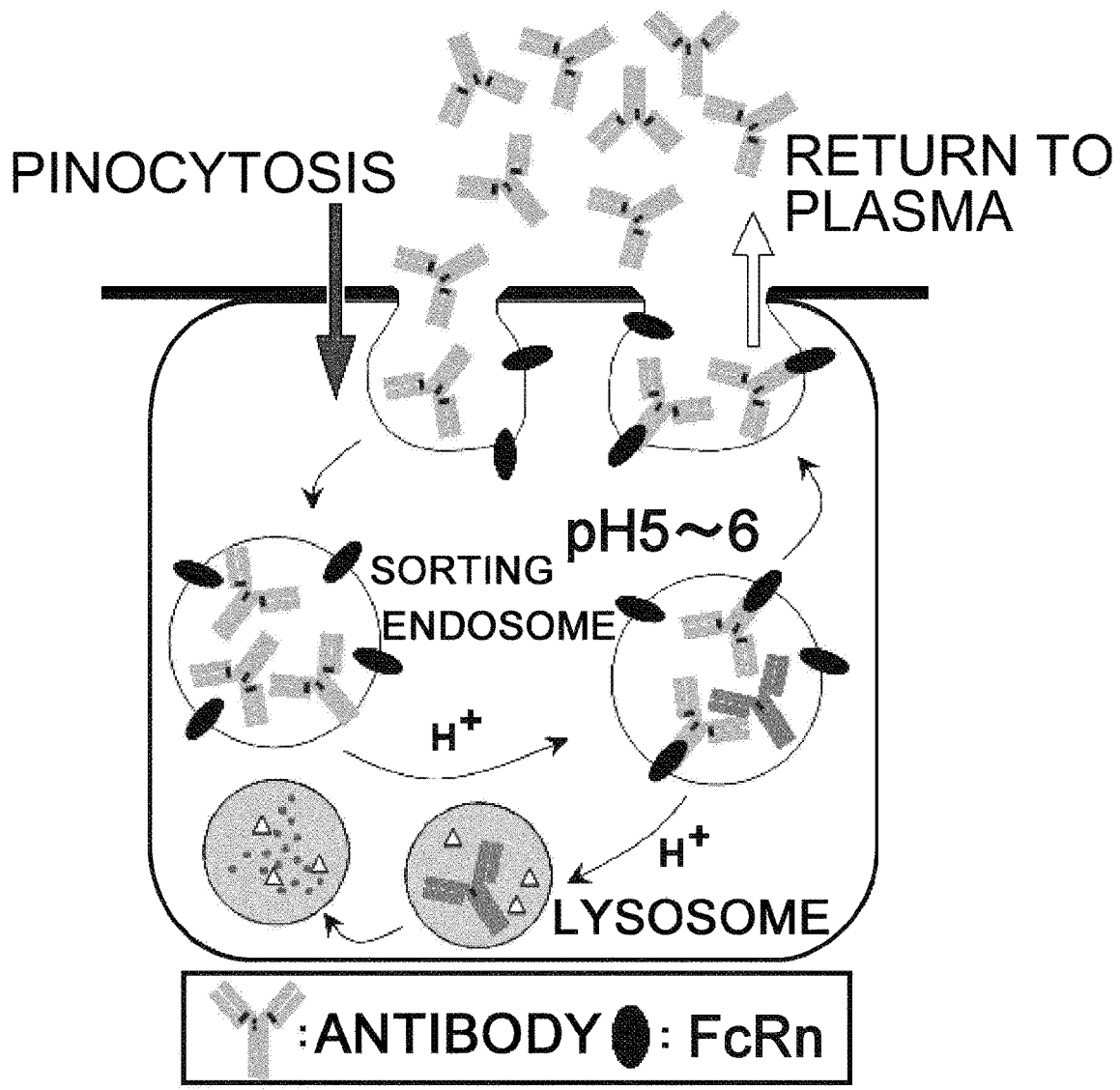
FIG. 2 is a diagram depicting a mechanism by which IgG molecules are salvaged by FcRn.

The reason for the long retention (slow elimination) of IgG molecules in plasma is that FcRn, known as an IgG molecule salvage receptor, functions (Nat. Rev. Immunol. 2007 September; 7(9): 715-25). IgG molecules that have been taken up into endosomes by pinocytosis bind to FcRn expressed in endosomes under intraendosomal acidic conditions. IgG molecules bound to FcRn move to the cell surface where they dissociate from FcRn under neutral conditions in plasma and return to plasma, while IgG molecules unable to bind to FcRn proceed into lysosomes where they are degraded (FIG. 2).

Figure 3:
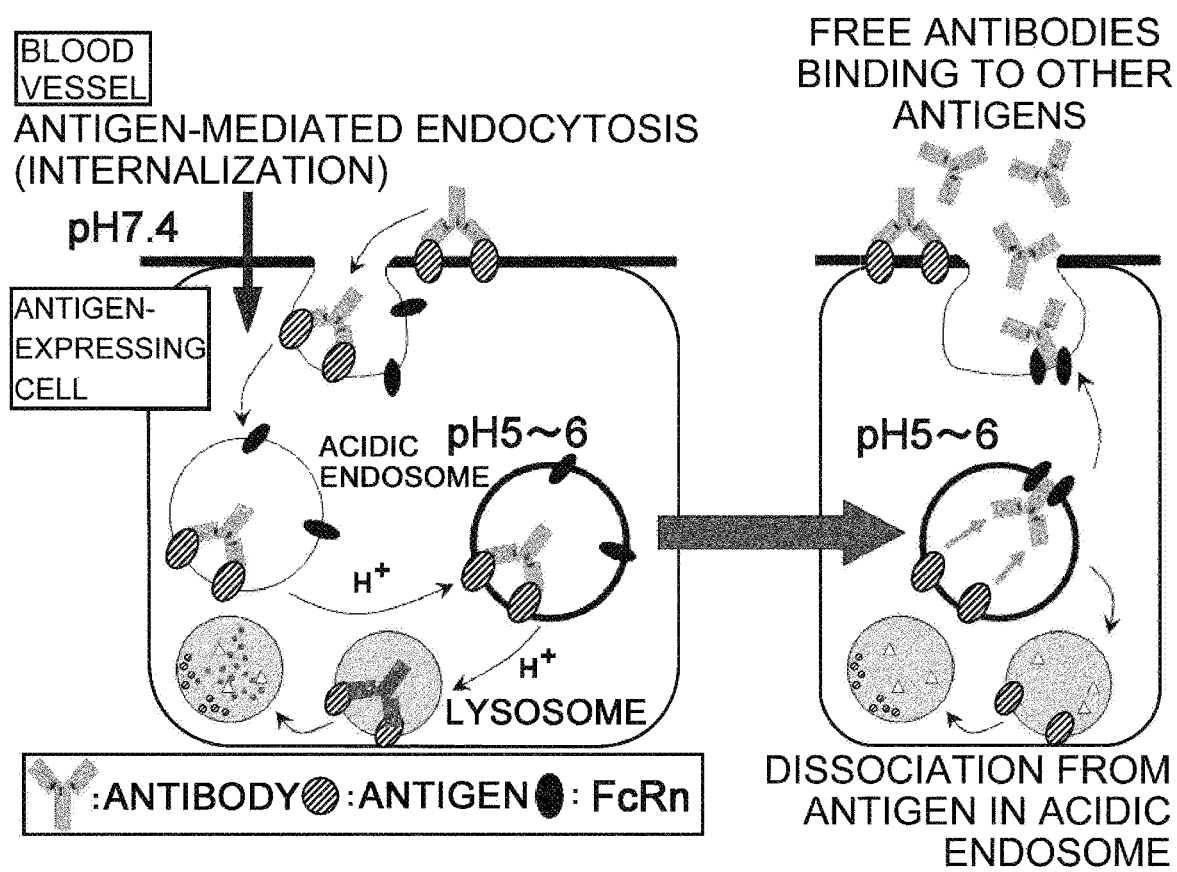
FIG. 3 is a schematic diagram depicting the re-binding of IgG molecules to new antigen following dissociation from membrane-bound antigen within endosomes.

IgG molecules bound to a membrane antigen are taken up into intracellular endosomes by internalization, move into lysosomes while bound to the antigen, and undergo degradation. When an IgG antibody divalently binds to antigens, it neutralizes two antigen molecules and undergoes degradation together with the antigens. If the IgG antibody, when taken up into intracellular endosomes by internalization, can dissociate from the antigen under intraendosomal acidic conditions, the dissociated antibody may be able to bind to FcRn expressed in the endosomes. The IgG molecule dissociated from the antigen and bound to FcRn is transferred to the cell surface and then dissociated from FcRn under neutral conditions in the plasma, thereby return to the plasma again. The IgG molecule that has returned to the plasma is able to bind to a new membrane antigen again. The repetition of this process allows a single IgG molecule to repeatedly bind to membrane antigens, thereby enabling neutralization of a multiple antigens with a single IgG molecule (FIG. 3).

Figure 4:
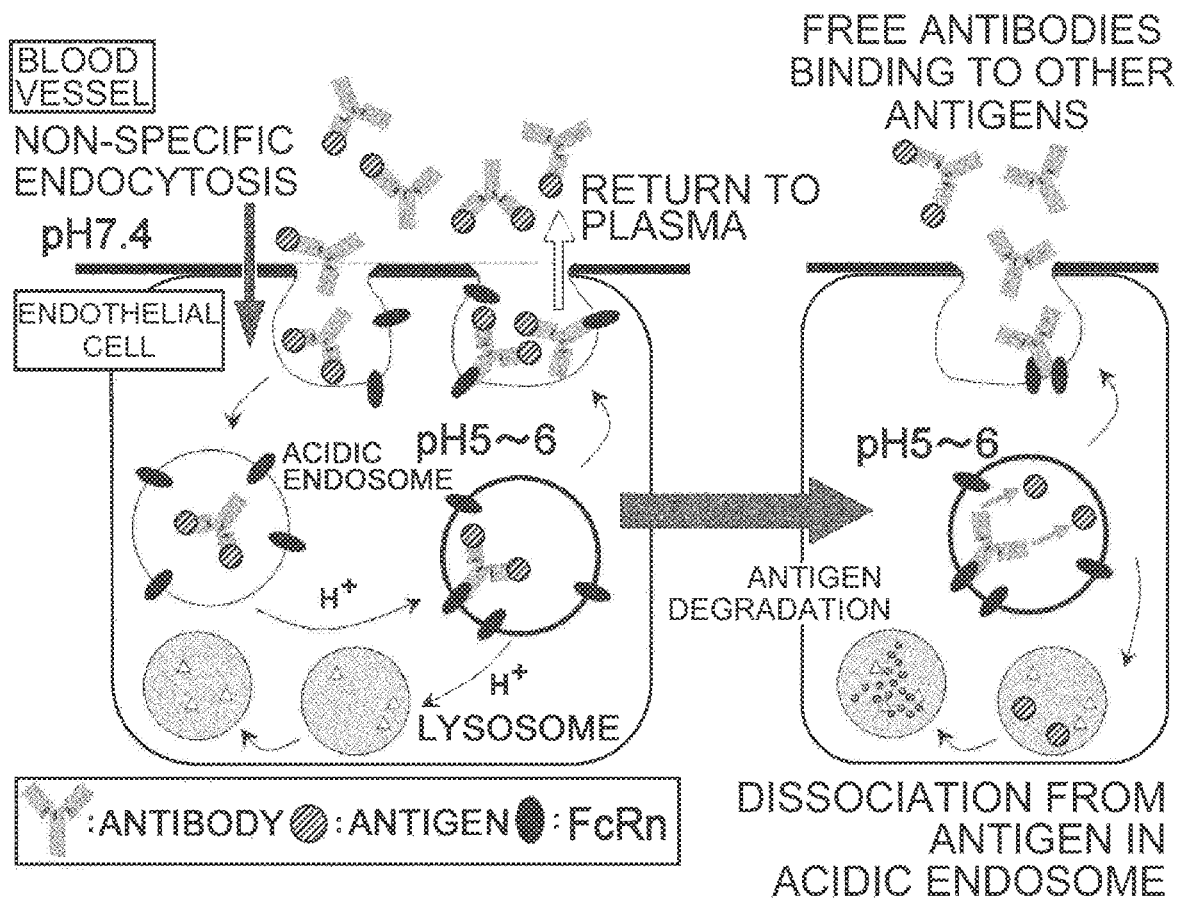
FIG. 4 is a schematic diagram depicting the re-binding of IgG molecules to new antigen following dissociation from soluble antigen within endosomes.

In the case of a soluble antigen, an antibody administered binds to the antigen in the plasma, and remains in the plasma in the form of an antigen-antibody complex. Normally, while the retention of antibody in plasma is very long (elimination rate is very slow) due to the function of FcRn as described above, the retention of antigen in plasma is short (elimination rate is fast). Thus, antibody-bound antigens show retention in plasma comparable to that of antibody (elimination rate is very slow). Antigens are produced in the body at a constant rate and, in the absence of antibody, present in plasma at a concentration at which the antigen production rate and the antigen elimination rate are under equilibrium. In the presence of antibody, most of the antigens are bound to antibodies, resulting in the very slow elimination of antigens. Thus, the antigen concentration in plasma increases as compared with that in the absence of antibody (Kidney Int. 2003, 64, 697-703; J. National Cancer Institute 2002, 94(19), 1484-1493; J. Allergy and Clinical Immunology 1997, 100(1), 110-121; Eur. J. Immunol. 1993, 23; 2026-2029). Even if the affinity of antibody for antigen is infinite, antigen concentration elevates as antibody is slowly eliminated from the plasma, and the neutralizing effect of antibody terminates after the concentrations of antibody and antigen become equal. Although antibodies with a stronger dissociation constant (KD) can neutralize soluble antigens at a lower antibody concentration, antibodies at a concentration half or less than the concentration of antigen present are unable to neutralize antigens regardless of how strong the affinity of antibody is (Biochem. Biophys. Res. Commun. 2005 Sep. 9; 334(4): 1004-13). As is the case with IgG molecules not bound to antigens, IgG molecules bound to antigens in the plasma are also taken up into endosomes by pinocytosis, and bind to FcRn expressed in endosomes under intraendosomal acidic conditions. The IgG molecules bound to FcRn moves to the cell surface while the antibody is kept bound to the antigen and then dissociate from the FcRn under neutral conditions in the plasma. Since the IgG molecules return to the plasma while bound to the antigen, they cannot bind to new antigens in the plasma. In this case, if IgG molecules can dissociate from the antigen under intraendosomal acidic conditions, the dissociated antigen will not be able to bind to FcRn and thereby may be degraded by lysosomes. On the other hand, the IgG molecules can return to the plasma again by binding to FcRn. Since the IgG molecules that have returned to the plasma have already dissociated from the antigen in endosomes, they are able to bind to a new antigen again in the plasma. The repetition of this process allows a single IgG molecule to repeatedly bind to soluble antigens. This enables a single IgG molecule to neutralize multiple antigens (FIG. 4).

Thus, regardless of whether the antigen is a membrane antigen or soluble antigen, if the dissociation of IgG antibody from the antigen is possible under intraendosomal acidic conditions, a single IgG molecule would be able to repeatedly neutralize antigens. In order for IgG antibodies to dissociate from antigens under intraendosomal acidic conditions, it is necessary that antigen-antibody binding be considerably weaker under acidic conditions than under neutral conditions. Since membrane antigens on the cell surface need to be neutralized, antibodies have to strongly bind to antigens at the cell surface pH, namely pH 7.4. Since the intraendosomal pH has been reported to be typically pH 5.5 to 6.0 (Nat. Rev. Mol. Cell. Biol. 2004 February; 5(2): 121-32), an antibody that weakly binds to an antigen at pH 5.5 to 6.0 is considered to dissociate from the antigen under intraendosomal acidic conditions. More specifically, a single IgG molecule that strongly binds to an antibody at the cell surface pH of 7.4 and weakly binds to the antigen at the intraendosomal pH of 5.5 to 6.0 may be able to neutralize a multiple antigens and thereby improve the pharmacokinetics.

In general, protein-protein interactions consist of hydrophobic interaction, electrostatic interaction and hydrogen bonding, and the binding strength is typically expressed as a binding constant (affinity) or apparent binding constant (avidity). pH-dependent binding, whose binding strength varies between neutral conditions (pH 7.4) and acidic conditions (pH 5.5 to 6.0), is present in naturally-occurring protein-protein interactions. For example, the above-mentioned binding between IgG molecules and FcRn known as a salvage receptor for IgG molecules is strong under acidic conditions (pH 5.5 to 6.0) but remarkably weak under neutral conditions (pH 7.4). Most of such pH-dependently changing protein-protein interactions are associated with histidine residues. Since the pKa of histidine residue is in the vicinity of pH 6.0 to 6.5, the proton dissociation state of histidine residues varies between neutral conditions (pH 7.4) and acidic conditions (pH 5.5 to 6.0). Specifically, histidine residues are not charged and function as hydrogen atom acceptors under neutral conditions (pH 7.4), while they become positively charged and function as hydrogen atom donors under acidic conditions (pH 5.5 to 6.0). It has been reported that the pH-dependent binding of the above-described IgG-FcRn interaction is also associated with histidine residues present in IgG (Mol. Cell. 2001 April; 7(4): 867-77).

Therefore, pH-dependence can be imparted to protein-protein interactions by substituting an amino acid residue involved in protein-protein interactions with a histidine residue, or by introducing a histidine into an interaction site. Such attempts have also been made in protein-protein interactions between antibodies and antigens, and a mutant antibody with antigen-binding ability decreased under acidic conditions has been successfully acquired by introducing histidine into the CDR sequence of an anti-egg white lysozyme antibody (FEBS Letter (vol. 309, No. 1, 85-88, 1992)). In addition, an antibody that is prepared by introducing histidine into its CDR sequence and specifically binds to an antigen at the low pH of cancer tissues but weakly binds under neutral conditions has been reported (WO 2003-105757).

Although methods for introducing pH dependency into antigen-antibody reactions have been reported as described above, an IgG molecule that neutralizes multiple antigens by strongly binding to antigens at the body fluid pH of 7.4 but weakly binding to antigens at the intraendosomal pH of pH 5.5 to 6.0 has not been reported. In other words, there have been no reports relating to modifications that significantly reduce the binding under acidic conditions while maintaining the binding under neutral conditions such that, as compared to an unmodified antibody, a modified antibody binds to antigens multiple times in vivo and thereby shows improved pharmacokinetics as well as improved duration of the neutralizing effect at the same dose.

The IL-6 receptor is present in the body in the form of either soluble IL-6 receptor or membrane IL-6 receptor (Nat. Clin. Pract. Rheumatol. 2006 November; 2(11): 619-26). Anti-IL-6 receptor antibodies bind to both the soluble IL-6 receptor and membrane IL-6 receptor, and neutralize their biological action. It is considered that, after binding to the membrane IL-6 receptor, anti-IL-6 receptor antibodies are taken up into intracellular endosomes by internalization while bound to the membrane IL-6 receptor, then move into lysosomes while the antibodies are kept bound to the membrane IL-6 receptor, and undergo degradation by lysosomes together with the membrane IL-6 receptor. In fact, it has been reported that a humanized anti-IL-6 receptor antibody exhibits non-linear clearance, and its antigen-dependent elimination greatly contributes to the elimination of the humanized anti-IL-6 receptor antibody (The Journal of Rheumatology, 2003, 30; 71426-1435). Thus, one humanized anti-IL-6 receptor antibody binds to one or two membrane IL-6 receptors (monovalently or divalently), and is then internalized and degraded in lysosomes. Therefore, if it is possible to produce modified antibodies that exhibit greatly reduced binding ability under acidic conditions but retain the same binding ability as the wild type humanized anti-IL-6 receptor antibody under neutral conditions (pH-dependent binding anti-IL-6 receptor antibody), multiple IL-6 receptors can be neutralized with a single humanized anti-IL-6 receptor antibody. Thus, in comparison with wild type humanized anti-IL-6 receptor antibodies, pH-dependent binding anti-IL-6 receptor antibodies may improve the duration of the neutralizing effect in vivo at the same dosage.

Production of pH-Dependently Binding Humanized Anti-IL-6 Receptor Antibody H3pI/L73

Introduction of histidine into a CDR has been reported as a method for introducing pH-dependent binding to antigen-antibody reaction (FEBS Letter (vol. 309, No. 1, 85-88, 1992)). In order to find amino acid residues exposed on the surface of the variable region of the H53/PF1L produced in Example 1 and possible residues interacting with the antigen, a Fv region model of H53/PF1L was created by homology modeling using MOE software (Chemical Computing Group Inc.). A three-dimensional model constructed on the basis of the sequence information of H53/PF1L was used to select H27, H31, H35, L28, L32 and L53 (Kabat numbering, Kabat, E. A. et al., 1991, Sequences of Proteins of Immunological Interest, NIH) as mutation sites that may introduce pH-dependent antigen-binding by histidine introduction. The product in which the residues at H27, H31 and H35 in H53 produced in Example 1 were substituted with histidines was designated as H3pI (amino acid sequence: SEQ ID NO: 3), and the product in which the residues at L28, L32 and L53 in PF1L produced in Example 1 were substituted with histidines was designated as L73 (amino acid sequence: SEQ ID NO: 6).

Production, Expression and Purification of H3pI/L73 Expression Vector

Amino acid modification was carried out to produce antibodies modified at the selected sites. Mutations were introduced into H53 (nucleotide sequence: SEQ ID NO: 13) and PF1L (nucleotide sequence: SEQ ID NO: 14) produced in Example 1 to produce H3pI (amino acid sequence: SEQ ID NO: 3) and L73 (amino acid sequence: SEQ ID NO: 6).

More specifically, the QuikChange Site-Directed Mutagenesis Kit (Stratagene) was used according to the method described in the instructions provided, and the resulting plasmid fragments were inserted into a mammalian cell expression vector to produce the desired H chain expression vector and L chain expression vector. The nucleotide sequences of the resulting expression vectors were determined using a method known to persons skilled in the art. H3pI/L73 which uses H3pI for the H chain and L73 for the L chain was expressed and purified by the method described in Example 1.

Example 3 Conferring pH-Dependent Antigen Binding Ability by his Modification of CDR Using Phage Display Technology Production of scFv Molecule of Humanized PM1 Antibody The humanized PM1 antibody, which is a humanized anti-IL-6R antibody (Cancer Res. 1993 Feb. 15; 53(4): 851-6), was converted into scFv. The VH and VL regions were amplified by PCR, and humanized PM1 HL scFv having the linker sequence GGGGSGGGGSGGGGS (SEQ ID NO. 15) between VH and VL was produced.

Selection of Histidine-Introducible Positions by Histidine Scanning

PCR was performed using the produced humanized PM1 HL scFv DNA as a template to produce a histidine library in which any one of the CDR amino acids is replaced with histidine. The library portions were constructed by PCR using primers in which the codon of an amino acid desired to be mutated for the library was replaced with CAT, a codon corresponding to histidine, and other portions were constructed by normal PCR. These portions were then linked by assemble PCR. The constructed library was digested with SfiI, inserted into a phagemid vector pELBG lacI that was also digested with SfiI, and then used to transform XL1-Blue (Stratagene). The resulting colonies were used to evaluate antigen binding by phage ELISA and analyze the sequence of HL scFv. Phage ELISA was carried out using a plate coated with SR344 at 1 μg/mL in accordance with J. Mol. Biol. 1992; 227: 381-388. Clones that were found to bind to SR344 were subjected to sequence analysis using specific primers.

Phage titer was determined by ELISA with an anti-Etag antibody (GE Healthcare) and anti-M13 antibody (GE Healthcare). This value was then used to select positions where substitution of the CDR residue with histidine did not significantly alter the binding ability as compared to humanized PM1 HL scFv, based on the results of phage ELISA for SR344. The selected positions are shown in Table 2. Numbering of each residue was in accordance with the Kabat numbering (Kabat, et al., 1991, Sequences of Proteins of Immunological Interest, NIH).

TABLE 2

Positions of Histidine Substitution Not Significantly Affecting Binding Ability

H31, H50, H54, H56, H57, H58, H59, H60, H61,
H62, H63, H64, H65, H100a, H100b, H102
L24, L26, L27, L28, L30, L31, L32, L52, L53,
L54, L56, L90, L92, L93, L94

Construction of Histidine-Modified CDR Library

A library was designed in which the amino acids of CDR residues that did not significantly alter the binding ability when substituted with histidine as shown in Table 2 (histidine-introducible positions) are their original sequence (wild type sequence) or histidine. The library was constructed based on the sequences of the H chain PF1H and the L chain PF1L produced in Example 1 such that the mutated positions for the library have the original sequences or histidines (either the original sequence or histidines).

The library portions were constructed by PCR using primers that were designed such that a position desired to be mutated for the library has the original amino acid codon or histidine codon, and other portions were produced by normal PCR, or by PCR using synthetic primers as in the library portions. These portions were then linked by assemble PCR (J. Mol. Biol. 1996; 256: 77-88).

This library was used to construct a ribosome display library in accordance with J. Immunological Methods 1999; 231: 119-135. In order to carry out Escherichia coli cell-free in vitro translation, an SDA sequence (ribosome binding site) and T7 promoter were added to the 5' side, and a gene3 partial sequence serving as a linker for ribosome display was ligated to the 3' side using SfiI.

Acquisition of pH-Dependent Binding scFv from Library by Bead Panning

In order to concentrate only scFv having the ability to bind to SR344, panning was carried out twice by the ribosome display method in accordance with Nature Biotechnology 2000 December; 18: 1287-1292. The prepared SR344 was biotinylated using NHS-PEO4-Biotin (Pierce) to obtain an antigen. Panning was carried out using 40 nM of the biotinylated antigen.

Using the resulting DNA pool as a template, HL scFv was restored by PCR using specific primers. After digesting with SfiI, the digested HL scFv was inserted into a phagemid vector pELBG lacI that was also digested with SfiI, and then used to transform XL1-Blue (Stratagene).

Escherichia coli cells carrying the desired plasmid were grown to 0.4 to 0.6 O.D./mL in 2YT medium containing 100 μg/mL ampicillin and 2% glucose. A helper phage (M13KO7, 4.5×10$^{11}$ pfu) was added thereto, statically cultured for 30 minutes at 37° C., and then cultured with shaking for 30 minutes at 37° C. The culture was transferred to a 50 mL Falcon tube, centrifuged for 10 minutes at 3000 rpm, resuspended in 2YT medium containing 100 μg/mL ampicillin, 25 μg/mL kanamycin, and 0.5 mM IPTG, and then incubated overnight at 30° C.

The culture incubated overnight was precipitated with 2.5 M NaCl and 10% PEG, and then diluted with PBS to obtain a phage library solution. 10% M-PBS (PBS containing 10% skim milk) and 1 M Tris-HCl were added to the phage library solution to the final concentration of 2.5% M-PBS and pH 7.4. Panning was carried out by a typical panning method using an antigen immobilized on magnetic beads (J. Immunol. Methods 2008 Mar. 20; 332(1-2): 2-9; J. Immunol. Methods 2001 Jan. 1; 247(1-2): 191-203; Biotechnol. Prog. 2002 March-April; 18(2): 212-20). More specifically, 40 pmol of biotin-labeled SR344 was added to the prepared phage library and the library was contacted with the antigen for 60 minutes at 37° C. Streptavidin-coated beads (Dynal M-280) washed with 5% M-PBS (PBS containing 5% skim milk) were added and allowed to bind for 15 minutes at 37° C. The beads were washed five times with both 0.5 ml of PBST (PBS containing 0.1% TWEEN® 20 polyoxyethylene sorbitan monolaurate, pH 7.4) and PBS (pH 7.4). The beads were then suspended in 1 mL of PBS (pH 5.5) at 37° C., and the phage was recovered immediately. The recovered phage solution was added to 10 mL of logarithmic-growth-phase XL1-Blue (OD600 of 0.4 to 0.5) and allowed to stand for 30 minutes at 37° C. for infection. The infected E. coli were plated onto a 225 mm×225 mm plate containing 2 YT, 100 µg/mL ampicillin and 2% glucose. These E. coli were used to begin additional phage culture in the same manner as described above and repeat the panning 8 times.

Evaluation by Phage ELISA

The above single colonies were inoculated in 100 µL of 2YT, 100 µg/mL ampicillin, 2% glucose and 12.5 µg/mL tetracycline and cultured overnight at 30° C. 2 µL of this culture was inoculated into 300 µL of 2YT, 100 µg/mL ampicillin and 2% glucose, and then cultured for 4 hours at 37° C. A helper phage (M13KO7) was added to the culture at 9×10$^8$ pfu, allowed to stand for 30 minutes at 37° C. and then shaken for 30 minutes at 37° C. for infection. Subsequently, the medium was replaced with 300 µL of 2 YT, 100 µg/mL ampicillin, 25 µg/mL kanamycin, and 0.5 mM IPTG. After culturing overnight at 30° C., the centrifuged supernatant was recovered. 360 µL of 50 mM PBS (pH 7.4) was added to 40 µL of the centrifuged supernatant and subjected to ELISA. A StreptaWell 96-well microtiter plate (Roche) was coated overnight with 100 µL of PBS containing 62.5 ng/mL of biotin-labeled SR344. After removing the antigen by washing with PBST, blocking was carried out with 250 µL of 2% BSA-PBS for 1 hour or more. After removing the 2% BSA-PBS, the prepared culture supernatant was added and allowed to stand for 1 hour at 37° C. for antibody binding. After washing, 50 mM PBS (pH 7.4) or 50 mM PBS (pH 5.5) was added and incubated by standing for 30 minutes at 37° C. After washing, detection was carried out with an HRP-conjugated anti-M13 antibody (Amersham Pharmacia Biotech) diluted with 2% BSA-PBS and TMB single solution (Zymed), followed by the addition of sulfuric acid to stop the reaction, and the measurement of absorbance at 450 nm.

However, no clones exhibiting potent pH-dependent binding ability were obtained by this panning using the antigen immobilized on the magnetic beads. Clones that were found to show weak pH-dependent binding ability were subjected to sequence analysis using specific primers. The positions in these clones where histidine was present at a high rate are shown in Table 3.

TABLE 3

Positions of Histidine Substitution Detected Using
Phage Library (Magnetic Bead Panning)

H50, H58, H61, H62, H63, H64, H65, H102
L24, L27, L28, L32, L53, L56, L90, L92, L94

Acquisition of pH-Dependently Binding scFv from Library by Column Panning

No clones having strong pH-dependent binding ability were obtained by typical panning using the magnetic bead-immobilized antigen. This may be due to the following reasons. In the panning using an antigen immobilized on magnetic beads or a plate, all phages dissociated from the magnetic beads or plate under acidic conditions are collected. Thus, phage clones having weak pH dependency recovered together reduce the likelihood that clones having strong pH dependency are included in the finally concentrated clones.

Figure 5:
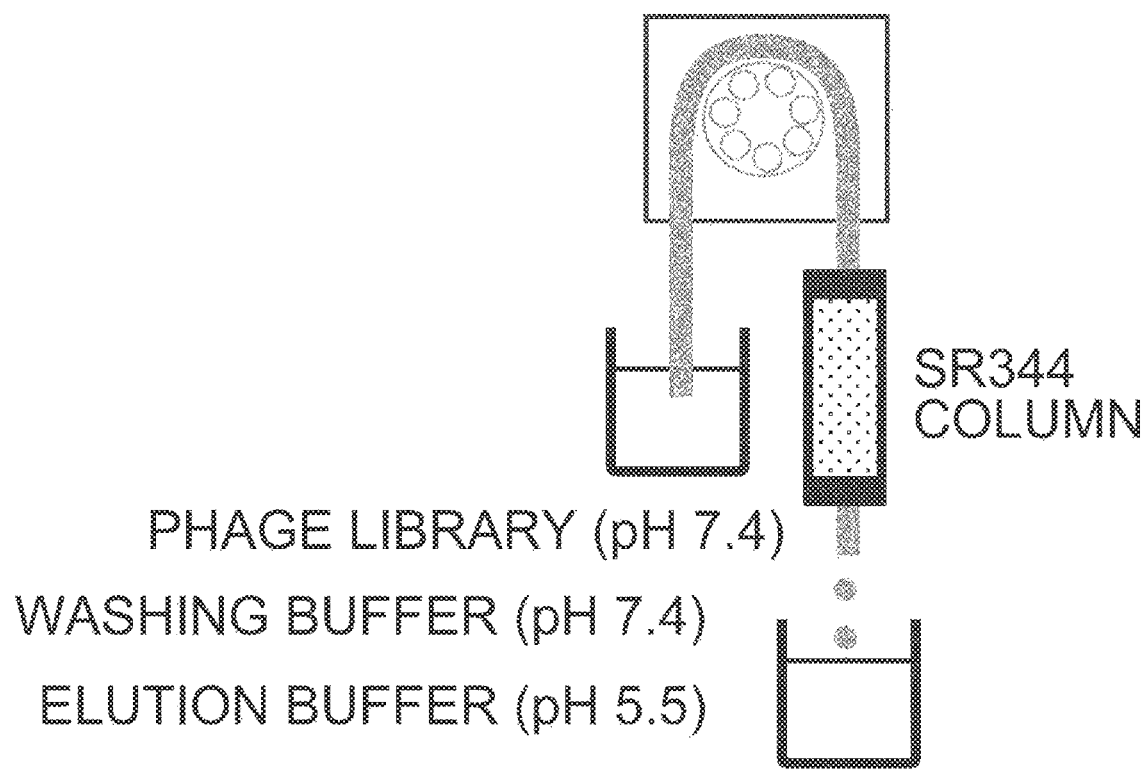
FIG. 5 is a diagram depicting the process of panning using an antigen-immobilized column.

Therefore, panning using a column immobilized with an antigen was examined as a more stringent panning method (FIG. 5). There have been no previous reports on the acquisition of clones having pH-dependent binding ability by using panning with an antigen-immobilized column. In the panning using an antigen-immobilized column, when phages that have been bound under neutral conditions are eluted under acidic conditions, clones having weak pH dependency rebind to the antigen within the column and are thereby less eluted, allowing strongly pH-dependent clones that less rebind within the column to be selectively eluted from the column. In addition, although "all" phages that have dissociated under acidic conditions are recovered in the panning using the antigen immobilized on magnetic beads or a plate, the panning using a column immobilized with the antigen enables selective recovery of phages having strong pH-dependent binding ability by allowing an acidic buffer to flow through the column to begin the elution and recovering only "appropriate fractions".

First, a column to which the antigen SR344 was immobilized was prepared. 200 µl of Streptavidin Sepharose (GE Healthcare) was washed with 1 ml of PBS, suspended in 500 µL of PBS, and contacted with 400 pmol of biotin-labeled SR344 for 1 hour at room temperature. Subsequently, an empty column (Amersham Pharmacia Biotech) was filled with the above sepharose and washed with about 3 mL of PBS. The above-mentioned PEG-precipitated library phages were diluted to 1/25 with 0.5% BSA-PBS (pH 7.4), passed through a 0.45 nm filter, and then added to the column. After washing with about 6 mL of PBS (pH 7.4), 50 mM MES-NaCl (pH5.5) was allowed to flow through the column to elute antibodies that dissociate under low pH. The appropriate eluted fractions were collected, and the recovered phage solution was added to 10 mL of logarithmic-growth-phase XL1-Blue (OD600 of 0.4 to 0.5) and allowed to stand for 30 minutes at 37° C.

The infected E. coli were plated onto a 225 mm×225 mm plate containing 2YT, 100 µg/mL ampicillin, and 2% glucose. These E. coli were used to begin additional phage culture in the same manner as described above and repeat the panning 6 times.

Evaluation by Phage ELISA

Figure 6:
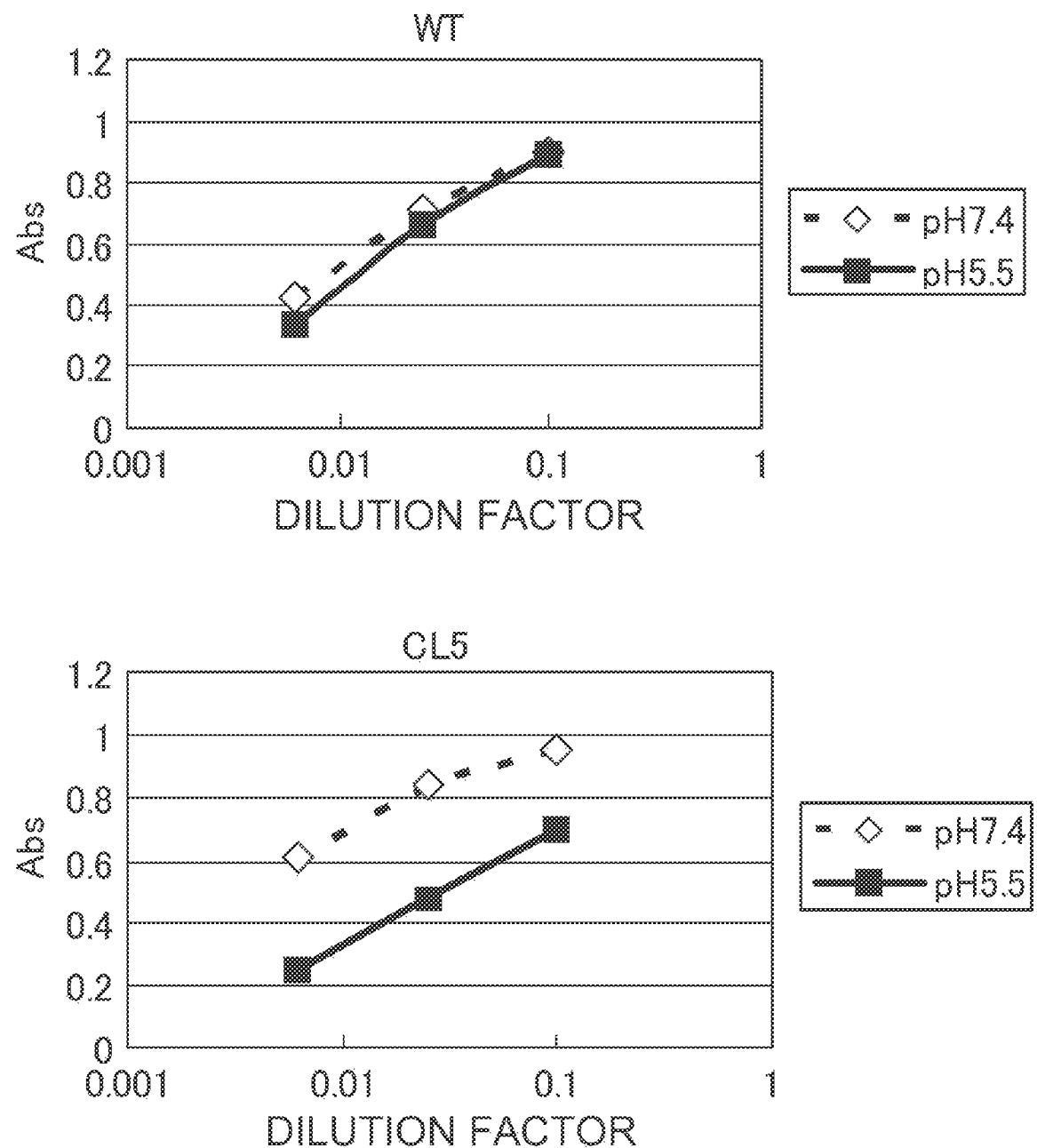
FIG. 6 presents graphs depicting the results of phage ELISA for clones acquired by column panning. The upper graph depicts WT and the lower graph depicts CL5.

The resulting phages were evaluated by phage ELISA. Clones that were found to have strong pH dependency were subjected to sequence analysis using specific primers. As a result, several clones showing strong pH-dependent binding as compared to WT were obtained. As shown in FIG. 6, clone CL5 (H chain: CLH5, L chain: CLL5) (CLH5: amino acid sequence of SEQ ID NO: 5, CLL5: amino acid sequence of SEQ ID NO: 8) was found to exhibit particularly strong pH-dependent binding as compared to WT. It was thus confirmed that antibodies exhibiting strong pH-dependent binding, while being unable to be obtained by typical panning using the antigen immobilized onto magnetic beads, can be obtained by panning using a column immobilized with the antigen. Therefore, panning using an antigen-immobilized column was found to be a highly effective method for obtaining pH-dependently binding antibodies from a library. The amino acid sequences of the clones showing pH-dependent binding were analyzed, and the positions where histidine was present at a high probability in the concentrated clones are shown in Table 4.

TABLE 4

Positions of Histidine Substitution found by Phage Library (Column Panning)

H31, H50, H58, H62, H63, H65, H100b, H102
L24, L27, L28, L32, L53, L56, L90, L92, L94

Example 4 Expression and Purification of Histidine-Modified Humanized IL-6 Receptor Antibody Production, Expression and Purification of Expression Vector of Histidine-Modified Humanized IL-6 Receptor Antibody In order to convert clones showing strong pH dependency in phage ELISA to IgG, VH and VL were respectively amplified by PCR, digested with XhoI/NheI and EcoRI, and inserted to a mammalian cell expression vector. The nucleotide sequence of each DNA fragment was determined by a method known to persons skilled in the art. CLH5/L73, in which CLH5 was used for the H chain and L73 obtained in Example 2 was used for the L chain, was expressed and purified as IgG. Expression and purification were carried out by the method described in Example 1.

Antibody having even higher pH dependency was produced by combining mutation sites. Based on the locations where His was concentrated in the phage library as well as the structural information and the like, H32, H58, H62 and H102 in H3pI which was obtained as an H chain in Example 2 were substituted with histidine, and H95 and H99 were further substituted with valine and isoleucine, respectively, to produce H170 (SEQ ID NO: 4). The variant production was carried out using the method described in Example 1. In addition, L82 (SEQ ID NO: 7) was produced by substituting the 28th histidine of L73, which was produced as an L chain in Example 2, with aspartic acid. The variant production was carried out using the method described in Example 1. H170/L82, in which H170 was used for the H chain and L82 was used for the L chain, was expressed and purified as IgG using the method described in Example 1.

Example 5 Evaluation of IL-6R-Neutralizing Activity of pH-Dependent Binding Antibody Evaluation of Human IL-6 Receptor-Neutralizing Activity of Clones Converted to IRG The IL-6 receptor-neutralizing activity was evaluated for four antibodies: humanized PM1 antibody (WT) and H3pI/L73, CLH5/L73 and H170/L82 produced in Examples 2 and 4.

Figure 7:
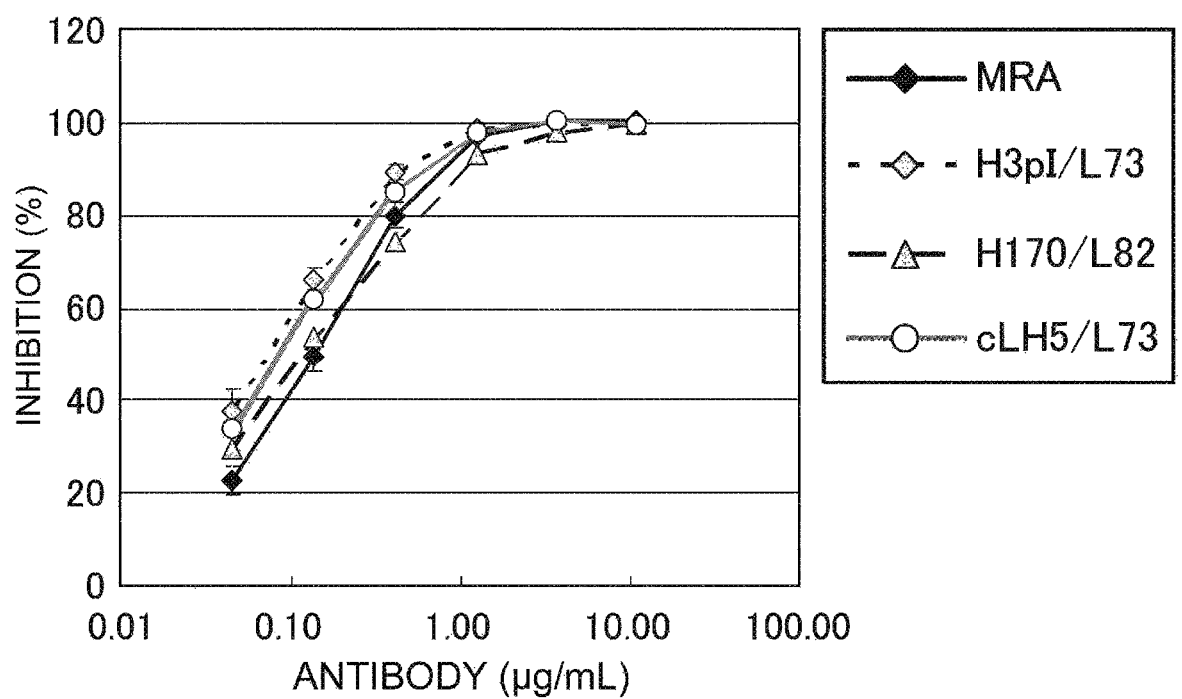
FIG. 7 is a graph depicting the biological neutralization activity of pH-dependently-binding anti-IL-6 receptor antibodies.

More specifically, the IL-6 receptor-neutralizing activity was evaluated using BaF3/gp130 exhibiting IL-6/IL-6 receptor-dependent growth. BaF3/gp130 was washed three times with RPMI1640 medium containing 10% FBS, then suspended at $5 \times 10^4$ cells/mL in RPMI1640 medium containing 60 ng/mL of human interleukin-6 (Toray), 60 ng/mL of recombinant soluble human IL-6 receptor (SR344) and 10% FBS. 50 μL of the suspension was dispensed into each of the wells of a 96-well plate (Corning). Next, the purified antibody was diluted with RMPI1640 containing 10% FBS, and 50 μl of the antibody was mixed into each well. After culturing for 3 days at 37° C. and 5% $CO_2$, WST-8 reagent (Cell Counting Kit-8, Dojindo Laboratories) diluted two-fold with PBS was added at 20 μL/well, and then immediately measured for absorbance at 450 nm (reference wavelength: 620 nm) using the Sunrise Classic (Tecan). After culturing for 2 hours, absorbance at 450 nm was measured again (reference wavelength: 620 nm). The IL-6 receptor-neutralizing activity was evaluated based on the change in absorbance after 2 hours. As a result, as shown in FIG. 7, H3pI/L73, CLH5/L73 and H170/L82 were shown to have equivalent biological neutralization activity in comparison with the humanized PM1 antibody (WT).

Figure 8:
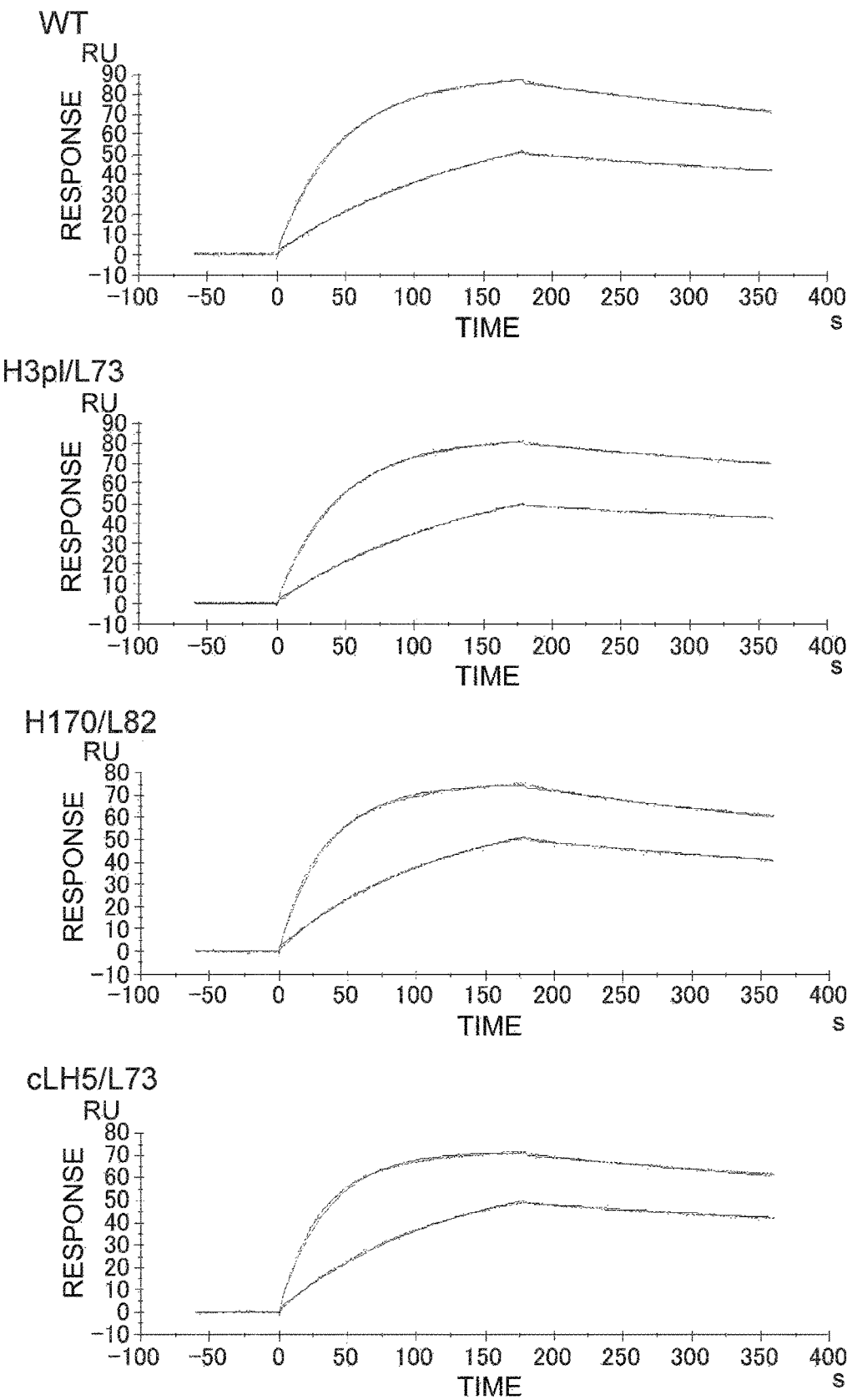
FIG. 8 presents Biacore™ sensorgrams depicting binding of pH-dependently-binding anti-IL-6 receptor antibodies to soluble IL-6 receptor at pH 7.4. The top graph depicts WT; the second graph from the top depicts H3pI/L73; the third graph from the top depicts H170/L82; and the bottom graph depicts CLH5/L73.
Figure 9:
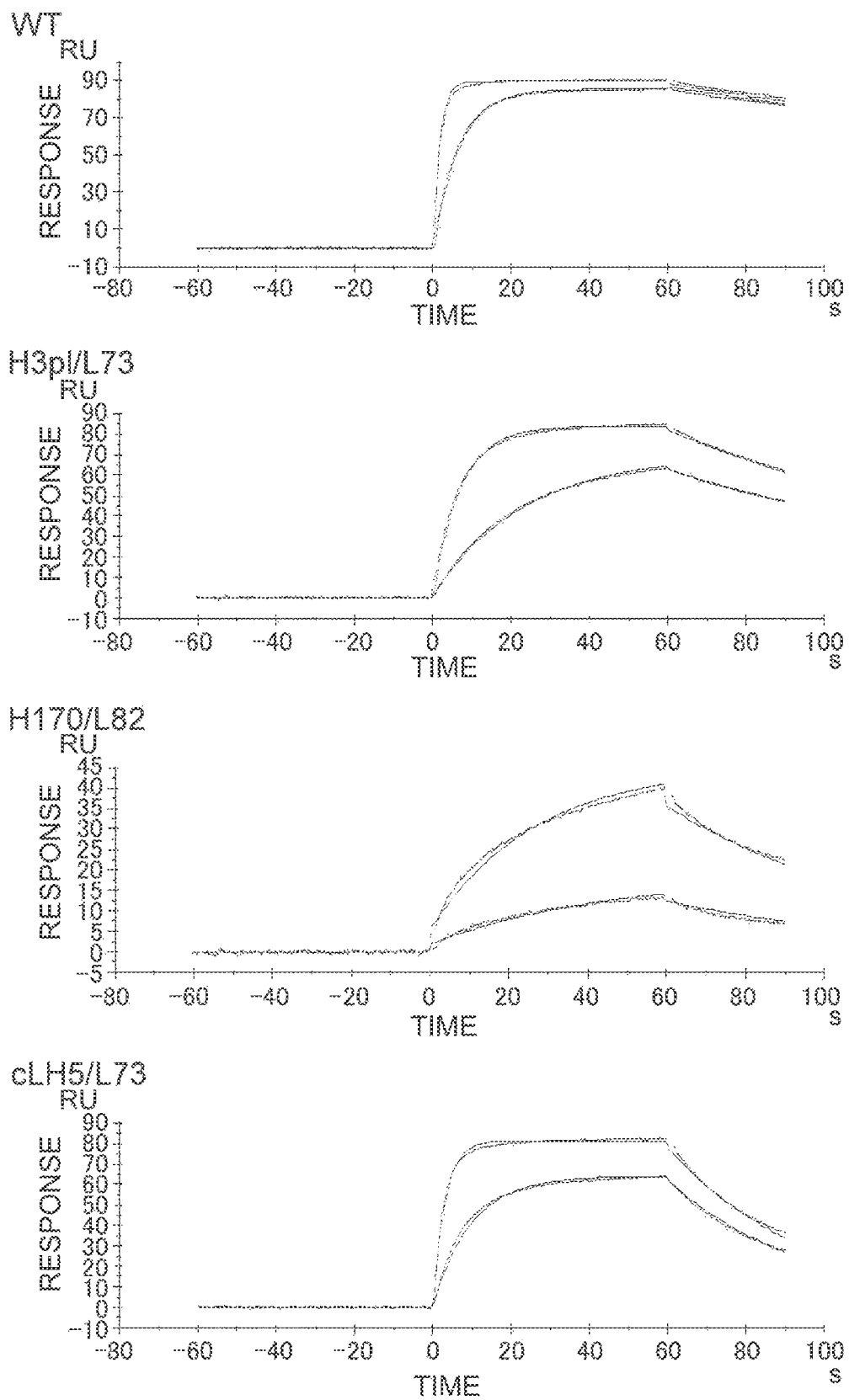
FIG. 9 presents Biacore™ sensorgrams depicting binding of pH-dependently-binding anti-IL-6 receptor antibodies to soluble IL-6 receptor at pH 5.8. The top graph depicts WT; the second graph from the top depicts H3pI/L73; the third graph from the top depicts H170/L82; and the bottom graph depicts CLH5/L73.

Example 6 Biacore™ Surface Plasmon Resonance Analysis of pH-Dependently Binding Antibody Analysis of Binding of pH-Dependently Binding Clones to Soluble IL-6 Receptor Kinetic analyses of antigen-antibody reactions at pH 5.8 and pH 7.4 were carried out using a Biacore™ T100 surface plasmon resonance system (GE Healthcare) on the four antibodies: humanized PM1 antibody (WT) and H3pI/L73, CLH5/L73, and H170/L82 produced in Examples 2 and 4 (buffer: 10 mM MES (pH 7.4 or pH 5.8), 150 mM NaCl, and 0.05% TWEEN® 20 (polyoxyethylene sorbitan monolaurate)). Various antibodies were bound onto a sensor chip immobilized with recomb-protein A/G (Pierce) by amine coupling. SR344 adjusted to concentrations of 9.8 to 400 nM was injected to the chip as an analyte. Association and dissociation of the pH-dependent binding clones to SR344 was observed in real time (FIGS. 8 and 9). All the measurements were carried out at 37° C. Association rate constants $k_a$ (1/Ms) and dissociation rate constants $k_d$ (1/s) were calculated using Biacore T100™ Evaluation Software (GE Healthcare), and dissociation constants KD (M) were calculated on the basis of those values (Table 5). Moreover, the ratio of the affinities at pH 5.8 and pH 7.4 were calculated for each clone to evaluate pH-dependent binding. All the measurements were carried out at 37° C.

As a result of calculating the affinity ratio between pH 5.8 and pH 7.4 for each clone, the pH-dependent binding (affinity) of H3pI/L73, H170/L82 and CLH5/L73 to SR344 was 41-fold, 394-fold and 66-fold, respectively, each showing the pH-dependent binding more than 15 times higher than WT.

Anti-IL-6 receptor antibodies that strongly bind to the antigen at the plasma pH of 7.4 but weakly bind to the antigen at the intraendosomal pH of 5.5 to 6.0 have not been reported yet. In this study, antibodies were obtained that retain the biological neutralization activity equivalent to the WT humanized IL-6 receptor antibody and the affinity at pH 7.4, but exhibit the affinity at pH 5.8 that has been specifically lowered more than 10 times.

TABLE 5

Comparison of Binding of pH-Dependently Binding Clones
Directed Against SR344 to Soluble IL-6 Receptor

|  | pH7.4 | | | pH5.8 | | | KD(pH5.8)/ |
| --- | --- | --- | --- | --- | --- | --- | --- |
|  | ka(1/Ms) | kd(1/s) | KD(M) | ka(1/Ms) | kd(1/s) | KD(M) | KD(pH7.4) |
| WT | 5.1E+05 | 1.0E−03 | 2.1 E−09 | 7.6E+05 | 3.8E−03 | 5.0E−09 | 2.4 |
| H3pI/L73 | 5.4E+05 | 7.4E−04 | 1.4E−09 | 1.7E+05 | 9.7E−03 | 5.7E−08 | 41.3 |
| H170/L82 | 6.8E+05 | 1.1E−03 | 1.6E−09 | 2.6E+04 | 1.7E−02 | 6.4E−07 | 393.5 |
| CLH5/L73 | 7.1E+05 | 7.9E−04 | 1.1E−09 | 3.8E+05 | 2.8E−02 | 7.4E−08 | 66.1 |

Analysis of Binding of pH-Dependently Binding Clones to Membrane IL-6 Receptor

Figure 10:
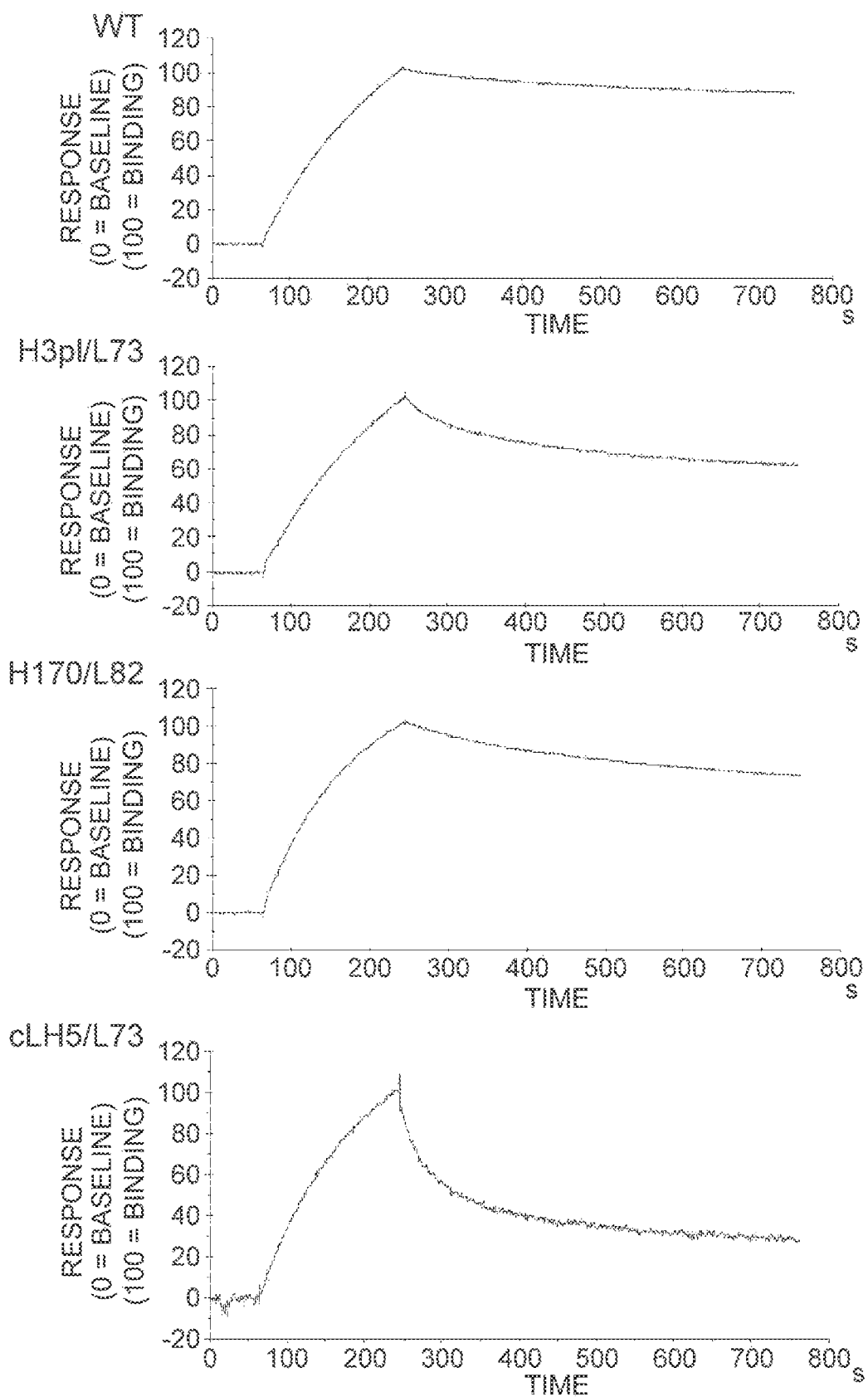
FIG. 10 presents Biacore™ sensorgrams depicting association (pH 7.4) and dissociation (pH 5.8) of pH-dependently-binding anti-IL-6 receptor antibodies to membrane-type IL-6 receptor. The top graph depicts WT; the second graph from the top depicts H3pI/L73; the third graph from the top depicts H170/L82; and the bottom graph depicts CLH5/L73.

Antigen-antibody reactions to membrane IL-6 receptor at pH 5.8 and pH 7.4 were observed for the above produced pH-dependent binding clones, using a Biacore T100™ Surface plasmon resonance system (GE Healthcare). The binding to membrane IL-6 receptor was evaluated by evaluating the binding to the IL-6 receptor immobilized onto a sensor chip. SR344 was biotinylated according to a method known to persons skilled in the art, and the biotinylated SR344 was immobilized on the sensor chip via streptavidin by utilizing the affinity between streptavidin and biotin. All the measurements were carried out at 37° C., and the mobile phase buffer contained 10 mM MES (pH 5.8), 150 mM NaCl and 0.05% TWEEN® 20 (polyoxyethylene sorbitan monolaurate). The pH-dependent binding clones were injected therein under the condition of pH 7.4 and allowed to bind to SR344 (injection sample buffer: 10 mM MES (pH 7.4), 150 mM NaCl, 0.05% TWEEN® 20 (polyoxyethylene sorbitan monolaurate)), and the pH-dependent dissociation of each clone at the mobile phase pH of 5.8 was observed (FIG. 10).

The dissociation rate ($k_d$(1/s)) at pH 5.8 was calculated using Biacore T100™ Evaluation Software (GE Healthcare) by fitting only the dissociation phase at pH 5.8, where 0.5 μg/mL of the sample was bound in 10 mM MES (pH 7.4), 150 mM NaCl, and 0.05% TWEEN® 20 (polyoxyethylene sorbitan monolaurate), and dissociated in 10 mM MES (pH 5.8), 150 mM NaCl, and 0.05% TWEEN® 20 (polyoxyethylene sorbitan monolaurate). Similarly, the dissociation rate ($k_d$(1/s)) at pH 7.4 was calculated using Biacore T100™ Evaluation Software (GE Healthcare) by fitting only the dissociation phase at pH 7.4, where 0.5 μg/mL of the sample was bound in 10 mM MES (pH 7.4), 150 mM NaCl, and 0.05% TWEEN® 20 (polyoxyethylene sorbitan monolaurate), and dissociated in 10 mM MES (pH 7.4), 150 mM NaCl, and 0.05% TWEEN® 20 (polyoxyethylene sorbitan monolaurate). The pH-dependent dissociation rate constant of each clone is shown in Table 6.

TABLE 6

Comparison of Rate Constant of Dissociation
of pH-Dependent Binding Clones
directed against SR344 from Membrane IL-6 Receptor

|  | kd(1/s) | | kd ratio |
| --- | --- | --- | --- |
|  | pH7.4 | pH5.8 | pH5.8/pH7.4 |
| WT | 4.84E−04 | 7.15E−04 | 1.5 |
| H3pI/L73 | 3.44E−04 | 3.78E−03 | 11.0 |
| H170/L82 | 7.70E−04 | 1.44E−03 | 1.9 |
| CLH5/L73 | 1.04E−03 | 5.67E−03 | 5.5 |

The highest pH dependency of the dissociation ratio was observed in H3pI/L73 followed by CLH5/L73 and H170/L82 in descending order, and each clone demonstrated higher pH-dependent dissociation from the membrane IL-6 receptor than WT. However, the rank of pH-dependent association/dissociation was different between the soluble IL-6 receptor and membrane IL-6 receptor. It was revealed that H170/L82, which exhibited the highest pH-dependent binding in the analysis of binding to soluble IL-6 receptor, showed the lowest pH-dependent binding in the analysis of binding to the membrane IL-6 receptor. In general, it is known that while IgG molecules monovalently bind to a soluble antigen (affinity), they divalently bind to membrane antigens (avidity). It is suggested that this difference in the binding mode between soluble antigens and membrane antigens influenced the pH-dependent binding of H170/L82.

Example 7 Confirmation of Multiple Binding to Antigen by pH-Dependent Binding Antibody As described in Example 2, pH-dependent binding antibodies may be able to bind to antigens multiple times. Specifically, a pH-dependent binding antibody that has bound to an antigen is non-specifically taken up into endosomes, but dissociated from the soluble antigen under the intraendosomal acidic conditions. The antibody binds to FcRn and thereby returns to the plasma. Since the antibody that has returned to the plasma is not bound to antigen, it is able to bind to a new antigen again. The repetition of this process enables pH-dependent binding antibodies to bind to antigens multiple times. However, for IgG antibodies that do not have pH-dependent binding ability, not all antigens are dissociated from the antibodies under the intraendosomal acidic conditions. Thus, such antibodies that have been returned to the plasma by FcRn remain bound to antigen, and therefore cannot bind to new antigens. Consequently, in nearly all cases, each single molecule of IgG antibodies is able to neutralize only two antigens (in the case of divalent binding).

Therefore, it was evaluated whether the three pH-dependently binding antibodies (H3pI/L73, CLH5/L73, and H170/L82) constructed in Examples 2 and 4 were able to bind to the antigen SR344 multiple times as compared to the humanized PM1 antibody (wild type, WT).

A Biacore™ surface plasmon resonance system (GE Healthcare) was used to evaluate that the antibodies binding at pH 7.4 and dissociating at pH 5.8 were able to bind to the antigen multiple times. The antibody to be evaluated was bound to a recomb-protein A/G (Pierce)-immobilized sensor chip by the amine coupling method, and a mobile phase of pH 7.4 was allowed to flow (step 1). SR344 solution adjusted to pH 7.4 was then allowed to flow as an analyte to bind SR344 to the antibody at pH 7.4 (step 2). This binding at pH 7.4 mimics the antigen binding in plasma. Subsequently, buffer adjusted to pH 5.8 alone (not containing SR344) was added as an analyte to expose the antigen bound to the antibody to acidic conditions (step 3). This dissociation at pH 5.8 mimics the binding state of antigen-antibody complexes in endosomes. Subsequently, step 2 was repeated. This mimics the rebinding of antibody that has been returned to plasma by FcRn to a new antigen. Subsequently, step 2 was repeated to expose the antibody-antigen complex to acidic conditions. Repeating "step 2 to step 3" multiple times at 37° C. as described above can mimic the in vivo state in which antibodies are repeatedly taken up from the plasma into endosomes by pinocytosis and returned to the plasma by FcRn (Nat. Rev. Immunol. 2007 September; 7(9): 715-25).

Figure 11:
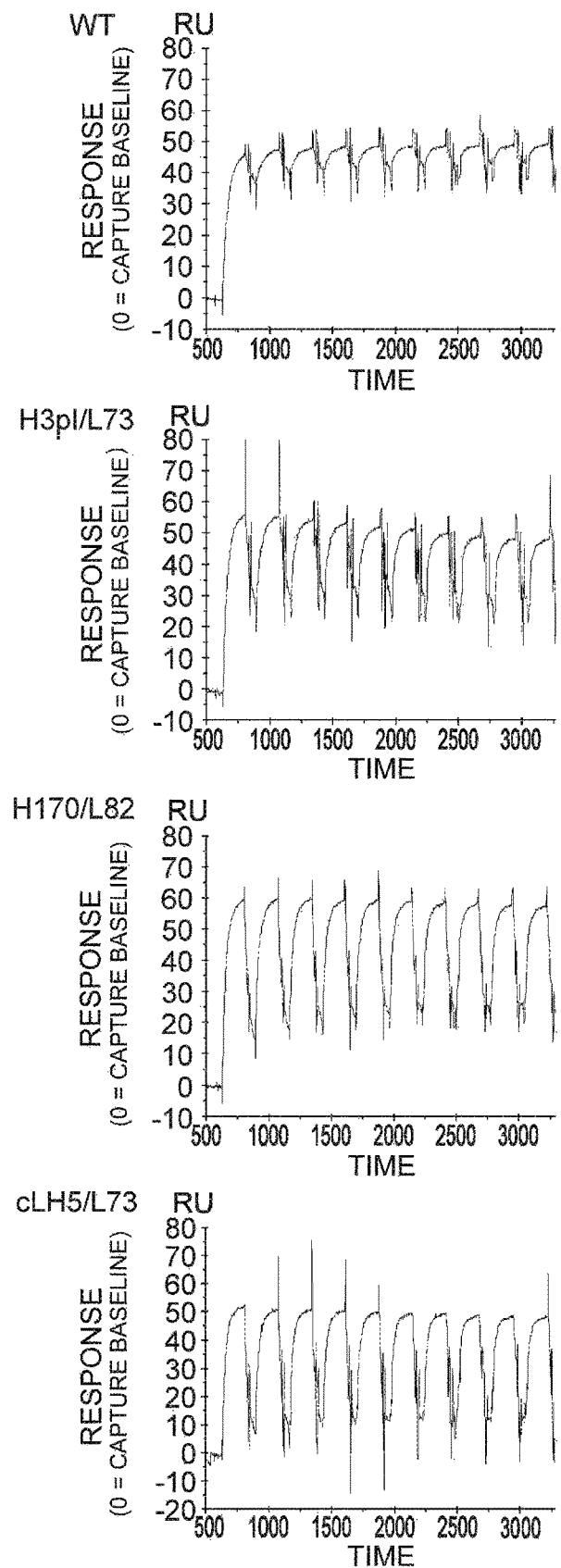
FIG. 11 is a Biacore™ sensorgram indicating repeated binding of pH-dependently-binding anti-IL-6 receptor antibodies to SR344.

The produced pH-dependent binding clones described above were analyzed using a Biacore T100™ surface plasmon resonance system (GE Healthcare) for their ability to bind to the antigen SR344 multiple times at pH 5.8 and pH 7.4. More specifically, the analysis was carried out as follows. All the measurements were carried out at 37° C. First, the sample antibodies described above were bound onto a recomb-protein A/G (Pierce)-immobilized sensor chip by amine-coupling, where the mobile phase buffer was 10 mM MES (pH 5.8), 150 mM NaCl, and 0.05% TWEEN® 20 (polyoxyethylene sorbitan monolaurate) (step 1). SR344 adjusted to a concentration of about 40 nM was injected as an analyte for 3 minutes at pH 7.4 and allowed to bind (the buffer for injected SR344 was 10 mM MES (pH 7.4), 150 mM NaCl, and 0.05% TWEEN® 20 (polyoxyethylene sorbitan monolaurate)) (step 2). Subsequently, the injection of SR344 was discontinued and a mobile phase of pH 5.8 was allowed to flow for about 70 seconds to expose the antibody/SR344 complex under acidic conditions (step 3). Ten sets of this binding (step 2)/acidity exposure (step 3) process were continuously repeated to observe the sensorgram in real-time, which is shown in FIG. 11. WT showed less dissociation of SR344 during the acidic exposure in step 3, and consequently the proportion of antibody capable of binding to new antigens in the subsequent step 2 was extremely low. In contrast, it was found that the pH-dependent binding clones, particularly H170/L82 and CLH5/L73, demonstrated so strong dissociation during the acidic exposure in step 3 that most of the bound SR344 was dissociated, and therefore nearly all antibodies were able to bind to new antigens in the subsequent step 2. In the 10-set repetition of the binding (step 2) and acidic exposure (step 3), almost all H170/L82 and CLH5/L73 antibodies were able to bind to new antigens in each set.

Figure 12:
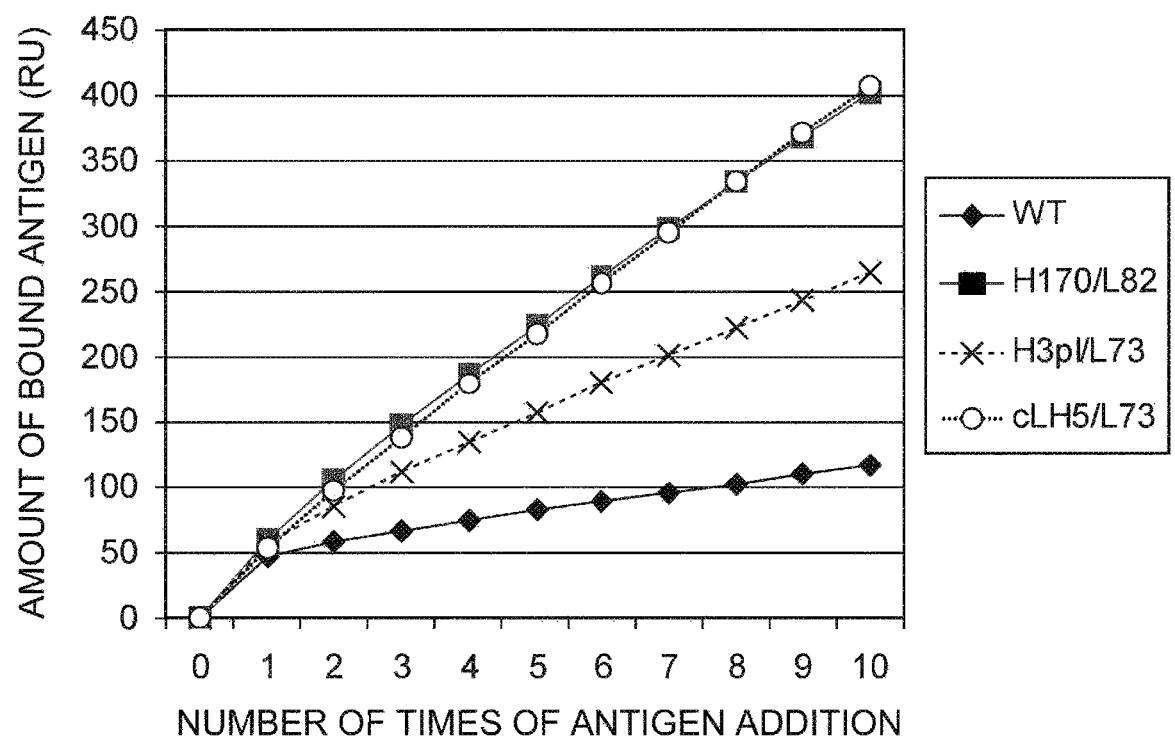
FIG. 12 is a graph depicting the total amount of bound antigen in a repetitive binding experiment of pH-dependently-binding anti-IL-6 receptor antibodies to SR344.

The obtained sensorgrams were used to calculate the binding amount of SR344 in each set for each sample using Biacore T100™ Evaluation Software (GE Healthcare). The integrated values in the time course of the 10 sets are shown in FIG. 12. The integrated RU values obtained at the 10th set are equivalent to the total amount of antigens bound during the ten cycles. The pH-dependent binding clones, particularly H170/L82 and CLH5/L73, showed the largest total amounts of bound antigens in comparison with WT, and were demonstrated to be able to repeatedly bind to roughly four times the amount of antigens bound by WT. Accordingly, it was revealed that by conferring pH-dependent binding ability to WT, such antibodies can repeatedly bind to antigens and thereby neutralize multiple antigens.

Example 8 PK/PD Test of pH-Dependently-Binding Antibody Using Human IL-6 Receptor Transgenic Mice IL-6 receptors are present in the body in both soluble IL-6 receptor form and membrane-type IL-6 receptor form (Nat. Clin. Pract. Rheumatol. 2006 November; 2(11): 619-26). Anti-IL-6 receptor antibodies bind to soluble IL-6 receptors and membrane-type IL-6 receptors and neutralize their biological action. It is believed that an anti-IL-6 receptor antibody binds to a membrane-type IL-6 receptor, is subsequently taken up into an endosome within a cell by internalization while the antibody is kept bound to the membrane-type IL-6 receptor, and then moves to a lysosome while still kept bound to the membrane-type IL-6 receptor where it is degraded by lysosome together with the membrane-type IL-6 receptor. If H3pI/L73, CLH5/L73, and H170/L82, which are the pH-dependent-binding IL-6 receptor antibodies evaluated in Example 6, are able to return to plasma via FcRn as a result of dissociation under acidic conditions within endosomes, the antibodies that have returned to the plasma can bind to antigens again. This enables neutralization of multiple membrane-type IL-6 receptors with a single antibody molecule. Whether or not the return to the plasma via FcRn as a result of dissociation under acidic conditions within endosomes is achieved with the constructed pH-dependent-binding anti-IL-6 receptor antibodies can be determined by evaluating whether the pharmacokinetics of these antibodies are improved as compared with that of WT.

Thus, the pharmacokinetics in human-IL-6-receptor transgenic mice (hIL-6R tg mice, Proc. Natl. Acad. Sci. USA 1995 May 23; 92(11): 4862-6) was evaluated for the four types of antibodies, that is, humanized PM1 antibody (wild type: WT) and H3pI/L73, CLH5/L73, and H170/L82 constructed in Examples 2 and 4. WT, H3pI/L73, CLH5/L73, or H170/L82 was administered by single-dose intravenous administration to hIL-6R tg mice at 25 mg/kg, and blood samples were collected, before administration and over time. Collected blood was immediately centrifuged for 15 minutes at 15,000 rpm and 4° C. to obtain plasma. Separated plasma was stored in a freezer set to −20° C. or lower until measurements were carried out.

Figure 13:
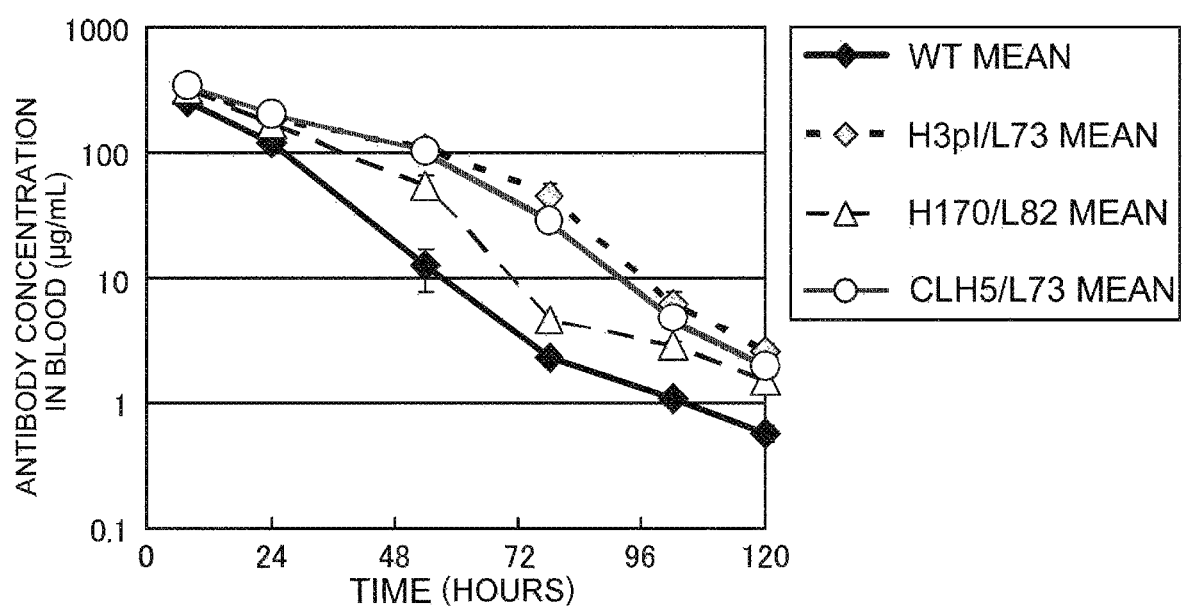
FIG. 13 is a graph depicting time courses of antibody plasma concentrations of pH-dependently-binding anti-IL-6 receptor antibodies in human IL-6 receptor transgenic mice.

The measurement of concentration in mouse plasma was carried out by ELISA. Samples for calibration curve were prepared at plasma concentrations of 6.4, 3.2, 1.6, 0.8, 0.4, 0.2 and 0.1 µg/mL. The calibration curve samples and mouse plasma measurement samples were dispensed into an immunoplate (Nunc-Immuno Plate, MaxiSorp (Nalge Nunc International)) immobilized with anti-human IgG (γ-chain specific) F(ab')2 (Sigma), and allowed to stand undisturbed for one hour at room temperature. Goat anti-human IgG-BIOT (Southern Biotechnology Associates) and streptavidin-alkaline phosphatase conjugate (Roche Diagnostics) were sequentially allowed to react, and a chromogenic reaction was carried out by using BluePhos Microwell Phosphatase Substrates System (Kirkegaard & Perry Laboratories) as substrate. Absorbance at 650 nm was measured with a microplate reader. The concentrations in mouse plasma were calculated from the absorbance of the calibration curve using the analytical software SOFTmax PRO (Molecular Devices). Time courses of plasma concentrations of WT as well as H3pI/L73, CLH5/L73, and H170/L82 are shown in FIG. 13.

The pharmacokinetics was improved for all of H3pI/L73, CLH5/L73, and H170/L82 as compared with WT. In particular, the pharmacokinetics of H3pI/L73 and CLH5/L73 were improved considerably. A wild type anti-IL-6 receptor antibody (WT) bound to membrane-type IL-6 receptor is taken up into an endosome within a cell by internalization, moves to a lysosome while the antibody is kept bound to the antigen, and then degraded; therefore, it has a short residence time in the plasma. In contrast, since the pharmacokinetics of the pH-dependent-binding anti-IL-6 receptor antibodies were improved considerably, the pH-dependent-binding anti-IL-6 receptor antibodies were thought to return to the plasma again via FcRn as a result of dissociation from the antigen, membrane-type IL-6 receptor, under acidic conditions within endosomes.

Although the pharmacokinetics was improved for all of H3pI/L73, CLH5/L73, and H170/L82 as compared with WT, the effect of prolonging plasma persistence time of H170/L82 was weaker than that of H3pI/L73 and CLH5/L73. Since IgG molecules are thought to normally bind divalently to membrane-bound antigen, it is thought that anti-IL-6 receptor antibodies also bind divalently (avidity) to membrane-type IL-6 receptors and then are internalized. As indicated in Example 6, the analysis using a Biacore™ surface plasmon resonance system revealed that H170/L82 rapidly dissociated from the IL-6 receptor at pH 5.8 when binding to soluble IL-6 receptor (FIG. 9), but the dissociation rate thereof from the IL-6 receptor at pH 5.8 when binding to membrane-type IL-6 receptor was extremely slow (FIG. 10). From this result, the reason for the weak effect of prolonging residence time in plasma of H170/L82 is thought to be that the antibody was unable to adequately dissociate within endosomes after having been internalized due to its slow dissociation at pH 5.8 when binding to membrane-type IL-6 receptor. Namely, as for the case relating to membrane antigens, it was determined that in order for a single IgG molecule to neutralize multiple membrane antigens, the pH dependency of dissociation from divalent binding (avidity) is more important than the pH dependency of monovalent binding (affinity).

Example 9 PK/PD Test of pH-Dependently-Binding Antibody Using Cynomolgus Monkeys Since the pharmacokinetics of the pH-dependently-binding anti-IL-6 receptor antibodies were improved considerably in Example 8, the pH-dependently-binding anti-IL-6 receptor antibodies were thought to return to plasma via FcRn as a result of dissociation from the antigen, membrane-type IL-6 receptor, under acidic conditions within endosomes. If antibodies that have returned to the plasma can bind to membrane-type IL-6 receptors again, neutralization of an antigen, the membrane-type IL-6 receptor, by pH-dependently-binding anti-IL-6 receptor antibodies is thought to persist longer than that by the wild-type anti-IL-6 receptor antibody, at the same dosage. In addition, since the soluble IL-6 receptor is also present among IL-6 receptors, the duration of neutralization is thought to be longer for the same dosage with respect to the soluble IL-6 receptor as well.

The pharmacokinetics in cynomolgus monkeys was evaluated for WT and H3pI/L73. WT or H3pI/L73 was administered to cynomolgus monkeys by single-dose intravenous administration at 1 mg/kg, and blood samples were collected, before administration and over time. Collected blood was immediately centrifuged for 15 minutes at 15,000 rpm and 4° C. to obtain plasma. The separated plasma was stored in a freezer set to −20° C. or lower until measurements were carried out.

Figure 14:
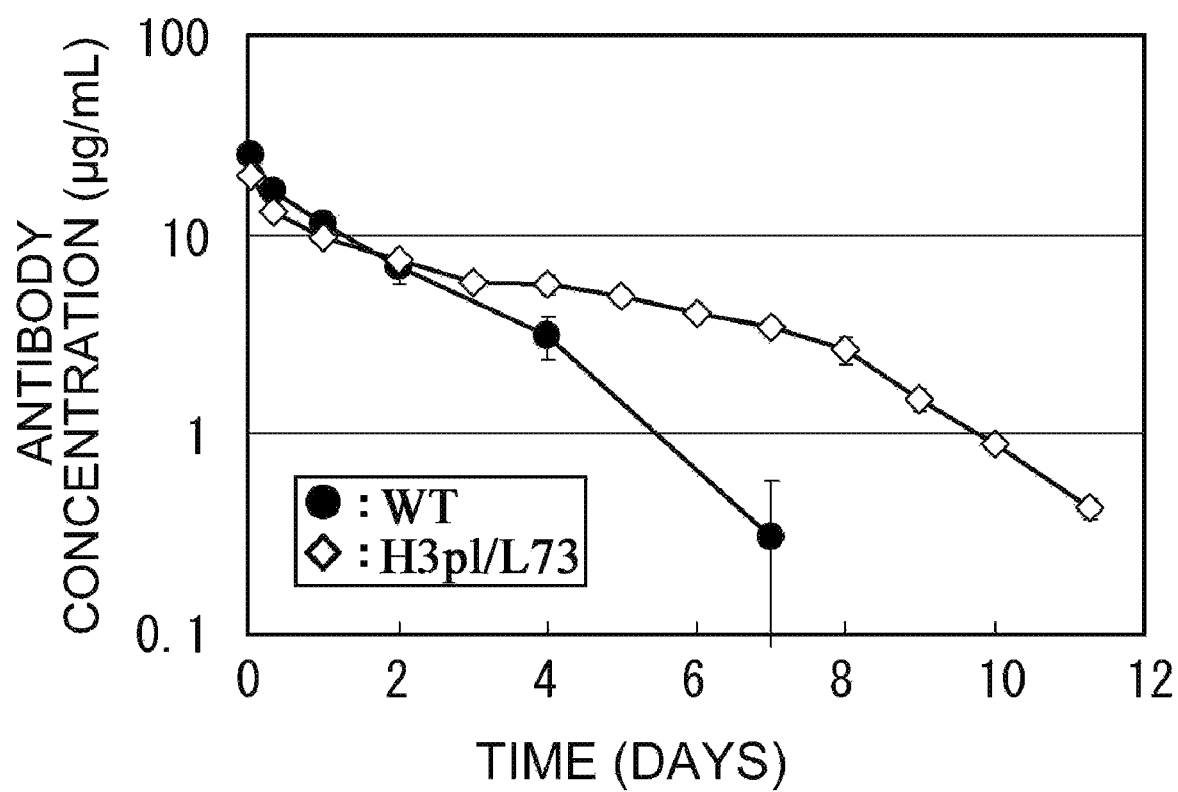
FIG. 14 is a graph depicting time courses of antibody plasma concentrations of pH-dependently-binding anti-IL-6 receptor antibodies in cynomolgus monkeys.

The measurement of concentration in cynomolgus monkey plasma was carried out by ELISA. First, anti-human IgG (γ-chain specific) F(ab')2 fragment of antibody (Sigma) was dispensed into a Nunc-ImmunoPlate MaxiSorp (Nalge Nunc International) and allowed to stand undisturbed overnight at 4° C. to prepare plates immobilized with anti-human IgG. Calibration curve samples having plasma concentrations of 3.2, 1.6, 0.8, 0.4, 0.2, 0.1 and 0.05 µg/mL and cynomolgus monkey plasma measurement samples diluted 100-fold or more were prepared; 200 µL of 20 ng/mL cynomolgus monkey IL-6R was added to 100 µL of the calibration curve samples and plasma measurement samples; and then, they were allowed to stand undisturbed for one hour at room temperature. Subsequently, the samples were dispensed into the anti-human IgG-immobilized plate and allowed to stand undisturbed for another one hour at room temperature. Biotinylated Anti-Human IL-6R Antibody (R&D) was allowed to react for one hour at room temperature, and then Streptavidin-PolyHRP80 (Stereospecific Detection Technologies) was allowed to react for one hour. A chromogenic reaction was carried out by using TMP One Component HRP Microwell Substrate (BioFX Laboratories) as substrate, then, the reaction was stopped with 1N sulfuric acid (Showa Chemical) and the absorbance at 450 nm was measured with a microplate reader. The concentrations in cynomolgus monkey plasma were calculated from the absorbance of the calibration curve using the analytical software SOFTmax PRO (Molecular Devices). The time courses of plasma concentrations of WT and H3pI/L73 after the intravenous administration are shown in FIG. 14. As a result, the pharmacokinetics of H3pI/L73 was improved considerably in comparison with WT in cynomolgus monkeys in the same manner as in human IL-6 receptor transgenic mice. Since the pharmacokinetics of a pH-dependent-binding anti-IL-6 receptor antibody, H3pI/L73, was improved considerably, H3pI/L73 was thought to return to the plasma via FcRn as a result of dissociation from the antigen, membrane-type IL-6 receptor, under acidic conditions within endosomes.

Figure 15:
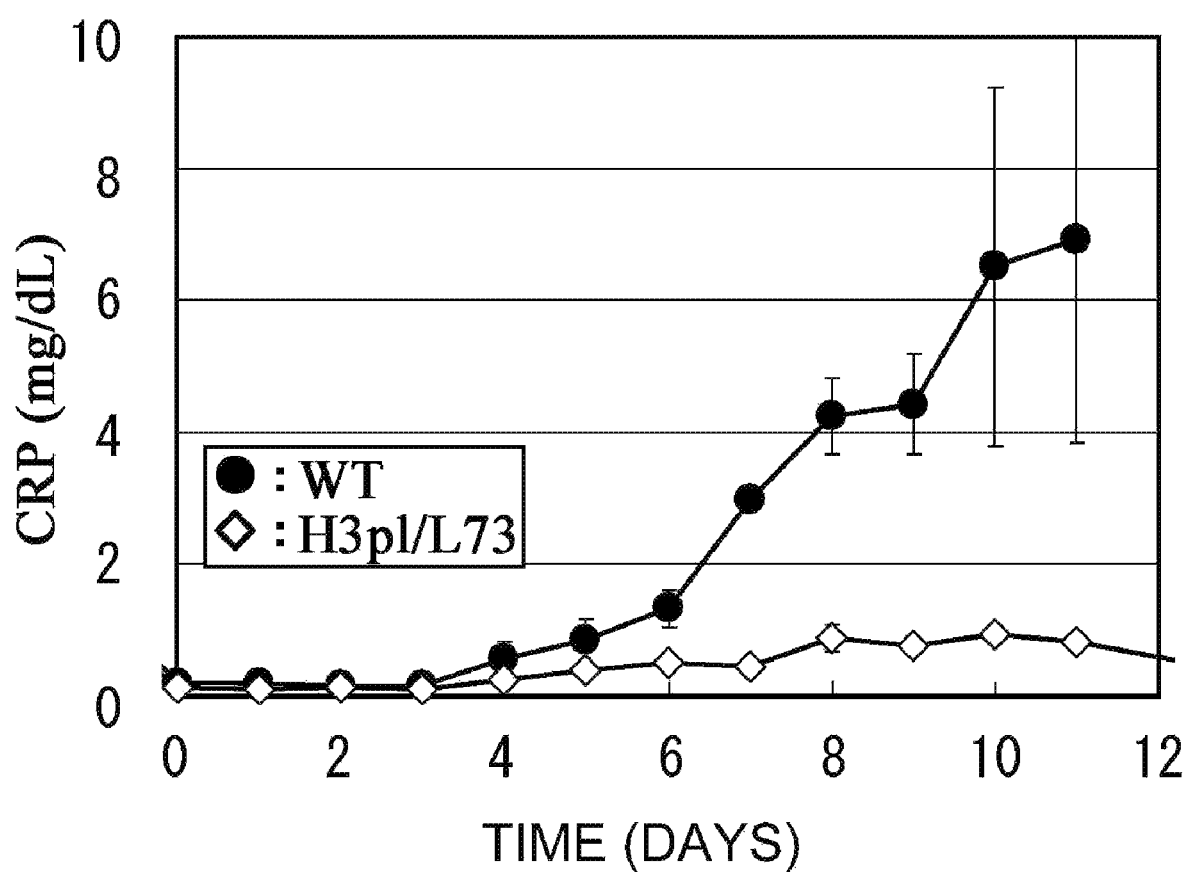
FIG. 15 is a graph depicting time courses of CRP concentrations in cynomolgus monkeys, in relation to pH-dependently-binding anti-IL-6 receptor antibodies.

In order to evaluate the degree to which cynomolgus monkey membrane-type IL-6 receptor is neutralized by the intravenous administration of WT and H3pI/L73, the effects of sample antibodies on plasma C-reactive protein (CRP) induced by cynomolgus monkey IL-6 were studied. Since CRP is secreted when IL-6 binds to membrane-type IL-6 receptors, CRP serves as an indicator of neutralization of membrane-type IL-6 receptors. Cynomolgus monkey IL-6 (cyno.IL-6 prepared in Example 1) containing 1% inactivated cynomolgus monkey plasma was administered subcutaneously into lower backs of the animals daily at 5 µg/kg from day 3 to day 10 after the administration of WT or H3pI/L73. Blood samples were collected from the saphenous vein immediately before the start of cynomolgus monkey IL-6 administration (day 3) and after the administration at 24-hour intervals (day 4 to day 11), then were separated into plasma. The CRP concentrations of individual animals were measured with Cias R CRP (Kanto Chemical) using an automated analyzer (TBA-120FR, Toshiba Medical Systems). The time courses of CRP concentration upon induction with cynomolgus IL-6 with respect to WT and H3pI/L73 are shown in FIG. 15. As a result, the duration of CRP suppression was prolonged considerably by H3pI/L73 in comparison with WT. On the basis of this finding, a pH-dependent-binding anti-IL-6 receptor antibody, H3pI/L73, was thought to return to the plasma via FcRn as a result of dissociation from its antigen, membrane-type IL-6 receptor, under acidic conditions within endosomes; and neutralize the membrane-type IL-6 receptor by re-binding thereto; and thereby suppress production of CRP for a longer period of time than WT. In other words, H3pI/L73 was shown to be able to bind to and neutralize the membrane-type IL-6 receptor more than once, as a single antibody molecule. Since the duration of suppression of CRP production by H3pI/L73 is prolonged in comparison to that by WT, the duration of time where an antigen, the membrane-type IL-6 receptor, is bound by antibodies was indicated to be prolonged for H3pI/L73 than WT.

Figure 16:
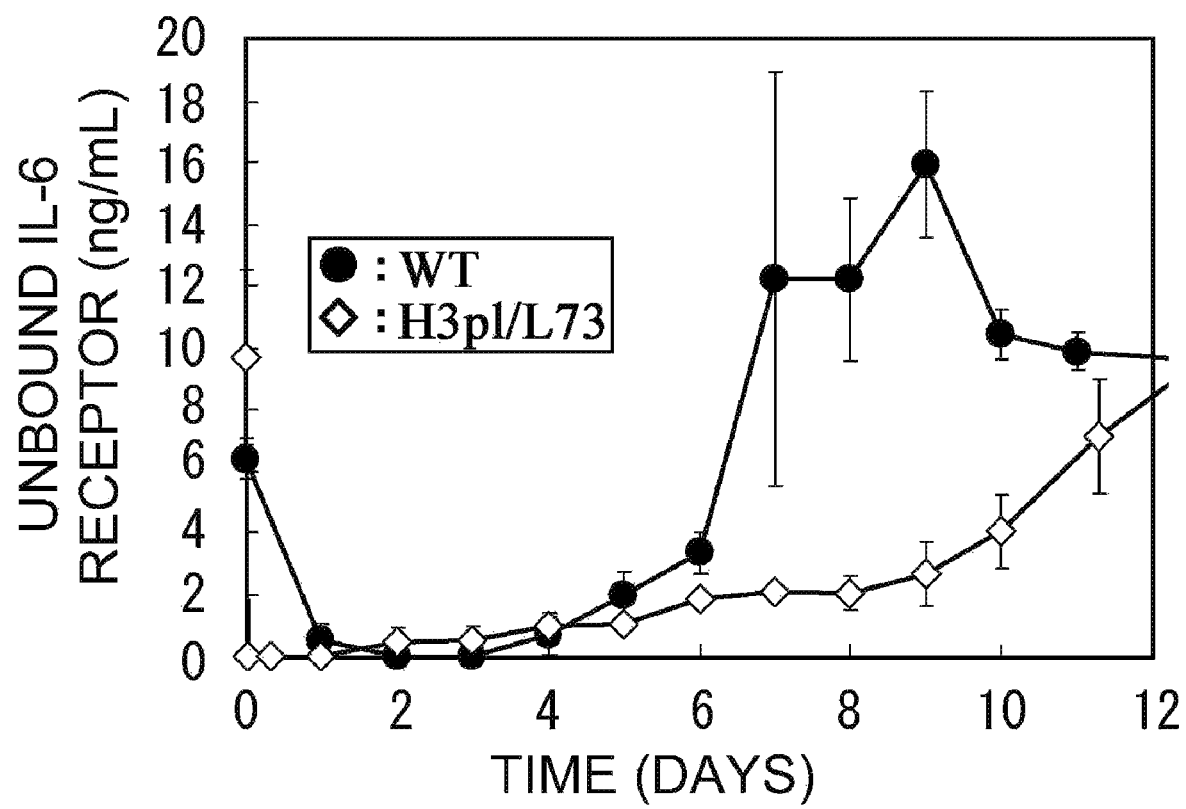
FIG. 16 is a graph depicting time courses of unbound-type cynomolgus monkey IL-6 receptor concentrations in cynomolgus monkeys, in relation to pH-dependently-binding anti-IL-6 receptor antibodies.

In order to evaluate the degree to which cynomolgus monkey soluble IL-6 receptor is neutralized by the intravenous administration of WT and H3pI/L73, the concentration of unbound cynomolgus monkey soluble IL-6 receptor in cynomolgus monkey plasma was measured. All IgG-type antibodies (cynomolgus monkey IgG, anti-human IL-6 receptor antibody, and a complex of anti-human-IL-6 receptor antibody and cynomolgus monkey soluble IL-6 receptor) present in the plasma were adsorbed to Protein A by adding 30 μL of cynomolgus monkey plasma to an appropriate amount of rProtein A Sepharose Fast Flow (GE Healthcare) resin dried in a 0.22 μm filter cup (Millipore). After spinning down with a high-speed centrifuge, the solution that passed through (hereinafter referred to as "pass solution") was recovered. Since the pass solution does not contain the complex of anti-human IL-6 receptor antibody and cynomolgus monkey soluble IL-6 receptor which is bound to protein A, the concentration of unbound soluble IL-6 receptor can be measured by measuring the concentration of cynomolgus monkey soluble IL-6 receptor in the pass solution. Monoclonal Anti-human IL-6R Antibody (R&D) that was ruthenium-labeled with Sulfo-Tag NHS Ester (Meso Scale Discovery) and Biotinylated Anti-human IL-6R Antibody (R&D) were mixed with cynomolgus monkey IL-6 receptor calibration curve samples adjusted to concentrations of 4000, 2000, 1000, 500, 250, 125, and 62.5 pg/mL and the plasma samples treated with Protein A as described above. The mixtures were allowed to react for one hour at room temperature. Subsequently, the mixtures were dispensed into an SA-Coated Standard MA2400 96-well plate (Meso Scale Discovery). After allowing to react for another one hour and washing, Read Buffer T (×4) (Meso Scale Discovery) was dispensed. Immediately thereafter, the measurement with Sector Imager 2400 (Meso Scale Discovery) was conducted. The concentrations of cynomolgus monkey IL-6 receptor were calculated from the response of the calibration curve by using the analytical software, SOFTmax PRO (Molecular Devices). The time courses of concentrations of unbound cynomolgus monkey soluble IL-6 receptor for WT and H3pI/L73 are shown in FIG. 16. As a result, the duration of neutralization of cynomolgus monkey soluble IL-6 receptor by H3pI/L73 was considerably prolonged as compared to that by WT. On the basis of this finding, the pH-dependent-binding anti-IL-6 receptor antibody H3pI/L73 was thought to dissociate from its antigen, soluble IL-6 receptor, under acidic conditions in endosomes; and return to the plasma via FcRn; and bind to and neutralize the soluble IL-6 receptor again. Since the duration of suppression of unbound cynomolgus monkey soluble IL-6 receptor by H3pI/L73 is prolonged in comparison to that by WT, the duration of time where an antigen, the soluble IL-6 receptor, is bound by antibodies was indicated to be prolonged for H3pI/L73 than WT.

From these findings, the time until the antibody disappears from the plasma as well as the time where soluble and membrane-type IL-6 receptors are bound by the antibody in the body were found to be considerably elongated for the pH-dependent-binding anti-IL-6 receptor antibodies that were made to bind strongly to the antigen at pH 7.4, which is the pH in the plasma, but bind weakly to the antigen at pH 5.8, which is the pH within endosomes, as compared to the wild-type anti-IL-6 receptor antibody. This makes it possible to reduce the dosage and frequency of administration to patients, and in consequence, the total administration dosage. Therefore, the pH-dependent-binding anti-IL-6 receptor antibody is thought to be particularly advantageous as a pharmaceutical for use as an IL-6 antagonist.

Example 10 Improvement of pH-Dependent Binding to Membrane-Type IL-6 Receptor by Optimization of Variable Region Optimization of Variable Regions H3pI/L73 and CLH5/L82

Antibodies having pH-dependent binding abilities were shown to demonstrate superior effects in Example 9. Therefore, to further improve the pH-dependent binding abilities, mutations were introduced into the CDR sequence of CLH5 obtained in Example 3 to construct VH1-IgG1 (SEQ ID NO: 21) and VH2-IgG1 (SEQ ID NO: 22). In addition, mutations were introduced into the framework sequence and CDR sequence of H3pI to construct the modified H chains VH3-IgG1 (SEQ ID NO: 23) and VH4-IgG1 (SEQ ID NO: 24). Mutations were introduced into the CDR sequences of L73 and L82 to construct the modified L chains VL1-CK (SEQ ID NO: 25), VL2-CK (SEQ ID NO: 26), and VL3-CK (SEQ ID NO: 27). More specifically, the mutants were constructed using the QuikChange Site-Directed Mutagenesis Kit (Stratagene) according to the method described in the appended instructions, and the resulting plasmid fragments were inserted into an mammalian cell expression vector to construct the desired H chain expression vectors and L chain expression vectors. The nucleotide sequences of the resulting expression vectors were determined by methods known to persons with ordinary skill in the art.

The antibody having VH2-IgG1 (SEQ ID NO: 22) as H chain and VL2-CK (SEQ ID NO: 26) as L chain was denoted as Fv1-IgG1, the antibody having VH1-IgG1 (SEQ ID NO: 21) as H chain and L82 as L chain was denoted as Fv2-IgG1, the antibody having VH4-IgG1 (SEQ ID NO: 24) as H chain and VL1-CK (SEQ ID NO: 25) as L chain was denoted as Fv3-IgG1, and the antibody having VH3-IgG1 (SEQ ID NO: 23) as H chain and VL3-CK (SEQ ID NO: 27) as L chain was denoted as Fv4-IgG1. Of these, Fv2-IgG1 and Fv4-IgG1 were expressed and purified. The expression and purification were carried out by the method described in Example 1.

Analysis of Binding of pH-Dependent-Binding Clones to Soluble IL-6 Receptor

Kinetic analyses of antigen-antibody reactions at pH 7.4 were carried out on the four types of antibodies, i.e., the humanized PM1 antibody (wild type: WT), and WT, H3pI/L73-IgG1, Fv2-IgG1, and Fv4-IgG1 constructed in Examples 2 and 10, by using a Biacore T100™ Surface plasmon resonance system (GE Healthcare) (buffer: 10 mM MES (pH 7.4), 150 mM NaCl, 0.05% TWEEN® 20 (polyoxyethylene sorbitan monolaurate)). Each antibody was bound on a sensor chip on which an anti-IgG γ chain specific F(ab)$_2$ (Pierce) was immobilized by amine coupling, and then, SR344 adjusted to a concentration of 9.8 to 40 nM was injected thereto as an analyte. The association to and dissociation from SR344 were observed on a real-time basis for the pH-dependent-binding clones. All the measurements were carried out at 37° C. Association rate constants $k_a$ (1/Ms) and dissociation rate constants $k_d$ (1/s) were calculated using Biacore T100™ Evaluation Software (GE Healthcare), and dissociation constants KD (M) were calculated on the basis of those values (Table 7).

TABLE 7

Comparison of Dissociation Rate Constants of
pH-Dependent-Binding Clones from
Soluble IL-6 Receptor, SR344

| Sample | $k_a$ (1/Ms) | $k_d$ (1/s) | KD (M) |
|---|---|---|---|
| WT | 4.0E+05 | 1.1E−03 | 2.7E−09 |
| H3pI/L73 | 4.1E+05 | 5.9E−04 | 1.4E−09 |
| Fv2-IgG1 | 3.9E+05 | 7.7E−04 | 2.0E−09 |
| Fv4-IgG1 | 7.2E+05 | 1.0E−03 | 1.4E−09 |

As a result of calculating the affinity at pH 7.4 for each clone, the dissociation constants (affinity, KD value) of WT, H3pI/L73-IgG1, Fv2-IgG1, and Fv4-IgG1 to SR344 were, respectively, 2.7 nM, 1.4 nM, 2.0 nM, and 1.4 nM, and they are nearly equivalent. Fv2-IgG1 and Fv4-IgG1 were demonstrated to have binding ability to the soluble IL-6 receptor that is equal to or greater than that of WT.

Figure 17:
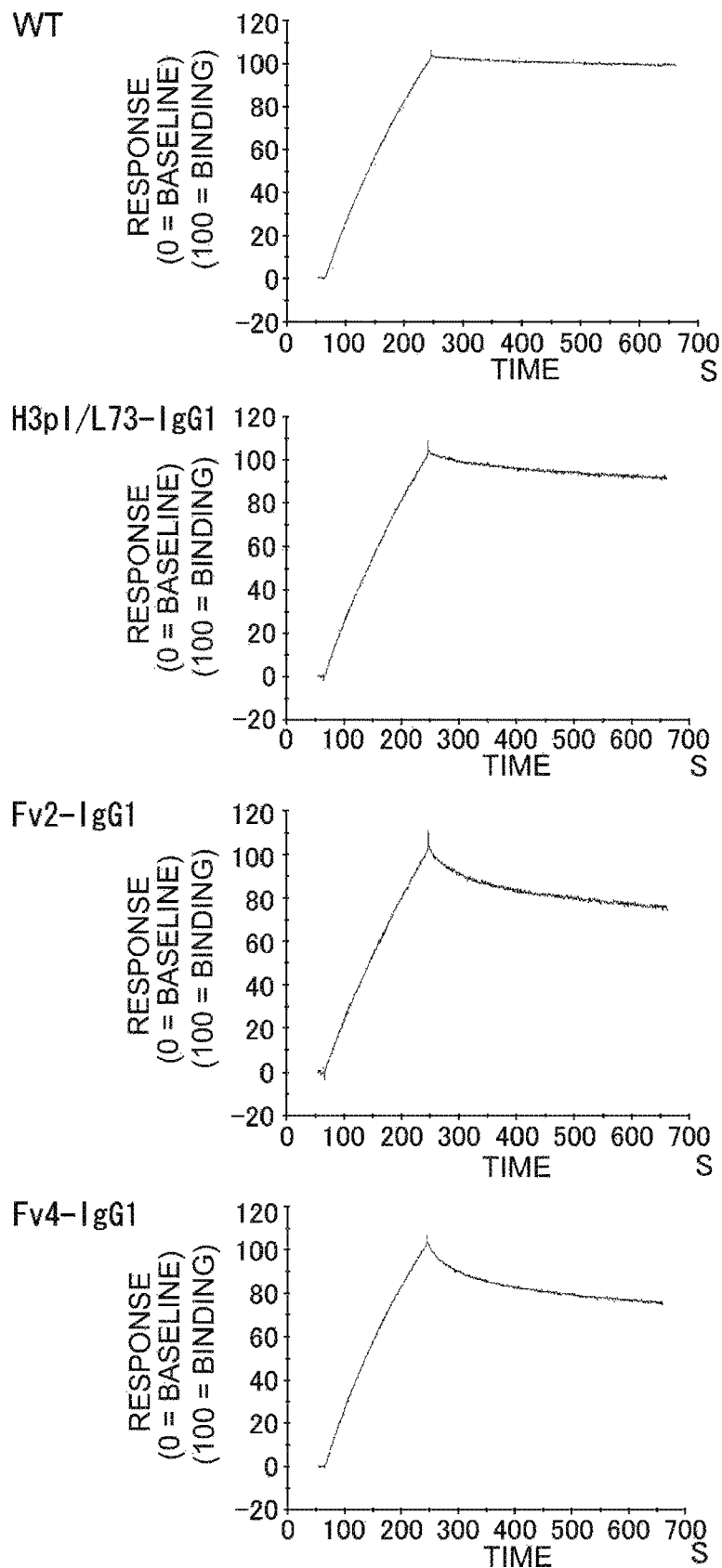
FIG. 17 presents Biacore™ sensorgrams depicting association (pH 7.4) and dissociation (pH 5.8) of pH-dependently-binding anti-IL-6 receptor antibodies to membrane-type IL-6 receptor. In order moving from the top, the results for WT, H3pI/L73-IgG1, Fv2-IgG1, and Fv4-IgG1 are shown.

Analysis of Binding of pH-Dependent-Binding
Clones to Membrane-Type IL-6 Receptor Antigen-antibody reactions to membrane-type IL-6 receptor were observed at pH 5.8 and pH 7.4 for the four types of constructed clones, WT, H3pI/L73-IgG1, Fv2-IgG1, and Fv4-IgG1 by using a Biacore T100™ surface plasmon resonance system (GE Healthcare). Binding to the membrane-type IL-6 receptor was evaluated by evaluating binding to the IL-6 receptor immobilized on a sensor chip. SR344 was biotinylated in accordance with a method known among persons with ordinary skill in the art, and the biotinylated SR344 was immobilized on the sensor chip via streptavidin using the affinity between streptavidin and biotin. All the measurements were carried out at 37° C. The mobile phase buffer was 10 mM MES (pH 5.8), 150 mM NaCl and 0.05% TWEEN® 20 (polyoxyethylene sorbitan monolaurate). The pH-dependent-binding clones were injected therein under conditions of pH 7.4 to allow them to bind to SR344 (injection sample buffer: 10 mM MES (pH 7.4), 150 mM NaCl, 0.05% TWEEN® 20 (polyoxyethylene sorbitan monolaurate)), then, pH-dependent dissociation of each clone was observed at the pH of the mobile phase of 5.8 (FIG. 17).

Sample concentrations were adjusted to 0.25 µg/mL. Binding was carried out in 10 mM MES (pH 7.4), 150 mM NaCl, and 0.05% TWEEN® 20 (polyoxyethylene sorbitan monolaurate). Dissociation was carried out in 10 mM MES (pH 5.8), 150 mM NaCl, and 0.05% TWEEN® 20 (polyoxyethylene sorbitan monolaurate). For this case, the dissociation rate constants ($k_d$(1/s)) at pH 5.8 were calculated by fitting only the dissociation phase at pH 5.8 using Biacore T100™ Evaluation Software (GE Healthcare). In a similar manner, sample concentrations were adjusted to 0.25 µg/mL, binding was carried out in 10 mM MES (pH 7.4), 150 mM NaCl, and 0.05% TWEEN® 20 (polyoxyethylene sorbitan monolaurate), dissociation was carried out in 10 mM MES (pH 7.4), 150 mM NaCl, and 0.05% TWEEN® 20 (polyoxyethylene sorbitan monolaurate), and the dissociation rate constants ($k_d$(1/s)) at pH 7.4 were calculated by fitting only the dissociation phase at pH 7.4 using Biacore T100™ Evaluation Software (GE Healthcare). The pH-dependent dissociation rate constants of each clone are shown in Table 8.

TABLE 8

Comparison of Dissociation Rate Constants of
pH-Dependent-Binding Clones from
Membrane-Type IL-6 Receptor, SR344

| Sample | pH7.4 kd (1/s) | pH5.8 kd (1/s) | pH Dependency kd(pH5.8)/kd(pH7.4) |
|---|---|---|---|
| WT | 2.5E−04 | 2.5E−04 | 1.00 |
| H3pI/L73 | 2.6E−04 | 6.7E−04 | 2.59 |
| Fv2-IgG1 | 3.4E−04 | 2.4E−03 | 7.18 |
| Fv4-IgG1 | 4.7E−04 | 2.6E−03 | 5.56 |

As a result of calculating pH dependency for each clone, the pH dependencies of binding to the membrane-type IL-6 receptor of the four clones, WT, H3pI/L73-IgG1, Fv2-IgG1, and Fv4-IgG1 with respect to SR344 were 1.0-fold, 2.59-fold, 7.18-fold, and 5.56-fold, respectively. Fv2-IgG1 and Fv4-IgG1 demonstrated higher pH-dependency in dissociation from the membrane-type IL-6 receptor than H3pI/L73-IgG1.

On the basis of the above, Fv2-IgG1 and Fv4-IgG1 were shown to demonstrate stronger pH-dependent binding to the membrane-type IL-6 receptor than H3pI/L73-IgG1 while maintaining the affinity for the soluble IL-6 receptor equal to or stronger than that of WT.

Figure 18:
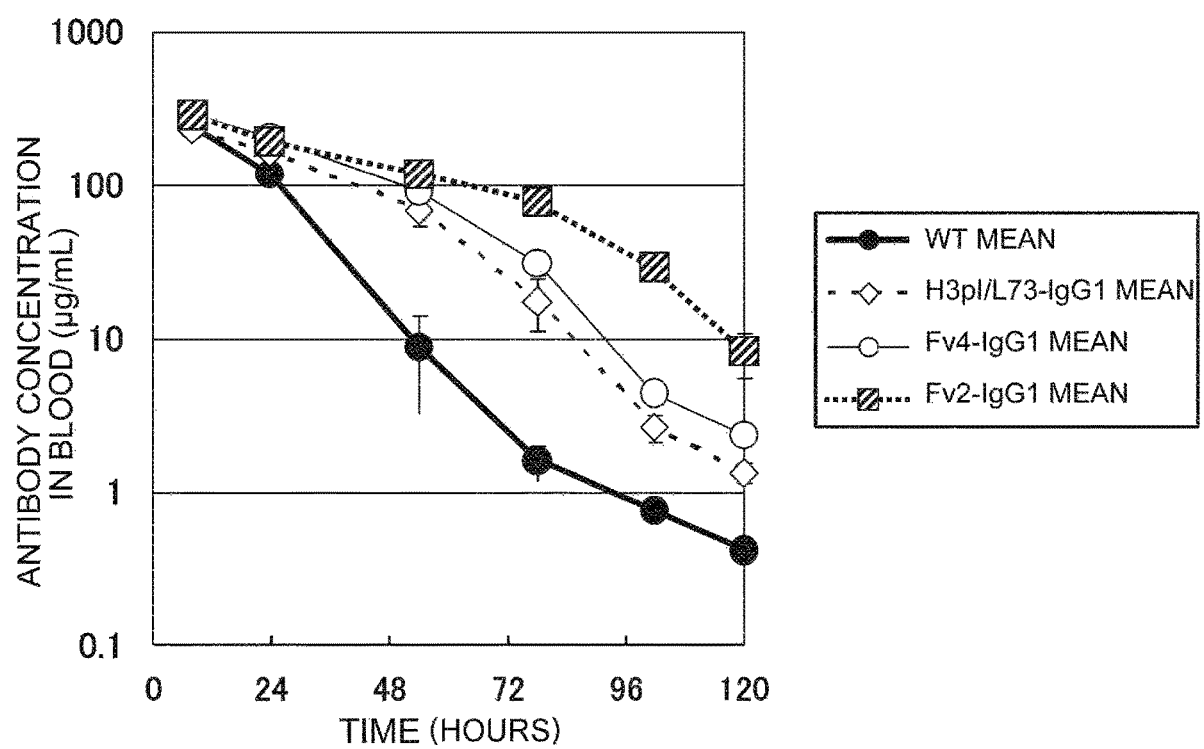
FIG. 18 is a graph depicting time courses of plasma antibody concentrations of pH-dependently-binding anti-IL-6 receptor antibodies (WT, H3pI/L73-IgG1, Fv2-IgG1, and Fv4-IgG1) in human IL-6 receptor transgenic mice.

Example 11 PK/PD Test of pH-Dependent-Binding
Antibodies with Optimized Variable Regions Using
Human IL-6 Receptor Transgenic Mice The pharmacokinetics of Fv2-IgG1 and Fv4-IgG1, as well as WT and H3pI/L73-IgG1 prepared and evaluated in Example 10 were evaluated using the human IL-6 receptor transgenic mice used in Example 8. WT, H3pI/L73-IgG1, Fv2-IgG1, or Fv4-IgG1 was administered by single-dose intravenous administration to hIL-6R tg mice at 25 mg/kg, and the concentration of each antibody in the plasma was measured in the same manner as in Example 8. The time courses of the plasma concentrations of WT, H3pI/L73-IgG1, Fv2-IgG1, and Fv4-IgG1 are shown in FIG. 18.

The pharmacokinetics of H3pI/L73-IgG1 improved in comparison with WT in the same manner as in Example 8, while the pharmacokinetics of Fv2-IgG1 and Fv4-IgG1 was further improved than H3pI/L73-IgG1. Measurement as to the unbound IL-6 receptor concentrations, as measured in cynomolgus monkeys in Example 9, was carried out in the hIL-6R tg mice in this test using the same method. As a result, prolongation of the duration of neutralization of the soluble IL-6 receptor was confirmed for Fv2-IgG1 and Fv4-IgG1 in comparison to that for H3pI/L73-IgG1 (data not shown). As indicated in Example 10, the pH-dependent binding to the membrane-type IL-6 receptor was improved for Fv2-IgG1 and Fv4-IgG1 as compared with H3pI/L73-IgG1. Therefore, it was indicated that further improvement in the pharmacokinetics and duration of neutralization of the soluble IL-6 receptor over those of H3pI/L73-IgG1 is possible by improving the pH-dependent binding to the membrane-type IL-6 receptor.

Example 12 Improvement of pH-Dependent
Binding to Membrane-Type IL-6 Receptor by
Optimization of Constant Region Optimization of Constant Region of Fv4-IgG1

Generally, binding to membrane-bound antigens has been reported to vary depending on the constant region of the antibody (J. Immunol. Methods 1997 Jun. 23; 205(1): 67-72). The constant regions of the pH-dependent-binding antibodies prepared above were of the IgG1 isotype. Therefore, a study was made for optimization of the constant region in order to improve the pH-dependent binding to the membrane-type IL-6 receptor.

A mutation was introduced into a naturally-occurring constant region, i.e., constant region IgG2 (SEQ ID NO: 28), to construct constant region IgG2ΔGK (SEQ ID NO: 29). Another mutation was introduced into the constant region IgG2ΔGK to construct constant region M58 (SEQ ID NO: 30). Mutations were further introduced into the constant regions IgG2 and M58 to construct constant regions M71 (SEQ ID NO: 31) and M73 (SEQ ID NO: 32).

VH3-IgG2ΔGK (SEQ ID NO: 33) was constructed by substituting the constant region of VH3-IgG1 prepared in Example 10 with IgG2ΔGK, VH3-M58 (SEQ ID NO: 34) was constructed by substituting the constant region with M58, and VH3-M73 (SEQ ID NO: 35) was constructed by substituting the constant region with M73. More specifically, expression vectors in which the constant region portion of VH3 used in Example 10 was substituted by a desired constant region by NheI/NotI digestion and ligation were constructed. The nucleotide sequences of the resulting expression vectors were determined using a method known among persons with ordinary skill in the art.

Expression and purification were carried out for the following: Fv4-IgG2 using VH3-IgG2ΔGK (SEQ ID NO: 33) for the H chain and VL3-CK (SEQ ID NO: 27) for the L chain; Fv4-M58 using VH3-M58 (SEQ ID NO: 34) for the H chain and VL3-CK (SEQ ID NO: 27) for the L chain; and Fv4-M73 using VH3-M73 (SEQ ID NO: 35) for the H chain and VL3-CK (SEQ ID NO: 27) for the L chain. Expression and purification were carried out using the method described in Example 1.

Analysis of Binding of Fv4 Having Optimized Constant Region to Soluble IL-6 Receptor The association with and dissociation from SR344 were observed on a real-time basis using the same method as Example 10 for thus-prepared Fv4-IgG1, Fv4-IgG2, Fv4-M58, and Fv4-M73 as well as WT. The association rate constants $k_a$ (1/Ms) and dissociation rate constants $k_d$(1/s) were calculated after analysis in the same manner, and then, dissociation constants KD (M) were calculated on the basis of those values (Table 9).

TABLE 9

Comparison of Dissociation Rate Constants of pH-Dependently-Binding Clones from Soluble IL-6 Receptor, SR344

| Sample | ka (1/Ms) | kd (1/s) | KD (M) |
|---|---|---|---|
| Fv4-IgG1 | 7.2E+05 | 1.0E−03 | 1.4E−09 |
| Fv4-IgG2 | 9.6E+05 | 1.2E−03 | 1.3E−09 |
| Fv4-M58 | 8.3E+05 | 1.1E−03 | 1.4E−09 |
| Fv4-M73 | 7.5E+05 | 1.0E−03 | 1.4E−09 |

As a result of calculating the affinity at pH 7.4 for each clone, the dissociation constants (affinity, KD value) of Fv4-IgG1, Fv4-IgG2, Fv4-M58, and Fv4-M73 to SR344 were 1.4 nM, 1.3 nM, 1.4 nM, and 1.4 nM, respectively, and they are almost equivalent. This indicates that the binding ability of pH-dependent-binding clones to the soluble IL-6 receptor, SR344, does not change even after modifying the constant region. On the basis of this finding, the binding ability to the soluble IL-6 receptor was thought to not change for Fv1, Fv2, and Fv3 even if the constant region was similarly modified.

Figure 19:
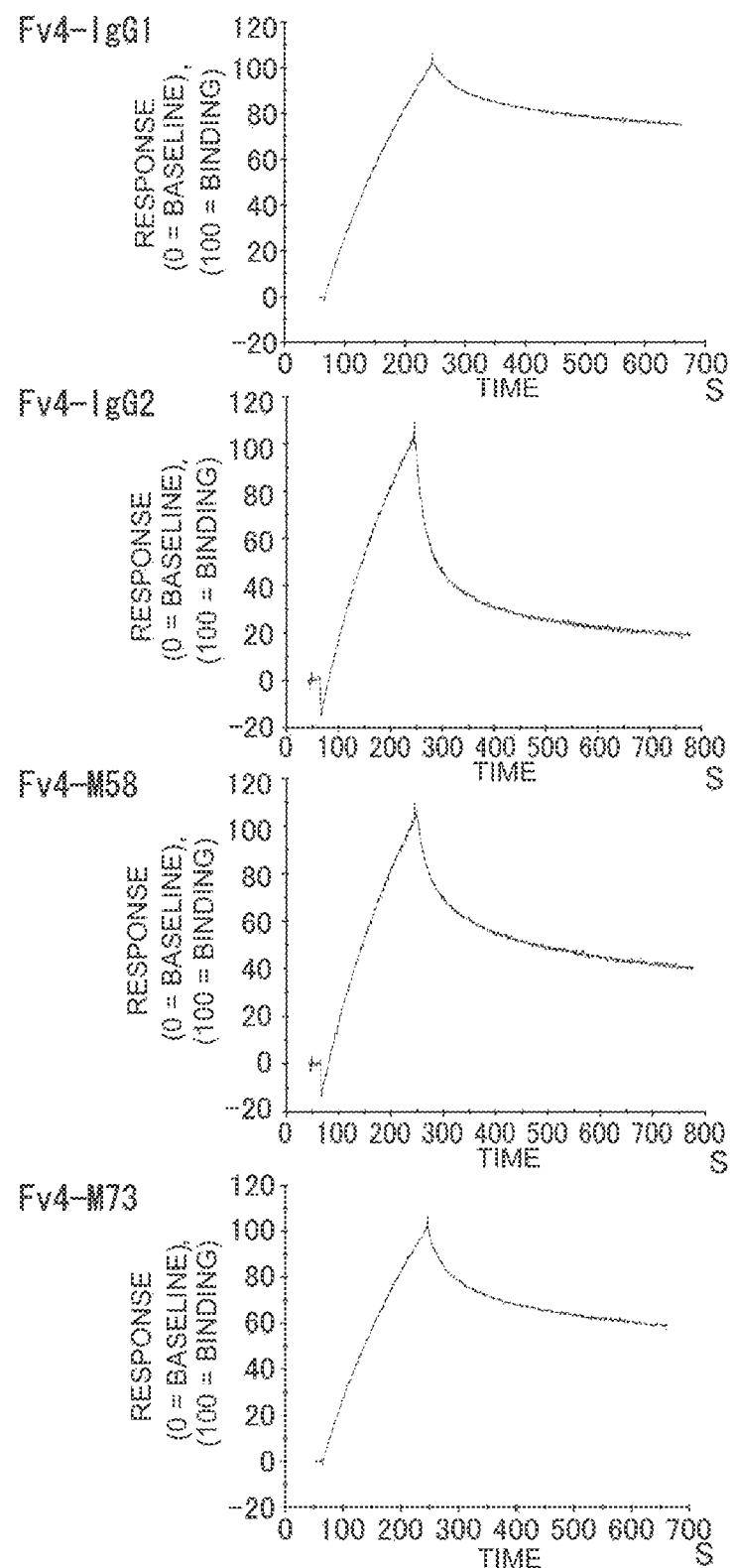
FIG. 19 presents Biacore™ sensorgrams depicting association (pH 7.4) and dissociation (pH 5.8) of pH-dependently-binding anti-IL-6 receptor antibodies to membrane-type IL-6 receptor. Moving from the top down, the results for WT, Fv4-IgG1, Fv4-IgG2, and Fv4-M58 are shown.

Analysis of Binding of Fv4 Having Optimized Constant Region to Membrane-Type IL-6 Receptor Antigen-antibody reactions to the membrane-type IL-6 receptor at pH 5.8 and pH 7.4 were observed for thus-prepared Fv4-IgG1, Fv4-IgG2, Fv4-M58, and Fv4-M73 as well as WT, in the same manner as in Example 10 using a Biacore T100™ surface plasmon resonance system (GE Healthcare). The results obtained by injecting the pH-dependent-binding clones under the conditions of pH 7.4 to allow binding to SR344, and by observing the pH-dependent dissociation of each clone in the pH 5.8 mobile phase, are shown in FIG. 19. Further analyses were conducted in the same manner as in Example 10, and the pH-dependent dissociation rates for each clone are shown in Table 10.

TABLE 10

Comparison of Dissociation Rate Constants of pH-Dependently-Binding Clone from Membrane-Type IL-6 Receptor, SR344

| Sample | pH7.4 kd (1/s) | pH5.8 kd (1/s) | pH Dependency kd(pH5.8)/kd(pH7.4) |
|---|---|---|---|
| Fv4-IgG1 | 4.7E−04 | 2.6E−03 | 5.56 |
| Fv4-IgG2 | 1.0E−03 | 1.8E−02 | 16.99 |
| Fv4-M58 | 5.4E−04 | 9.5E−03 | 17.64 |
| Fv4-M73 | 5.1E−04 | 5.1E−03 | 10.06 |

As a result of calculating the pH dependency for each clone, the pH dependencies of Fv4-IgG1, Fv4-IgG2, Fv4-M58, and Fv4-M73 to SR344 were 5.6-fold, 17.0-fold, 17.6-fold, and 10.1-fold, respectively; thus, Fv4-IgG2, Fv4-M58, and Fv4-M73 all demonstrated higher pH-dependent dissociation from the membrane-type IL-6 receptor than Fv4-IgG1.

Based on the results of analyzing binding to the soluble IL-6 receptor and binding to the membrane-type IL-6 receptor using the variable region of Fv4, it was found that substitution of the constant region from IgG1 to IgG2, M58, or M73 could improve the pH-dependent binding to the membrane-type IL-6 receptor, without causing a change in the affinity to the soluble IL-6 receptor. This was considered to similarly hold for Fv1, Fv2, and Fv3.

Figure 20:
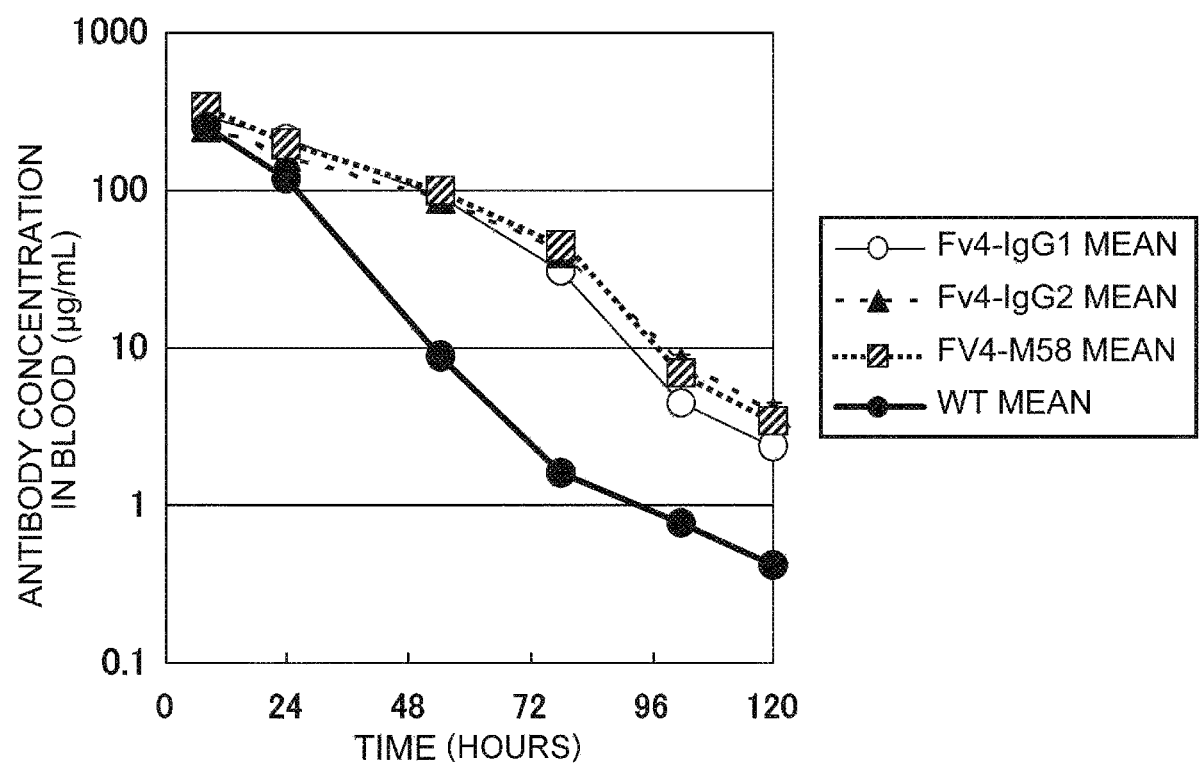
FIG. 20 is a graph showing time courses of antibody plasma concentrations of pH-dependently-binding anti-IL-6 receptor antibodies (WT, Fv4-IgG1, Fv4-IgG2, and Fv4-M58) in human IL-6 receptor transgenic mice.

Example 13 PK/PD Test of pH-Dependently-Binding Antibodies Having Optimized Constant Region Using Human IL-6 Receptor Transgenic Mice The pharmacokinetics of Fv4-IgG1, Fv4-IgG2, and Fv4-M58 prepared in Example 13 were evaluated using the human IL-6 receptor transgenic mice (hIL-6R tg mice) used in Example 8 to examine the effects of the constant region on the pharmacokinetics. WT, Fv4-IgG1, Fv4-IgG2, or Fv4-M58 was administered to the hIL-6R tg mice by single-dose intravenous administration at 25 mg/kg, and then, measurement of the plasma concentrations of each antibody was carried out in the same manner as in Example 8. The time courses of plasma concentrations of WT, Fv4-IgG1, Fv4-IgG2, and Fv4-M58 are shown in FIG. 20.

Similar to Example 11, the pharmacokinetics of Fv4-IgG1 was improved in comparison with WT, and the pharmacokinetics of Fv4-IgG2 and Fv4-M58 was further improved in comparison with Fv4-IgG1. Measurement as to the unbound IL-6 receptor concentrations, as measured in cynomolgus monkeys in Example 9, was carried out in the hIL-6R tg mice in this test using the same method. As a result, prolongation of the duration of neutralization of the soluble IL-6 receptor was confirmed for Fv4-IgG2 and Fv4-M58 in comparison to that of Fv4-IgG1 (data not shown). As indicated in Example 10, the pH-dependent binding to the membrane-type IL-6 receptor was improved for Fv4-IgG2 and Fv4-M58 as compared with Fv4-IgG1. Therefore, it was shown that improvement in the pH-dependent binding to the membrane-type IL-6 receptor and improvement in the pharmacokinetics and duration of neutralization of the soluble IL-6 receptor are possible by substituting the constant region from IgG1 to IgG2 or M58. On the basis of this finding, it was thought that the pharmacokinetics and duration of neutralization of the soluble IL-6 receptor, not only in the case of Fv4, but also in the cases of Fv1, Fv2, and Fv3, can be improved as compared to IgG1 by substituting the constant region from IgG1 to IgG2 or M58.

Example 14 Construction of pH-Dependently-Binding Antibodies Having Optimized Variable and Constant Regions VH2-M71 (SEQ ID NO: 36) and VH2-M73 (SEQ ID NO: 37), having M71 and M73 for the constant region of VH2-IgG1, and VH4-M71 (SEQ ID NO: 38) and VH4-M73 (SEQ ID NO: 39), having M71 and M73 for the constant region of VH4-IgG1, were constructed using the same method as described above.

Fv1-M71 using VH2-M71 for the H chain and VL2-CK for the L chain, Fv1-M73 using VH2-M73 for the H chain and VL2-CK for the H chain, Fv3-M71 using VH4-M71 for the H chain and VL1-CK for the L chain, and Fv3-M73 using VH4-M73 for the H chain and VL1-CK for the L chain, were expressed and purified. Expression and purification were carried out using the method described in Example 1.

Analyses of Binding of pH-Dependent-Binding Antibodies Having Optimized Variable and Constant Regions to Soluble IL-6 Receptor The association to and dissociation from SR344 were observed on a real-time basis using the same method as Example 10 for the eleven types of antibodies, humanized PM1 antibody (wild type: WT) and H3pI/L73-IgG1, Fv1-M71, Fv1-M73, Fv2-IgG1, Fv3-M71, Fv3-M73, Fv4-IgG1, Fv4-IgG2, Fv4-M58, and Fv4-M73, constructed as described above. The association rate constants $k_a$ (1/Ms) and dissociation rate constants $k_d$ (1/s) were calculated by analysis in the same manner, and the dissociation constants KD (M) were calculated on the basis of those values (Table 11).

TABLE 11

Comparison of Dissociation Rate Constants of pH-Dependently-Binding Clones from Soluble IL-6 Receptor, SR344

| Sample | $k_a$ (1/Ms) | $k_d$ (1/s) | KD (M) |
| --- | --- | --- | --- |
| WT | 4.0E+05 | 1.1E−03 | 2.7E−09 |
| H3pI/L73 | 4.1E+05 | 5.9E−04 | 1.4E−09 |
| Fv1-M71 | 5.5E+05 | 5.4E−04 | 9.7E−10 |

TABLE 11-continued

Comparison of Dissociation Rate Constants of pH-Dependently-Binding Clones from Soluble IL-6 Receptor, SR344

| Sample | $k_a$ (1/Ms) | $k_d$ (1/s) | KD (M) |
| --- | --- | --- | --- |
| Fv1-M73 | 6.1E+05 | 5.5E−04 | 9.1E−10 |
| Fv2-IgG1 | 3.9E+05 | 7.7E−04 | 2.0E−09 |
| Fv3-M71 | 7.8E+05 | 8.2E−04 | 1.1E−09 |
| Fv3-M73 | 8.5E+05 | 8.7E−04 | 1.0E−09 |
| Fv4-IgG1 | 7.2E+05 | 1.0E−03 | 1.4E−09 |
| Fv4-IgG2 | 9.6E+05 | 1.2E−03 | 1.3E−09 |
| Fv4-M58 | 8.3E+05 | 1.1E−03 | 1.4E−09 |
| Fv4-M73 | 7.5E+05 | 1.0E−03 | 1.4E−09 |

All of the resulting ten types of pH-dependent-binding clones were found to have dissociation constants (affinity, KD values) to the soluble IL-6 receptor equal to or stronger than that of WT.

Figure 21:
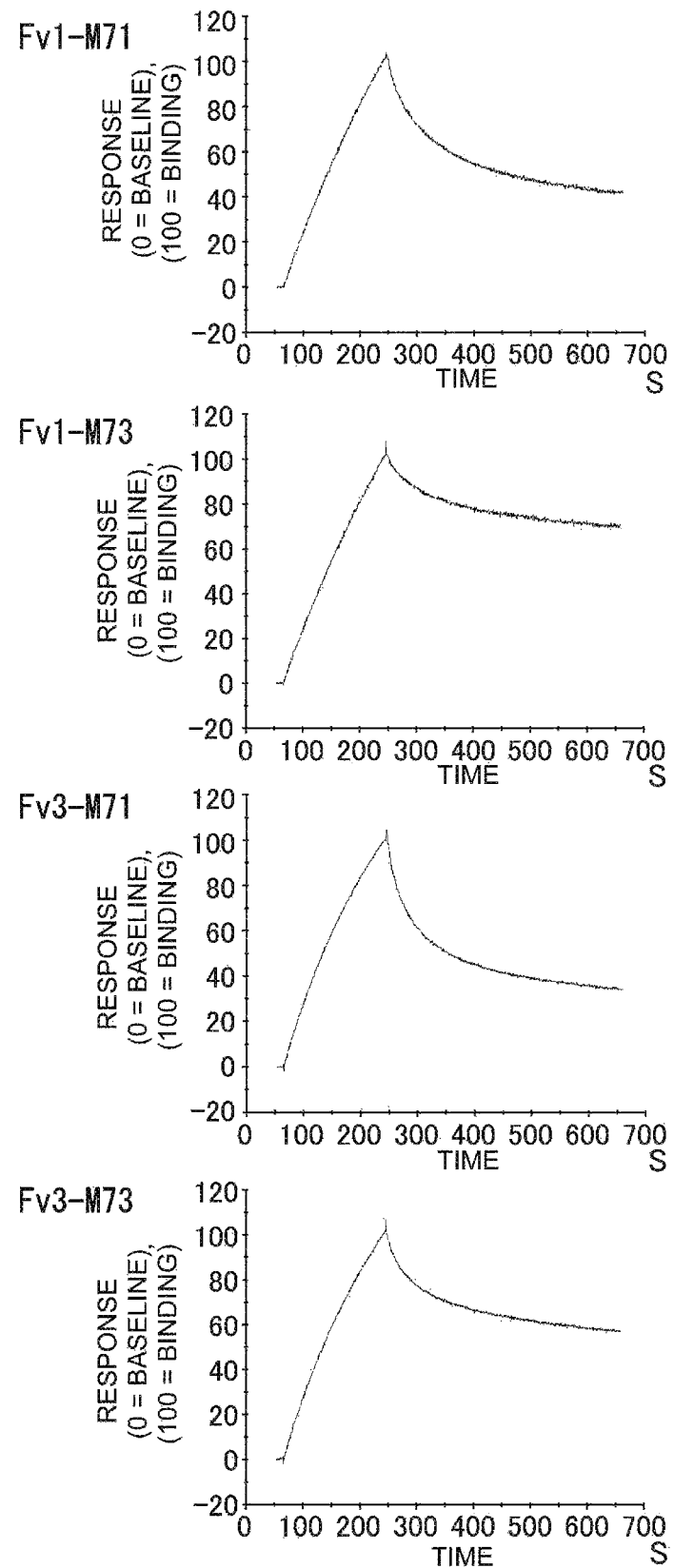
FIG. 21 presents Biacore™ sensorgrams depicting association (pH 7.4) and dissociation (pH 5.8) of pH-dependently-binding anti-IL-6 receptor antibodies to membrane-type IL-6 receptor. Moving from the top down, the results for Fv1-M71, Fv1-M73, Fv3-M71, and Fv3-M73 are shown.

Analyses of Binding of pH-Dependently-Binding Antibodies Having Optimized Variable and Constant Regions to Membrane-Type IL-6 Receptor Antigen-antibody reactions to the membrane-type IL-6 receptor at pH 5.8 and pH 7.4 were observed in the same manner as in Example 10 using a Biacore T100™ surface plasmon resonance system (GE Healthcare) for the eleven types of antibodies, humanized PM1 antibody (wild type: WT) and H3pI/L73-IgG1, Fv1-M71, Fv1-M73, Fv2-IgG1, Fv3-M71, Fv3-M73, Fv4-IgG1, Fv4-IgG2, Fv4-M58, and Fv4-M73, prepared as described above. The pH-dependently-binding clones were injected under the condition of pH 7.4 to allow them to bind to SR344, and then, the pH-dependent dissociation of each clone at the pH of the mobile phase, pH 5.8, was observed. The results are shown in FIG. 21 (results for Fv1-M71, Fv1-M73, Fv3-M71, and Fv3-M73 are shown in FIG. 21, while results for other clones are shown in FIGS. 17 and 19). Analyses were carried out in the same manner as in Example 10 and the pH dependencies of the dissociation rate constants of all of the eleven types of clones are shown in Table 12.

TABLE 12 pH Dependencies of Dissociation Rate Constants of pH-Dependently-Binding Clones from Membrane-Type IL-6 Receptor, SR344

| Sample | pH7.4 kd (1/s) | pH5.8 kd (1/s) | pH Dependency kd(pH5.8)/kd(pH7.4) |
| --- | --- | --- | --- |
| WT | 2.5E−04 | 2.5E−04 | 1.00 |
| H3pI/L73 | 2.6E−04 | 6.7E−04 | 2.59 |
| Fv1-M71 | 6.1E−04 | 6.9E−03 | 11.29 |
| Fv1-M73 | 3.7E−04 | 3.2E−03 | 8.80 |
| Fv2-IgG1 | 3.4E−04 | 2.4E−03 | 7.18 |
| Fv3-M71 | 9.1E−04 | 9.7E−03 | 10.74 |
| Fv3-M73 | 4.9E−04 | 5.3E−03 | 10.88 |
| Fv4-IgG1 | 4.7E−04 | 2.6E−03 | 5.56 |
| Fv4-IgG2 | 1.0E−03 | 1.8E−02 | 16.99 |
| Fv4-M58 | 5.4E−04 | 9.5E−03 | 17.64 |
| Fv4-M73 | 5.1E−04 | 5.1E−03 | 10.06 |

The ten types of obtained pH-dependently-binding clones demonstrated pH-dependent binding ability to the membrane-type IL-6 receptor. Moreover, all of Fv1-M71, Fv1-M73, Fv2-IgG1, Fv3-M71, Fv3-M73, Fv4-IgG1, Fv4-IgG2, Fv4-M58, and Fv4-M73 were found to demonstrate improved pH-dependent binding to the membrane-type IL-6 receptor, in comparison with H3pI/L73-IgG1, for which the time until the antibody disappears from the plasma as well as the time where the soluble IL-6 receptor and membrane-type IL-6 receptor are bound by the antibody in the body were found to be prolonged considerably in comparison with WT, as shown in cynomolgus monkeys in Example 9.

Example 15 PK/PD Test of pH-Dependently-Binding Antibodies Having Optimized Variable and Constant Regions Using Cynomolgus Monkeys Construction of Known High-Affinity Anti-IL-6 Receptor Antibody A mammalian cell expression vector was constructed to express the high-affinity anti-IL-6 receptor antibody VQ8F11-21 hIgG1 described in US 2007/0280945 A1 (US 2007/0280945 A1, amino acid sequences 19 and 27), as a known high-affinity anti-IL-6 receptor antibody. An antibody variable region was constructed by PCR combining synthetic oligo-DNAs (assembly PCR). The constant region was amplified by PCR from the expression vector used in Example 1. The antibody variable region and antibody constant region were ligated by assembly PCR and inserted into a vector for expression in mammals. The resulting H chain and L chain DNA fragments were inserted into mammalian cell expression vectors to construct the H chain expression vector and L chain expression vector of interest. The nucleotide sequences of the resulting expression vectors were determined by a method known among persons with ordinary skill in the art. Expression and purification were carried out using the constructed expression vectors. Expression and purification were carried out using the method described in Example 1 to obtain the high-affinity anti-IL-6 receptor antibody (high affinity Ab).

PK/PD Test in Cynomolgus Monkeys

Figure 22:
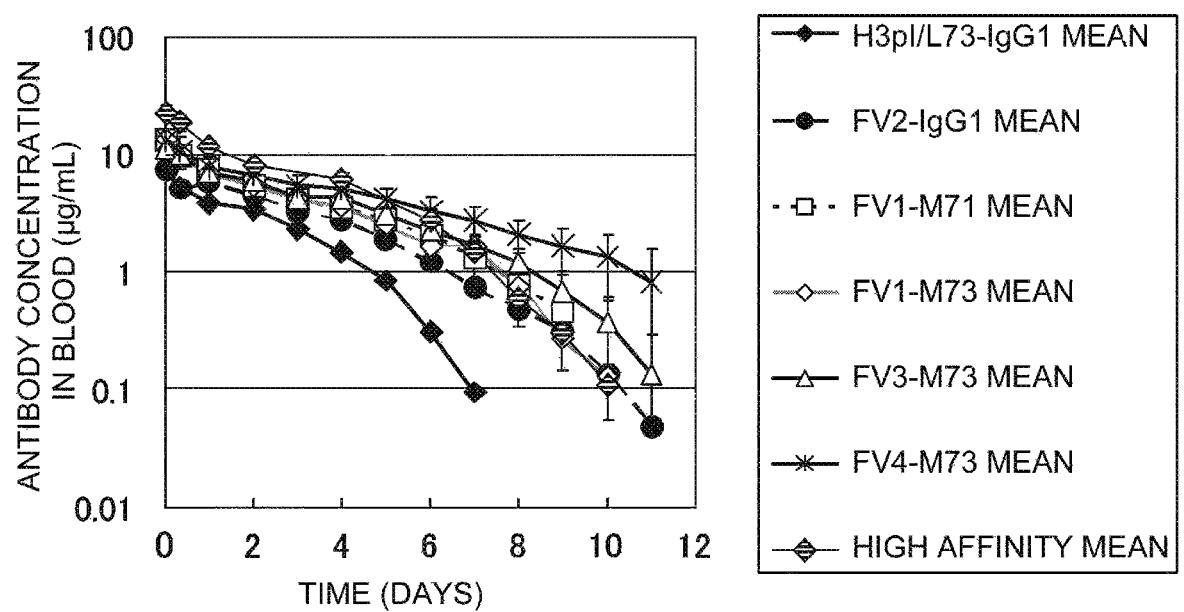
FIG. 22 is a graph depicting time courses of antibody plasma concentrations of pH-dependently-binding anti-IL-6 receptor antibodies in cynomolgus monkeys, during administration of H3pI/L73-IgG1, Fv1-M71, Fv1-M73, Fv2-IgG1, Fv3-M73, and Fv4-M73 at 0.5 mg/kg and during administration of high affinity Ab at 1.0 mg/kg.
Figure 23:
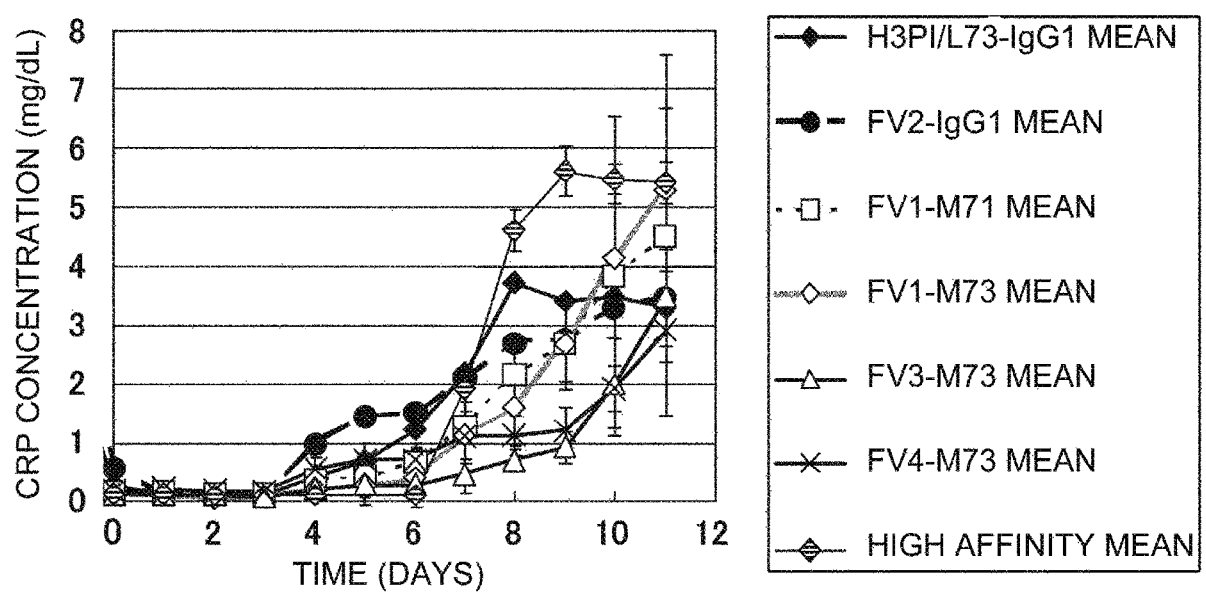
FIG. 23 is a graph depicting time courses of CRP concentrations in cynomolgus monkeys, in relation to pH-dependently-binding anti-IL-6 receptor antibodies (H3pI/L73-IgG1-, Fv1-M71-, Fv1-M73-, Fv2-IgG1-, Fv3-M73-, Fv4-M73-, and high-affinity-Ab-administered groups).
Figure 24:
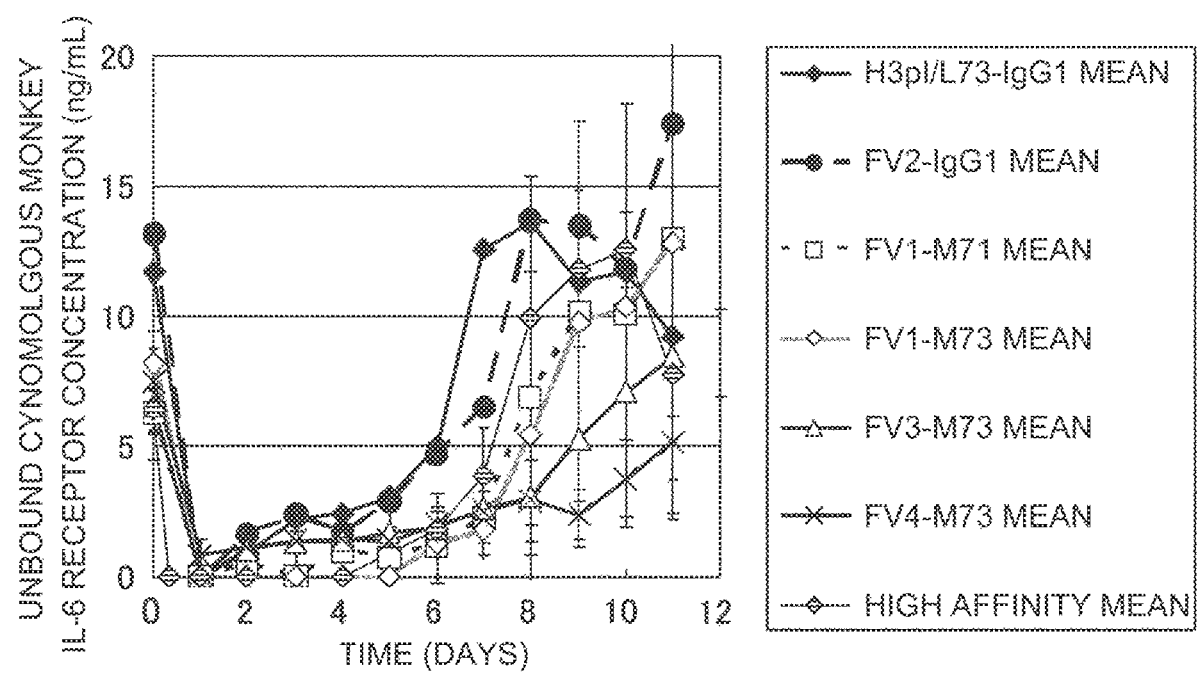
FIG. 24 is a graph depicting time courses of unbound-type cynomolgus monkey IL-6 receptor concentrations in cynomolgus monkeys, in relation to pH-dependently-binding anti-IL-6 receptor antibodies (H3pI/L73-IgG1-, Fv1-M71-, Fv1-M73-, Fv2-IgG1-, Fv3-M73-, Fv4-M73-, and high-affinity-Ab-administered groups).

The pharmacokinetics and pharmacological efficacy were evaluated in cynomolgus monkeys for the pH-dependently-binding antibodies H3pI/L73-IgG1 and Fv1-M71, Fv1-M73, Fv2-IgG1, Fv3-M73, and Fv4-M73 and the known high-affinity anti-IL-6 receptor antibody (high affinity Ab). H3pI/L73-IgG1, Fv1-M71, Fv1-M73, Fv2-IgG1, Fv3-M73, or Fv4-M73 was administered to cynomolgus monkeys by single-dose intravenous administration at 0.5 mg/kg, while the high affinity Ab was administered by single-dose intravenous administration at 1.0 mg/kg. Blood samples were collected before administration and over time. The plasma concentration of each antibody was measured in the same manner as in Example 9. The time courses of plasma concentrations of H3pI/L73-IgG1, Fv1-M71, Fv1-M73, Fv2-IgG1, Fv3-M73, and Fv4-M73, as well as the high affinity Ab are shown in FIG. 21. In order to evaluate the pharmacological efficacy in terms of the degree to which the cynomolgus monkey membrane-type IL-6 receptor is neutralized, cynomolgus monkey IL-6 was administered subcutaneously into the lower backs of the animals daily at 5 µg/kg from day 3 to day 10 (from day 6 to day 10 with respect to the high affinity Ab) after the administration of antibody, in the same manner as in Example 9. The CRP concentration of each animal was measured 24 hours after each administration. The time courses of CRP concentrations with the administration of each antibody are shown in FIG. 22. In order to evaluate the pharmacological efficacy in terms of the degree of neutralization of cynomolgus monkey soluble IL-6 receptor, the concentration of the unbound cynomolgus monkey soluble IL-6 receptor in cynomolgus monkey plasma was measured in the same manner as Example 9. The time courses of the unbound cynomolgus monkey soluble IL-6 receptor concentrations with the administration of each antibody are shown in FIG. 23.

As a result, the antibody concentrations in plasma were maintained high for each of Fv1-M71, Fv1-M73, Fv2-IgG1, Fv3-M73 and Fv4-M73 in comparison with H3pI/L73-IgG1, while the concentrations of CRP and the unbound cynomolgus monkey soluble IL-6 receptor were maintained at low levels. Namely, this result showed that the time where the membrane-type and soluble IL-6 receptors are bound by the antibody (or in other words, the duration of neutralization) was prolonged by the antibodies in comparison with H3pI/L73-IgG1.

In addition, these pH-dependently-binding anti-IL-6 receptor antibodies were confirmed for their neutralization effects and sustained efficacy equal to or greater than that of the known high-affinity anti-IL-6 receptor antibody (high affinity Ab) administered at 1.0 mg/kg, at only half the dosage thereof, i.e., at 0.5 mg/kg. Therefore, the pH-dependently-binding antibodies were elucidated to have the neutralization effects and sustained efficacy superior to those of the known high-affinity anti-IL-6 receptor antibody.

Those antibodies shown in Table 12 for which PK/PD tests were not carried out using cynomolgus monkeys as in this test, have also been confirmed to demonstrate improved pH-dependent binding to the membrane-type IL-6 receptor in comparison with H3pI/L73-IgG1. Therefore, the time during which the membrane-type and soluble IL-6 receptor are bound by the antibodies (or in other words, the duration of neutralization and sustained neutralization effects) are also thought to be prolonged for the antibodies in comparison with H3pI/L73-IgG1.

In Example 9, for H3pI/L73-IgG1, the time until the antibody disappears from the plasma as well as the time where the soluble IL-6 receptor and membrane-type IL-6 receptor are bound by the antibody in the body (sustained neutralization effects) were found to be prolonged considerably as compared with WT. Fv1-M71, Fv1-M73, Fv2-IgG1, Fv3-M71, Fv3-M73, Fv4-IgG1, Fv4-IgG2, Fv4-M58, and Fv4-M73, having superior sustained neutralization effects to H3pI/L73-IgG1, are therefore thought to have remarkably improved sustained neutralization effects as compared with WT.

In contrast to anti-IL-6 receptor antibodies, the pH-dependent-binding anti-IL-6 receptor antibodies that are made to strongly bind to the antigen at the pH in the plasma of pH 7.4 but only weakly bind to the antigen at the pH in endosomes of pH 5.8, make it possible to reduce the patient dosage and administration frequency of the anti-IL-6 receptor antibody, and as a result, they can considerably reduce the total administration amount. Therefore, the pH-dependently-binding anti-IL-6 receptor antibodies are thought to be extremely superior as a pharmaceutical for use as an IL-6 antagonist.

Example 16 Construction of pH-Dependently Binding Anti-IL-6 Antibody

Expression and Purification of Anti-IL-6 Antibody

In Examples 1 to 15, a plurality of humanized anti-IL-6 receptor antibodies that pH-dependently bind to the IL-6 receptor were successfully created by imparting the dependency through introducing histidine substitutions and the like into the variable region, in particular, the CDR sequences of the humanized anti-IL-6 receptor antibodies. It was found that all of these antibodies repeatedly bind to the IL-6 receptor and demonstrate a considerable improvement in PK/PD.

Therefore, it was confirmed that the pH-dependent ability of an antibody to bind to an antigen could be conferred to another antibody that binds to an antigen other than the IL-6 receptor using a similar method. Human IL-6 was selected as the antigen, and an anti-IL-6 antibody including the H chain (WT) (amino acid sequence: SEQ ID NO: 62) and L chain (WT) (amino acid sequence: SEQ ID NO: 63), which binds to IL-6 as described in WO 2004/039826, ("Anti-IL6 wild type") was constructed. Using a method known to those skilled in the art, gene fragments encoding the antibody amino acid sequences of interest were inserted into mammalian cell expression vectors to construct the H chain expression vector and L chain expression vector of interest. The nucleotide sequences of the resulting expression vectors were determined using a method known to a skilled person. Anti-IL6 wild type was expressed and purified by the method described in Example 1.

Construction of pH-Dependent Anti-IL-6 Antibody

To confer the pH-dependent ability of the antibody to bind to IL-6, histidine substitutions were introduced into the amino acids in CDR of the anti-IL-6 antibody (Anti-IL6 wild type) including the H chain (WT) (amino acid sequence: SEQ ID NO: 62) and L chain (WT) (amino acid sequence: SEQ ID NO: 63). By substituting histidine in the CDR amino acids and subsequently screening, several clones that demonstrate the pH-dependent binding were obtained. The binding at pH 5.5 was significantly reduced as compared with the binding at pH 7.4. The positions of histidine substitution in the pH-dependent clones are shown in Table 13. The examples include "Anti-IL6 clone 1" including the H chain (c1) (amino acid sequence: SEQ ID NO: 64) and L chain (c1) (amino acid sequence: SEQ ID NO: 65), and "Anti-IL-6 clone 2" including the H chain (c1) (amino acid sequence: SEQ ID NO: 64) and L chain (c2) (amino acid sequence: SEQ ID NO: 66). Anti-IL6 clone 1 and Anti-IL-6 clone 2 were expressed and purified by the method described in Example 1.

TABLE 13

Positions of Histidine Substitution in pH-dependent clones

H32, H59, H61, H99
L53, L54, L90, L94

Analysis of Binding of pH-Dependent Clones to Human IL-6

Kinetic analysis of antigen-antibody reactions at pH 5.5 and pH 7.4 was carried out using a Biacore T100™ surface plasmon resonance system (GE Healthcare) for the three types of antibodies prepared as mentioned above: Anti-IL6 wild type, Anti-IL6 clone 1, and Anti-IL-6 clone 2 (buffer: DPBS(−) (pH 7.4 or pH 5.5), 150 mM NaCl). The antibodies were bound to a sensor chip on which recomb-protein A/G (Pierce) was immobilized by amine coupling, and then human IL-6 (Toray) adjusted to an appropriate concentration was injected on the chip as an analyte. All the measurements were carried out at 37° C. Association rate constants $k_a$ (1/Ms) and dissociation rate constants $k_d$ (1/s) were calculated using Biacore T100™ Evaluation Software (GE Healthcare), and dissociation constants KD (M) were calculated based on those values (Table 14). Furthermore, the ratio of affinity at pH 5.5 and pH 7.4 was calculated for each clone to evaluate the pH-dependent binding.

TABLE 14

Comparison of Binding of pH-Dependent Clones to IL-6

| Sample | PH | ka(1/Ms) | kd(1/s) | KD(M) | KD(pH5.5)/ KD(pH7.4) |
|---|---|---|---|---|---|
| Wild type | pH7.4 | 2.05E+07 | 3.91E−04 | 1.91E−11 | 0.8 |
|  | pH5.5 | 1.52E+07 | 2.45E−04 | 1.61E−11 |  |
| clone1 | pH7.4 | 1.07E+07 | 4.71E−03 | 4.38E−10 | 10.3 |
|  | pH5.5 | 2.05E+06 | 9.26E−03 | 4.52E−09 |  |
| clone2 | pH7.4 | 8.96E+06 | 2.63E−03 | 2.94E−10 | 13.5 |
|  | pH5.5 | 2.76E+06 | 1.10E−02 | 3.98E−09 |  |

The ratio of affinity at pH 5.5 and pH 7.4 ((KD)(pH 5.5)/(KD)(pH 7.4)) calculated, which indicates the pH-dependent binding to human IL-6, was 0.8, 10.3, and 13.5 for Anti-IL6 wild type, Anti-IL6 clone 1, and Anti-IL6 clone 2, respectively. That is, the pH-dependent binding ability of each clone is more than 10 times greater than that of WT. The sensorgrams of Anti-IL-6 clone 2 at pH 7.4 and pH 5.5 are shown in FIG. 26.

Thus, it was shown that, as in the case of the anti-IL-6 receptor antibodies, pH-dependently binding anti-IL-6 antibodies that bind to the antigen strongly under plasma neutral conditions, but weakly under intraendosomal acidic conditions can be constructed by introducing histidine substitutions and the like mainly into the CDR amino acid sequences. As indicated in Examples 1 to 15, an anti-IL-6 receptor antibody that has the pH-dependent binding ability repeatedly binds to the IL-6 receptor and PK/PD is remarkably improved. That is, it was suggested that Anti-IL-6 clone 1 and Anti-IL-6 clone 2, which have the pH-dependent binding ability, repeatedly bind to more antigens with significantly improved PK/PD, as compared with Anti-IL6 wild type.

Example 17 Construction of pH-Dependently Binding Anti-IL-31 Receptor Antibody

Expression and Purification of Anti-IL-31 Receptor Antibody

In Examples 1 to 15, a plurality of humanized anti-IL-6 receptor antibodies that pH-dependently bind to the IL-6 receptor were successfully created by conferring the pH dependency through introducing histidine substitutions and the like into the variable region, in particular, the CDR sequences of the humanized anti-IL-6 receptor antibodies. It was found that all of these antibodies repeatedly bind to the IL-6 receptor and demonstrate a considerable improvement of PK/PD.

Therefore, it was confirmed that the pH dependent ability of an antibody to bind to an antigen could be conferred to another antibody that binds to an antigen other than the IL-6 receptor using a similar method. Mouse IL-31 receptor was selected as the antigen, and an anti-IL-31 receptor antibody including the H chain (WT) (amino acid sequence: SEQ ID NO: 67) and L chain (WT) (amino acid sequence: SEQ ID NO: 68), which binds to the mouse IL-31 receptor as described in WO 2007/142325, ("Anti-IL31R wild type") was constructed. Using a method known to those skilled in the art, gene fragments encoding the amino acid sequences of interest were inserted into mammalian cell expression vectors to construct the H chain expression vector and L chain expression vector of interest. The nucleotide sequences of the resulting expression vectors were determined using a method known to a skilled person. Anti-IL31R wild type was expressed and purified by the method described in Example 1.

Construction of pH-Dependent Anti-IL-31 Receptor Antibody

To confer the pH-dependent ability of the antibody to bind to the IL-31 receptor, histidine substitutions were introduced into the amino acids of CDR of the anti-IL-31 receptor antibody (Anti-IL31R wild type) including the H chain (WT) (amino acid sequence: SEQ ID NO: 67) and L chain (WT) (amino acid sequence: SEQ ID NO: 68). By histidine substitutions in the CDR amino acids and subsequent screening, several clones that demonstrate the pH-dependent binding were obtained. The binding at pH 5.5 was significantly reduced as compared with the binding at pH 7.4. The position of histidine substitution in the pH-dependent clones is shown in Table 15. An example is "Anti-IL31R clone 1" including the H chain (c1) (amino acid sequence: SEQ ID NO: 69) and L chain (WT). Anti-IL31R clone 1 was expressed and purified using the method described in Example 1.

[Table 15] Position of Histidine Substitution in pH-dependent clones
H33

Analysis of Binding of pH-Dependent Clones to Soluble IL-31 Receptor

Kinetic analysis of antigen-antibody reactions at pH 5.5 and pH 7.4 was carried out using a Biacore T100™ surface plasmon resonance system (GE Healthcare) for the two types of antibodies prepared as mentioned above: Anti-IL31R wild type and Anti-IL31R clone 1 (buffer: DPBS(-) (pH 7.4 or pH 5.5), 150 mM NaCl, 0.01% TWEEN® 20 (polyoxyethylene sorbitan monolaurate), 0.02% NaN$_3$). The antibodies were bound to a sensor chip on which recomb-protein A/G (Pierce) was immobilized by amine coupling, and then the soluble mouse IL-31 receptor (prepared according to the method described in WO 2007/142325) adjusted to an appropriate concentration was injected therein as an analyte. All the measurements were carried out at 25° C. Association rate constants $k_a$ (1/Ms) and dissociation rate constants $k_d$ (1/s) were calculated using Biacore T100™ Evaluation Software (GE Healthcare), and dissociation constants KD (M) were calculated based on those values (Table 16). Furthermore, the ratio of affinity at pH 5.5 and pH 7.4 was calculated for each clone to evaluate the pH-dependent binding.

TABLE 16

Comparison of Binding of pH-Dependent Clones to Mouse IL-31 Receptor

| Sample | pH | ka(1/Ms) | kd(1/s) | KD(M) | KD(pH5.5)/KD(pH7.4) |
|---|---|---|---|---|---|
| Wild type | pH7.4 | 1.40E+05 | 3.40E-03 | 2.30E-08 | 3.2 |
|  | pH5.5 | 5.10E+05 | 3.80E-03 | 7.40E-08 |  |
| clone1 | pH7.4 | 1.70E+05 | 3.30E-03 | 2.20E-08 | 1000.0 |
|  | pH5.5 | 1.10E+03 | 2.40E-02 | 2.20E-05 |  |

Figure 27:
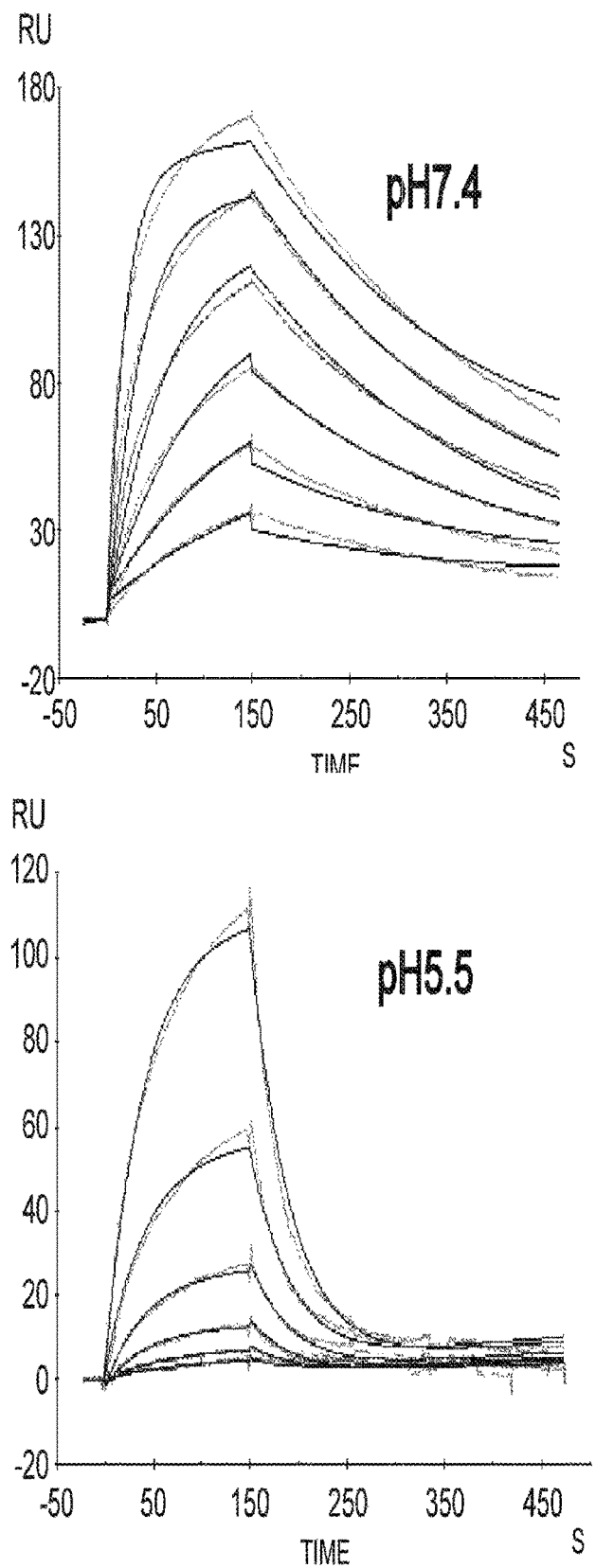
FIG. 27 presents Biacore™ sensorgrams depicting the pH-dependent binding of an anti-IL-31 receptor antibody, Anti-IL31R clone 1, to the IL-31 receptor at pH 7.4 and pH 5.5. The curves in the sensorgram at pH 5.5 correspond to 100, 50, 25, and 12.5 ng/mL IL-31 receptor, from above.

The ratio of affinity at pH 5.5 and pH 7.4 ((KD)(pH 5.5)/(KD)(pH 7.4)) calculated, which indicates the pH-dependent binding to the mouse IL-31 receptor, was 3.2 and 1000 for Anti-IL31R wild type and Anti-IL31R clone 1, respectively. That is, the pH-dependent binding ability of Anti-IL31R clone 1 is about 300 times greater than that of WT. The sensorgrams for Anti-IL31R clone 1 at pH 7.4 and pH 5.5 are shown in FIG. 27.

Thus, it was shown that, as in the cases of the anti-IL-6 receptor antibodies and anti-IL-6 antibodies, pH-dependent binding anti-IL-31 receptor antibodies that bind to the antigen strongly under plasma neutral conditions, but weakly under intraendosomal acidic conditions can be constructed by introducing histidine substitutions and the like mainly into the CDR amino acid sequences. As indicated in Examples 1 to 15, an anti-IL-6 receptor antibody that has the pH-dependent binding ability repeatedly binds to the IL-6 receptor and PK/PD is remarkably improved. That is, it was suggested that Anti-IL31R clone 1, which has the pH-dependent binding ability, repeatedly binds to more antigens with significantly improved PK/PD, as compared with Anti-IL31R wild type.

Example 18 Repetitive Binding to Antigen by pH-Dependently Binding Antibody

Expression and Purification of Antibody Administered to Mice

The four types of humanized IL-6 receptor antibodies described below were prepared. As the antibodies that do not pH-dependently bind to the IL-6 receptor, WT-IgG1 including H (WT) (amino acid sequence: SEQ ID NO: 9) and L (WT) (amino acid sequence: SEQ ID NO: 10), and H54/L28-IgG1 including H54 (amino acid sequence: SEQ ID NO: 70) and L28 (amino acid sequence: SEQ ID NO: 12) were expressed and purified using the method indicated in Example 1. As the antibodies that pH-dependently bind to the IL-6 receptor, H170/L82-IgG1 of Example 3 including H170 (amino acid sequence: SEQ ID NO: 4) and L82 (amino acid sequence: SEQ ID NO: 7), and Fv4-IgG1 of Example 10 including VH3-IgG1 (SEQ ID NO: 23) and VL3-CK (SEQ ID NO: 27), were expressed and purified using the method indicated in Example 1.

Analysis of Binding of Each Type of Antibody to Soluble IL-6 Receptor

Kinetic analysis of antigen-antibody reactions at pH 7.4 and pH 5.8 was carried out using a Biacore T100™ surface plasmon resonance system (GE Healthcare) for the four types of antibodies prepared: WT-IgG1, H54/L28-IgG1, H170/L82-IgG1, and Fv4-IgG1 (buffer: 10 mM MES (pH 7.4 or pH 5.8), 150 mM NaCl, 0.05% Surfactant P20 (polyoxyethylene sorbitan monolaurate)). The antibodies were bound to a sensor chip on which recomb-protein A/G (Pierce) was immobilized by amine coupling, and SR344 adjusted to an appropriate concentration was injected therein as an analyte. The association with and dissociation from SR344 of each type of antibody were observed on a real-time basis. All the measurements were carried out at 37° C. Association rate constants $k_a$ (1/Ms) and dissociation rate constants $k_d$ (1/s) were calculated using Biacore T100™ Evaluation Software (GE Healthcare), and dissociation constants KD (M) were calculated based on those values (Table 17).

TABLE 17

Comparison of Association Rates (k_a), Dissociation Rates (k_d), and Dissociation Constants of Each Type of Antibody Against Soluble IL-6 Receptor (SR344)

| Sample | pH 7.4 | | | pH 5.8 | | | pH Dependency | |
| --- | --- | --- | --- | --- | --- | --- | --- | --- |
| | ka(1/Ms) | kd(1/s) | KD(M) | ka(1/Ms) | kd(1/s) | KD(M) | kd(pH 5.8)/ kd(pH 7.4) | KD(pH 5.8)/ KD(pH 7.4) |
| WT-IgG1 | 4.9E+05 | 9.4E−04 | 1.9E−09 | 8.9E−05 | 2.7E−03 | 3.1E−09 | 2.9 | 1.6 |
| H54/L28-IgG1 | 8.3E+05 | 1.4E−03 | 1.7E−09 | 2.4E−06 | 2.7E−03 | 1.1E−09 | 2.0 | 0.7 |
| H170/L28-IgG1 | 6.7E+05 | 1.1E−03 | 1.6E−09 | 1.2E−05 | 1.3E−02 | 1.0E−07 | 11.4 | 61.9 |
| Fv4-IgG1 | 9.8E+05 | 9.5E−04 | 9.7E−10 | 1.4E−06 | 3.7E−02 | 2.6E−08 | 38.8 | 27.3 |

The ratio of affinity (KD) at pH 5.8 and pH 7.4 for each antibody was calculated. The KD ratio, which indicates the pH-dependent binding to SR344, was 1.6, 0.7, 61.9, and 27.3 for WT-IgG1, H54/L28-IgG1, H170/L82-IgG1, and Fv4-IgG1, respectively. In addition, the ratio of dissociation rate ($k_d$) at pH 5.8 and pH 7.4 for each antibody was calculated. The $k_d$ ratio, which indicates the pH-dependent dissociation rate for SR344, was 2.9, 2.0, 11.4, and 38.8 for WT-IgG1, H54/L28-IgG1, H170/L82-IgG1, and Fv4-IgG1, respectively. Thus, it was confirmed that H170/L82-IgG1 and Fv4-IgG1 demonstrate the pH-dependent binding, while the conventional antibodies WT-IgG1 and H54/L28-IgG1 hardly exhibit the ability. In addition, since the affinity (KD) of these antibodies at pH 7.4 was nearly equal, their ability to bind to SR344 in the plasma was thought to be equivalent.

In Vivo Pharmacokinetics Test Using Mice

The pharmacokinetics of SR344 and the anti-human IL-6 receptor antibody were evaluated following administration of SR344 (human IL-6 receptor, prepared in Example 1) only or simultaneous administration of SR344 and the anti-human IL-6 receptor antibody to mice that do not express the human IL-6 receptor (C57BL/6J; the anti-human IL-6 receptor antibodies do not bind to the mouse IL-6 receptor). An SR344 solution (5 μg/mL) or a mixed solution containing SR344 and the anti-human IL-6 receptor antibody (5 μg/mL and 0.1 mg/mL, respectively) was administered into a caudal vein by single-dose administration at 10 mL/kg. Since the anti-human IL-6 receptor antibody was present in an adequate excess amount relative to SR344, it was thought that nearly all of the SR344 molecules were bound by the antibody. Blood samples were collected at 15 minutes, 2 hours, 8 hours, 1 day, 2 days, 3 days, 4 days, 7 days, 14 days, 21 days, and 28 days after administration. The collected blood samples were immediately centrifuged for 15 minutes at 15,000 rpm and 4° C. to obtain the plasma. The plasma separated was stored in a freezer set to −20° C. or lower until the time of measurement. Above-described WT-IgG1, H54/L28-IgG1, H170/L82-IgG1, and Fv4-IgG1 were used as the anti-human IL-6 receptor antibodies.

Measurement of Anti-Human IL-6 Receptor Antibody Plasma Concentration by ELISA

Figure 28:
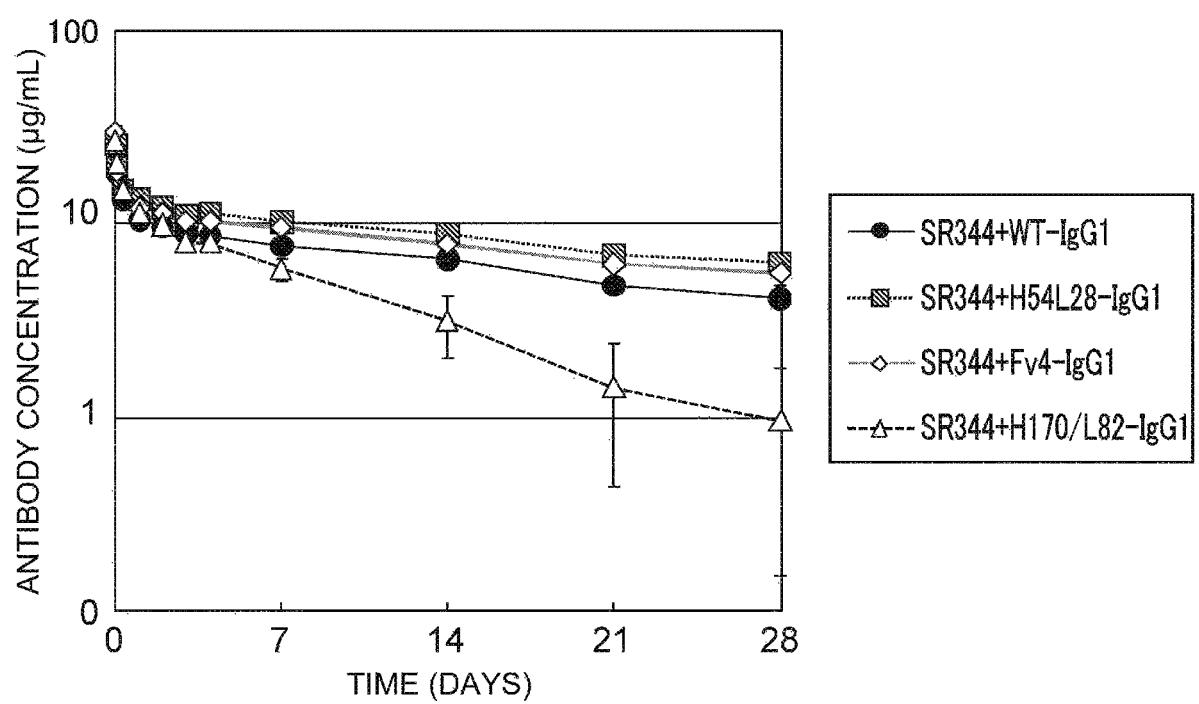
FIG. 28 depicts the time course of plasma antibody concentration after intravenous administration of a mixture solution containing SR344 and an anti-human IL-6 receptor antibody to mouse.

The concentration of human IL-6 receptor antibody in mouse plasma was measured by ELISA. Anti-human IgG (γ-chain specific) F(ab')2 antibody fragment (Sigma) was dispensed onto a Nunc-ImmunoPlate MaxiSorp (Nalge Nunc International) and allowed to stand overnight at 4° C. to prepare anti-human IgG-immobilized plates. Calibration curve samples having plasma concentrations of 0.8, 0.4, 0.2, 0.1, 0.05, 0.025, and 0.0125 μg/mL, and mouse plasma samples diluted 100-fold or more were prepared. 200 μL of 20 ng/mL SR344 was added to 100 μL of the calibration curve samples and plasma samples, and then the samples were allowed to stand for 1 hour at room temperature. Subsequently, the samples were dispensed into the anti-human IgG-immobilized plates, and allowed to stand for 1 hour at room temperature. Then, Biotinylated Anti-Human IL-6R Antibody (R&D) was added to react for 1 hour at room temperature. Subsequently, Streptavidin-PolyHRP80 (Stereospecific Detection Technologies) was added to react for 1 hour at room temperature, and chromogenic reaction was carried out using TMP One Component HRP Microwell Substrate (BioFX Laboratories) as a substrate. After stopping the reaction with 1 N sulfuric acid (Showa Chemical), the absorbance at 450 nm was measured by a microplate reader. The concentration in mouse plasma was calculated from the absorbance of the calibration curve using the analytical software SOFTmax PRO (Molecular Devices). The time course of plasma concentration after intravenous administration as measured by this method is shown in FIG. 28.

Measurement of SR344 Plasma Concentration by Electrochemiluminescence

Figure 29:
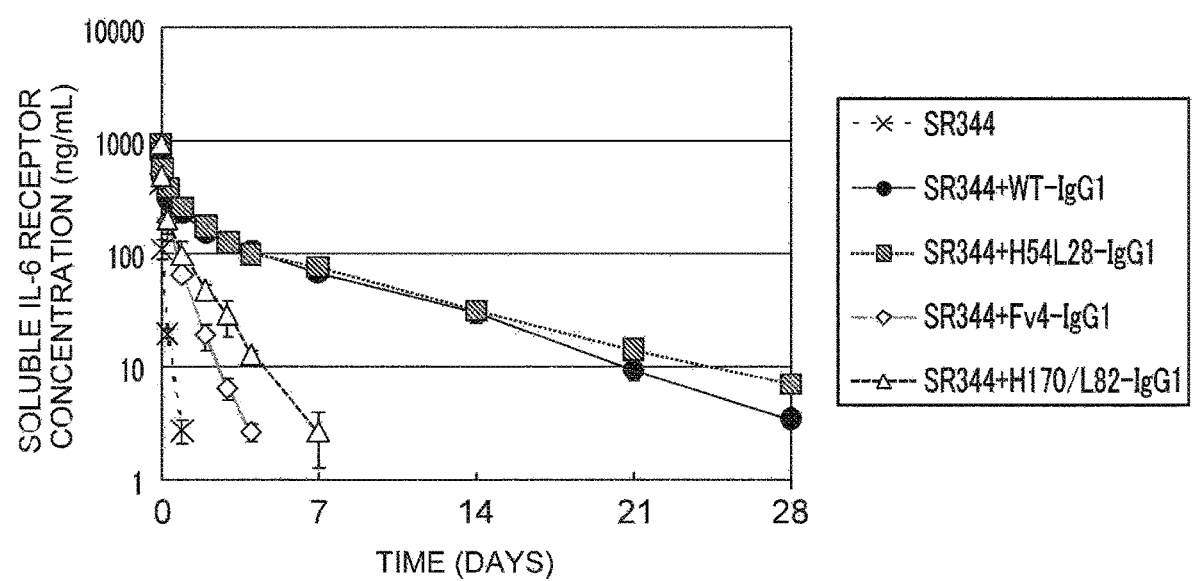
FIG. 29 depicts the time course of plasma SR344 concentration after intravenous administration of a mixture solution containing SR344 and an anti-human IL-6 receptor antibody to mouse.

The concentration of SR344 in mouse plasma was measured by electrochemiluminescence. SR344 calibration curve samples adjusted to concentrations of 2000, 1000, 500, 250, 125, 62.5, and 31.25 pg/mL, and mouse plasma samples diluted 50-fold or more were prepared. The samples were mixed with a solution of Monoclonal Anti-human IL-6R Antibody (R&D) ruthenium-labeled with Sulfo-Tag NHS Ester (Meso Scale Discovery), Biotinylated Anti-human IL-6R Antibody (R&D), and WT-IgG1, and then allowed to react overnight at 37° C. The final concentration of WT-IgG1 was 333 μg/mL, which is in excess of the concentration of anti-human IL-6 receptor antibody contained in the samples, for the purpose of binding nearly all of the SR344 molecules in the samples to WT-IgG1. Subsequently, the samples were dispensed into an MA400 PR Streptavidin Plate (Meso Scale Discovery), and allowed to react for 1 hour at room temperature, and washing was performed. Immediately after Read Buffer T (×4) (Meso Scale Discovery) was dispensed, the measurement was performed by the Sector PR 400 Reader (Meso Scale Discovery). The SR344 concentration was calculated based on the response of the calibration curve using the analytical software SOFTmax PRO (Molecular Devices). The time course of SR344 plasma concentration after intravenous administration as measured by this method is shown in FIG. 29.

Effects of pH-Dependent Binding

With respect to the time course of antibody concentration of WT-IgG1 and H54/L28-IgG1, which do not demonstrate the pH-dependent binding, and H170/L82-IgG1 and Fv4-IgG1, which demonstrate the pH-dependent binding, the time course of concentration was roughly identical for WT-IgG1, H54/L28-IgG1 and Fv4-IgG1, while H170/L82-IgG1 was eliminated slightly more rapidly. The data of the time course of plasma concentration was analyzed by the pharmacokinetics analysis software WinNonlin (Pharsight). The half-lives in the plasma of WT-IgG1, H54/L28-IgG1, Fv4-IgG1, and H170/L28-IgG1 were 21.0, 28.8, 26.2, and 7.5 days, respectively.

As described in Example 2, when the antigen is a soluble antigen, an administered antibody binds to the antigen in the plasma, and is retained in the plasma in the form of an antigen-antibody complex. Generally, in contrast to extremely long plasma retention time of an antibody (the elimination rate is extremely low) due to the function of FcRn, the plasma retention time of an antigen is short (the elimination rate is high). Thus, an antigen that is bound to an antibody has a prolonged plasma retention time similar to that of an antibody (the elimination rate is extremely low). Similarly, when the antigen of humanized IL-6 receptor antibody, SR344 (soluble human IL-6 receptor), was administered alone, SR344 was extremely rapidly eliminated (plasma half-life: 0.2 days). However, in the case of concurrent administration of SR344 with a conventional antibody, WT-IgG1 or H54/L28-IgG1, which does not demonstrate the pH-dependent binding, the elimination rate of SR344 was considerably reduced, and the plasma retention time of SR344 was prolonged (plasma half-life: 5.3 days for WT-IgG1, 6.3 days for H54/L28-IgG1). This is because nearly all of the SR344 molecules were bound by the antibodies administered together, and thus SR344 bound by the antibodies had a prolonged plasma retention time similar to that of the antibody, due to the function of FcRn as described above.

In the case of concurrent administration of SR344 with the H170/L82-IgG1 or Fv4-IgG1 antibody, which demonstrates the pH-dependent binding, the elimination of SR344 was significantly rapid (plasma half-life: 1.3 days for H170/L82-IgG1, 0.6 days for Fv4-IgG1), as compared to the case of concurrent administration with WT-IgG1 or H54/L28-IgG1. This tendency was particularly prominent for Fv4-IgG1. Since the affinity of Fv4-IgG1 at pH 7.4 is equivalent to or stronger than that of WT-IgG1 and H54/L28-IgG1, it is thought that nearly all of the SR344 molecules were bound to Fv4-IgG1. Even though Fv4-IgG1 demonstrates equivalent or slightly longer plasma retention and slower elimination compared to WT-IgG1 and H54/L28-IgG1, the elimination of SR344 bound to Fv4-IgG1 was extremely rapid. This can be explained by the concept of the present technology shown in FIG. 4. In the case of conventional antibodies that do not demonstrate the pH-dependent binding, an antibody-soluble antigen complex is taken up into endosomes by pinocytosis in the plasma, and binds to FcRn expressed in endosomes under intraendosomal acidic conditions. Since the antibody-soluble antigen complex bound to FcRn transfers to the cell surface as it is, and again returns to the plasma, the antigen bound to the antibody has a prolonged plasma retention time similar to that of the antibody (the elimination is extremely slow). On the other hand, in the case of antibodies that demonstrate the pH-dependent binding, the antigen dissociates from the antibody under intraendosomal acidic conditions, and thus only the antibody binds to FcRn and returns again to the plasma. Since the antigen dissociated from the antibody is degraded in lysosomes without returning to the plasma, the elimination of antigen is extremely rapid as compared to the case of antibodies that do not demonstrate the pH-dependent binding. Namely, in the case of concurrent administration of SR344 with the WT-IgG1 or H54/L28-IgG1 antibody, which does not demonstrate the pH-dependent binding, the elimination of SR344 is slow to the similar degree as the antibody, since SR344 binds to WT-IgG1 or H54/L28-IgG1 both in plasma and endosomes. In contrast, in the case of concurrent administration of SR344 with the H170/L28-IgG1 or Fv4-IgG1 antibody, which demonstrates the pH-dependent binding, the elimination of SR344 is extremely rapid, since SR344 dissociates from the antibody in the intraendosomal low-pH environment. That is, since the H170/L28-IgG1 and Fv4-IgG1 antibodies, which demonstrate the pH-dependent binding, dissociate from SR344 in the intraendosomal low-pH environment, the majority of H170/L82-IgG1 or Fv4-IgG1 that has returned again to the plasma with FcRn is thought to be not bound to SR344. Thus, as shown in FIG. 4, it was revealed that, by dissociating from an antigen in the intraendosomal low-pH environment and returning to the plasma with FcRn without binding to the antigen, an antibody that demonstrates the pH-dependent binding can again bind to an antigen in the plasma. It was also shown that, by repeating this process, the antibody that demonstrates the pH-dependent binding can repeatedly bind to multiple antigens. This is consistent with the Biacore™ surface plasmon resonance data shown in Example 7, demonstrating that pH-dependent antibodies can repeatedly bind to antigens. Thus, by enhancing the pH-dependent binding of an antibody to an antigen, the number of times of repetitive antigen binding can be increased.

When the antigen is a soluble antigen, and the antigen binds to an antibody under plasma neutral conditions, but dissociates from the antibody in endosomes and the antibody returns to the plasma with FcRn, the antibody can again bind to an antigen under plasma neutral conditions. Thus, an antibody that has the ability to dissociate from an antigen under intraendosomal acidic conditions can bind to antigens multiple times. As compared to when an antigen bound to an antibody does not dissociate from the antibody in endosomes (i.e., the antigen bound to the antibody returns to the plasma), if an antigen bound to an antibody dissociates from the antibody in endosomes, the plasma elimination rate of the antigen is increased, since the antigen is transported to lysosomes and degraded. Thus, the plasma elimination rate of an antigen can be used as an index to determine whether an antibody can bind to the antigen multiple times. Determination of the plasma elimination rate of an antigen can be performed, for example, by administering an antigen and an antibody in vivo, and then measuring the plasma antigen concentration after the administration, as shown in the Examples.

An antibody that demonstrates the pH-dependent binding can repeatedly bind to multiple antigens in contrast to the case of a conventional antibody that does not demonstrate the pH-dependent binding. Thus, the amount of antibody administered can be considerably reduced, and the administration intervals can be greatly prolonged.

The repetitive binding to multiple antigens of this mechanism is based on pH-dependent antigen-antibody reaction. Thus, regardless of the type of antigen, if an antibody demonstrating the pH-dependent binding that binds to an antigen at pH 7.4 of plasma but dissociates from the antigen at intraendosomal acidic pH can be constructed, then such an antibody can repeatedly bind to multiple antigens. Accordingly, the present technology is useful in that it can be applied not only to antibodies to the IL-6 receptor, IL-6, and the IL-31 receptor, but generally to any antibody to any antigen, regardless of the type of antigen.

The invention claimed is:

1. A method of neutralizing an antigen in vivo, comprising:
  administering an antibody to a human subject for a therapeutic purpose, wherein the antibody binds to the antigen through the antigen-binding domain of the antibody and has a KD(pH5.8)/KD(pH7.4) value, defined as the ratio of KD for the antigen at pH 5.8 and KD for the antigen at pH 7.4, of 40 to 1,000, wherein the antibody binds to the antigen under conditions present in plasma in vivo and dissociates from the bound antigen under conditions present in an endosome in vivo, and wherein the antibody is a human IgG or a humanized IgG.

2. The method of claim 1, wherein the antigen is a soluble antigen.

3. The method of claim 1, wherein the antibody is a humanized IgG.

4. The method of claim 1, wherein KD is determined using a surface plasmon resonance technique in which the antibody is immobilized, the antigen serves as analyte, and the following conditions are used: 10 mM MES buffer, 0.05% polyoxyethylene sorbitan monolaurate, and 150 mM NaCl at 37° C.

5. The method of claim 1, wherein the KD(pH5.8)/KD(pH7.4) value is 40 to 400.

6. A method of neutralizing an antigen in vivo, comprising:
  administering an antibody to a human subject for a therapeutic purpose, wherein the antibody binds to the antigen through the antigen-binding domain of the antibody comprising one or more histidine substitutions at one or more heavy chain or light chain variable region positions and has a KD(pH5.8)/KD(pH7.4) value, defined as the ratio of KD for the antigen at pH 5.8 and KD for the antigen at pH 7.4, of 10 to 1,000, wherein the antibody binds to the antigen under conditions present in plasma in vivo and dissociates from the bound antigen under conditions present in an endosome in vivo, and wherein the antibody is a human IgG or a humanized IgG.

7. The method of claim 6, wherein the antigen is a soluble antigen.

8. The method of claim 6, wherein the KD(pH5.8)/KD(pH7.4) value is 10 to 400.

9. The method of claim 6, wherein the KD(pH5.8)/KD(pH7.4) value is 30 to 400.

10. The method of claim 6, wherein the KD(pH5.8)/KD(pH7.4) value is 40 to 400.

11. The method of claim 6, wherein KD is determined using a surface plasmon resonance technique in which the antibody is immobilized, the antigen serves as analyte, and the following conditions are used: 10 mM MES buffer, 0.05% polyoxyethylene sorbitan monolaurate, and 150 mM NaCl at 37° C.

12. The method of claim 2, wherein the antibody is a humanized IgG.

13. The method of claim 2, wherein KD is determined using a surface plasmon resonance technique in which the antibody is immobilized, the antigen serves as analyte, and the following conditions are used: 10 mM MES buffer, 0.05% polyoxyethylene sorbitan monolaurate, and 150 mM NaCl at 37° C.

14. The method of claim 2, wherein the KD(pH5.8)/KD(pH7.4) value is 40 to 400.

15. The method of claim 12, wherein KD is determined using a surface plasmon resonance technique in which the antibody is immobilized, the antigen serves as analyte, and the following conditions are used: 10 mM MES buffer, 0.05% polyoxyethylene sorbitan monolaurate, and 150 mM NaCl at 37° C.

16. The method of claim 12, wherein the KD(pH5.8)/KD(pH7.4) value is 40 to 400.

17. The method of claim 15, wherein the KD(pH5.8)/KD(pH7.4) value is 40 to 400.

18. The method of claim 7, wherein the antibody is a humanized IgG.

19. The method of claim 7, wherein KD is determined using a surface plasmon resonance technique in which the antibody is immobilized, the antigen serves as analyte, and the following conditions are used: 10 mM MES buffer, 0.05% polyoxyethylene sorbitan monolaurate, and 150 mM NaCl at 37° C.

20. The method of claim 7, wherein the KD(pH5.8)/KD(pH7.4) value is 10 to 400.

21. The method of claim 7, wherein the KD(pH5.8)/KD(pH7.4) value is 30 to 400.

22. The method of claim 7, wherein the KD(pH5.8)/KD(pH7.4) value is 40 to 400.

23. The method of claim 18, wherein KD is determined using a surface plasmon resonance technique in which the antibody is immobilized, the antigen serves as analyte, and the following conditions are used: 10 mM MES buffer, 0.05% polyoxyethylene sorbitan monolaurate, and 150 mM NaCl at 37° C.

24. The method of claim 18, wherein the KD(pH5.8)/KD(pH7.4) value is 10 to 400.

25. The method of claim 18, wherein the KD(pH5.8)/KD(pH7.4) value is 30 to 400.

26. The method of claim 18, wherein the KD(pH5.8)/KD(pH7.4) value is 40 to 400.

27. The method of claim 23, wherein the KD(pH5.8)/KD(pH7.4) value is 10 to 400.

28. The method of claim 23, wherein the KD(pH5.8)/KD(pH7.4) value is 30 to 400.

29. The method of claim 23, wherein the KD(pH5.8)/KD(pH7.4) value is 40 to 400.

* * * * *

SEQUENCE LISTING

<160> NUMBER OF SEQ ID NOS: 70

<210> SEQ ID NO 1
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115

<210> SEQ ID NO 2
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 2

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105

<210> SEQ ID NO 3
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 3

Gln Val Gln Leu Gln Glu Ser Gly Pro Gly Leu Val Lys Pro Ser Glu
1               5                   10                  15

```
Thr Leu Ser Leu Thr Cys Ala Val Ser Gly His Ser Ile Ser His Asp
            20                  25                  30

His Ala His Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
 50                  55                  60

Lys Gly Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Ala Tyr Tyr Cys
                 85                  90                  95

Ala Arg Ser Leu Ala Arg Thr Thr Ala Met Asp Tyr Trp Gly Glu Gly
            100                 105                 110

Thr Leu Val Thr Val Ser Ser
        115
```

<210> SEQ ID NO 4
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 4

```
Gln Val Gln Leu Gln Glu Ser Gly Pro Gly Leu Val Lys Pro Ser Glu
 1               5                  10                  15

Thr Leu Ser Leu Thr Cys Ala Val Ser Gly His Ser Ile Ser His His
            20                  25                  30

His Ala His Ser Trp Val Arg Gln Pro Pro Gly Glu Gly Leu Glu Trp
        35                  40                  45

Ile Gly Tyr Ile Ser Tyr Ser Gly Ile Thr His Tyr Asn Pro His Leu
 50                  55                  60

Lys Gly Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Ala Tyr Tyr Cys
                 85                  90                  95

Ala Arg Val Leu Ala Arg Ile Thr Ala Met Asp His Trp Gly Glu Gly
            100                 105                 110

Thr Leu Val Thr Val Ser Ser
        115
```

<210> SEQ ID NO 5
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 5

```
Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Ser His Asp
            20                  25                  30

His Ala Trp Ser Trp Val Arg Gln Pro Pro Gly Glu Gly Leu Glu Trp
        35                  40                  45

Ile Gly His Ile Ser Tyr Ser Gly Ile Thr Asn Tyr Asn Pro His Leu
 50                  55                  60
```

```
Lys Gly Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Ala Tyr Tyr Cys
                 85                  90                  95

Ala Arg Phe Leu Ala Arg Ile Thr Ala His Asp His Trp Gly Glu Gly
            100                 105                 110

Thr Leu Val Thr Val Ser Ser
            115

<210> SEQ ID NO 6
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 6

Asp Ile Gln Met Thr Gln Ser Pro Ser Ser Leu Ser Ala Ser Val Gly
  1               5                  10                  15

Asp Ser Val Thr Ile Thr Cys Gln Ala Ser Gln His Ile Ser Ser His
                 20                  25                  30

Leu Asn Trp Tyr Gln Gln Lys Pro Gly Lys Ala Pro Glu Leu Leu Ile
             35                  40                  45

Tyr Tyr Gly Ser His Leu His Ser Gly Val Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gly Gln Gly Asn Arg Leu Pro Tyr
                 85                  90                  95

Thr Phe Gly Gln Gly Thr Lys Val Glu Ile Glu
            100                 105

<210> SEQ ID NO 7
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 7

Asp Ile Gln Met Thr Gln Ser Pro Ser Ser Leu Ser Ala Ser Val Gly
  1               5                  10                  15

Asp Ser Val Thr Ile Thr Cys Gln Ala Ser Gln Asp Ile Ser Ser His
                 20                  25                  30

Leu Asn Trp Tyr Gln Gln Lys Pro Gly Lys Ala Pro Glu Leu Leu Ile
             35                  40                  45

Tyr Tyr Gly Ser His Leu His Ser Gly Val Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gly Gln Gly Asn Arg Leu Pro Tyr
                 85                  90                  95

Thr Phe Gly Gln Gly Thr Lys Val Glu Ile Glu
            100                 105

<210> SEQ ID NO 8
<211> LENGTH: 107
<212> TYPE: PRT
```

```
<213> ORGANISM: Artificial
<220> FEATURE:
<223> OTHER INFORMATION: An artificially synthesized peptide sequence

<400> SEQUENCE: 8

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu His His Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly His Arg Leu Pro Tyr
                85                  90                  95

Thr Phe Gly Gln Gly Thr Lys Val Glu Ile Glu
            100                 105

<210> SEQ ID NO 9
<211> LENGTH: 448
<212> TYPE: PRT
<213> ORGANISM: Artificial
<220> FEATURE:
<223> OTHER INFORMATION: An artificially synthesized peptide sequence

<400> SEQUENCE: 9

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 10
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
            85                  90                  95

Ala Arg Val Leu Ala Arg Ile Thr Ala Met Asp Tyr Trp Gly Glu Gly
        100                 105                 110

Thr Leu Val Thr Val Ser Ser
        115

<210> SEQ ID NO 12
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 12

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Leu Glu Ala
65                  70                  75                  80

Glu Asp Ala Ala Thr Tyr Tyr Cys Gln Gln Gly Asn Ser Leu Pro Tyr
            85                  90                  95

Thr Phe Gly Gln Gly Thr Lys Val Glu Ile Glu
        100                 105

<210> SEQ ID NO 13
<211> LENGTH: 1404
<212> TYPE: DNA
<213> ORGANISM: Artificial
<220> FEATURE:
<223> OTHER INFORMATION: An artificially synthesized nucleotide sequence

<400> SEQUENCE: 13

| | | | | | |
|---|---|---|---|---|---|
| atgggatgga | gctgtatcat | cctcttcttg | gtagcaacag | ctacaggtgt | ccactcccag | 60 |
| gtccaactgc | aggagagcgg | tccaggtctt | gtgaaaccta | gcgagaccct | gagcctgacc | 120 |
| tgcgccgtgt | ctggctactc | aattagcgac | gatcatgcct | ggagctgggt | tcgccagcca | 180 |
| cctggagaag | gtcttgagtg | gattggatac | attagttata | gtggaatcac | aaactataat | 240 |
| ccatctctca | aggcagagt | gacaatatcg | agagacacca | gcaagaacca | gttcagcctg | 300 |
| aaactcagca | gcgtgacagc | cgccgacacc | gcggcttatt | attgtgcaag | atccctagct | 360 |
| cggactacgg | ctatggacta | ctggggtgaa | ggcacccteg | tcacagtctc | ctcagcctcc | 420 |
| accaagggcc | catcggtctt | cccctggca | ccctcctcca | gagcacctc | tgggggcaca | 480 |
| gcggccctgg | gctgcctggt | caaggactac | ttccccgaac | cggtgacggt | gtcgtggaac | 540 |
| tcaggcgccc | tgaccagcgg | cgtgcacacc | ttcccggctg | tcctacagtc | ctcaggactc | 600 |
| tactccctca | gcagcgtggt | gaccgtgccc | tccagcagct | tgggcaccca | gacctacatc | 660 |
| tgcaacgtga | atcacaagcc | cagcaacacc | aaggtggaca | agaaagttga | gcccaaatct | 720 |
| tgtgacaaaa | ctcacacatg | cccaccgtgc | ccagcacctg | aactcctggg | gggaccgtca | 780 |
| gtcttcctct | tccccccaaa | acccaaggac | accctcatga | tctcccggac | ccctgaggtc | 840 |
| acatgcgtgg | tggtggacgt | gagccacgaa | gaccctgagg | tcaagttcaa | ctggtacgtg | 900 |
| gacggcgtgg | aggtgcataa | tgccaagaca | aagccgcggg | aggagcagta | caacagcacg | 960 |
| taccgtgtgg | tcagcgtcct | caccgtcctg | caccaggact | ggctgaatgg | caaggagtac | 1020 |
| aagtgcaagg | tctccaacaa | agccctccca | gcccccatcg | agaaaaccat | ctccaaagcc | 1080 |
| aaagggcagc | cccgagaacc | acaggtgtac | accctgcccc | catcccggga | tgagctgacc | 1140 |
| aagaaccagg | tcagcctgac | ctgcctggtc | aaaggcttct | atcccagcga | catcgccgtg | 1200 |
| gagtgggaga | gcaatgggca | gccggagaac | aactacaaga | ccacgcctcc | cgtgctggac | 1260 |
| tccgacggct | ccttcttcct | ctacagcaag | ctcaccgtgg | acaagagcag | gtggcagcag | 1320 |
| gggaacgtct | tctcatgctc | cgtgatgcat | gaggctctgc | acaaccacta | cacgcagaag | 1380 |
| agcctctccc | tgtctccggg | taaa | | | | 1404 |

<210> SEQ ID NO 14
<211> LENGTH: 321
<212> TYPE: DNA
<213> ORGANISM: Artificial
<220> FEATURE:
<223> OTHER INFORMATION: An artificially synthesized nucleotide sequence

<400> SEQUENCE: 14

| | | | | | |
|---|---|---|---|---|---|
| gacatccaga | tgacccagag | cccaagcagc | ctgagcgcca | gcgtgggtga | cagcgtgacc | 60 |
| atcacctgtc | aagccagcca | ggacatcagc | agttacctga | attggtacca | gcagaagcca | 120 |
| ggaaaggctc | cagagctgct | gatctactac | ggctccgaac | tgcactctgg | tgtgccaagc | 180 |
| agattcagcg | gtagcggtag | cggtaccgac | ttcaccttca | ccatcagcag | cctcgaggca | 240 |

```
gaggacgccg ctacctacta ctgcgggcag ggtaaccggc ttccatacac gttcggccaa    300
gggaccaagg tggaaatcga a                                              321
```

<210> SEQ ID NO 15
<211> LENGTH: 15
<212> TYPE: PRT
<213> ORGANISM: Artificial
<220> FEATURE:
<223> OTHER INFORMATION: An artificially synthesized peptide sequence

<400> SEQUENCE: 15

```
Gly Gly Gly Gly Ser Gly Gly Gly Gly Ser Gly Gly Gly Gly Ser
1               5                   10                  15
```

<210> SEQ ID NO 16
<211> LENGTH: 24
<212> TYPE: DNA
<213> ORGANISM: Artificial
<220> FEATURE:
<223> OTHER INFORMATION: An artificially syntheisized primer sequence

<400> SEQUENCE: 16

```
ttcccaccag cctgtccgcc tctg                                            24
```

<210> SEQ ID NO 17
<211> LENGTH: 24
<212> TYPE: DNA
<213> ORGANISM: Artificial
<220> FEATURE:
<223> OTHER INFORMATION: An artificially syntheisized primer sequence

<400> SEQUENCE: 17

```
cgtgaagcca aaggccccac tccc                                            24
```

<210> SEQ ID NO 18
<211> LENGTH: 32
<212> TYPE: DNA
<213> ORGANISM: Artificial
<220> FEATURE:
<223> OTHER INFORMATION: An artificially syntheisized primer sequence

<400> SEQUENCE: 18

```
tagaattcca ccatgctggc cgtcggctgc gc                                   32
```

<210> SEQ ID NO 19
<211> LENGTH: 57
<212> TYPE: DNA
<213> ORGANISM: Artificial
<220> FEATURE:
<223> OTHER INFORMATION: An artificially syntheisized primer sequence

<400> SEQUENCE: 19

```
attgcggccg cttatcagtg gtgatgatga tgatgtggta ccgaagaaga atcttgc        57
```

<210> SEQ ID NO 20
<211> LENGTH: 1131
<212> TYPE: DNA
<213> ORGANISM: Artificial
<220> FEATURE:
<223> OTHER INFORMATION: An artificially synthesized nucleotide sequence

<400> SEQUENCE: 20

```
gaattccacc atgctggccg tcggctgcgc gctgctggct gccctgctgg ccgcgccggg    60
ggcggcgctg gccccggggg gctgccctgc acaggaggtg gcgagaggtg tgctgaccag   120
```

```
tctgccagga gacagcgtga ctctgacctg cccaggggga gagccggaag acaatgccac    180
tgttcactgg gttctcagga agccagctgt aggctcccac ctcagcagat gggctggcgt    240
gggaaggagg ctgctgctga ggtcggtgca gctccatgac tctggaaact attcatgcta    300
ccgggccggc cgcccggctg gaactgtgca cttgctggtg gatgttcccc ccgaggagcc    360
ccagctctcc tgcttccgga gagccccct cagcaacgtt gtttgtgagt ggggtcctcg     420
gagcacccca tctccgacga ccaaggctgt gctgttggtg aggaagtttc agaacagtcc    480
ggccgaagac ttccaggagc cgtgccagta ttcccaggag tcccagaagt ctcctgcca    540 gttggcagtc ccgagggag acagctcttt ctacatagtg tccatgtgcg tcgccagtag    600
tgtcgggagc aagctcagca aaactcagac ctttcagggt tgtggaatct gcagcctga    660 tccgcctgcc aacatcacag tcactgccgt ggccagaaac ccccgctggc tcagtgtcac    720
ctggcaagac ccccactcct ggaactcatc tttctacaga ctacggtttg agctcagata    780
tcgagctgaa cggtcaaaga cattcacaac atggatggtc aaggacctcc agcatcactg    840
tgtcatccac gacgcctgga gcggcctgag gcacgtggtg cagcttcgtg cccaggagga    900
gttcgggcaa ggcgagtgga gcgagtggag cccggaggcc atgggcacgc cttggacaga    960
atccaggagt cctccagctg agaacgaggt gtccaccccc acgcaggcac ctactactaa   1020
taaagatgat gataatattc tctccagaga ttctgcaaat gcgacaagcc tcccagtgca   1080
agattcttct tcggtaccac atcatcatca tcaccactga taagcggccg c            1131

<210> SEQ ID NO 21
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser His Asp
            20                  25                  30

His Ala Trp Ser Trp Val Arg Gln Pro Pro Gly Glu Gly Leu Glu Trp
        35                  40                  45

Ile Gly His Ile Ser Tyr Ser Gly Ile Thr Asn Tyr Asn Pro His Leu
    50                  55                  60

Gln Asp Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Phe Leu Ala Arg Ile Thr Ala His Asp His Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 22
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 22

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser His Asp
                20                  25                  30

His Ala Trp Ser Trp Val Arg Gln Pro Pro Gly Glu Gly Leu Glu Trp
                35                  40                  45

Ile Gly His Ile Ser Tyr Ser Gly Ile Thr Asn Tyr Asn Pro His Leu
        50                  55                  60

Gln Asp Arg Val Thr Ile Ser Arg Asp Thr Ser Lys Asn Gln Phe Ser
65                  70                  75                  80

-continued

```
Leu Lys Leu Ser Ser Val Thr Ala Ala Asp Thr Ala Val Tyr Tyr Cys
                85                  90                  95
Ala Arg Phe Leu Ala Arg Ile Thr Ala His Asp His Trp Gly Glu Gly
            100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
130             135                 140
Gly Cys Leu Val Lys Asp Tyr Phe Pro Glu Pro Val Thr Val Ser Trp
145             150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys Asp Lys
            210                 215                 220
Thr His Thr Cys Pro Pro Cys Pro Ala Pro Glu Leu Leu Gly Gly Pro
225             230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305             310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys
```

<210> SEQ ID NO 23
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 23

```
Gln Val Gln Leu Gln Glu Ser Gly Pro Gly Leu Val Lys Pro Ser Glu
1               5                   10                  15
Thr Leu Ser Leu Thr Cys Ala Val Ser Gly His Ser Ile Ser His Asp
            20                  25                  30
His Ala Trp Ser Trp Val Arg Gln Pro Pro Gly Glu Gly Leu Glu Trp
        35                  40                  45
Ile Gly Phe Ile Ser Tyr Ser Gly Ile Thr Asn Tyr Asn Pro Ser Leu
    50                  55                  60
Gln Gly Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
```

-continued

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 24
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Thr Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

Lys

<210> SEQ ID NO 25
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 25

Asp Ile Gln Met Thr Gln Ser Pro Ser Ser Leu Ser Ala Ser Val Gly
1               5                   10                  15

Asp Ser Val Thr Ile Thr Cys Gln Ala Ser Arg Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 26
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 26

Asp Ile Gln Met Thr Gln Ser Pro Ser Ser Leu Ser Ala Ser Val Gly
1               5                   10                  15

Asp Ser Val Thr Ile Thr Cys Gln Ala Ser Arg Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Glu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 27

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95
```

-continued

```
Thr Phe Gly Gln Gly Thr Lys Val Glu Ile Glu Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 28
<211> LENGTH: 326
<212> TYPE: PRT
<213> ORGANISM: Homo sapiens

<400> SEQUENCE: 28

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
```

```
Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 29
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285
```

```
Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro

<210> SEQ ID NO 30
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300
```

Ser Val Met His Glu Ala Leu His Asn His Tyr Thr Gln Lys Ser Leu
305                 310                 315                 320

Ser Leu Ser Pro

<210> SEQ ID NO 31
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 31

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Ala His Tyr Thr Gln Lys Ser Leu
305                 310                 315                 320

Ser Leu Ser Pro Gly Lys
                325

<210> SEQ ID NO 32
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 32

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300

Ser Val Met His Glu Ala Leu His Ala His Tyr Thr Gln Lys Ser Leu
305                 310                 315                 320

Ser Leu Ser Pro
```

<210> SEQ ID NO 33
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 33

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400
```

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
            435                 440

<210> SEQ ID NO 34
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 34

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

```
Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro
            435                 440

<210> SEQ ID NO 35
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 35

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
        435                 440

<210> SEQ ID NO 36
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 36

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser His Asp
            20                  25                  30

His Ala Trp Ser Trp Val Arg Gln Pro Pro Gly Glu Gly Leu Glu Trp
        35                  40                  45

Ile Gly His Ile Ser Tyr Ser Gly Ile Thr Asn Tyr Asn Pro His Leu
    50                  55                  60

Gln Asp Arg Val Thr Ile Ser Arg Asp Thr Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Phe Leu Ala Arg Ile Thr Ala His Asp His Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Ala
            420                 425                 430

His Tyr Thr Gln Lys Ser Leu Ser Leu Ser Pro Gly Lys
        435                 440                 445

<210> SEQ ID NO 37
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser His Asp
            20                  25                  30

His Ala Trp Ser Trp Val Arg Gln Pro Pro Gly Glu Gly Leu Glu Trp
        35                  40                  45

Ile Gly His Ile Ser Tyr Ser Gly Ile Thr Asn Tyr Asn Pro His Leu
    50                  55                  60

Gln Asp Arg Val Thr Ile Ser Arg Asp Thr Ser Lys Asn Gln Phe Ser
65                  70                  75                  80

```
Leu Lys Leu Ser Ser Val Thr Ala Ala Asp Thr Ala Val Tyr Tyr Cys
                85                  90                  95

Ala Arg Phe Leu Ala Arg Ile Thr Ala His Asp His Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Ser Cys Val Glu
        210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
        290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
                420                 425                 430

His Tyr Thr Gln Lys Ser Leu Ser Leu Ser Pro
            435                 440
```

<210> SEQ ID NO 38
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 38

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Thr Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Ala
            420                 425                 430

His Tyr Thr Gln Lys Ser Leu Ser Leu Ser Pro Gly Lys
        435                 440                 445

<210> SEQ ID NO 39
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Thr Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

```
Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
            405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
            435                 440

<210> SEQ ID NO 40
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 40

His Asp His Ala Trp Ser
1               5

<210> SEQ ID NO 41
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 41

His Ile Ser Tyr Ser Gly Ile Thr Asn Tyr Asn Pro His Leu Gln Asp
1               5                   10                  15

<210> SEQ ID NO 42
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 42

Phe Ile Ser Tyr Ser Gly Ile Thr Asn Tyr Asn Pro Ser Leu Gln Gly
1               5                   10                  15

<210> SEQ ID NO 43
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 43

Phe Ile Ser Tyr Ser Gly Ile Thr Asn Tyr Asn Pro Thr Leu Gln Gly
1               5                   10                  15

<210> SEQ ID NO 44
```

```
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 44

Phe Leu Ala Arg Ile Thr Ala His Asp His
1               5                   10

<210> SEQ ID NO 45
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 45

Ser Leu Ala Arg Thr Thr Ala Met Asp Tyr
1               5                   10

<210> SEQ ID NO 46
<211> LENGTH: 30
<212> TYPE: PRT
<213> ORGANISM: Artificial
<220> FEATURE:
<223> OTHER INFORMATION: An artificially synthesized peptide sequence

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser
            20                  25                  30

<210> SEQ ID NO 47
<211> LENGTH: 30
<212> TYPE: PRT
<213> ORGANISM: Artificial
<220> FEATURE:
<223> OTHER INFORMATION: An artificially synthesized peptide sequence

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser
            20                  25                  30

<210> SEQ ID NO 48
<211> LENGTH: 14
<212> TYPE: PRT
<213> ORGANISM: Artificial
<220> FEATURE:
<223> OTHER INFORMATION: An artificially synthesized peptide sequence

<400> SEQUENCE: 48

Trp Val Arg Gln Pro Pro Gly Glu Gly Leu Glu Trp Ile Gly
1               5                   10

<210> SEQ ID NO 49
<211> LENGTH: 32
<212> TYPE: PRT
<213> ORGANISM: Artificial
<220> FEATURE:
<223> OTHER INFORMATION: An artificially synthesized peptide sequence
```

<400> SEQUENCE: 49

Arg Val Thr Ile Ser Arg Asp Thr Ser Lys Asn Gln Phe Ser Leu Lys
1               5                   10                  15

Leu Ser Ser Val Thr Ala Ala Asp Thr Ala Ala Tyr Tyr Cys Ala Arg
            20                  25                  30

<210> SEQ ID NO 50
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 50

Arg Val Thr Ile Ser Arg Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 51
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 51

Arg Val Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 52
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 52

Trp Gly Glu Gly Thr Leu Val Thr Val Ser Ser
1               5                   10

<210> SEQ ID NO 53
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 53

Gln Ala Ser Arg Asp Ile Ser Ser His Leu Asn
1               5                   10

<210> SEQ ID NO 54
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 54

Gln Ala Ser Thr Asp Ile Ser Ser His Leu Asn
1               5                   10

```
<210> SEQ ID NO 55
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 55

Tyr Gly Ser His Leu Leu Ser
1               5

<210> SEQ ID NO 56
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 56

Tyr Gly Ser His Leu Glu Ser
1               5

<210> SEQ ID NO 57
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 57

Gly Gln Gly Asn Arg Leu Pro Tyr Thr
1               5

<210> SEQ ID NO 58
<211> LENGTH: 23
<212> TYPE: PRT
<213> ORGANISM: Artificial
<220> FEATURE:
<223> OTHER INFORMATION: An artificially synthesized peptide sequence

<400> SEQUENCE: 58

Asp Ile Gln Met Thr Gln Ser Pro Ser Ser Leu Ser Ala Ser Val Gly
1               5                   10                  15

Asp Ser Val Thr Ile Thr Cys
            20

<210> SEQ ID NO 59
<211> LENGTH: 15
<212> TYPE: PRT
<213> ORGANISM: Artificial
<220> FEATURE:
<223> OTHER INFORMATION: An artificially synthesized peptide sequence

<400> SEQUENCE: 59

Trp Tyr Gln Gln Lys Pro Gly Lys Ala Pro Glu Leu Leu Ile Tyr
1               5                   10                  15

<210> SEQ ID NO 60
<211> LENGTH: 32
<212> TYPE: PRT
<213> ORGANISM: Artificial
<220> FEATURE:
<223> OTHER INFORMATION: An artificially synthesized peptide sequence
```

<400> SEQUENCE: 60

```
Gly Val Pro Ser Arg Phe Ser Gly Ser Gly Thr Asp Phe Thr
 1               5                  10                  15

Phe Thr Ile Ser Ser Leu Glu Ala Glu Asp Ala Ala Thr Tyr Tyr Cys
             20                  25                  30
```

<210> SEQ ID NO 61
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 61

```
Phe Gly Gln Gly Thr Lys Val Glu Ile Glu
 1               5                  10
```

<210> SEQ ID NO 62
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 62

```
Glu Val Gln Leu Val Glu Ser Gly Gly Lys Leu Leu Lys Pro Gly Gly
 1               5                  10                  15

Ser Leu Lys Leu Ser Cys Ala Ala Ser Gly Phe Thr Phe Ser Ser Phe
             20                  25                  30

Ala Met Ser Trp Phe Arg Gln Ser Pro Glu Lys Arg Leu Glu Trp Val
         35                  40                  45

Ala Glu Ile Ser Ser Gly Gly Ser Tyr Thr Tyr Tyr Pro Asp Thr Val
     50                  55                  60

Thr Gly Arg Phe Thr Ile Ser Arg Asp Asn Ala Lys Asn Thr Leu Tyr
 65                  70                  75                  80

Leu Glu Met Ser Ser Leu Arg Ser Glu Asp Thr Ala Met Tyr Tyr Cys
                 85                  90                  95

Ala Arg Gly Leu Trp Gly Tyr Tyr Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 63
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 63

Gln Ile Val Leu Ile Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Gly Tyr Pro Tyr Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 64
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 64

Glu Val Gln Leu Val Glu Ser Gly Gly Lys Leu Leu Lys Pro Gly Gly
1               5                   10                  15

Ser Leu Lys Leu Ser Cys Ala Ala Ser Gly Phe Thr Phe Ser Ser His
            20                  25                  30

Ala Met Ser Trp Phe Arg Gln Ser Pro Glu Lys Arg Leu Glu Trp Val
        35                  40                  45

Ala Glu Ile Ser Ser Gly Gly Ser Tyr Thr Tyr His Pro His Thr Val
    50                  55                  60

Thr Gly Arg Phe Thr Ile Ser Arg Asp Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Ala Arg Gly Leu Trp Gly His Tyr Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 65
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 65

Gln Ile Val Leu Ile Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn His Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln His Trp Ser His Pro Tyr Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 66
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 66

Gln Ile Val Leu Ile Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser His His Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln His Trp Ser Gly His Pro Tyr Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 67
<211> LENGTH: 456
<212> TYPE: PRT
<213> ORGANISM: Artificial
<220> FEATURE:
<223> OTHER INFORMATION: An artificially synthesized peptide sequence

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Glu Asp Val Val Pro Ala Ala Met Ser Phe Tyr Tyr Gly Met
        100                 105                 110

Asp Val Trp Gly Arg Gly Thr Leu Val Thr Val Ser Ser Ala Ser Thr
    115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Gly
450                 455

<210> SEQ ID NO 68
<211> LENGTH: 214

```
<212> TYPE: PRT
<213> ORGANISM: Artificial
<220> FEATURE:
<223> OTHER INFORMATION: An artificially synthesized peptide sequence

<400> SEQUENCE: 68

Leu Pro Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Thr Val
            20                  25                  30

Tyr Trp Tyr Gln Gln Glu Pro Gly Gln Ala Pro Val Leu Val Val Tyr
        35                  40                  45

Asp Asp Thr Asp Arg Pro Ala Gly Ile Pro Glu Arg Phe Ser Gly Ala
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Thr Asp His
                85                  90                  95

Gly Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 69
<211> LENGTH: 456
<212> TYPE: PRT
<213> ORGANISM: Artificial
<220> FEATURE:
<223> OTHER INFORMATION: An artificially synthesized peptide sequence

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Asp Val Val Pro Ala Ala Met Ser Phe Tyr Tyr Gly Met
            100                 105                 110
```

```
Asp Val Trp Gly Arg Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Gly
    450                 455

<210> SEQ ID NO 70
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 70

Gln Val Gln Leu Gln Glu Ser Gly Pro Gly Leu Val Lys Pro Ser Glu
1               5                   10                  15
```

-continued

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
            85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

```
Ala Leu His Asn His Tyr Thr Gln Lys Ser Leu Ser Leu Ser Pro Gly
        435                 440                 445
Lys
```